United States Patent

Parham et al.

(10) Patent No.: US 9,334,260 B2
(45) Date of Patent: May 10, 2016

(54) MATERIALS FOR ELECTRONIC DEVICES

(75) Inventors: Amir Hossain Parham, Frankfurt am Main (DE); Christof Pflumm, Frankfurt am Main (DE); Arne Buesing, Frankfurt am Main (DE); Teresa Mujica-Fernaud, Darmstadt (DE); Irina Martynova, Frankfurt am Main (DE); Holger Heil, Frankfurt am Main (DE); Rémi Manouk Anémian, Seoul (KR)

(73) Assignee: Merck Patent GmbH, Darmstadt (DE)

( * ) Notice: Subject to any disclaimer, the term of this patent is extended or adjusted under 35 U.S.C. 154(b) by 663 days.

(21) Appl. No.: 13/509,399

(22) PCT Filed: Oct. 20, 2010

(86) PCT No.: PCT/EP2010/006415
§ 371 (c)(1),
(2), (4) Date: May 11, 2012

(87) PCT Pub. No.: WO2011/057706
PCT Pub. Date: May 19, 2011

(65) Prior Publication Data
US 2012/0223276 A1    Sep. 6, 2012

(30) Foreign Application Priority Data

Nov. 14, 2009   (DE) .................. 10 2009 053 382

(51) Int. Cl.
| | | |
|---|---|---|
| *H01L 51/50* | (2006.01) | |
| *C07D 403/14* | (2006.01) | |
| *C07D 403/10* | (2006.01) | |
| *C07D 403/12* | (2006.01) | |
| *C07D 405/14* | (2006.01) | |
| *C07D 409/14* | (2006.01) | |
| *C07D 471/04* | (2006.01) | |
| *H01L 51/00* | (2006.01) | |
| *C09B 57/00* | (2006.01) | |

(52) U.S. Cl.
CPC ............ *C07D 403/14* (2013.01); *C07D 403/10* (2013.01); *C07D 403/12* (2013.01); *C07D 405/14* (2013.01); *C07D 409/14* (2013.01); *C07D 471/04* (2013.01); *C09B 57/00* (2013.01); *H01L 51/0067* (2013.01); *H01L 51/0072* (2013.01); *H01L 51/0074* (2013.01); *H01L 51/0077* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 2004/0086745 A1 | 5/2004 | Iwakuma | |
| 2004/0110031 A1 | 6/2004 | Fukuda et al. | |
| 2006/0186796 A1 | 8/2006 | Yabe et al. | |
| 2008/0145699 A1 | 6/2008 | Yabe et al. | |
| 2009/0284138 A1* | 11/2009 | Yasukawa et al. | ............ 313/504 |
| 2011/0062429 A1 | 3/2011 | Kai et al. | |
| 2012/0175598 A1* | 7/2012 | Balaganesan | ........ C07D 209/88 257/40 |

FOREIGN PATENT DOCUMENTS

| | | |
|---|---|---|
| EP | 2080762 A1 | 7/2009 |
| GB | 1119824 A | 7/1968 |
| JP | 2004-071500 A | 3/2004 |
| JP | 2004-178895 A | 6/2004 |
| JP | 2004/288381 A | 10/2004 |
| JP | 2005-268199 A | 9/2005 |
| JP | 2009-306783  * 11/2006 ............. H01L 51/50 |
| JP | 2008-247895 A | 10/2008 |
| JP | 2009-021336 A | 1/2009 |
| JP | 2009-029726 A | 2/2009 |
| JP | 2009051788 A | 3/2009 |
| JP | 2009057307 A | 3/2009 |
| JP | 2009123976 A | 6/2009 |
| JP | 2010-140976 A | 6/2010 |
| WO | 03/080760 A1 | 10/2003 |
| WO | 2006/067976 A1 | 6/2006 |
| WO | 2009/069442 A1 | 6/2009 |
| WO | 2009/086028 | 7/2009 |
| WO | WO-2009086028 A2 | 7/2009 |
| WO | 2009/136595 A1 | 11/2009 |

OTHER PUBLICATIONS

International Search Report for PCT/EP2010/006415 mailed Jul. 14, 2011.
Shaw et al., "1,3,5-Triazines, Part XII: The Reaction of Trichtoro 1,3,5-triazine (Cyanuric Chloride) with N-Phenyl-pyrrole, -indole, carbazole, and -diphenylemine, and N-Ethyl-pyrrole, -carbazole and -diphenylamine", Journal of the Chemical Society Perkin Transactions II, 1973, No. 15, pp. 2075-2078.
Brandl et al., "An Efficient New Pyrimidlne Synthesis—A Pathway to Octupoles", J. Prakt. Chem., 1996, vol. 338, pp. 451-459.
Wong et al., "Synthesis, properties, and electrogenerated chemiluminescence (ECL) of a novel carbazole-based chromophore", Tetrahedron Letters, 2005, vol. 46, No. 5, pp. 855-858.
English Translation of Japanese Office Action dated Aug. 26, 2014 for Application No. 2012-538211.

* cited by examiner

*Primary Examiner* — Gregory Clark
(74) *Attorney, Agent, or Firm* — Drinker Biddle & Reath LLP

(57) ABSTRACT

The present adventure relates to novel compounds of the formula (I) or (II), to the use of the compounds in electronic devices, to a process for the preparation of the compounds, and to electronic devices comprising the compounds, preferably as matrix materials or as electron-transport materials.

21 Claims, No Drawings

MATERIALS FOR ELECTRONIC DEVICES

CROSS-REFERENCE TO RELATED APPLICATIONS

This application is a national stage application (under 35 U.S.C. §371) of PCT/EP2010/006415, filed Oct. 20, 2010, which claims benefit of German Application 10 2009 053 382.6, filed Nov. 14, 2009.

The invention relates to novel compounds of the formula (I) or (II). The invention furthermore relates to polymers which comprise the compounds according to the invention as structural units, to a process for the preparation of the compounds according to the invention, and to electronic devices comprising the compounds according to the invention.

Organic semiconductors like the compounds in accordance with the present application are being developed for a number of electronic applications of different types. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, further developments and improvements are desirable, in particular with respect to the lifetime, efficiency and operating voltage of organic electroluminescent devices. Furthermore, the compounds employed are in many cases required to have high thermal stability and a high glass-transition temperature and to be sublimable without decomposition.

Especially also in the case of phosphorescent electroluminescent devices, improvements in the above-mentioned properties are desired. In particular, there is a demand for matrix materials for phosphorescent emitters which simultaneously result in good efficiency, a long lifetime and a low operating voltage. In particular, the properties of the matrix materials are frequently limiting for the lifetime and efficiency of the organic electroluminescent device.

In accordance with the prior art, carbazole derivatives, for example bis(carbazolyl)biphenyl, are frequently used as matrix materials for phosphorescent emitters. There is a demand here for alternative materials, which preferably have a high glass-transition temperature and effect an extended lifetime of the electronic devices.

Furthermore, ketones (WO 04/093207), phosphine oxides and sulfones (WO 05/003253) are used as matrix materials for phosphorescent emitters.

Low operating voltages and long lifetimes are achieved, in particular, with ketones. There is still a need for improvement here, in particular with respect to the efficiency and compatibility with metal complexes which contain ketoketonate ligands, for example acetylacetonate. Furthermore, metal complexes, for example BAlq or bis[2-(2-benzothiazole)phenolate]-zinc(II), are used as matrix materials for phosphorescent emitters. There is a need for improvement here, in particular with respect to the operating voltage and chemical stability. Purely organic compounds are frequently more stable than the metal complexes. Thus, some of the metal complexes are sensitive to hydrolysis, which makes handling thereof more difficult.

In summary, there is a demand for matrix materials for phosphorescent emitters which simultaneously result in high efficiencies, long lifetimes and low operating voltages and which are also compatible with phosphorescent emitters which carry ketoketonate ligands.

The provision of novel electron-transport materials is likewise desirable, since the properties of the electron-transport material in particular also exert a significant influence on the above-mentioned properties of the organic electroluminescent device. In particular, there is a demand for electron-transport materials which simultaneously result in good efficiency, a long lifetime and a low operating voltage.

It would be desirable here to have available electron-transport materials which result in better electron injection into the emitting layer, since an electron-richer emission layer is accompanied by better efficiency. In addition, better injection enables the operating voltage to be lowered.

The applications WO 2006/067976, WO 2005/085387, WO 2008/123189 and JP 2002/193952 disclose carbazole derivatives which have been derivatised by means of electron-deficient heterocycles, such as, for example, triazine, and the use thereof in electronic devices. However, the systems, material combinations and compounds disclosed in the said applications still have potential for improvement in some areas, inter alia in the life of the electronic devices, the operating voltage and the glass-transition temperature of the compounds employed.

Consequently, there continues to be a demand for matrix materials for phosphorescent dopants which preferably have the following properties: an increase in the efficiency of the electroluminescent device, an extension of the lifetime of the device and technically straightforward processability. In addition, there is a demand for novel electron-transport materials which preferably have the advantageous properties mentioned above.

The present technical object thus consists in the provision of compounds of this type.

It has been found in accordance with the invention that compounds of the formulae (I) and (II) defined below are eminently suitable for use as matrix materials in electronic devices, in particular as matrix materials for phosphorescent emitters. Higher efficiencies and longer lifetimes can preferably be achieved with these materials than with materials in accordance with the prior art. In addition, the operating voltage can preferably be lowered, which corresponds to higher power efficiencies.

It has furthermore been found that the compounds of the formulae (I) and (II) can be used as electron-transport materials in organic electroluminescent devices. An improved performance profile of the devices, in particular higher power efficiency, a longer lifetime and a reduction in the operating voltage, can preferably be achieved with the compounds according to the invention.

The invention thus relates to a compound of the formula (I) or (II):

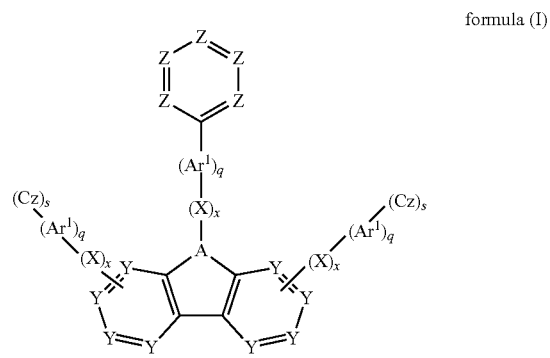

formula (I)

-continued

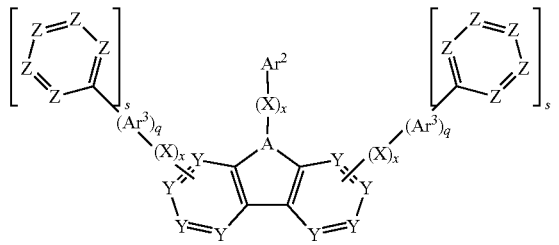

formula (II)

where the symbols and indices occurring are defined as follows:
$Ar^1$, $Ar^2$, $Ar^3$ are on each occurrence, identically or differently, an aromatic or heteroaromatic ring system having 5 to 60 aromatic ring atoms, which is optionally substituted by one or more radicals $R^1$;
Cz is on each occurrence, identically or differently, a group of the formula (A)

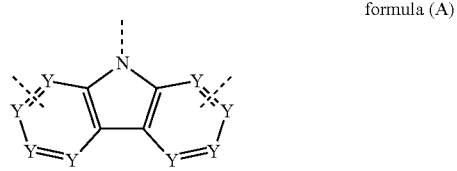

formula (A)

in which the dashed lines represent possible bonding positions to $Ar^1$ or X or to the central carbazole derivative, and the nitrogen is the preferred bonding position;
A is N or P;
X is on each occurrence, identically or differently, selected from —B($R^1$)—, —N($R^1$)—, —P($R^1$)—, —P($R^1$)$_3$—, —P(=O)($R^1$)—, —C($R^1$)$_2$—, —Si($R^1$)$_2$—, C=O, C=N$R^1$, C=C($R^1$)$_2$, —O—, —S—, —Se—, —S(=O)— and —S(=O)$_2$—;
Y is on each occurrence, identically or differently, C$R^{Cz}$ or N, or is C if a group X or $Ar^1$ or $Ar^3$ or Cz is bonded to this group;
Z is on each occurrence, identically or differently, C$R^{HetAr}$ or N, where at least one Z per six-membered ring is equal to N;
q is on each occurrence, identically or differently, 0 or 1, where, in the case where q=0, the two groups bonded to the group $Ar^1$ or $Ar^3$ in question are bonded directly to one another;
S is on each occurrence, identically or differently, 0 or 1, with the proviso that at least one index s is equal to 1;
x is on each occurrence, identically or differently, 0 or 1, where, in the case where x=0, the two groups bonded to the group X in question are bonded directly to one another;
$R^1$, $R^{HetAr}$, $R^{Cz}$ are on each occurrence, identically or differently, H, D, F, Cl, Br, I, N($R^2$)$_2$, CN, NO$_2$, Si($R^2$)$_3$, B(O$R^2$)$_2$, C(=O)$R^2$, P(=O)($R^2$)$_2$, S(=O)$R^2$, S(=O)$_2R^2$, OSO$_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkoxy or thioalkoxy group having 3 to 40 C atoms, each of which may be substituted by one or more radicals $R^2$, where one or more CH$_2$ groups may be replaced by —$R^2$C=C$R^2$—, —Si($R^2$)$_2$—, —Ge($R^2$)$_2$—, —Sn($R^2$)$_2$—, C=O, C=S, C=Se, C=N$R^2$, —P(=O) ($R^2$)—, —S(=O)—, —S(=O)$_2$—, —N($R^2$)—, —O—, —S—, —C(=O)O— or —C(=O)N$R^2$—, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or an aralkyl or heteroaralkyl group having 5 to 60 aromatic ring atoms, which may in each case be substituted by one or more radicals $R^2$; two or more substituents $R^1$, $R^{HetAr}$ or $R^{Cz}$ here may be linked to one another and may optionally form a mono- or polycyclic aliphatic, aromatic or heteroaromatic ring system;
$R^2$ is on each occurrence, identically or differently, H, D or an aliphatic, aromatic or heteroaromatic organic radical having 1 to 20 C atoms, in which, in addition, one or more H atoms may be replaced by D or F; two or more radicals $R^2$ here may be linked to one another and may optionally form a mono- or polycyclic aliphatic, aromatic or heteroaromatic ring system.

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S.

An aryl group or heteroaryl group here is taken to mean either a simple aromatic ring, i.e. benzene, or a simple heteroaromatic ring, for example pyridine, pyrimidine or thiophene, or a condensed (fused) aromatic or heteroaromatic polycyclic group, for example naphthalene, phenanthrene, quinoline or carbazole. A condensed (fused) aromatic or heteroaromatic polycyclic group in the sense of the present application consists of two or more simple aromatic or heteroaromatic rings which are condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp³-hybridised C, Si, N or O atom, an sp²-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanmidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH₂ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

It is preferred in accordance with the invention for no, precisely one or two groups Y per six-membered ring of the carbazole derivative in the compounds of the formula (I) or formula (II) to stand for N and for all other groups Y to stand for $CR^{Cz}$ or C. It is particularly preferred for no or precisely one group Y per six-membered ring of the carbazole derivative in compounds of the formula (I) or formula (II) to stand for N and for all other groups Y to stand for $CR^{Cz}$ or C.

It is furthermore particularly preferred for no group Y in compounds of the formula (I) to stand for N.

It is furthermore particularly preferred for one or more groups Y in compounds of the formula (II) to stand for N.

It is furthermore preferred in accordance with the invention for all indices s in the compounds of the formula (I) or formula (II) to adopt the value 1.

In a further preferred embodiment of the invention, one index s in the compounds according to the invention adopts the value 1 and the other adopts the value 0, where in this case 1, 2 or 3 groups X are preferably present, i.e. the index x in question is equal to 1.

It is furthermore preferred in accordance with the invention for A to be equal to N.

In accordance with a preferred embodiment of the invention, the group

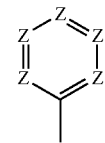

in a compound of the formula (I) or (II) represents triazine, pyrazine, pyridazine, pyrimidine or pyridine, which may be substituted by one or more radicals $R^{HetAr}$.

It is furthermore preferred for 1, 2 or 3 groups Z per six-membered ring in the compounds according to the invention to be equal to N, more preferred for 2 or 3 groups Z per six-membered ring in the compounds according to the invention to be equal to N, even more preferred for precisely 3 groups Z per six-membered ring in the compounds according to the invention to equal to N, where the other groups Z in the six-membered ring are equal to $CR^{HetAr}$.

The heteroaromatic six-membered ring in question very particularly preferably represents a 1,3,5-triazine derivative which is substituted by identical or different groups $R^{HetAr}$.

The following preferred embodiments apply to the groups $Ar^1$, $Ar^2$ and $Ar^3$:

$Ar^1$ preferably represents on each occurrence, identically or differently, an aromatic or heteroaromatic ring system having 5 to 30 aromatic ring atoms, which is optionally substituted by one or more radicals $R^1$.

Ar² preferably represents on each occurrence, identically or differently, an aromatic ring system having 6 to 30 aromatic ring atoms, which is optionally substituted by one or more radicals R¹, particularly preferably an aryl group having 6 to 18 aromatic ring atoms, which is optionally substituted by one or more radicals R¹.

Ar³ preferably represents on each occurrence, identically or differently, a heteroaromatic ring system having 5 to 30 aromatic ring atoms, which is optionally substituted by one or more radicals R¹, particularly preferably a heteroaryl group having 5 to 18 aromatic ring atoms, which is optionally substituted by one or more radicals R¹.

It is furthermore preferred for R¹ to be selected on each occurrence, identically or differently, from H, D, F, N(R²)₂, C(=O)R², CR²=C(R²)₂, CN, a straight-chain alkyl group having 1 to 10 C atoms, an alkenyl or alkynyl group having 2 to 10 C atoms or a branched or cyclic alkyl group having 3 to 10 C atoms, where the above-mentioned groups may each be substituted by one or more radicals R² and where one or more adjacent or non-adjacent CH₂ groups in the above-mentioned groups may be replaced by —C≡C—, —R²C=CR²—, Si(R²)₂, C=O, C=NR², —NR—, —O—, —S—, —C(=O)O— or —C(=O)NR²—, or an aryl or heteroaryl group having 5 to 20 aromatic ring atoms, which may be substituted by one or more radicals R².

It is furthermore preferred for $R^{Cz}$ to be selected on each occurrence, identically or differently, from H, D, F, N(R²)₂, C(=O)R², CR²=C(R²)₂, CN, a straight-chain alkyl group having 1 to 10 C atoms, an alkenyl or alkynyl group having 2 to 10 C atoms or a branched or cyclic alkyl group having 3 to 10 C atoms, where the above-mentioned groups may each be substituted by one or more radicals R² and where one or more adjacent or non-adjacent CH₂ groups in the above-mentioned groups may be replaced by —C≡C—, —R²C=CR²—, Si(R²)₂, C=O, C=NR², —NR²—, —O—, —S—, —C(=O)O— or —C(=O)NR²—, or an aryl or heteroaryl group having 5 to 20 aromatic ring atoms, which may be substituted by one or more radicals R².

At least one radical $R^{Cz}$ preferably represents a group of the formula (A)

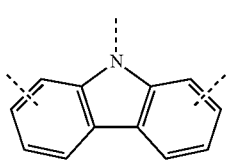

formula (A)

where the dashed lines represent possible links from the group of the formula (A) to further structural units of the compounds according to the invention.

It is furthermore preferred for $R^{HetAr}$ to be selected on each occurrence, identically or differently, from H, D, F, N(R²)₂, C(=O)R², CR²=C(R²)₂, CN, a straight-chain alkyl group having 1 to 10 C atoms, an alkenyl or alkynyl group having 2 to 10 C atoms or a branched or cyclic alkyl group having 3 to 10 C atoms, where the above-mentioned groups may each be substituted by one or more radicals R² and where one or more adjacent or non-adjacent CH₂ groups in the above-mentioned groups may be replaced by —C≡C—, —R²C=CR²—, Si(R²)₂, C=O, C=NR², —NR²—, —O—, —S—, —C(=O)O— or —C(=O)NR²—, or an aryl or heteroaryl group having 5 to 20 aromatic ring atoms, which may be substituted by one or more radicals R².

$R^{HetAr}$ is particularly preferably selected from H or aryl or heteroaryl groups having 5 to 20 aromatic ring atoms, of which preferably phenyl, biphenyl, terphenyl, pyrazinyl, pyridazyl, pyrimidyl, triazinyl, carbazolyl or dibenzothiophenyl groups, where the said groups may each be substituted by one or more radicals R².

It is preferred in accordance with the invention for X to be selected on each occurrence, identically or differently, from —N(R¹)—, —C(R¹)₂—, C=O, C=NR¹, —O—, —S—, —S(=O)— and —S(=O)₂—.

In a further preferred embodiment of the compounds according to the invention, at least one index x is equal to 1.

In a preferred embodiment of the invention, the compound of the formula (I) represents a compound of the formula (I-1) or (I-2):

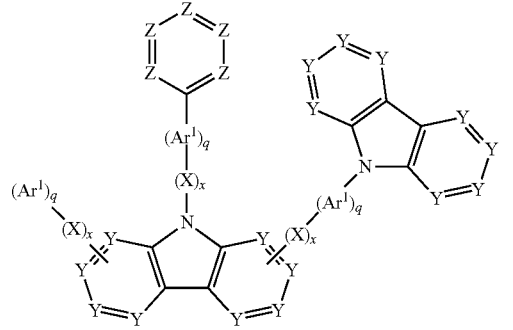

formula (I-1)

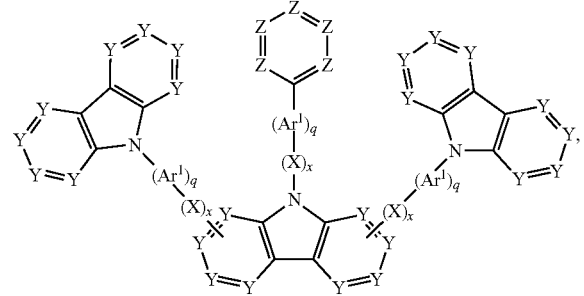

formula (I-2)

where the symbols and indices occurring are as defined above.

In particular, the preferred embodiments of the groups Ar¹, X, Y, Z, R¹, $H^{HetAr}$ and $R^{Cz}$ indicated above apply to the compounds of the formulae (I-1) and (I-2).

In a further preferred embodiment of the invention, the compound of the formula (II) represents a compound of the formula (II-1) or (II-2):

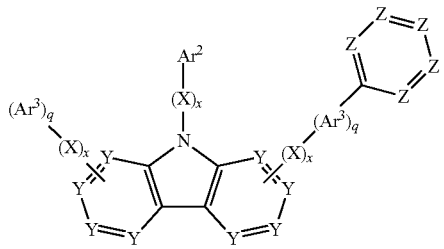

formula (II-1)

-continued

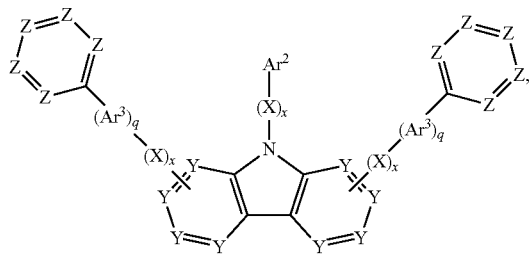
formula (II-2)

where the symbols and indices occurring are as defined above.

In particular, the preferred embodiments of the groups $Ar^r$, $Ar^3$, X, Y, Z, $R^1$, $H^{HetAr}$ and $R^{Cz}$ indicated above apply to the compounds of the formulae (II-1) and (II-2).

Particularly preferred embodiments of the compounds of the formulae (I-1) and (I-2) conform to the following formulae (I-1a) to (I-1d) and (I-2a) to (I-2f):

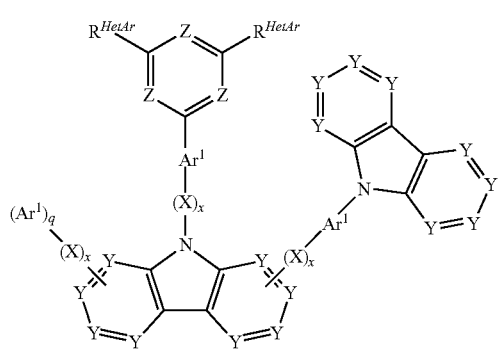
formula (I-1a)

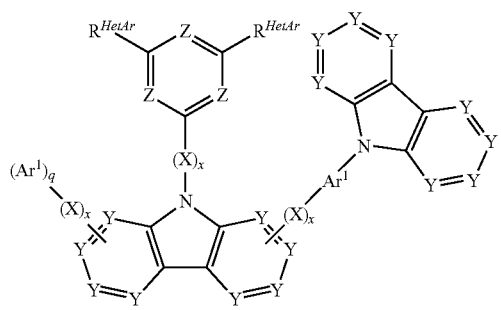
formula (I-1b)

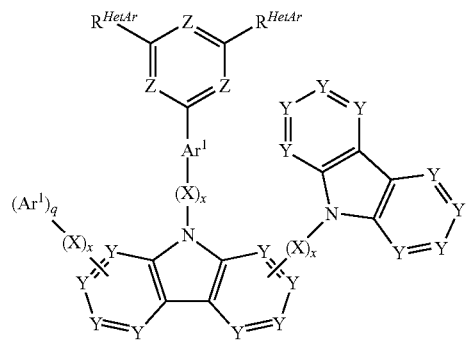
formula (I-1c)

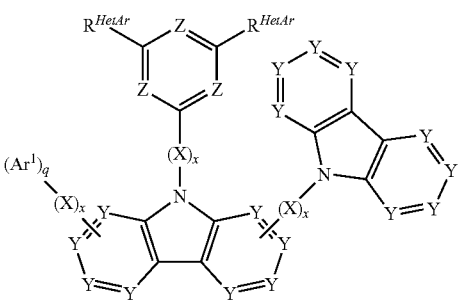
formula (I-1d)

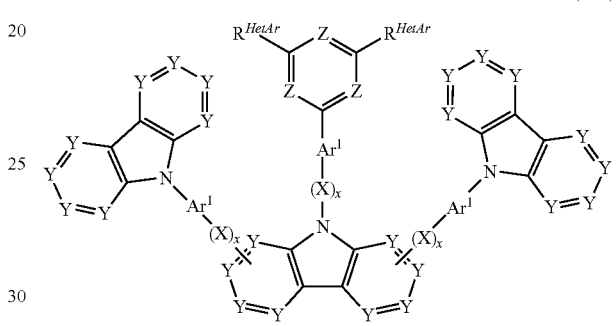
formula (I-2a)

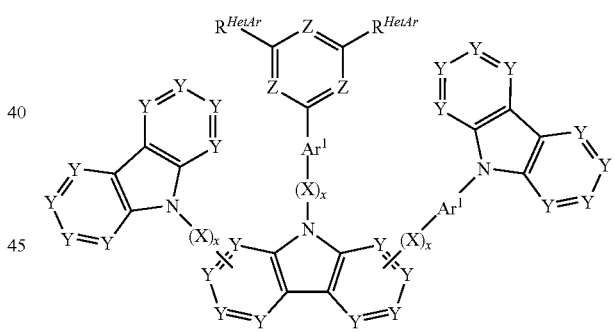
formula (I-2b)

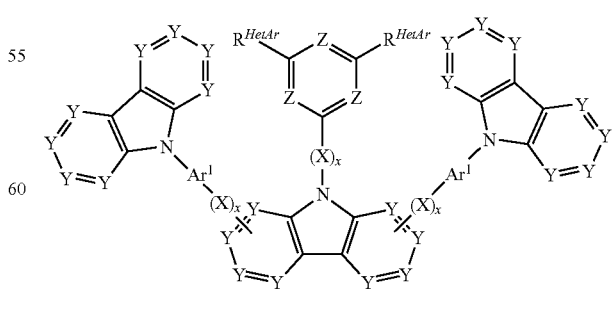
formula (I-2c)

formula (I-2d)

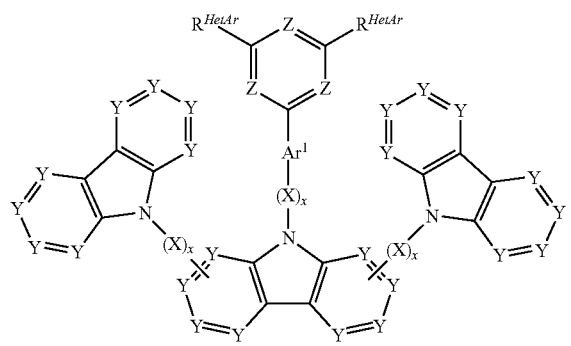

formula (I-2e)

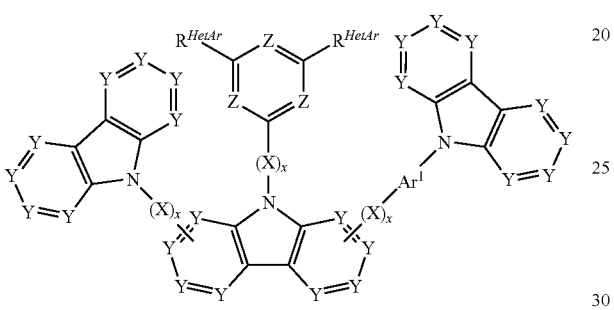

formula (I-2f)

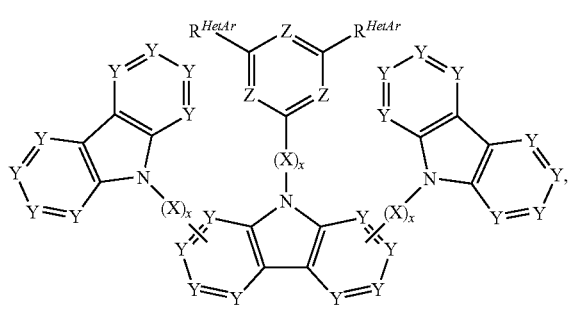

where the symbols and indices occurring are defined as indicated above.

Particularly preferred embodiments of the compounds of the formulae (II-1) and (II-2) conform to the following formulae (II-1a) to (II-1b) and (II-2a) to (II-2c):

formula (II-1a)

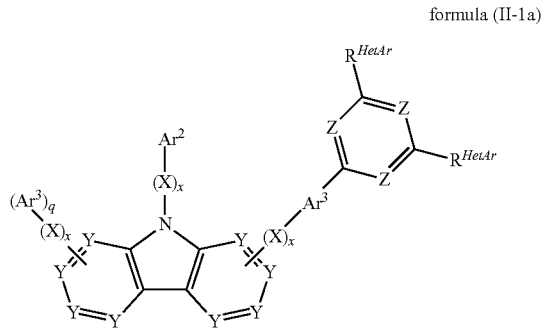

formula (II-1b)

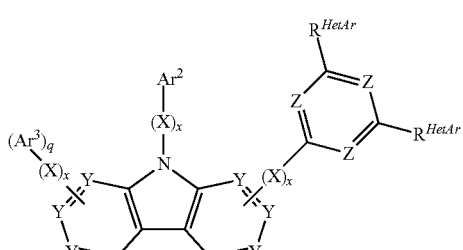

formula (II-2a)

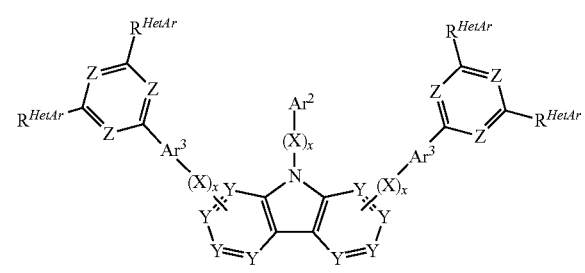

formula (II-2b)

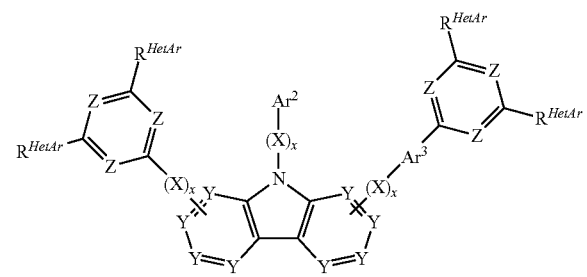

formula (II-2c)

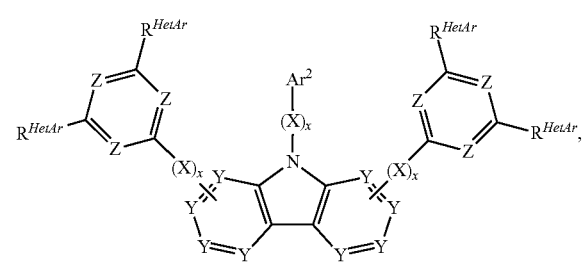

where the symbols and indices occurring are defined as indicated above. It is furthermore particularly preferred for the formulae (II-1a) and (II-1b) for $Ar^3$ to represent a heteroaryl group having 5 to 18 aromatic ring atoms, which may be substituted by one or more radicals $R^1$.

It is furthermore particularly preferred for the following preferred embodiments to apply simultaneously to the preferred embodiments of the formulae (I-1a) to (I-1d), (I-2a) to (I-2f), (II-1a) to (II-1b) and (II-2a) to (II-2c):

$Ar^1$ represents on each occurrence, identically or differently, an aromatic or heteroaromatic ring system having 5 to 30 aromatic ring atoms, which is optionally substituted by one or more radicals $R^1$; and $Ar^2$ represents on each occurrence, identically or differently, an aromatic ring system having 6 to 30 aromatic ring atoms, which is optionally substituted by one or more radicals $R^1$; and Ar³ represents on each occurrence, identically or differently, a heteroaromatic ring system having 5 to 30 aromatic ring atoms, which is optionally substituted by one or more radicals R¹; and X is selected on each occurrence, identically or differently, from —N(R¹)—, —C(R¹)₂—, C=O, C=NR¹, —O—, —S—, —S(=O)— and —S(=O)₂—; and R¹ is selected on each occurrence, identically or differently, from H, D, F, N(R²)₂, C(=O)R², CR²=C(R²)₂, CN, a straight-chain alkyl group having 1 to 10 C atoms, an alkenyl or alkynyl group having 2 to 10 C atoms or a branched or cyclic alkyl group having 3 to 10 C atoms, where the above-mentioned groups may each be substituted by one or more radicals R² and where one or more adjacent or non-adjacent CH₂ groups in the above-mentioned groups may be replaced by —C≡C—, —R²C=CR²—, Si(R²)₂, C=O, C=NR², —NR²—, —O—, —S—, —C(=O)O— or —C(=O)NR²—, or an aryl or heteroaryl group having 5 to 20 aromatic ring atoms, which may be substituted by one or more radicals R²; and $R^{Cz}$ is selected on each occurrence, identically or differently, from H, D, F, N(R²)₂, C(=O)R², CR²=C(R²)₂, CN, a straight-chain alkyl group having 1 to 10 C atoms, an alkenyl or alkynyl group having 2 to 10 C atoms or a branched or cyclic alkyl group having 3 to 10 C atoms, where the above-mentioned groups may each be substituted by one or more radicals R² and where one or more adjacent or non-adjacent CH₂ groups in the above-mentioned groups may be replaced by —C≡C—, —R²C=CR²—, Si(R²)₂, C=O, C=NR², —NR²—, —O—, —S—, —C(=O)O— or —C(=O)NR²—, or an aryl or heteroaryl group having 5 to 20 aromatic ring atoms, which may be substituted by one or more radicals R²; and $R^{HetAr}$ is selected on each occurrence, identically or differently, from H, D, F, N(R²)₂, C(=O)R², CR²=C(R²)₂, CN, a straight-chain alkyl group having 1 to 10 C atoms, an alkenyl or alkynyl group having 2 to 10 C atoms or a branched or cyclic alkyl group having 3 to 10 C atoms, where the above-mentioned groups may each be substituted by one or more radicals R² and where one or more adjacent or non-adjacent CH₂ groups in the above-mentioned groups may be replaced by —C≡C—, —R²C=CR²—, Si(R²)₂, C=O, C=NR², —NR²—, —O—, —S—, —C(=O)O— or —C(=O)NR²—, or an aryl or heteroaryl group having 5 to 20 aromatic ring atoms, which may be substituted by one or more radicals R².

Examples of compounds according to the invention are given in the following table.

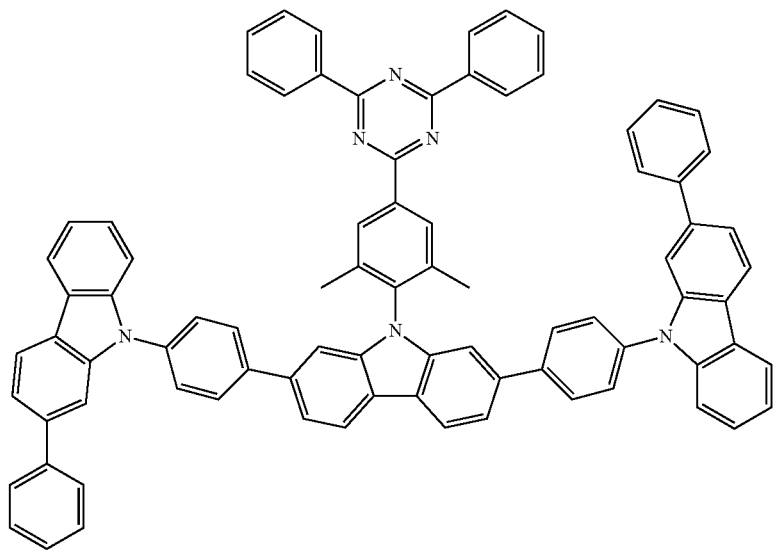 [SMILES: Cc1cc(-c2nc(-c3ccccc3)nc(-c3ccccc3)n2)cc(C)c1-n1c2cc(-c3ccc(-n4c5ccccc5c5ccc(-c6ccccc6)cc54)cc3)ccc2c2ccc(-c3ccc(-n4c5ccccc5c5ccc(-c6ccccc6)cc54)cc3)cc21]

1

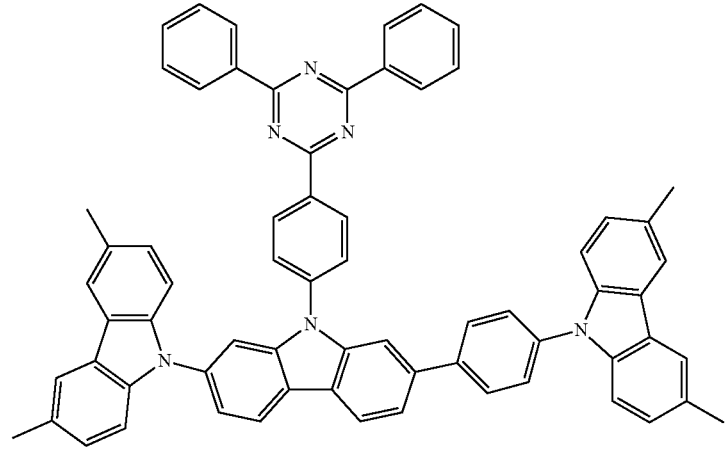

2

-continued
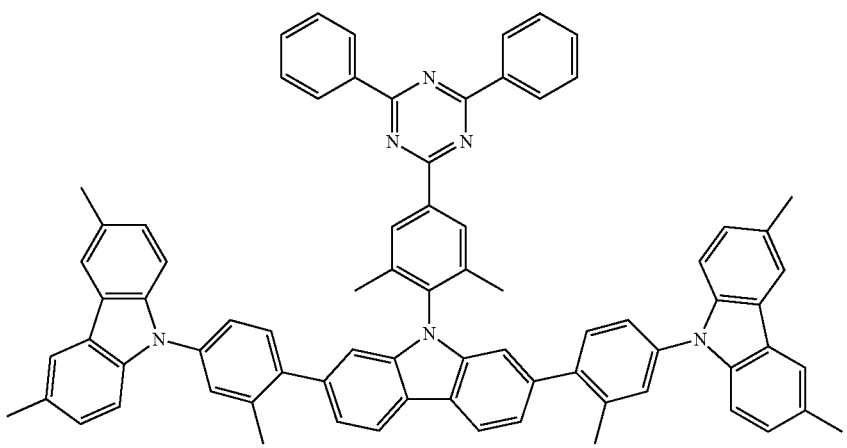
3
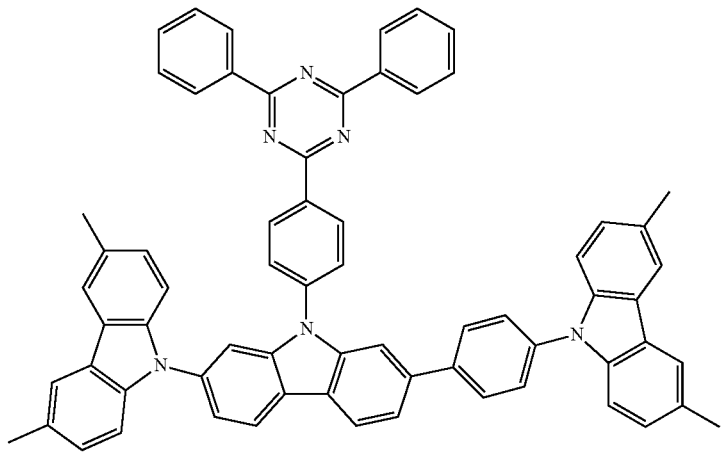
4
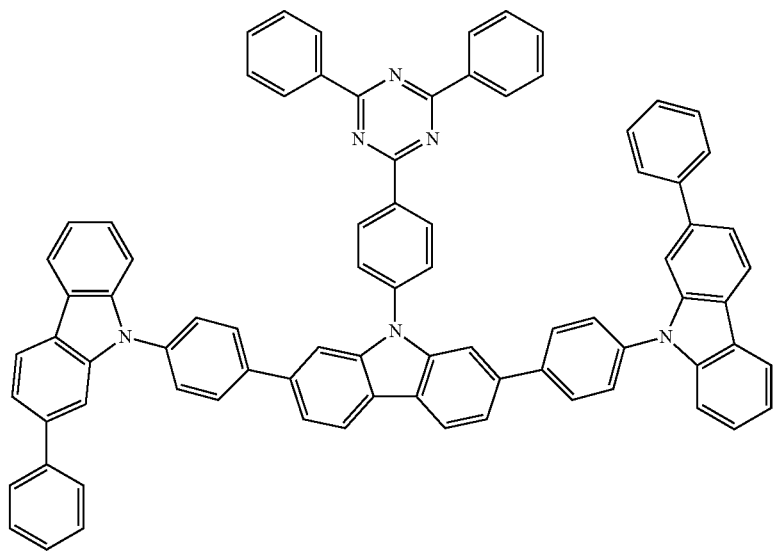 [SMILES: c1ccc(-c2ccc3c4ccccc4n(-c4ccc(-c5ccc6c7ccc(-c8ccc(-n9c%10ccccc%10c%10ccc(-c%11ccccc%11)cc%109)cc8)cc7n(-c7ccc(-c8nc(-c9ccccc9)nc(-c9ccccc9)n8)cc7)c6c5)cc4)c3c2)cc1]
5

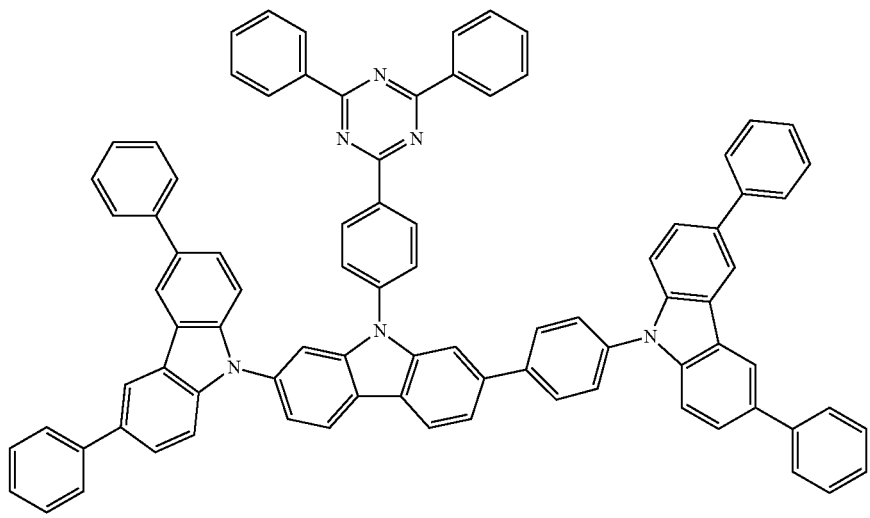 [SMILES: c1ccc(-c2ccc3c(c2)c2cc(-c4ccccc4)ccc2n3-c2ccc(-c3ccc4c5ccc(-n6c7ccc(-c8ccccc8)cc7c7cc(-c8ccccc8)ccc76)cc5n(-c5ccc(-c6nc(-c7ccccc7)nc(-c7ccccc7)n6)cc5)c4c3)cc2)cc1]
6
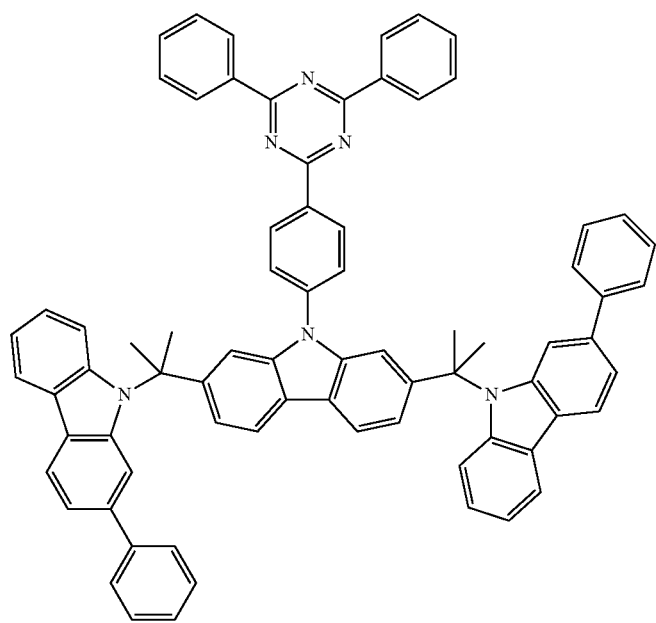 [SMILES: CC(C)(c1ccc2c3ccc(C(C)(C)n4c5ccccc5c5ccc(-c6ccccc6)cc54)cc3n(-c3ccc(-c4nc(-c5ccccc5)nc(-c5ccccc5)n4)cc3)c2c1)n1c2ccccc2c2ccc(-c3ccccc3)cc21]
7

-continued
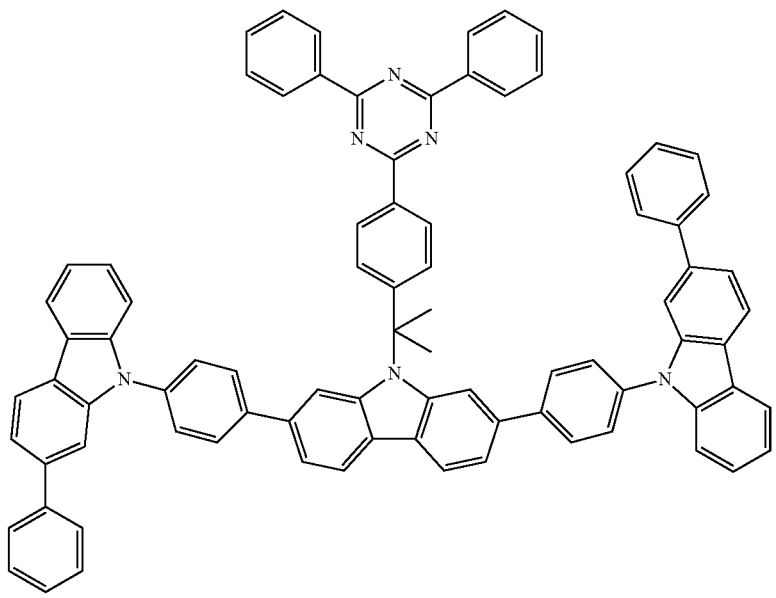 [SMILES: CC(C)(c1ccc(-c2nc(-c3ccccc3)nc(-c3ccccc3)n2)cc1)n1c2cc(-c3ccc(-n4c5ccccc5c5ccc(-c6ccccc6)cc54)cc3)ccc2c2ccc(-c3ccc(-n4c5ccccc5c5ccc(-c6ccccc6)cc54)cc3)cc21]
8
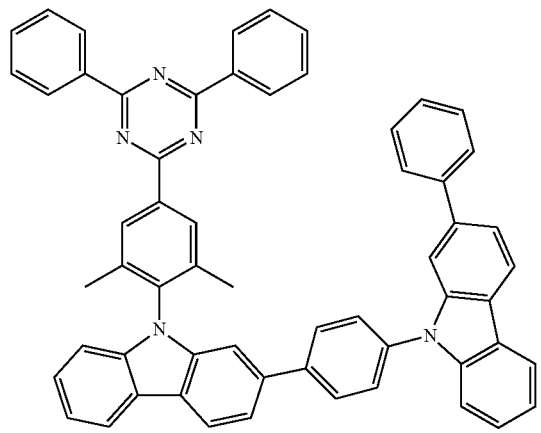 [SMILES: Cc1cc(-c2nc(-c3ccccc3)nc(-c3ccccc3)n2)cc(C)c1-n1c2ccccc2c2ccc(-c3ccc(-n4c5ccccc5c5ccc(-c6ccccc6)cc54)cc3)cc21]
9
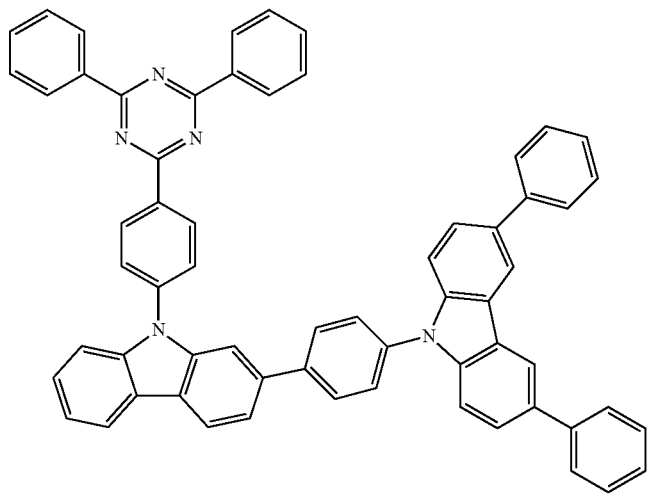 [SMILES: c1ccc(-c2ccc3c(c2)c2cc(-c4ccccc4)ccc2n3-c2ccc(-c3ccc4c5ccccc5n(-c5ccc(-c6nc(-c7ccccc7)nc(-c7ccccc7)n6)cc5)c4c3)cc2)cc1]
10

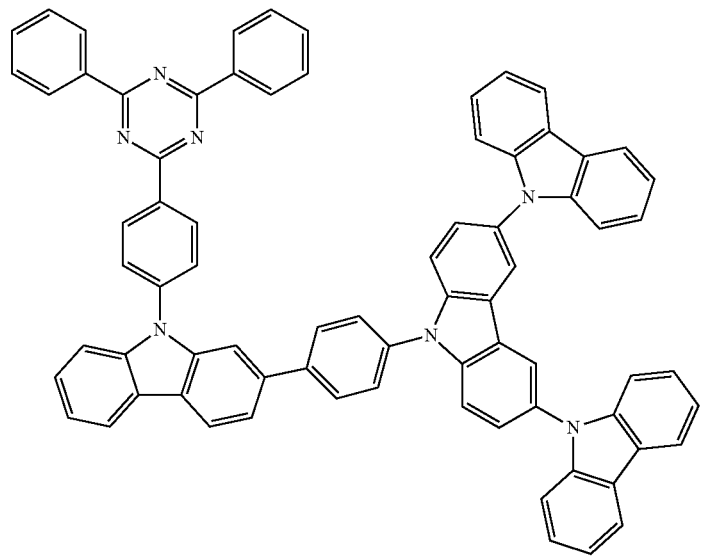 [SMILES: c1ccc(-c2nc(-c3ccccc3)nc(-c3ccc(-n4c5ccccc5c5ccc(-c6ccc(-n7c8ccc(-n9c%10ccccc%10c%10ccccc%109)cc8c8cc(-n9c%10ccccc%10c%10ccccc%109)ccc87)cc6)cc54)cc3)n2)cc1]
11
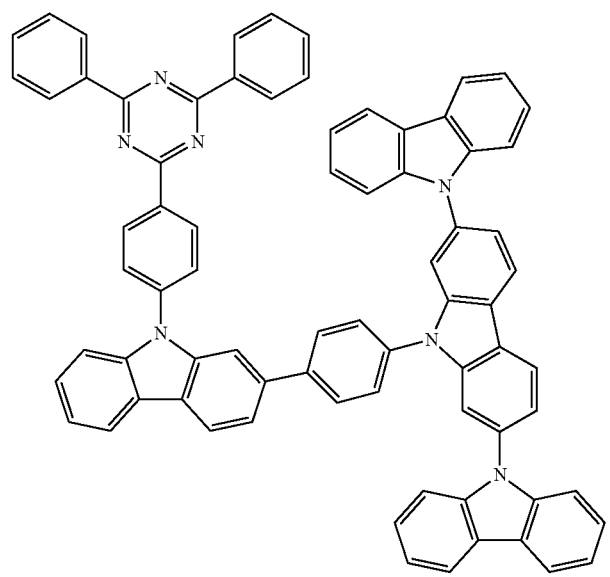 [SMILES: c1ccc(-c2nc(-c3ccccc3)nc(-c3ccc(-n4c5ccccc5c5ccc(-c6ccc(-n7c8cc(-n9c%10ccccc%10c%10ccccc%109)ccc8c8ccc(-n9c%10ccccc%10c%10ccccc%109)cc87)cc6)cc54)cc3)n2)cc1]
12

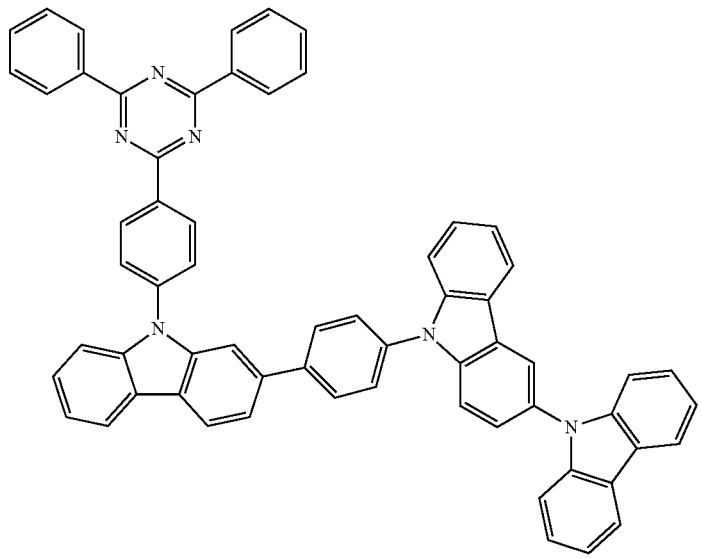 [SMILES: c1ccc(-c2nc(-c3ccccc3)nc(-c3ccc(-n4c5ccccc5c5ccc(-c6ccc(-n7c8ccccc8c8cc(-n9c%10ccccc%10c%10ccccc%109)ccc87)cc6)cc54)cc3)n2)cc1]
13
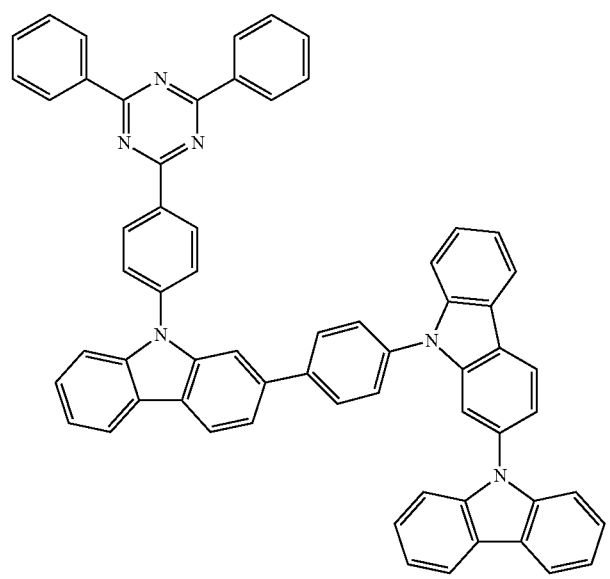 [SMILES: c1ccc(-c2nc(-c3ccccc3)nc(-c3ccc(-n4c5ccccc5c5ccc(-c6ccc(-n7c8ccccc8c8ccc(-n9c%10ccccc%10c%10ccccc%109)cc87)cc6)cc54)cc3)n2)cc1]
14
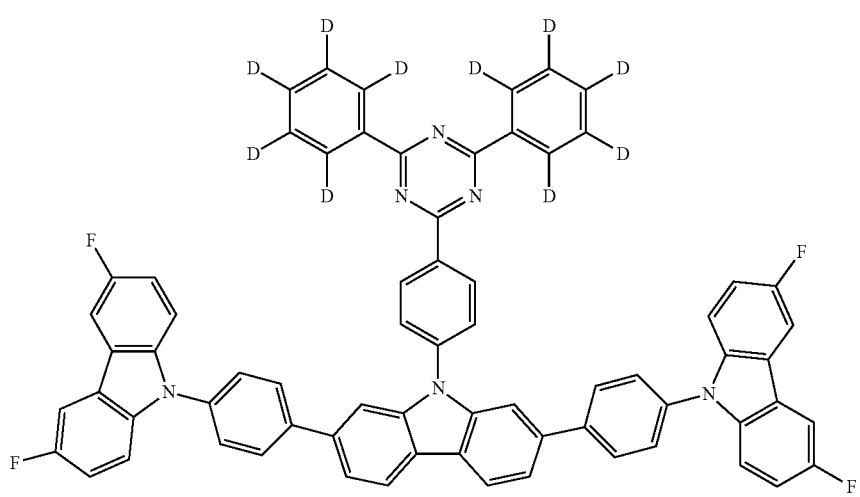 [SMILES: [2H]c1c([2H])c([2H])c(-c2nc(-c3ccc(-n4c5cc(-c6ccc(-n7c8ccc(F)cc8c8cc(F)ccc87)cc6)ccc5c5ccc(-c6ccc(-n7c8ccc(F)cc8c8cc(F)ccc87)cc6)cc54)cc3)nc(-c3c([2H])c([2H])c([2H])c([2H])c3[2H])n2)c([2H])c1[2H]]
15

-continued
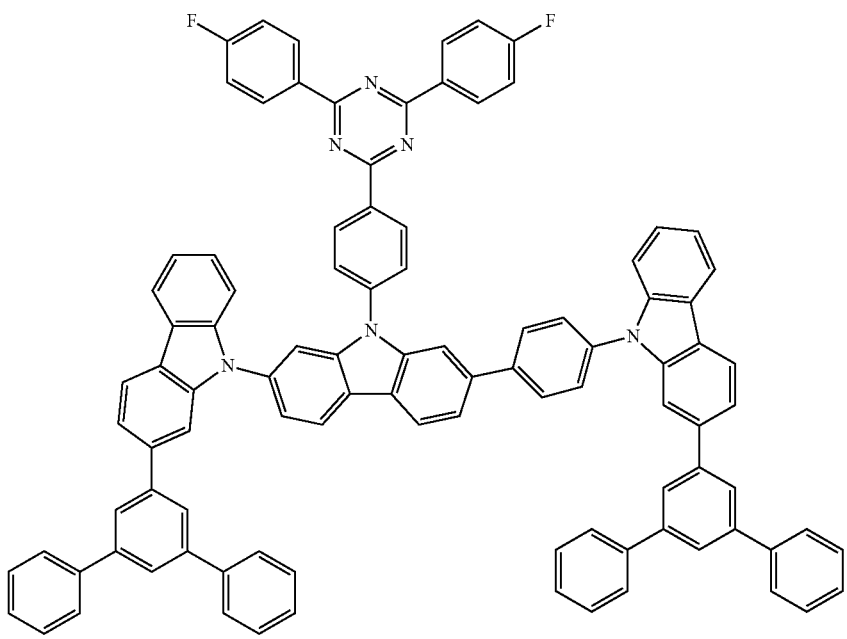 [SMILES: Fc1ccc(-c2nc(-c3ccc(F)cc3)nc(-c3ccc(-n4c5cc(-c6ccc(-n7c8ccccc8c8ccc(-c9cc(-c%10ccccc%10)cc(-c%10ccccc%10)c9)cc87)cc6)ccc5c5ccc(-n6c7ccccc7c7ccc(-c8cc(-c9ccccc9)cc(-c9ccccc9)c8)cc76)cc54)cc3)n2)cc1]
16
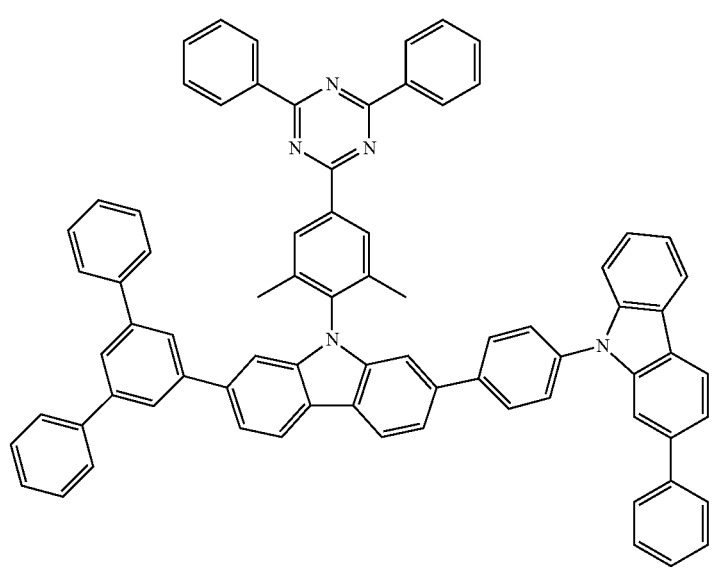 [SMILES: Cc1cc(-c2nc(-c3ccccc3)nc(-c3ccccc3)n2)cc(C)c1-n1c2cc(-c3ccc(-n4c5ccccc5c5ccc(-c6ccccc6)cc54)cc3)ccc2c2ccc(-c3cc(-c4ccccc4)cc(-c4ccccc4)c3)cc21]
17

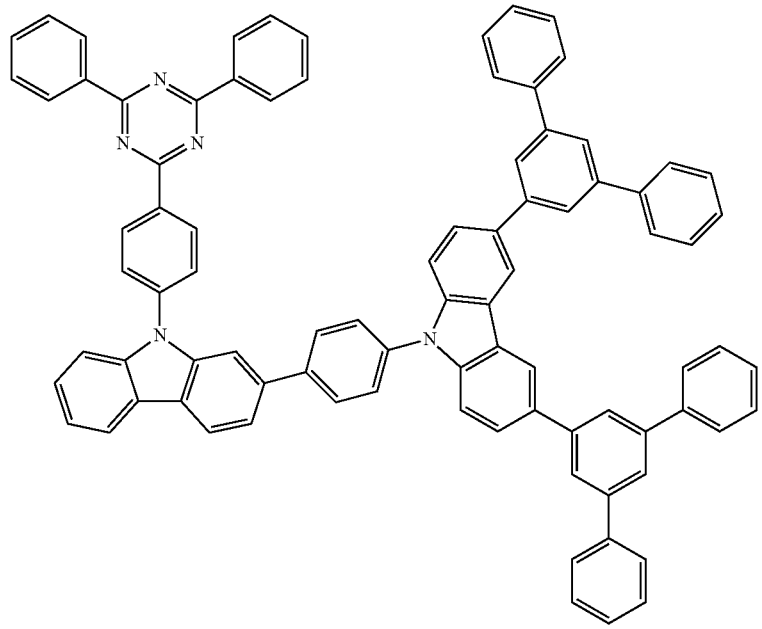 [SMILES: c1ccc(-c2cc(-c3ccccc3)cc(-c3ccc4c(c3)c3cc(-c5cc(-c6ccccc6)cc(-c6ccccc6)c5)ccc3n4-c3ccc(-c4ccc5c6ccccc6n(-c6ccc(-c7nc(-c8ccccc8)nc(-c8ccccc8)n7)cc6)c5c4)cc3)c2)cc1]
18
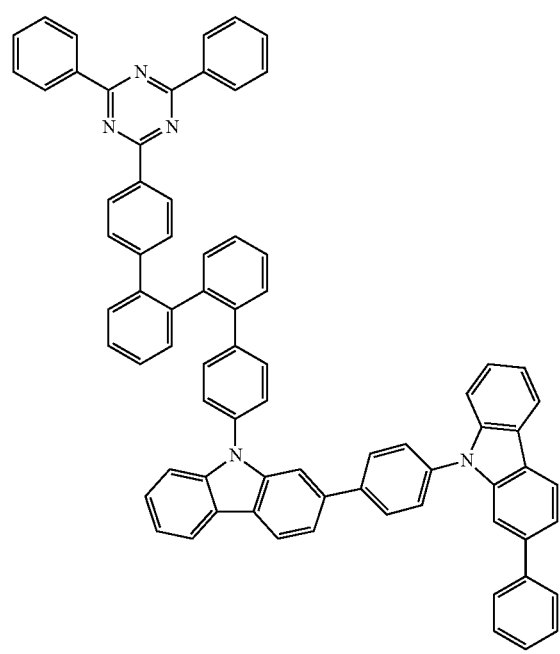 [SMILES: c1ccc(-c2ccc3c4ccccc4n(-c4ccc(-c5ccc6c7ccccc7n(-c7ccc(-c8ccccc8-c8ccccc8-c8ccc(-c9nc(-c%10ccccc%10)nc(-c%10ccccc%10)n9)cc8)cc7)c6c5)cc4)c3c2)cc1]
19

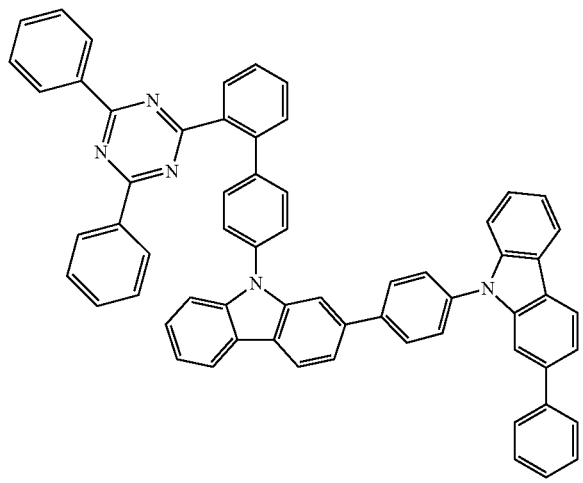 [SMILES: c1ccc(-c2ccc3c4ccccc4n(-c4ccc(-c5ccc6c7ccccc7n(-c7ccc(-c8ccccc8-c8nc(-c9ccccc9)nc(-c9ccccc9)n8)cc7)c6c5)cc4)c3c2)cc1]

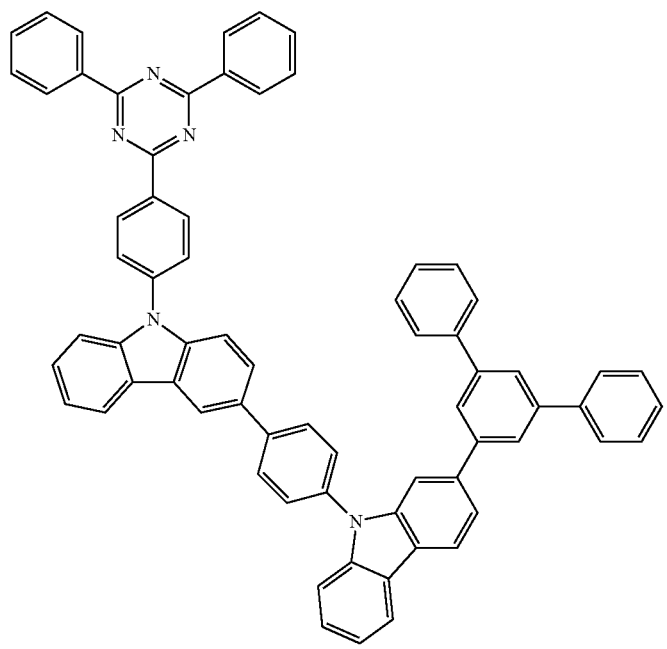 [SMILES: c1ccc(-c2cc(-c3ccccc3)cc(-c3ccc4c5ccccc5n(-c5ccc(-c6ccc7c(c6)c6ccccc6n7-c6ccc(-c7nc(-c8ccccc8)nc(-c8ccccc8)n7)cc6)cc5)c4c3)c2)cc1]
22
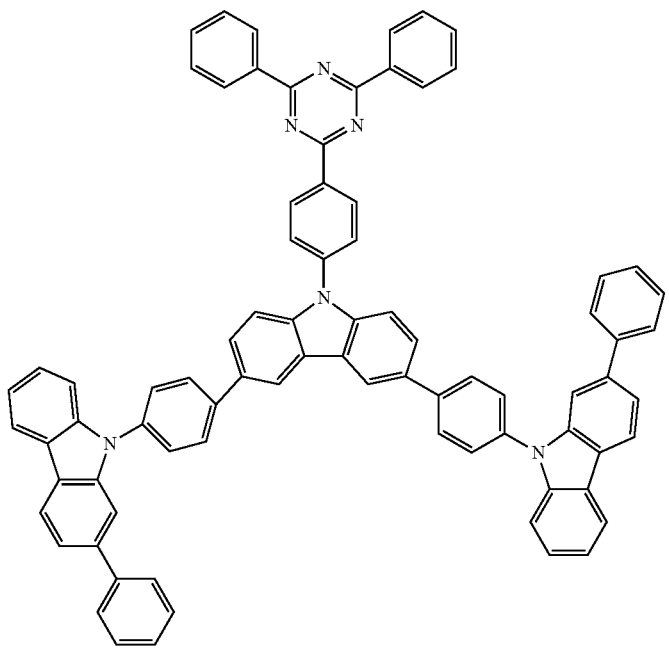 [SMILES: c1ccc(-c2ccc3c4ccccc4n(-c4ccc(-c5ccc6c(c5)c5cc(-c7ccc(-n8c9ccccc9c9ccc(-c%10ccccc%10)cc98)cc7)ccc5n6-c5ccc(-c6nc(-c7ccccc7)nc(-c7ccccc7)n6)cc5)cc4)c3c2)cc1]
23

-continued
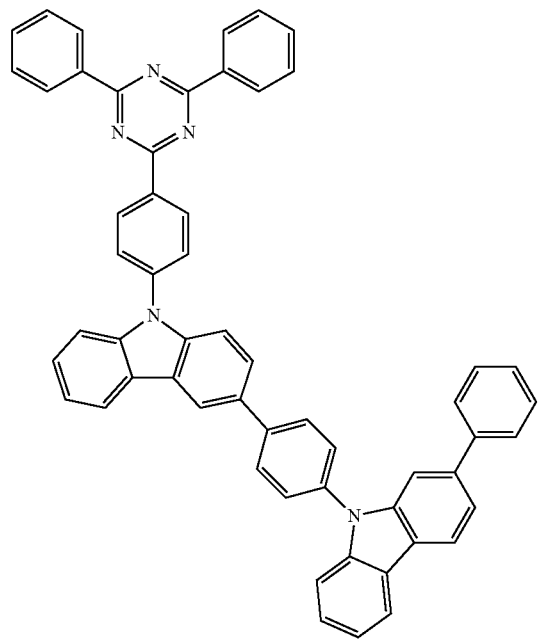 [SMILES: c1ccc(-c2ccc3c4ccccc4n(-c4ccc(-c5ccc6c(c5)c5ccccc5n6-c5ccc(-c6nc(-c7ccccc7)nc(-c7ccccc7)n6)cc5)cc4)c3c2)cc1]
24
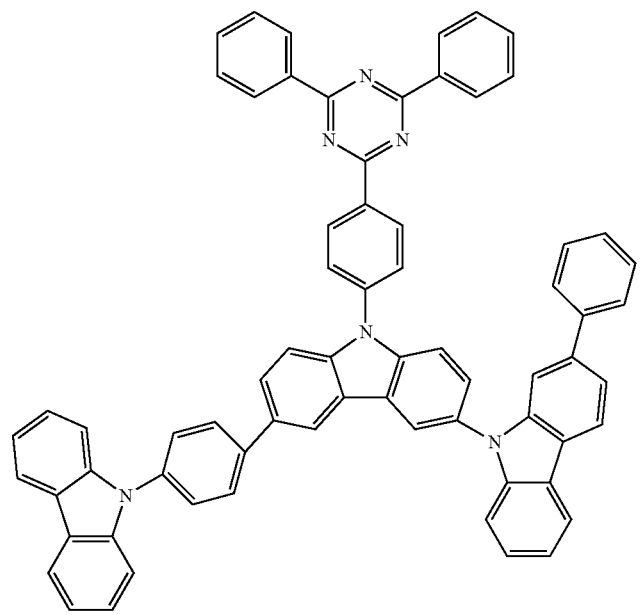 [SMILES: c1ccc(-c2ccc3c4ccccc4n(-c4ccc5c(c4)c4cc(-c6ccc(-n7c8ccccc8c8ccccc87)cc6)ccc4n5-c4ccc(-c5nc(-c6ccccc6)nc(-c6ccccc6)n5)cc4)c3c2)cc1]
25

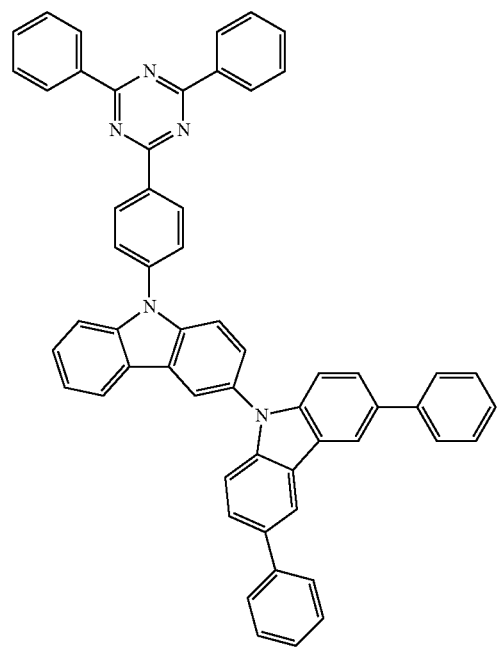 [SMILES: c1ccc(-c2ccc3c(c2)c2cc(-c4ccccc4)ccc2n3-c2ccc3c(c2)c2ccccc2n3-c2ccc(-c3nc(-c4ccccc4)nc(-c4ccccc4)n3)cc2)cc1]
26
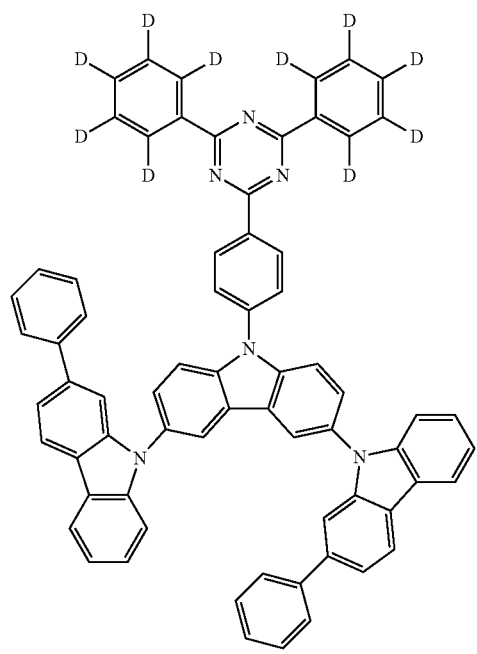 [SMILES: [2H]c1c([2H])c([2H])c(-c2nc(-c3ccc(-n4c5ccc(-n6c7ccccc7c7ccc(-c8ccccc8)cc76)cc5c5cc(-n6c7ccccc7c7ccc(-c8ccccc8)cc76)ccc54)cc3)nc(-c3c([2H])c([2H])c([2H])c([2H])c3[2H])n2)c([2H])c1[2H]]
27

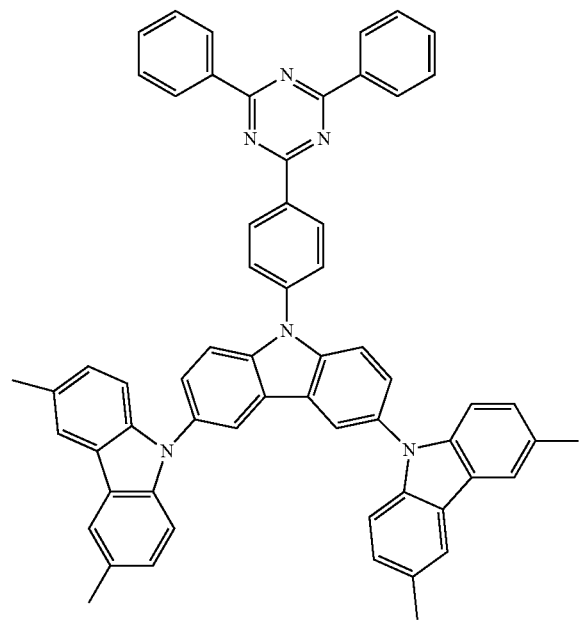
28
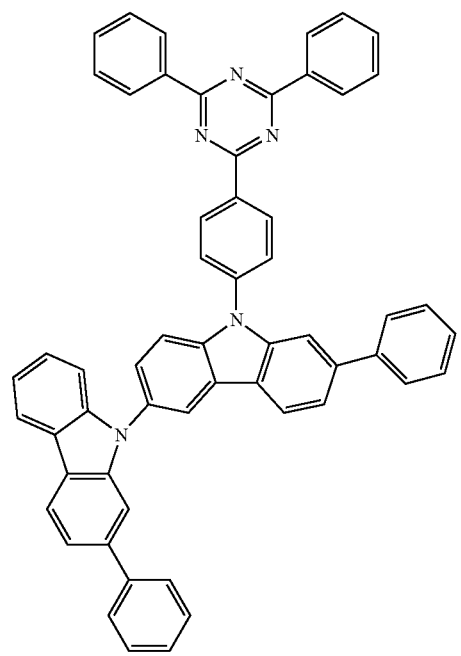 [SMILES: c1ccc(-c2ccc3c4ccccc4n(-c4ccc5c(c4)c4ccc(-c6ccccc6)cc4n5-c4ccc(-c5nc(-c6ccccc6)nc(-c6ccccc6)n5)cc4)c3c2)cc1]
29

-continued
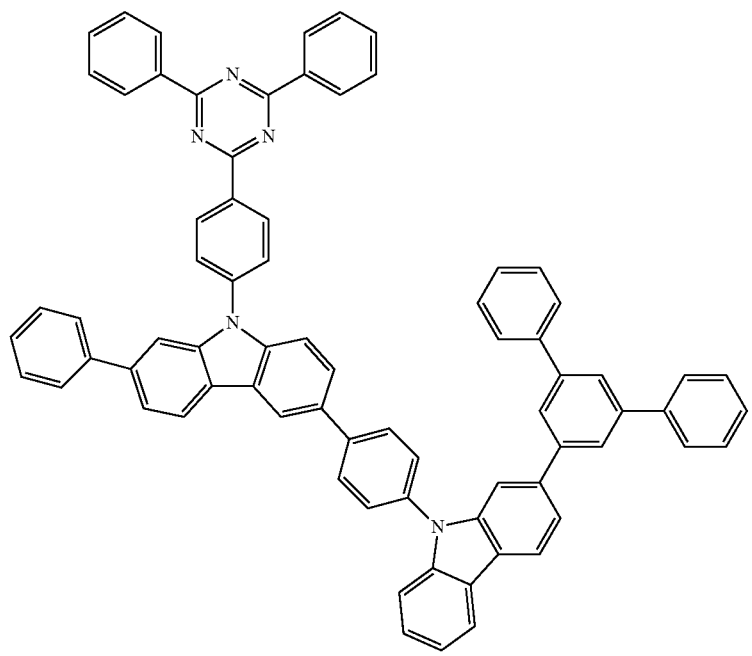 [SMILES: c1ccc(-c2cc(-c3ccccc3)cc(-c3ccc4c5ccccc5n(-c5ccc(-c6ccc7c(c6)c6ccc(-c8ccccc8)cc6n7-c6ccc(-c7nc(-c8ccccc8)nc(-c8ccccc8)n7)cc6)cc5)c4c3)c2)cc1]
30
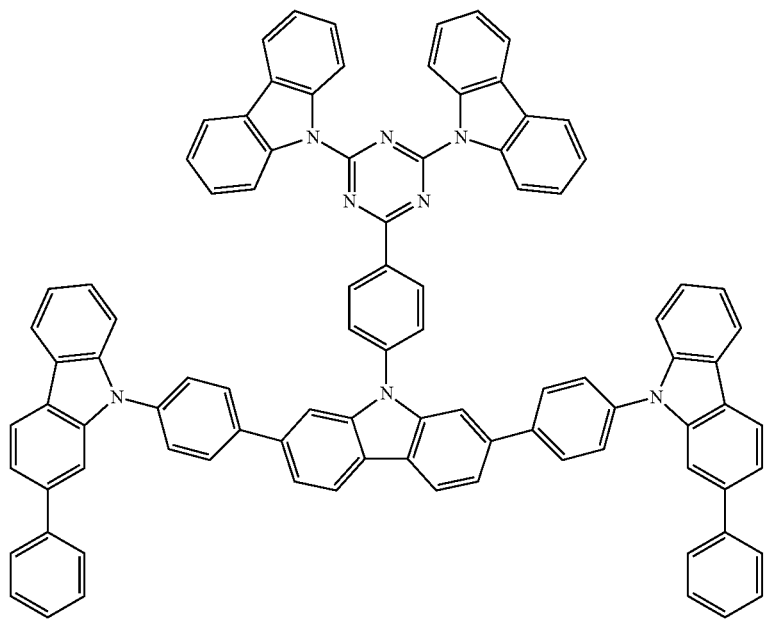 [SMILES: c1ccc(-c2ccc3c4ccccc4n(-c4ccc(-c5ccc6c7ccc(-c8ccc(-n9c%10ccccc%10c%10ccc(-c%11ccccc%11)cc%109)cc8)cc7n(-c7ccc(-c8nc(-n9c%10ccccc%10c%10ccccc%109)nc(-n9c%10ccccc%10c%10ccccc%109)n8)cc7)c6c5)cc4)c3c2)cc1]
31

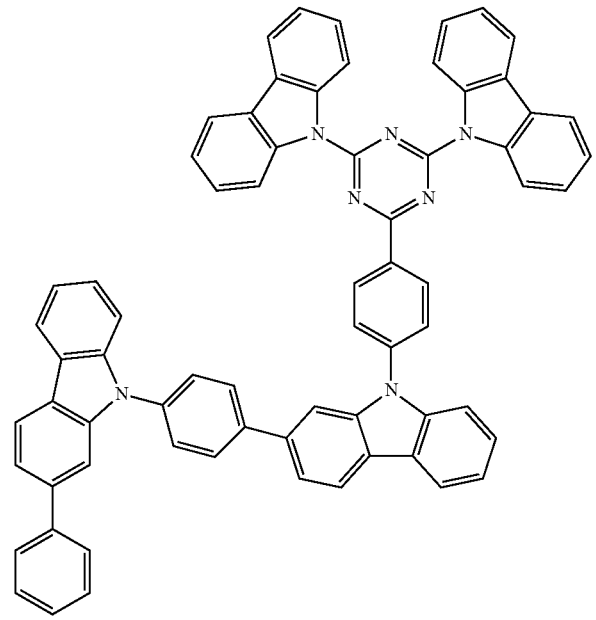 [SMILES: c1ccc(-c2ccc3c4ccccc4n(-c4ccc(-c5ccc6c7ccccc7n(-c7ccc(-c8nc(-n9c%10ccccc%10c%10ccccc%109)nc(-n9c%10ccccc%10c%10ccccc%109)n8)cc7)c6c5)cc4)c3c2)cc1]
32
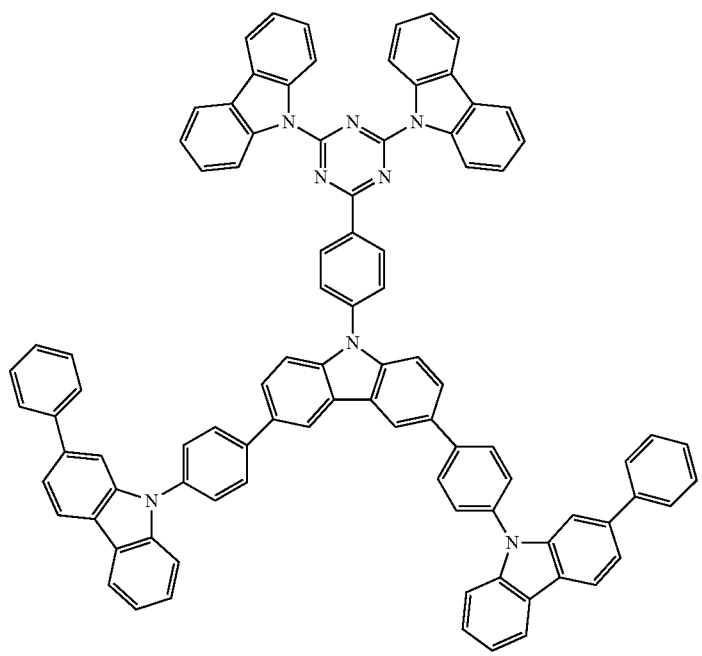 [SMILES: c1ccc(-c2ccc3c4ccccc4n(-c4ccc(-c5ccc6c(c5)c5cc(-c7ccc(-n8c9ccccc9c9ccc(-c%10ccccc%10)cc98)cc7)ccc5n6-c5ccc(-c6nc(-n7c8ccccc8c8ccccc87)nc(-n7c8ccccc8c8ccccc87)n6)cc5)cc4)c3c2)cc1]
33

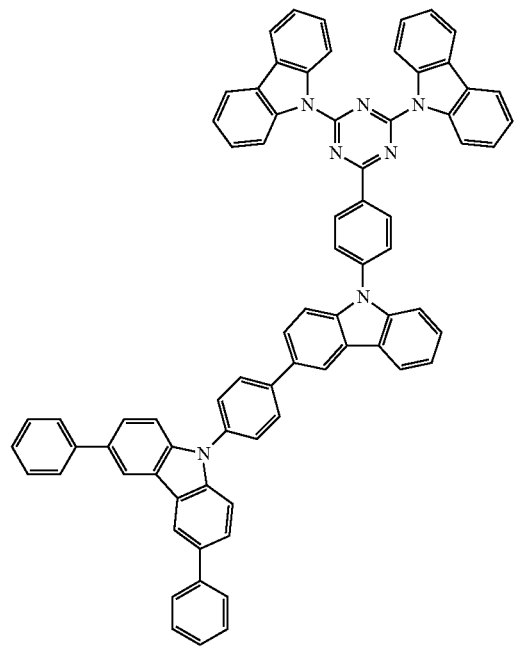 [SMILES: c1ccc(-c2ccc3c(c2)c2cc(-c4ccccc4)ccc2n3-c2ccc(-c3ccc4c(c3)c3ccccc3n4-c3ccc(-c4nc(-n5c6ccccc6c6ccccc65)nc(-n5c6ccccc6c6ccccc65)n4)cc3)cc2)cc1]
34
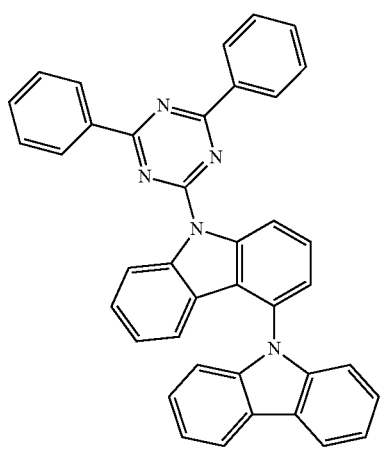 [SMILES: c1ccc(-c2nc(-c3ccccc3)nc(-n3c4ccccc4c4c(-n5c6ccccc6c6ccccc65)cccc43)n2)cc1]
35
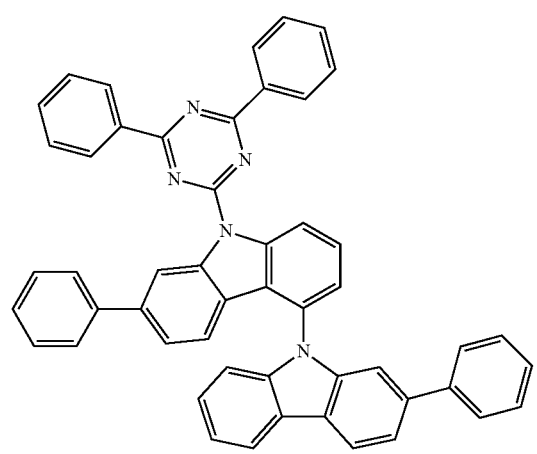 [SMILES: c1ccc(-c2ccc3c4ccccc4n(-c4cccc5c4c4ccc(-c6ccccc6)cc4n5-c4nc(-c5ccccc5)nc(-c5ccccc5)n4)c3c2)cc1]
36

-continued
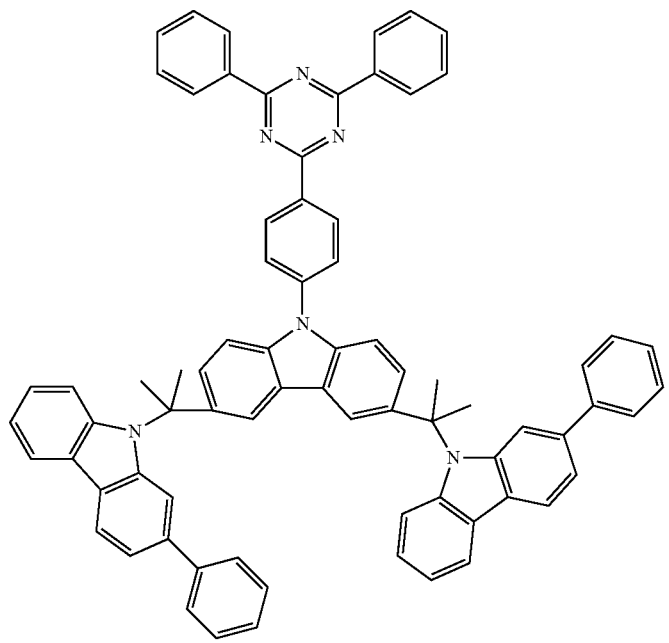 [SMILES: CC(C)(c1ccc2c(c1)c1cc(C(C)(C)n3c4ccccc4c4ccc(-c5ccccc5)cc43)ccc1n2-c1ccc(-c2nc(-c3ccccc3)nc(-c3ccccc3)n2)cc1)n1c2ccccc2c2ccc(-c3ccccc3)cc21]
37
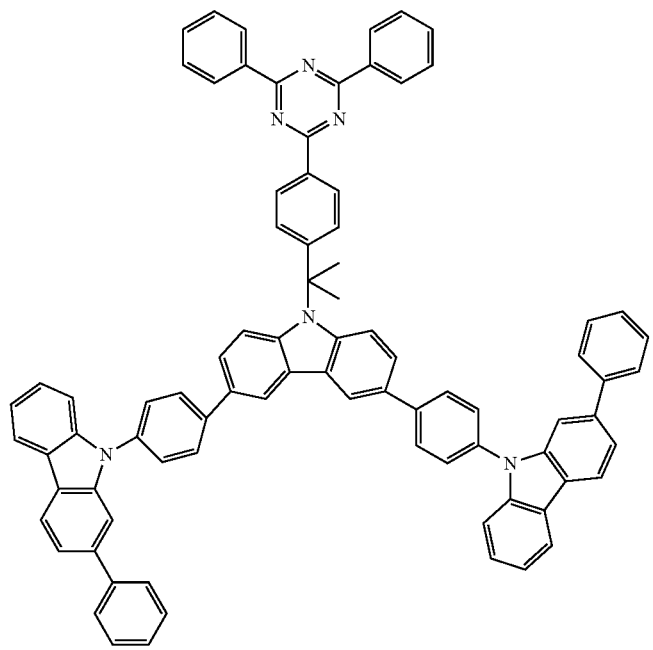 [SMILES: CC(C)(c1ccc(-c2nc(-c3ccccc3)nc(-c3ccccc3)n2)cc1)n1c2ccc(-c3ccc(-n4c5ccccc5c5ccc(-c6ccccc6)cc54)cc3)cc2c2cc(-c3ccc(-n4c5ccccc5c5ccc(-c6ccccc6)cc54)cc3)ccc21]
38

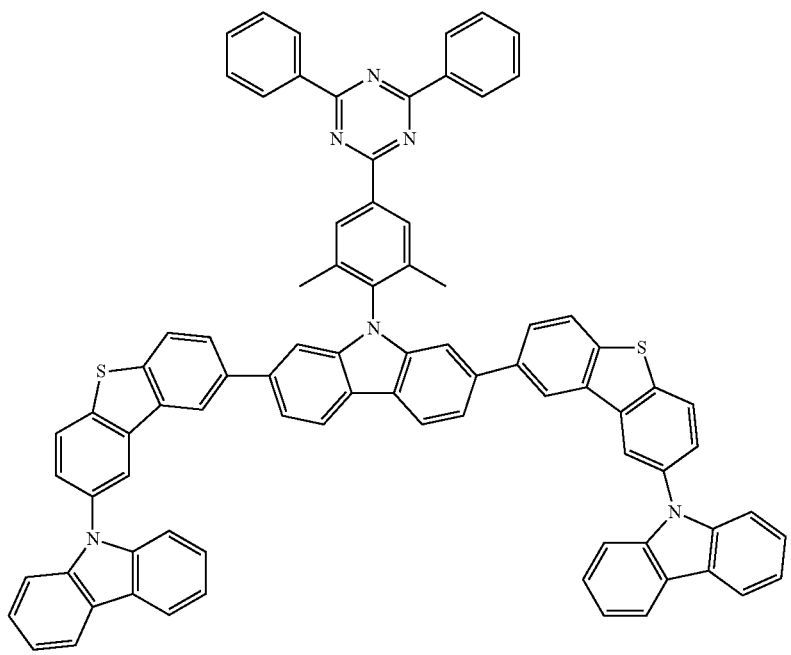 [SMILES: Cc1cc(-c2nc(-c3ccccc3)nc(-c3ccccc3)n2)cc(C)c1-n1c2cc(-c3ccc4sc5ccc(-n6c7ccccc7c7ccccc76)cc5c4c3)ccc2c2ccc(-c3ccc4sc5ccc(-n6c7ccccc7c7ccccc76)cc5c4c3)cc21]
39
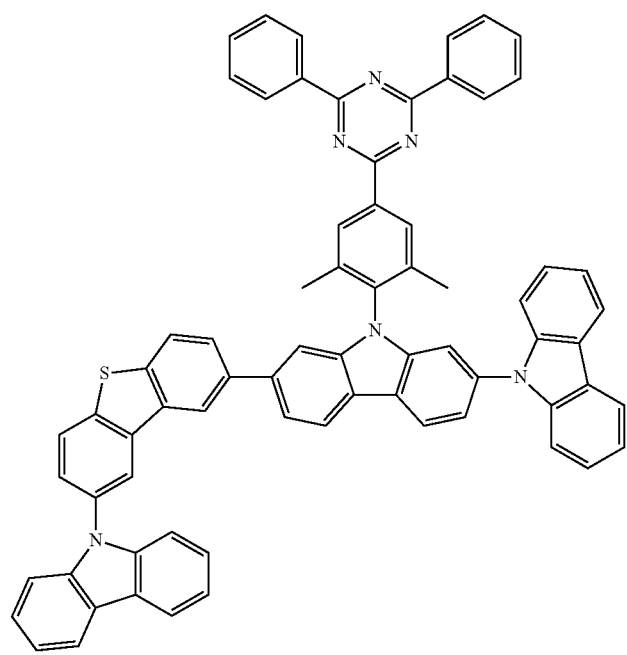 [SMILES: Cc1cc(-c2nc(-c3ccccc3)nc(-c3ccccc3)n2)cc(C)c1-n1c2cc(-c3ccc4sc5ccc(-n6c7ccccc7c7ccccc76)cc5c4c3)ccc2c2ccc(-n3c4ccccc4c4ccccc43)cc21]
40

-continued
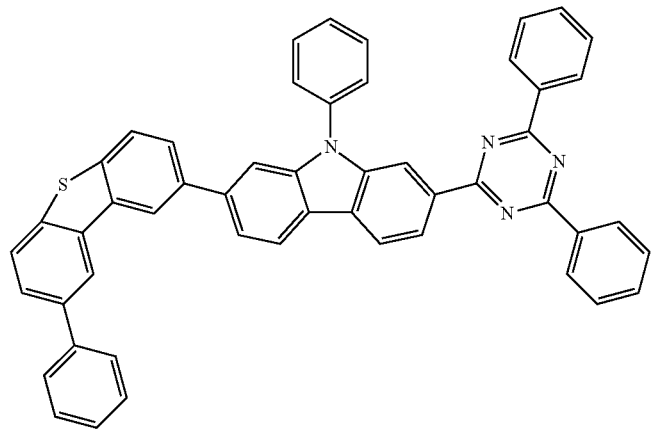 [SMILES: c1ccc(-c2ccc3sc4ccc(-c5ccc6c7ccc(-c8nc(-c9ccccc9)nc(-c9ccccc9)n8)cc7n(-c7ccccc7)c6c5)cc4c3c2)cc1]
41
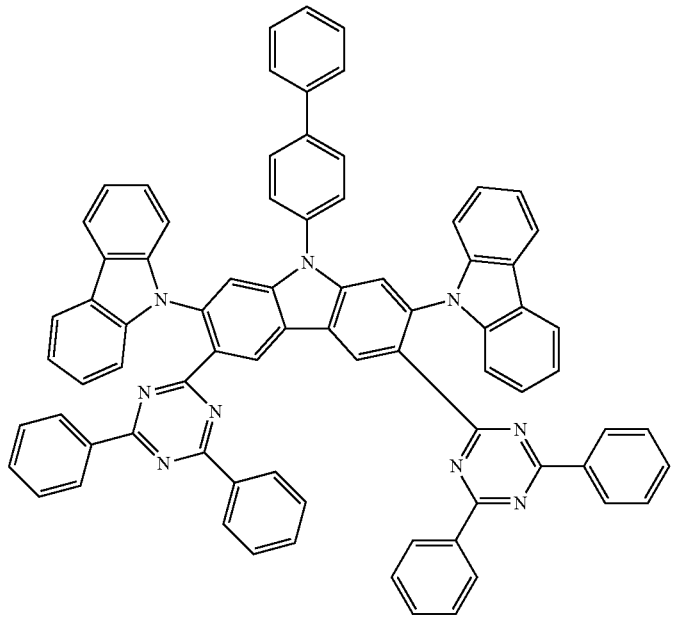 [SMILES: c1ccc(-c2ccc(-n3c4cc(-n5c6ccccc6c6ccccc65)c(-c5nc(-c6ccccc6)nc(-c6ccccc6)n5)cc4c4cc(-c5nc(-c6ccccc6)nc(-c6ccccc6)n5)c(-n5c6ccccc6c6ccccc65)cc43)cc2)cc1]
42
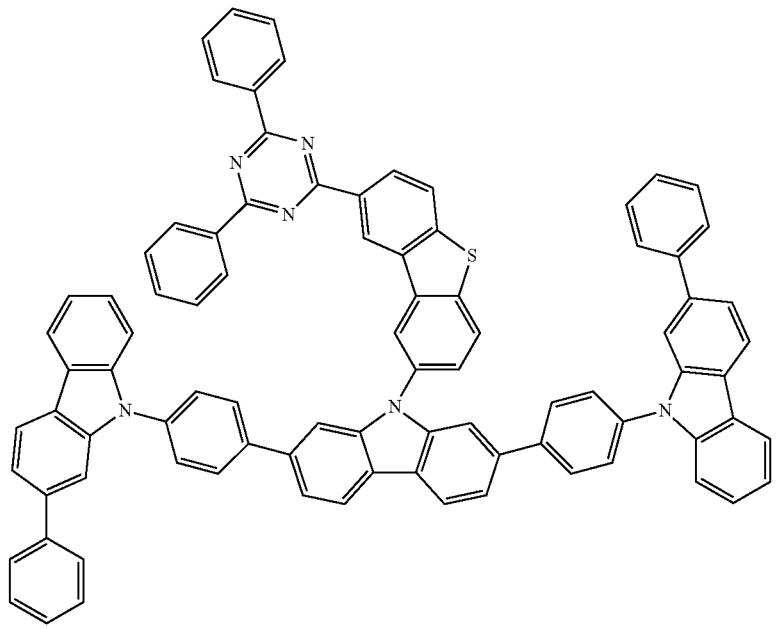 [SMILES: c1ccc(-c2ccc3c4ccccc4n(-c4ccc(-c5ccc6c7ccc(-c8ccc(-n9c%10ccccc%10c%10ccc(-c%11ccccc%11)cc%109)cc8)cc7n(-c7ccc8sc9ccc(-c%10nc(-c%11ccccc%11)nc(-c%11ccccc%11)n%10)cc9c8c7)c6c5)cc4)c3c2)cc1]
43

-continued
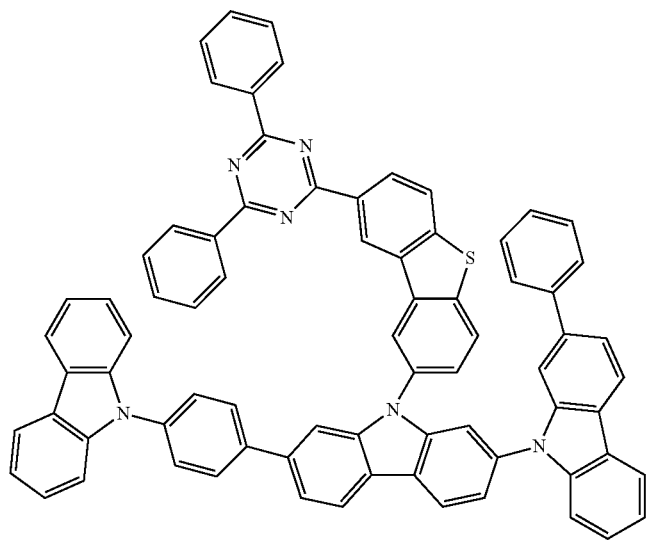 [SMILES: c1ccc(-c2ccc3c4ccccc4n(-c4ccc5c6ccc(-c7ccc(-n8c9ccccc9c9ccccc98)cc7)cc6n(-c6ccc7sc8ccc(-c9nc(-c%10ccccc%10)nc(-c%10ccccc%10)n9)cc8c7c6)c5c4)c3c2)cc1]
44
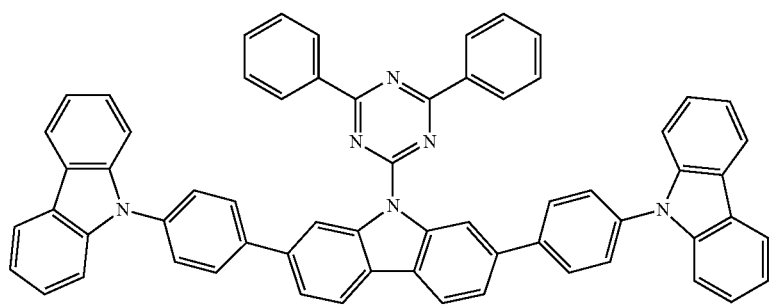 [SMILES: c1ccc(-c2nc(-c3ccccc3)nc(-n3c4cc(-c5ccc(-n6c7ccccc7c7ccccc76)cc5)ccc4c4ccc(-c5ccc(-n6c7ccccc7c7ccccc76)cc5)cc43)n2)cc1]
45
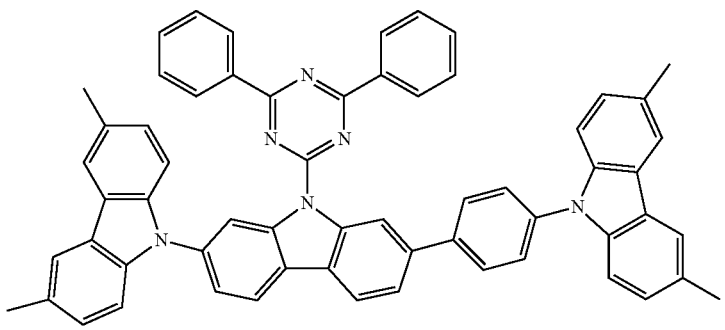
46
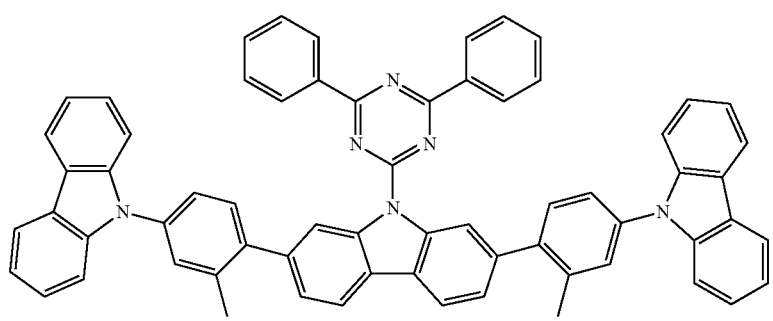 [SMILES: Cc1cc(-n2c3ccccc3c3ccccc32)ccc1-c1ccc2c3ccc(-c4ccc(-n5c6ccccc6c6ccccc65)cc4C)cc3n(-c3nc(-c4ccccc4)nc(-c4ccccc4)n3)c2c1]
47

-continued
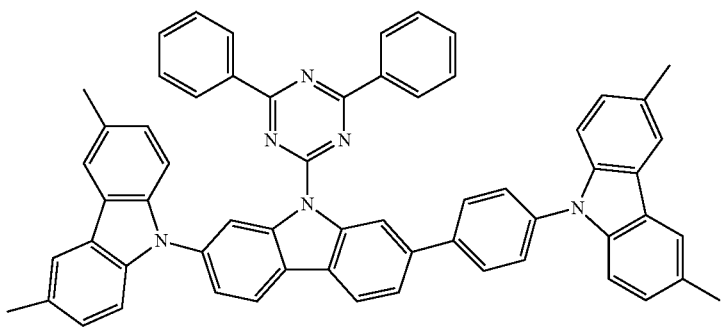
48
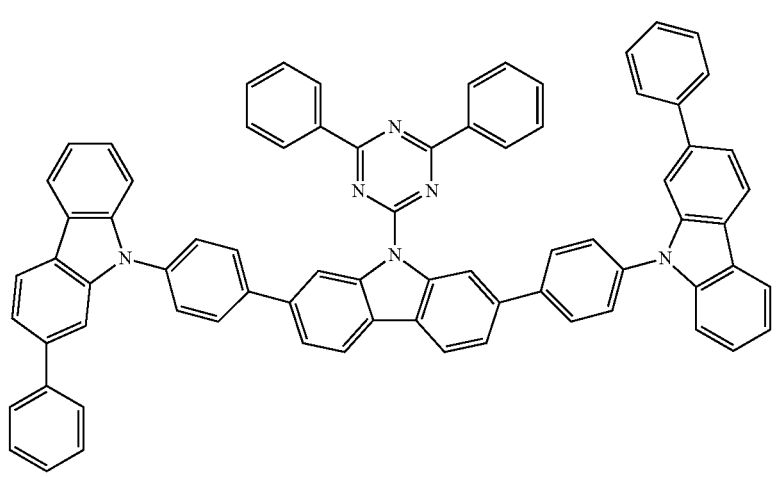 [SMILES: c1ccc(-c2ccc3c4ccccc4n(-c4ccc(-c5ccc6c7ccc(-c8ccc(-n9c%10ccccc%10c%10ccc(-c%11ccccc%11)cc%109)cc8)cc7n(-c7nc(-c8ccccc8)nc(-c8ccccc8)n7)c6c5)cc4)c3c2)cc1]
49
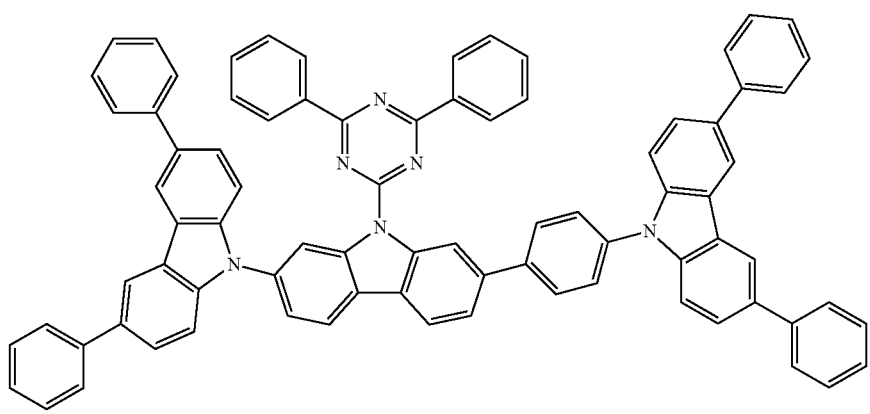 [SMILES: c1ccc(-c2ccc3c(c2)c2cc(-c4ccccc4)ccc2n3-c2ccc(-c3ccc4c5ccc(-n6c7ccc(-c8ccccc8)cc7c7cc(-c8ccccc8)ccc76)cc5n(-c5nc(-c6ccccc6)nc(-c6ccccc6)n5)c4c3)cc2)cc1]
50
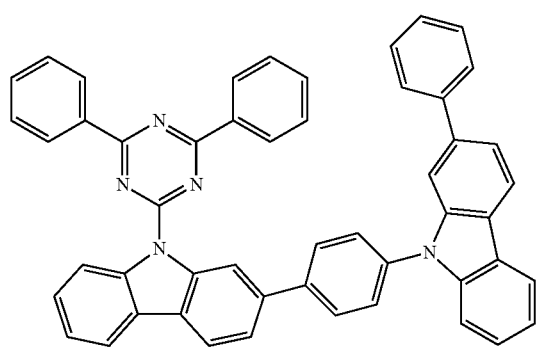 [SMILES: c1ccc(-c2ccc3c4ccccc4n(-c4ccc(-c5ccc6c7ccccc7n(-c7nc(-c8ccccc8)nc(-c8ccccc8)n7)c6c5)cc4)c3c2)cc1]
51

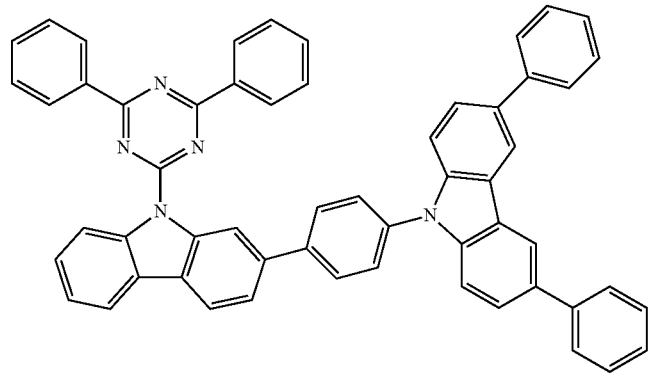 [SMILES: c1ccc(-c2ccc3c(c2)c2cc(-c4ccccc4)ccc2n3-c2ccc(-c3ccc4c5ccccc5n(-c5nc(-c6ccccc6)nc(-c6ccccc6)n5)c4c3)cc2)cc1]
52
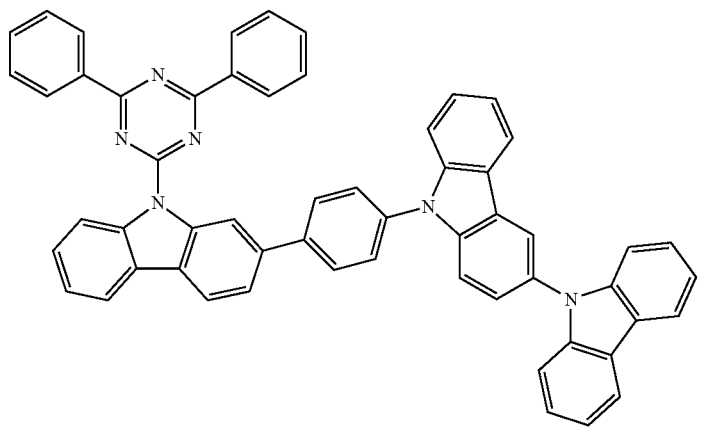 [SMILES: c1ccc(-c2nc(-c3ccccc3)nc(-n3c4ccccc4c4ccc(-c5ccc(-n6c7ccccc7c7cc(-n8c9ccccc9c9ccccc98)ccc76)cc5)cc43)n2)cc1]
53
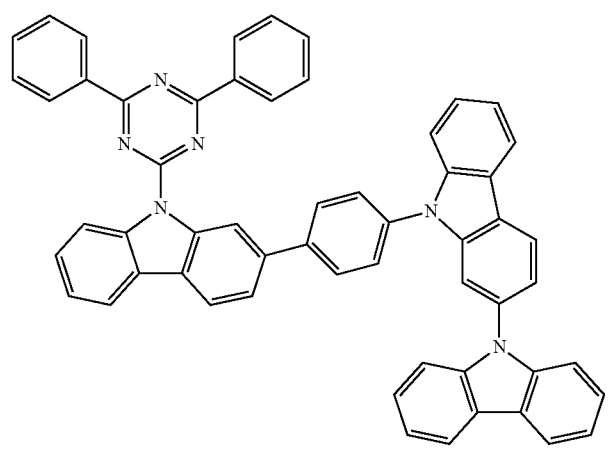 [SMILES: c1ccc(-c2nc(-c3ccccc3)nc(-n3c4ccccc4c4ccc(-c5ccc(-n6c7ccccc7c7ccc(-n8c9ccccc9c9ccccc98)cc76)cc5)cc43)n2)cc1]
54

55
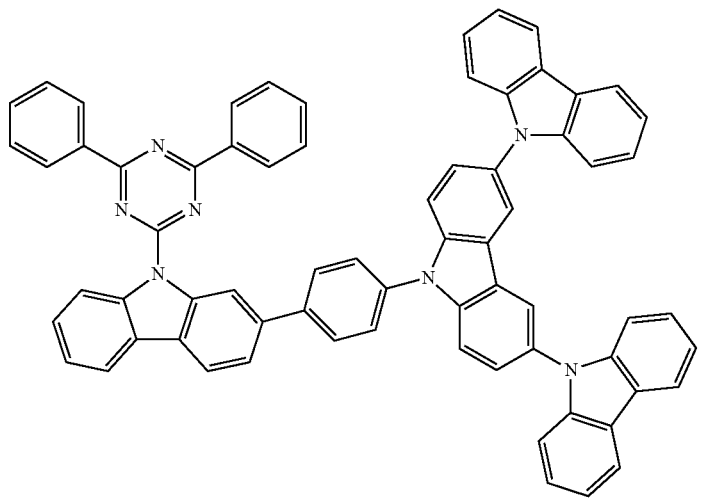 [SMILES: c1ccc(-c2nc(-c3ccccc3)nc(-n3c4ccccc4c4ccc(-c5ccc(-n6c7ccc(-n8c9ccccc9c9ccccc98)cc7c7cc(-n8c9ccccc9c9ccccc98)ccc76)cc5)cc43)n2)cc1]
56
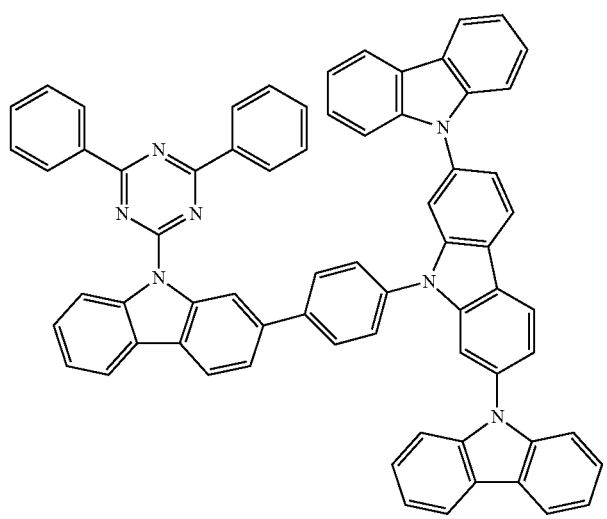 [SMILES: c1ccc(-c2nc(-c3ccccc3)nc(-n3c4ccccc4c4ccc(-c5ccc(-n6c7cc(-n8c9ccccc9c9ccccc98)ccc7c7ccc(-n8c9ccccc9c9ccccc98)cc76)cc5)cc43)n2)cc1]
57
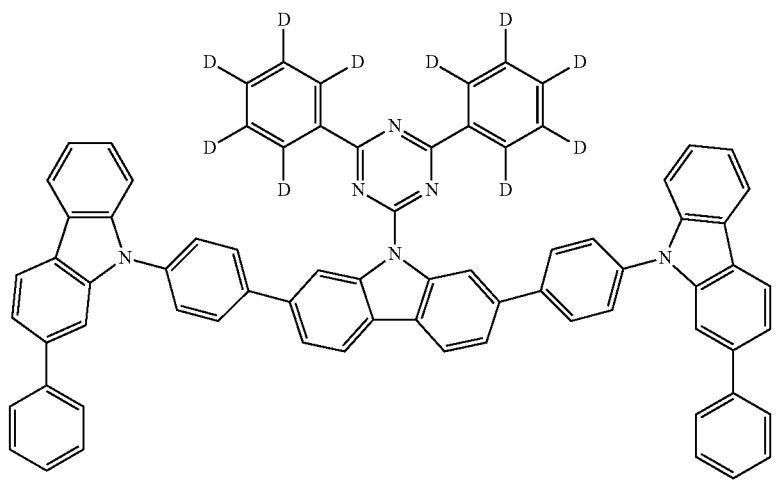 [SMILES: [2H]c1c([2H])c([2H])c(-c2nc(-c3c([2H])c([2H])c([2H])c([2H])c3[2H])nc(-n3c4cc(-c5ccc(-n6c7ccccc7c7ccc(-c8ccccc8)cc76)cc5)ccc4c4ccc(-c5ccc(-n6c7ccccc7c7ccc(-c8ccccc8)cc76)cc5)cc43)n2)c([2H])c1[2H]]

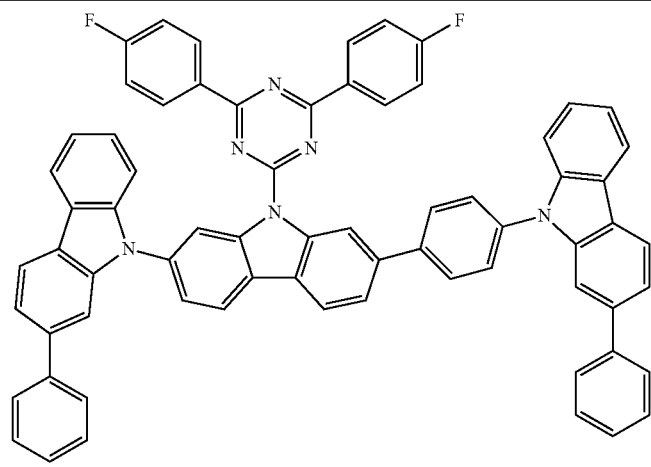
58
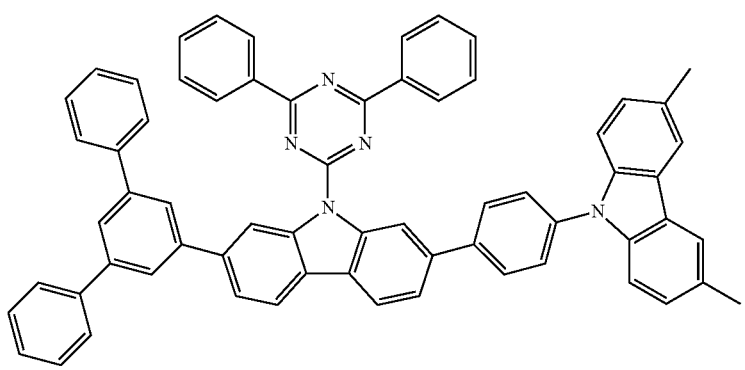 [SMILES: Cc1ccc2c(c1)c1cc(C)ccc1n2-c1ccc(-c2ccc3c4ccc(-c5cc(-c6ccccc6)cc(-c6ccccc6)c5)cc4n(-c4nc(-c5ccccc5)nc(-c5ccccc5)n4)c3c2)cc1]
59
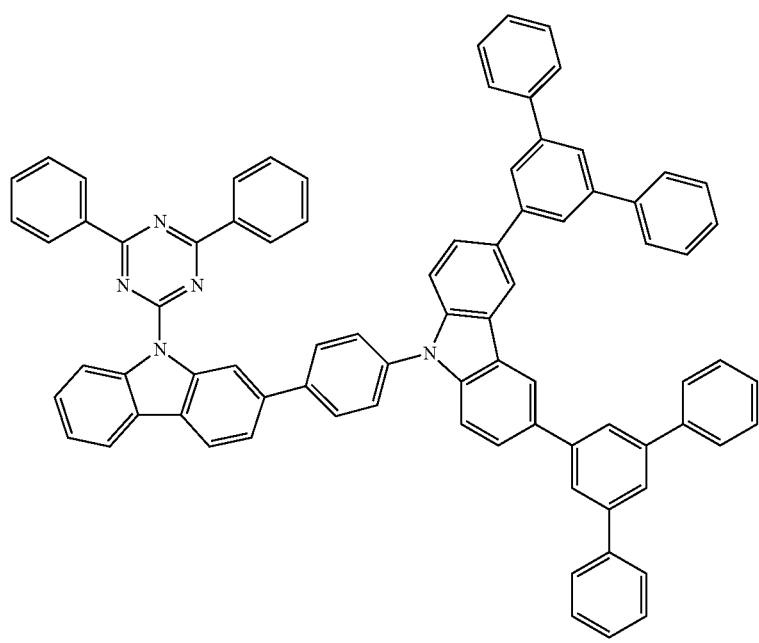 [SMILES: c1ccc(-c2cc(-c3ccccc3)cc(-c3ccc4c(c3)c3cc(-c5cc(-c6ccccc6)cc(-c6ccccc6)c5)ccc3n4-c3ccc(-c4ccc5c6ccccc6n(-c6nc(-c7ccccc7)nc(-c7ccccc7)n6)c5c4)cc3)c2)cc1]
60

-continued
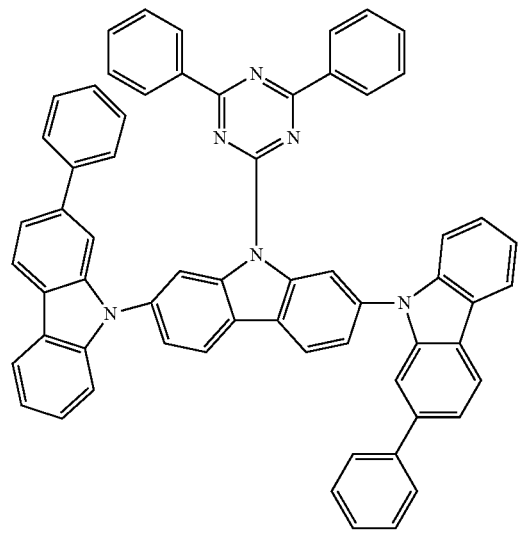 [SMILES: c1ccc(-c2ccc3c4ccccc4n(-c4ccc5c6ccc(-n7c8ccccc8c8ccc(-c9ccccc9)cc87)cc6n(-c6nc(-c7ccccc7)nc(-c7ccccc7)n6)c5c4)c3c2)cc1]
61
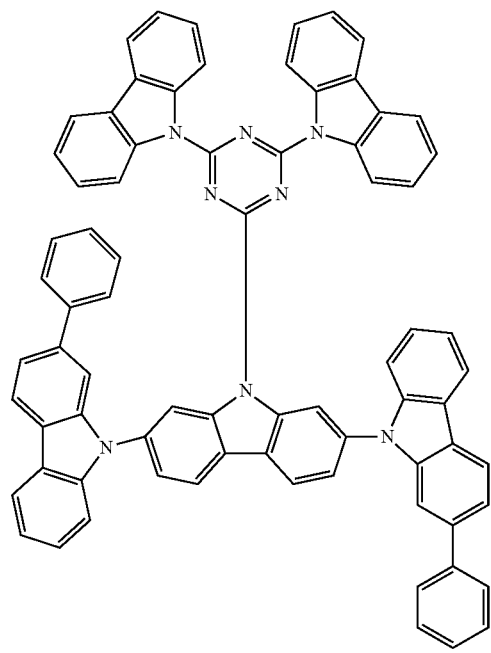 [SMILES: c1ccc(-c2ccc3c4ccccc4n(-c4ccc5c6ccc(-n7c8ccccc8c8ccc(-c9ccccc9)cc87)cc6n(-c6nc(-n7c8ccccc8c8ccccc87)nc(-n7c8ccccc8c8ccccc87)n6)c5c4)c3c2)cc1]
62
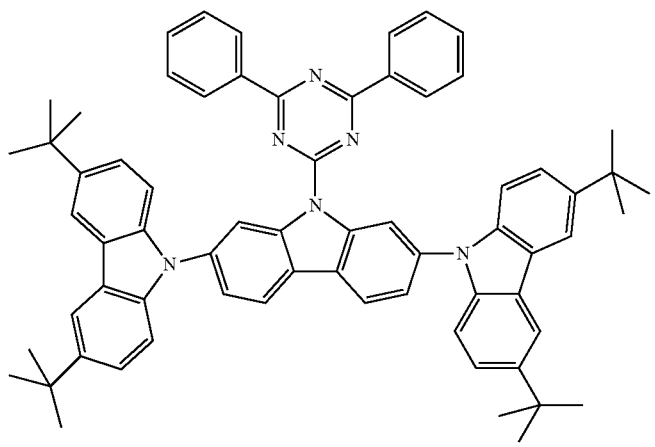 [SMILES: CC(C)(C)c1ccc2c(c1)c1cc(C(C)(C)C)ccc1n2-c1ccc2c3ccc(-n4c5ccc(C(C)(C)C)cc5c5cc(C(C)(C)C)ccc54)cc3n(-c3nc(-c4ccccc4)nc(-c4ccccc4)n3)c2c1]
63

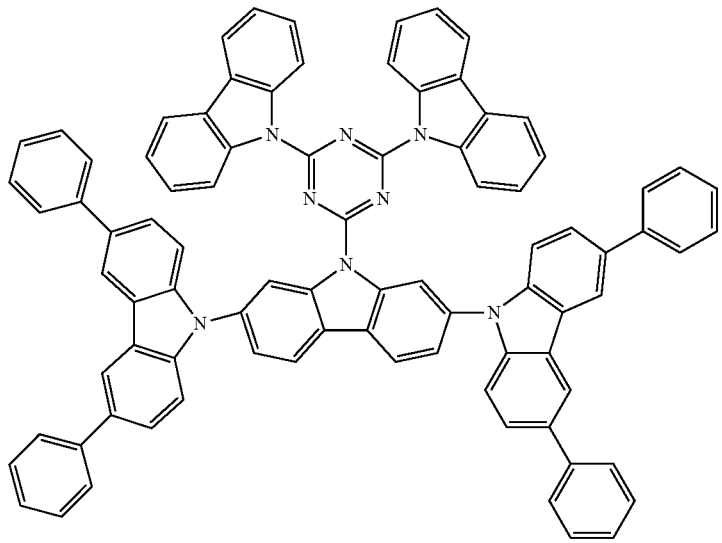 [SMILES: c1ccc(-c2ccc3c(c2)c2cc(-c4ccccc4)ccc2n3-c2ccc3c4ccc(-n5c6ccc(-c7ccccc7)cc6c6cc(-c7ccccc7)ccc65)cc4n(-c4nc(-n5c6ccccc6c6ccccc65)nc(-n5c6ccccc6c6ccccc65)n4)c3c2)cc1]
64
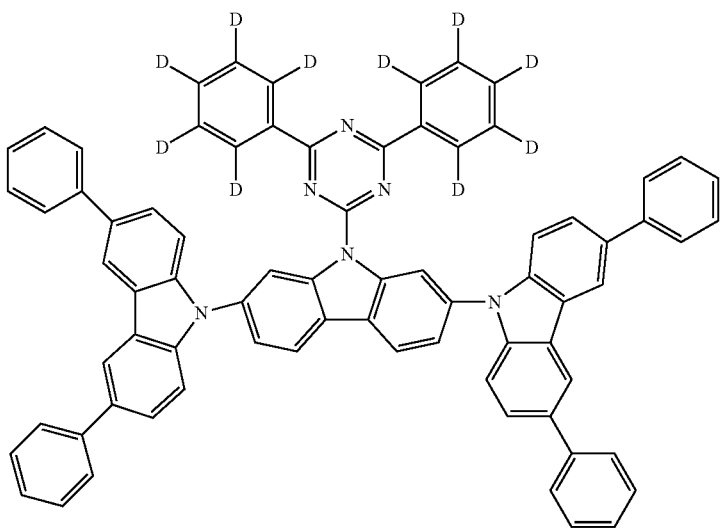 [SMILES: [2H]c1c([2H])c([2H])c(-c2nc(-c3c([2H])c([2H])c([2H])c([2H])c3[2H])nc(-n3c4cc(-n5c6ccc(-c7ccccc7)cc6c6cc(-c7ccccc7)ccc65)ccc4c4ccc(-n5c6ccc(-c7ccccc7)cc6c6cc(-c7ccccc7)ccc65)cc43)n2)c([2H])c1[2H]]
65
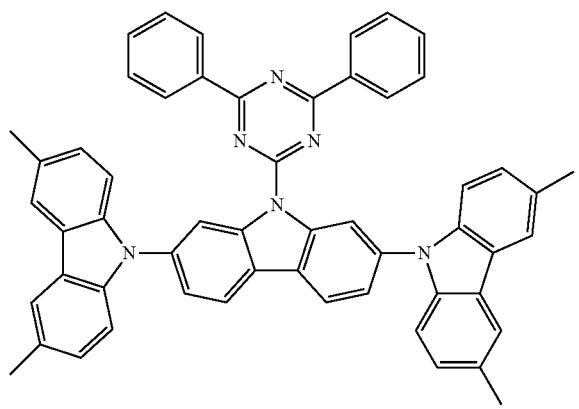
66

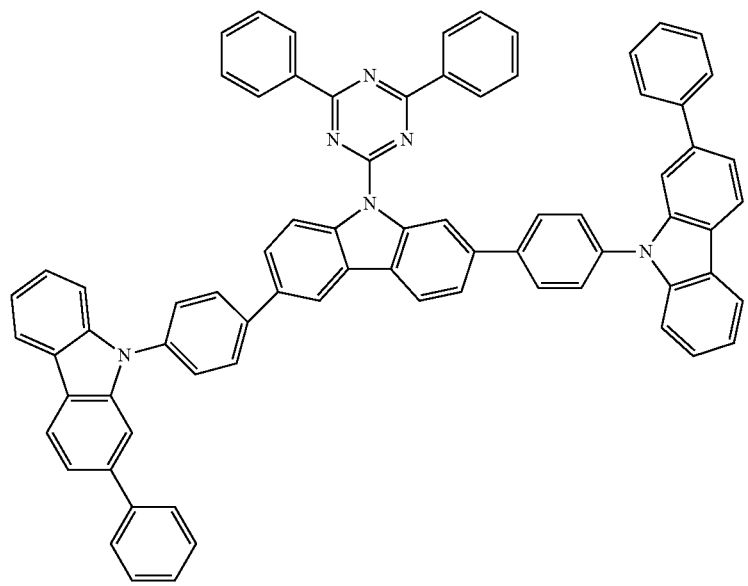 [SMILES: c1ccc(-c2ccc3c4ccccc4n(-c4ccc(-c5ccc6c(c5)c5ccc(-c7ccc(-n8c9ccccc9c9ccc(-c%10ccccc%10)cc98)cc7)cc5n6-c5nc(-c6ccccc6)nc(-c6ccccc6)n5)cc4)c3c2)cc1]
67
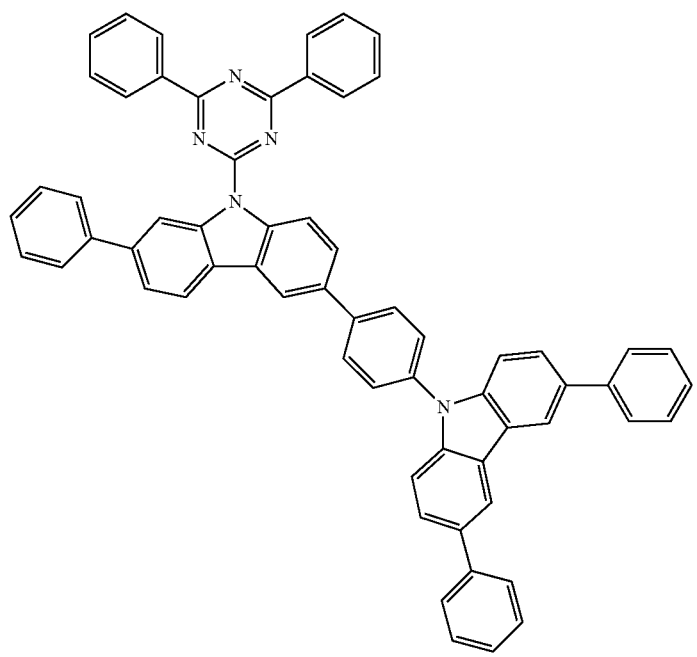 [SMILES: c1ccc(-c2ccc3c(c2)c2cc(-c4ccccc4)ccc2n3-c2ccc(-c3ccc4c(c3)c3ccc(-c5ccccc5)cc3n4-c3nc(-c4ccccc4)nc(-c4ccccc4)n3)cc2)cc1]
68

69
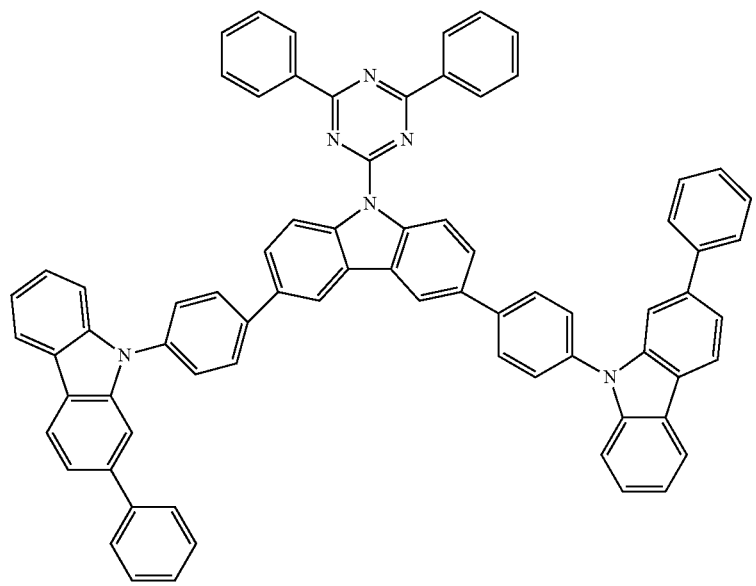 [SMILES: c1ccc(-c2ccc3c4ccccc4n(-c4ccc(-c5ccc6c(c5)c5cc(-c7ccc(-n8c9ccccc9c9ccc(-c%10ccccc%10)cc98)cc7)ccc5n6-c5nc(-c6ccccc6)nc(-c6ccccc6)n5)cc4)c3c2)cc1]
70
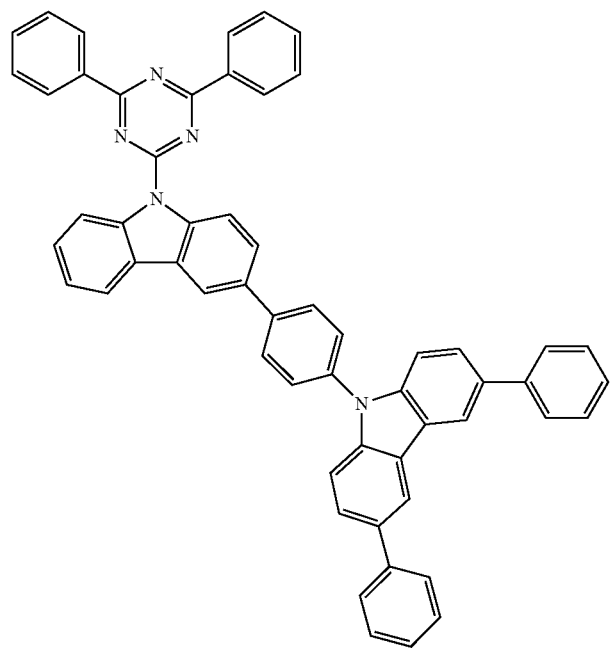 [SMILES: c1ccc(-c2ccc3c(c2)c2cc(-c4ccccc4)ccc2n3-c2ccc(-c3ccc4c(c3)c3ccccc3n4-c3nc(-c4ccccc4)nc(-c4ccccc4)n3)cc2)cc1]

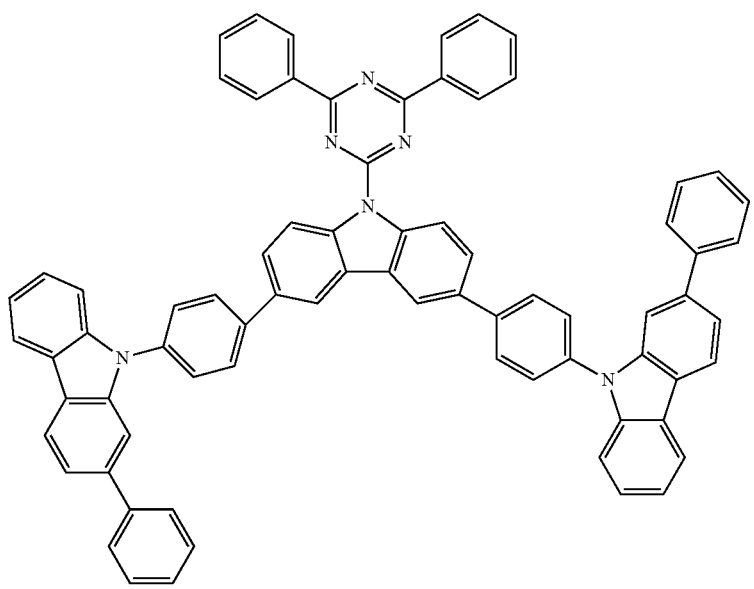 [SMILES: c1ccc(-c2ccc3c4ccccc4n(-c4ccc(-c5ccc6c(c5)c5cc(-c7ccc(-n8c9ccccc9c9ccc(-c%10ccccc%10)cc98)cc7)ccc5n6-c5nc(-c6ccccc6)nc(-c6ccccc6)n5)cc4)c3c2)cc1]
71
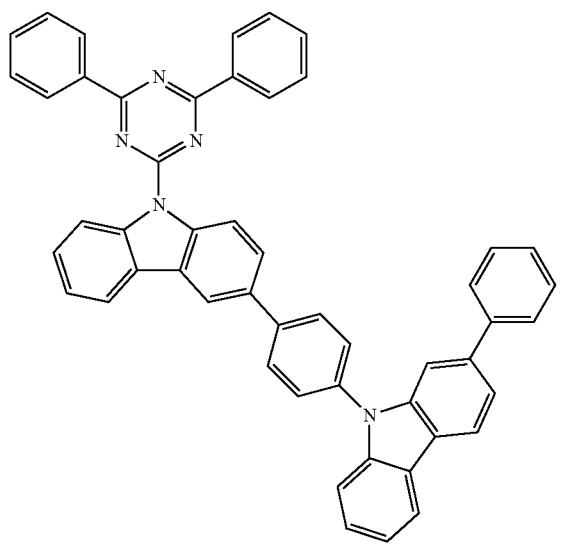 [SMILES: c1ccc(-c2ccc3c4ccccc4n(-c4ccc(-c5ccc6c(c5)c5ccccc5n6-c5nc(-c6ccccc6)nc(-c6ccccc6)n5)cc4)c3c2)cc1]
72
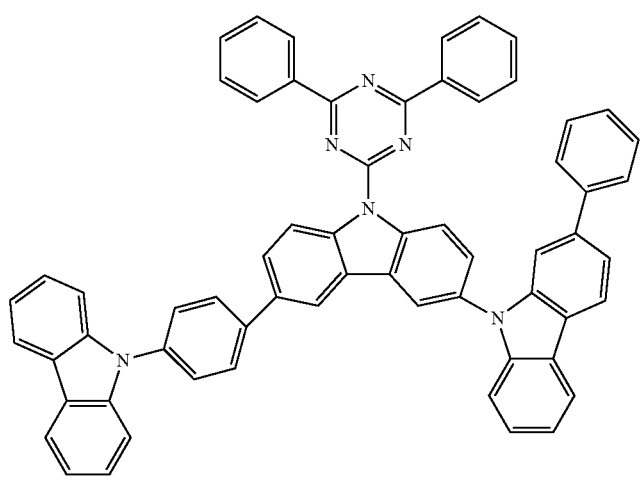 [SMILES: c1ccc(-c2ccc3c4ccccc4n(-c4ccc5c(c4)c4cc(-c6ccc(-n7c8ccccc8c8ccccc87)cc6)ccc4n5-c4nc(-c5ccccc5)nc(-c5ccccc5)n4)c3c2)cc1]
73

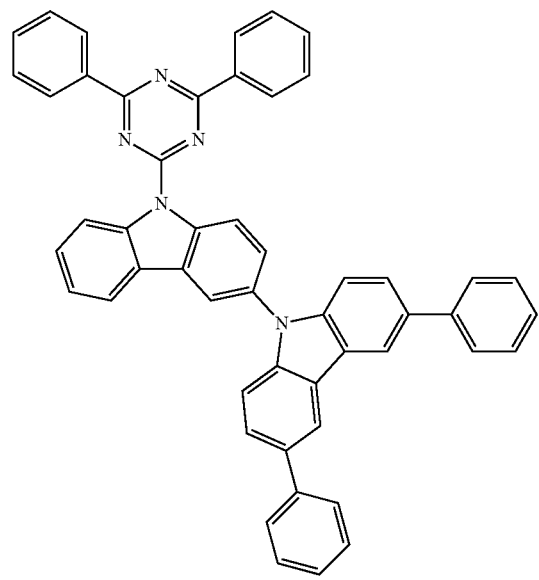 [SMILES: c1ccc(-c2ccc3c(c2)c2cc(-c4ccccc4)ccc2n3-c2ccc3c(c2)c2ccccc2n3-c2nc(-c3ccccc3)nc(-c3ccccc3)n2)cc1]
74
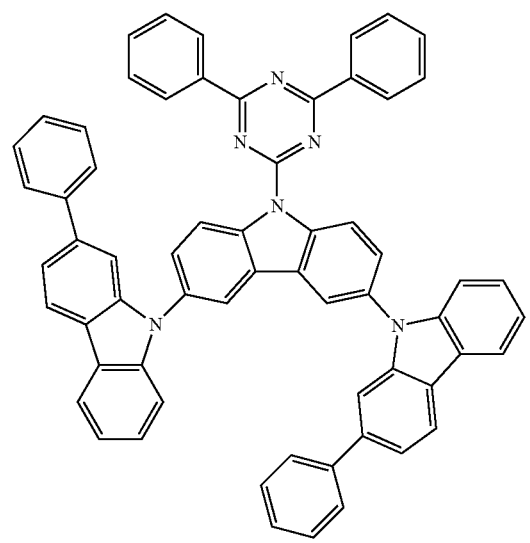 [SMILES: c1ccc(-c2ccc3c4ccccc4n(-c4ccc5c(c4)c4cc(-n6c7ccccc7c7ccc(-c8ccccc8)cc76)ccc4n5-c4nc(-c5ccccc5)nc(-c5ccccc5)n4)c3c2)cc1]
75

-continued
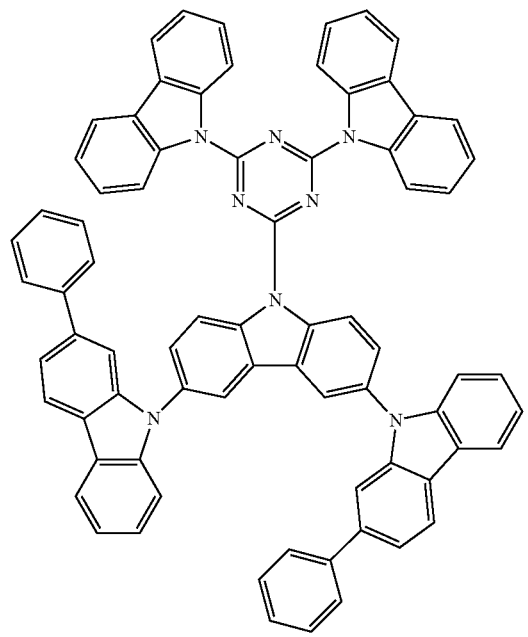 [SMILES: c1ccc(-c2ccc3c4ccccc4n(-c4ccc5c(c4)c4cc(-n6c7ccccc7c7ccc(-c8ccccc8)cc76)ccc4n5-c4nc(-n5c6ccccc6c6ccccc65)nc(-n5c6ccccc6c6ccccc65)n4)c3c2)cc1]
76
77

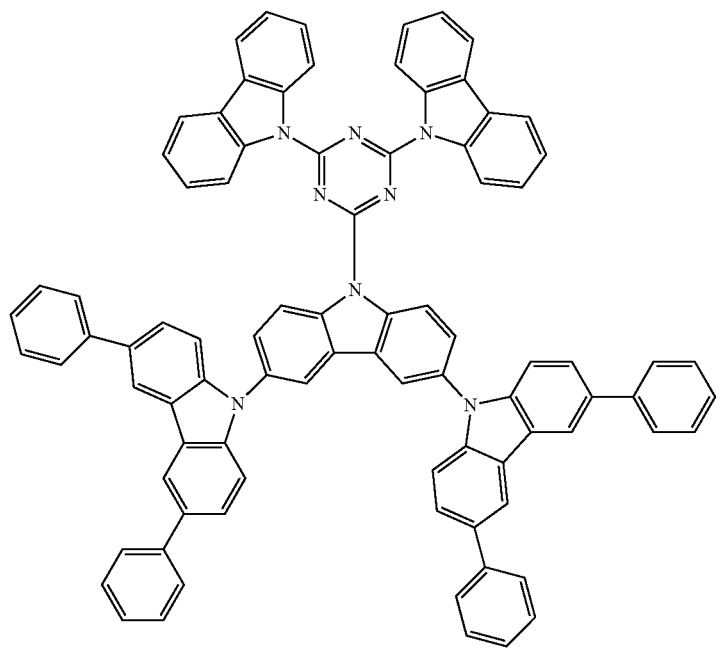 [SMILES: c1ccc(-c2ccc3c(c2)c2cc(-c4ccccc4)ccc2n3-c2ccc3c(c2)c2cc(-n4c5ccc(-c6ccccc6)cc5c5cc(-c6ccccc6)ccc54)ccc2n3-c2nc(-n3c4ccccc4c4ccccc43)nc(-n3c4ccccc4c4ccccc43)n2)cc1]
78
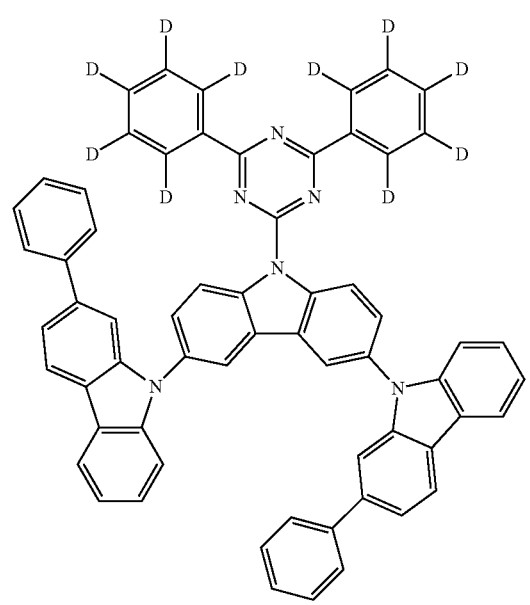 [SMILES: [2H]c1c([2H])c([2H])c(-c2nc(-c3c([2H])c([2H])c([2H])c([2H])c3[2H])nc(-n3c4ccc(-n5c6ccccc6c6ccc(-c7ccccc7)cc65)cc4c4cc(-n5c6ccccc6c6ccc(-c7ccccc7)cc65)ccc43)n2)c([2H])c1[2H]]
79

-continued
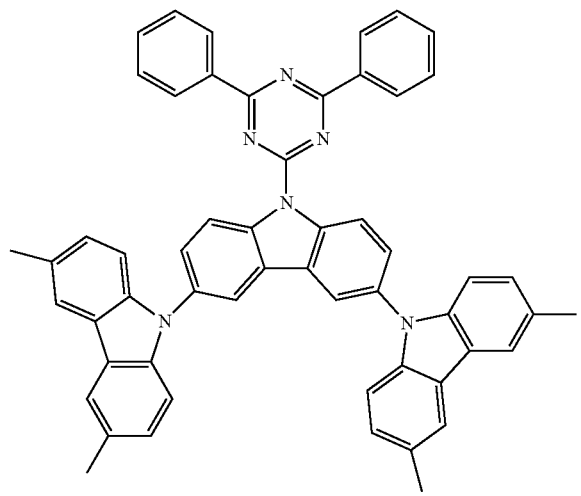
80
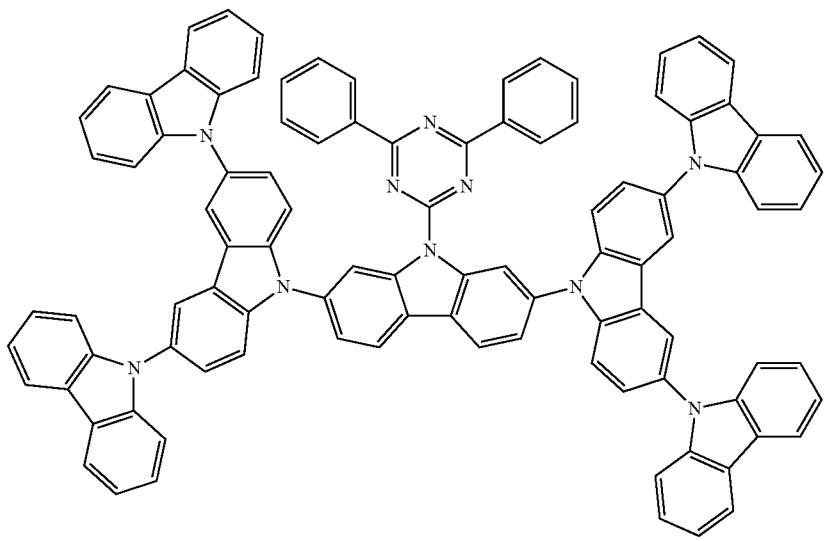 [SMILES: c1ccc(-c2nc(-c3ccccc3)nc(-n3c4cc(-n5c6ccc(-n7c8ccccc8c8ccccc87)cc6c6cc(-n7c8ccccc8c8ccccc87)ccc65)ccc4c4ccc(-n5c6ccc(-n7c8ccccc8c8ccccc87)cc6c6cc(-n7c8ccccc8c8ccccc87)ccc65)cc43)n2)cc1]
81
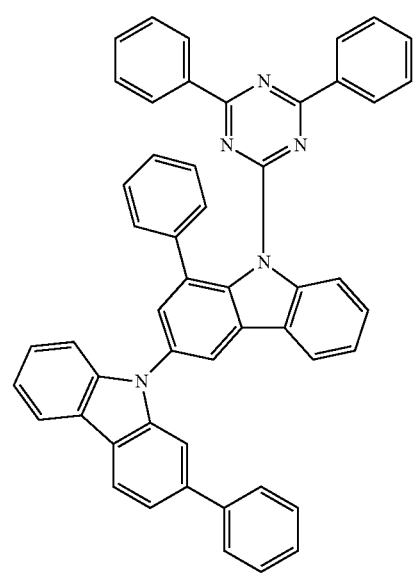 [SMILES: c1ccc(-c2ccc3c4ccccc4n(-c4cc(-c5ccccc5)c5c(c4)c4ccccc4n5-c4nc(-c5ccccc5)nc(-c5ccccc5)n4)c3c2)cc1]
82

-continued
83
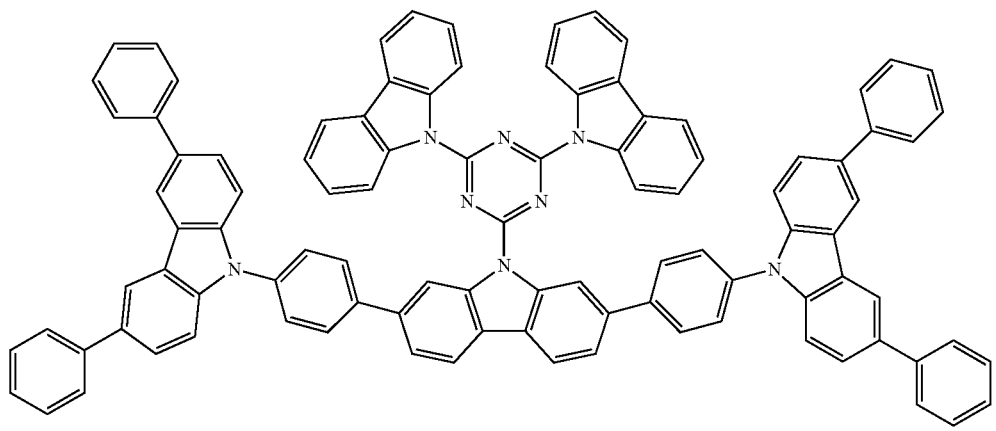 [SMILES: c1ccc(-c2ccc3c(c2)c2cc(-c4ccccc4)ccc2n3-c2ccc(-c3ccc4c5ccc(-c6ccc(-n7c8ccc(-c9ccccc9)cc8c8cc(-c9ccccc9)ccc87)cc6)cc5n(-c5nc(-n6c7ccccc7c7ccccc76)nc(-n6c7ccccc7c7ccccc76)n5)c4c3)cc2)cc1]
84
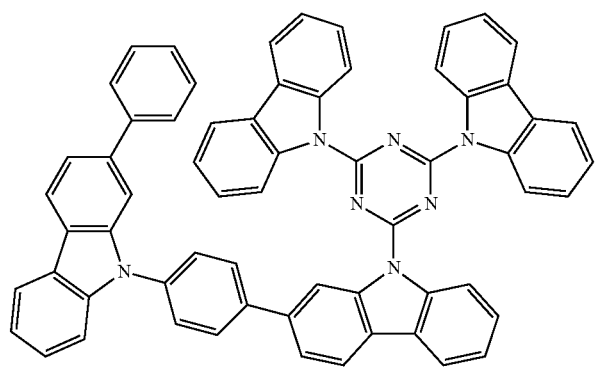 [SMILES: c1ccc(-c2ccc3c4ccccc4n(-c4ccc(-c5ccc6c7ccccc7n(-c7nc(-n8c9ccccc9c9ccccc98)nc(-n8c9ccccc9c9ccccc98)n7)c6c5)cc4)c3c2)cc1]
85
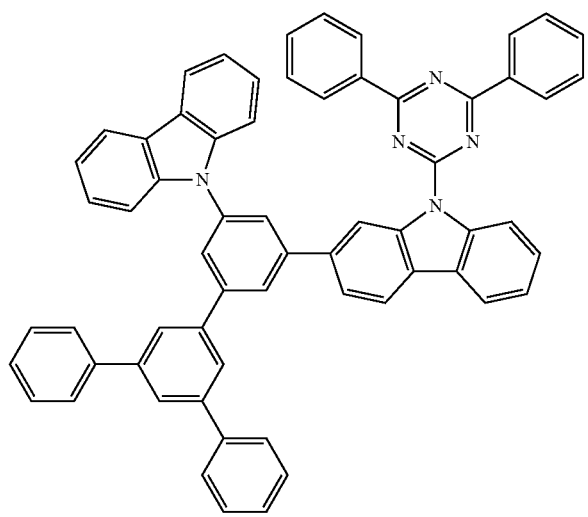 [SMILES: c1ccc(-c2cc(-c3ccccc3)cc(-c3cc(-c4ccc5c6ccccc6n(-c6nc(-c7ccccc7)nc(-c7ccccc7)n6)c5c4)cc(-n4c5ccccc5c5ccccc54)c3)c2)cc1]

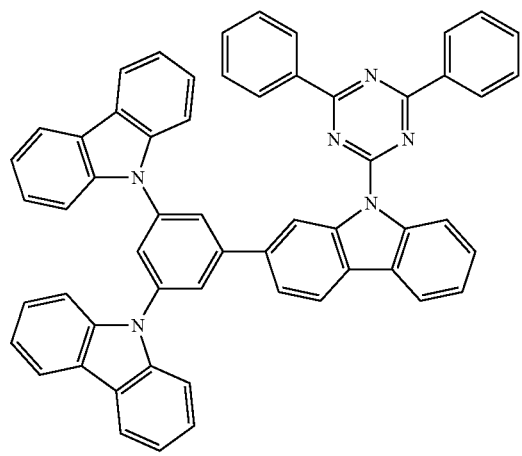 [SMILES: c1ccc(-c2nc(-c3ccccc3)nc(-n3c4ccccc4c4ccc(-c5cc(-n6c7ccccc7c7ccccc76)cc(-n6c7ccccc7c7ccccc76)c5)cc43)n2)cc1]
86
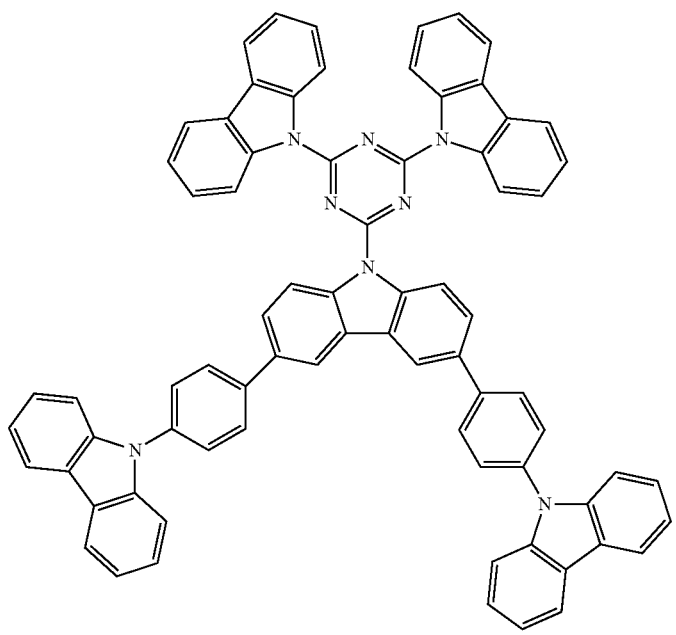 [SMILES: c1ccc2c(c1)c1ccccc1n2-c1ccc(-c2ccc3c(c2)c2cc(-c4ccc(-n5c6ccccc6c6ccccc65)cc4)ccc2n3-c2nc(-n3c4ccccc4c4ccccc43)nc(-n3c4ccccc4c4ccccc43)n2)cc1]
87

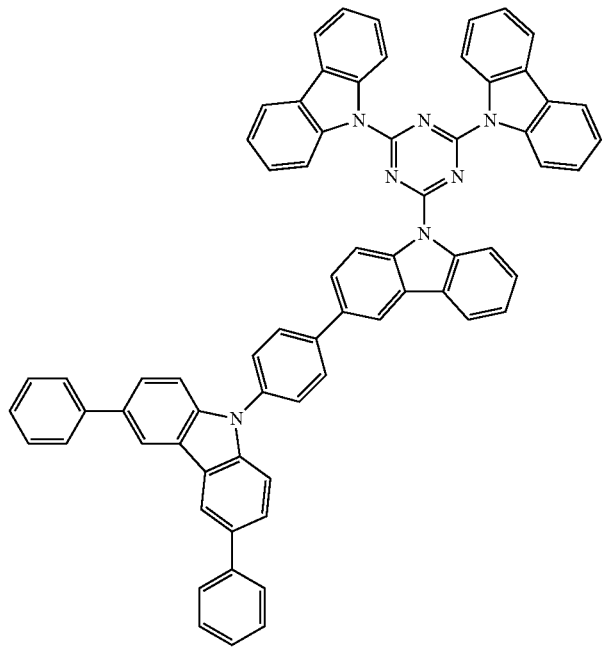 [SMILES: c1ccc(-c2ccc3c(c2)c2cc(-c4ccccc4)ccc2n3-c2ccc(-c3ccc4c(c3)c3ccccc3n4-c3nc(-n4c5ccccc5c5ccccc54)nc(-n4c5ccccc5c5ccccc54)n3)cc2)cc1]
88
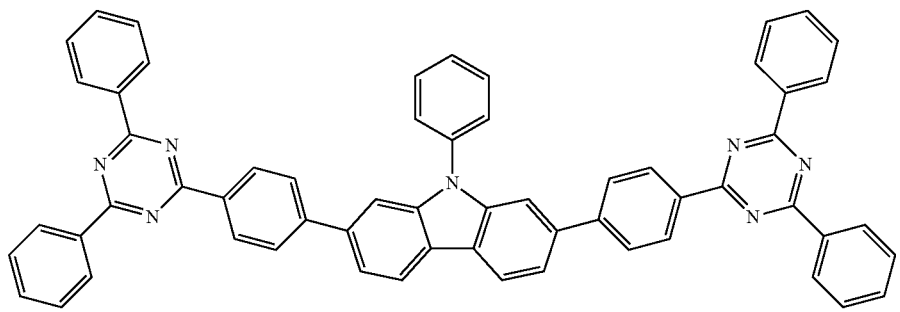 [SMILES: c1ccc(-c2nc(-c3ccccc3)nc(-c3ccc(-c4ccc5c6ccc(-c7ccc(-c8nc(-c9ccccc9)nc(-c9ccccc9)n8)cc7)cc6n(-c6ccccc6)c5c4)cc3)n2)cc1]
89
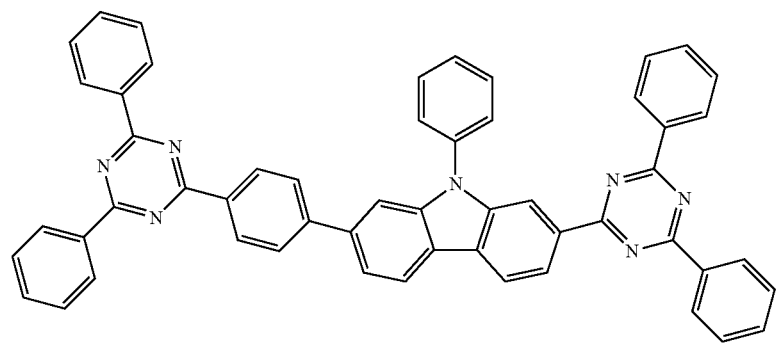 [SMILES: c1ccc(-c2nc(-c3ccccc3)nc(-c3ccc(-c4ccc5c6ccc(-c7nc(-c8ccccc8)nc(-c8ccccc8)n7)cc6n(-c6ccccc6)c5c4)cc3)n2)cc1]
90

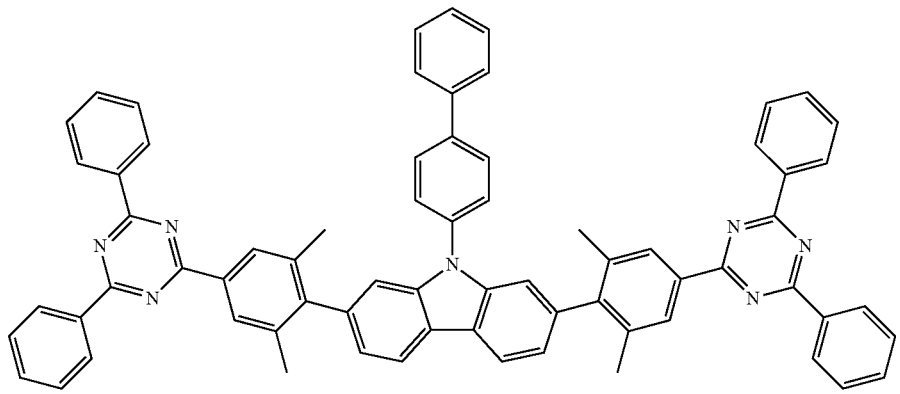 [SMILES: Cc1cc(-c2nc(-c3ccccc3)nc(-c3ccccc3)n2)cc(C)c1-c1ccc2c3ccc(-c4c(C)cc(-c5nc(-c6ccccc6)nc(-c6ccccc6)n5)cc4C)cc3n(-c3ccc(-c4ccccc4)cc3)c2c1]
91
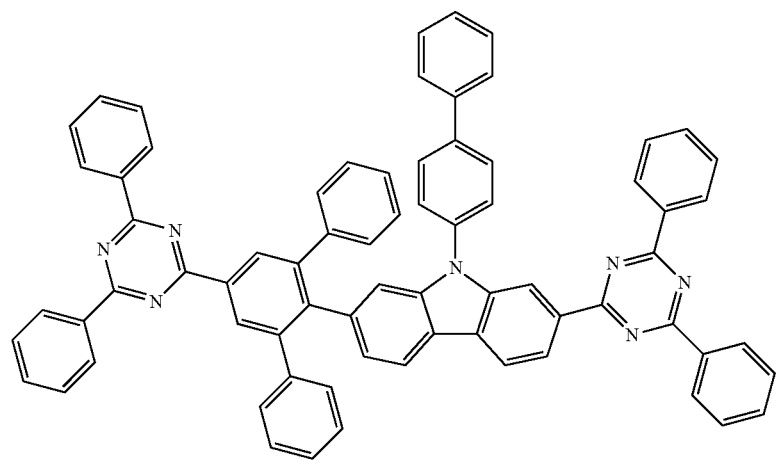 [SMILES: c1ccc(-c2ccc(-n3c4cc(-c5nc(-c6ccccc6)nc(-c6ccccc6)n5)ccc4c4ccc(-c5c(-c6ccccc6)cc(-c6nc(-c7ccccc7)nc(-c7ccccc7)n6)cc5-c5ccccc5)cc43)cc2)cc1]
92
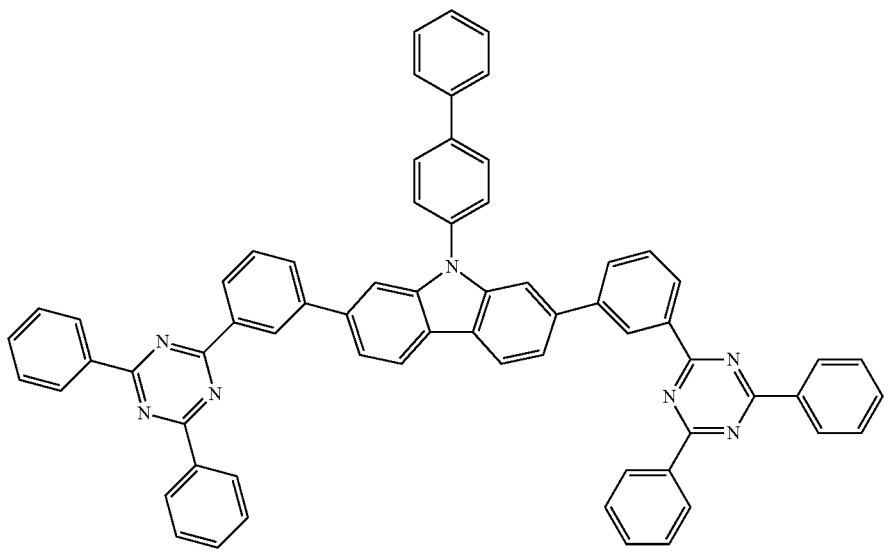 [SMILES: c1ccc(-c2ccc(-n3c4cc(-c5cccc(-c6nc(-c7ccccc7)nc(-c7ccccc7)n6)c5)ccc4c4ccc(-c5cccc(-c6nc(-c7ccccc7)nc(-c7ccccc7)n6)c5)cc43)cc2)cc1]
93

94
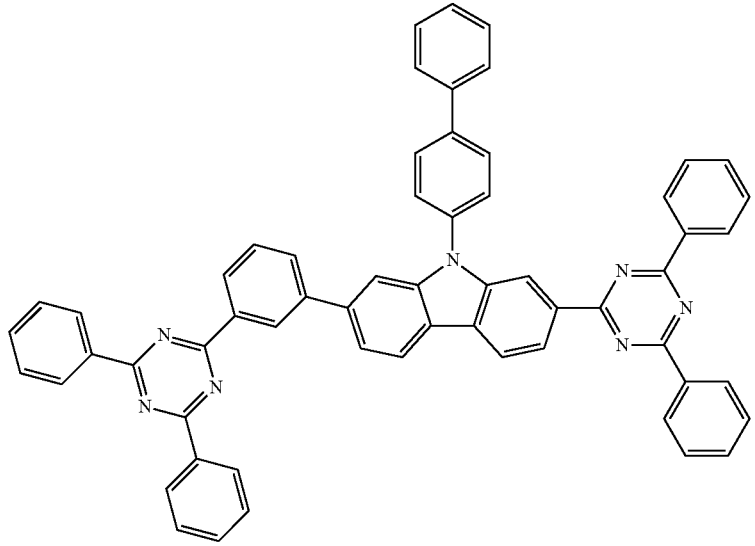 [SMILES: c1ccc(-c2ccc(-n3c4cc(-c5cccc(-c6nc(-c7ccccc7)nc(-c7ccccc7)n6)c5)ccc4c4ccc(-c5nc(-c6ccccc6)nc(-c6ccccc6)n5)cc43)cc2)cc1]
95
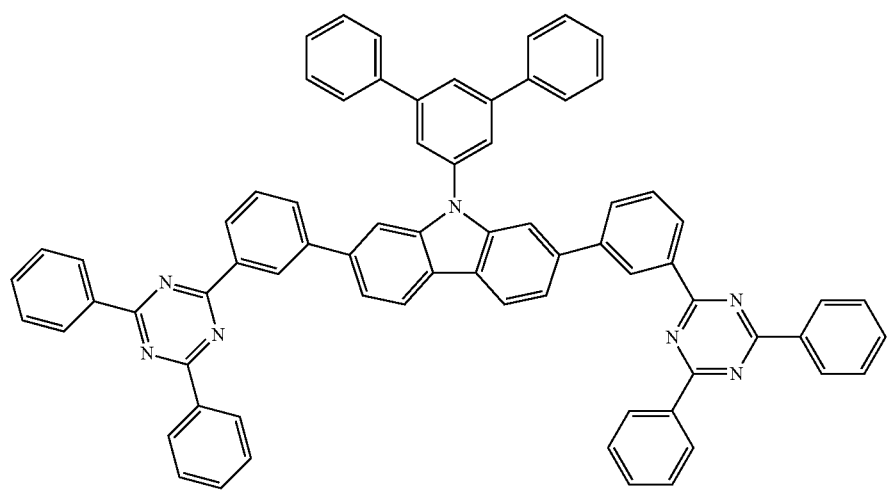 [SMILES: c1ccc(-c2cc(-c3ccccc3)cc(-n3c4cc(-c5cccc(-c6nc(-c7ccccc7)nc(-c7ccccc7)n6)c5)ccc4c4ccc(-c5cccc(-c6nc(-c7ccccc7)nc(-c7ccccc7)n6)c5)cc43)c2)cc1]
96
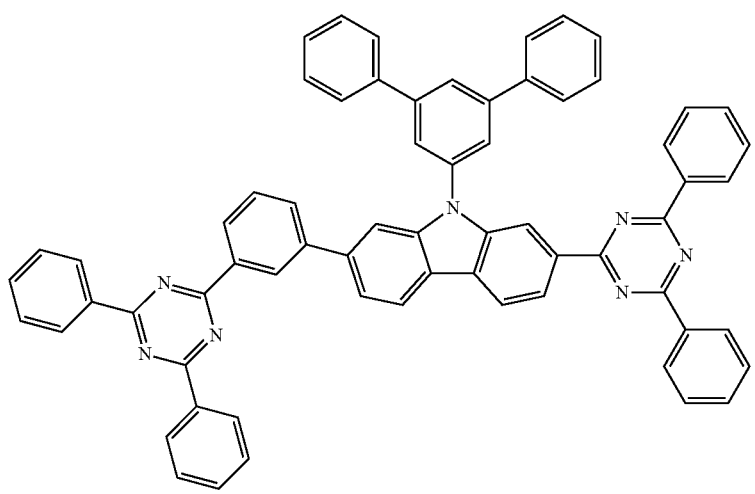 [SMILES: c1ccc(-c2cc(-c3ccccc3)cc(-n3c4cc(-c5cccc(-c6nc(-c7ccccc7)nc(-c7ccccc7)n6)c5)ccc4c4ccc(-c5nc(-c6ccccc6)nc(-c6ccccc6)n5)cc43)c2)cc1]

97
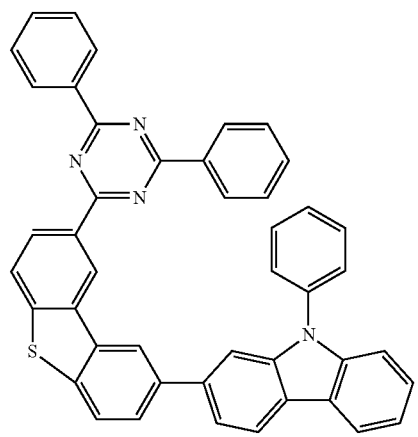 [SMILES: c1ccc(-c2nc(-c3ccccc3)nc(-c3ccc4sc5ccc(-c6ccc7c8ccccc8n(-c8ccccc8)c7c6)cc5c4c3)n2)cc1]
98
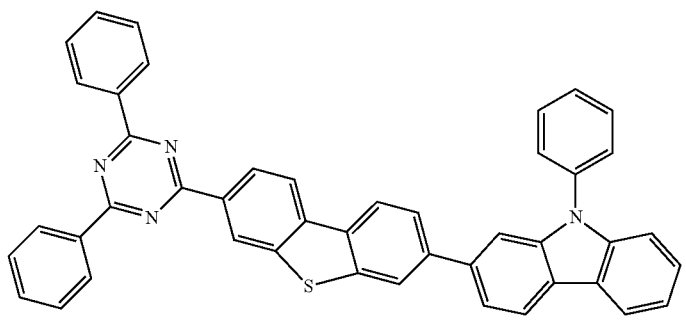 [SMILES: c1ccc(-c2nc(-c3ccccc3)nc(-c3ccc4c(c3)sc3cc(-c5ccc6c7ccccc7n(-c7ccccc7)c6c5)ccc34)n2)cc1]
99
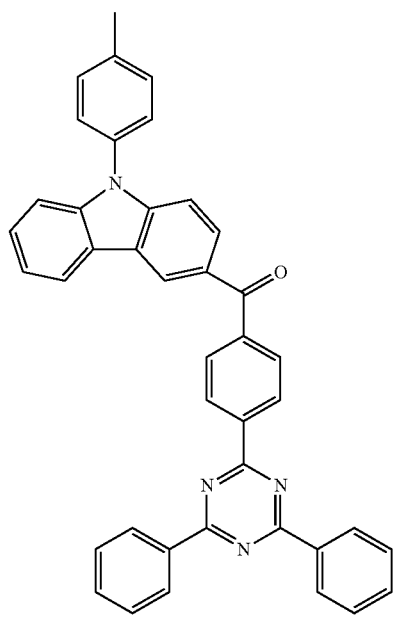 [SMILES: Cc1ccc(-n2c3ccccc3c3cc(C(=O)c4ccc(-c5nc(-c6ccccc6)nc(-c6ccccc6)n5)cc4)ccc32)cc1]

100
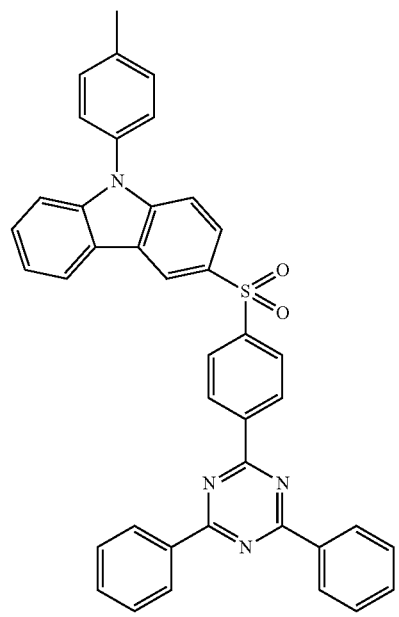 [SMILES: Cc1ccc(-n2c3ccccc3c3cc(S(=O)(=O)c4ccc(-c5nc(-c6ccccc6)nc(-c6ccccc6)n5)cc4)ccc32)cc1]
101
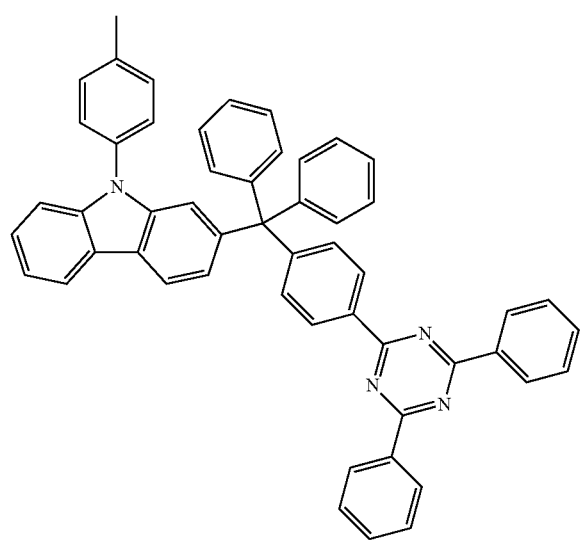 [SMILES: Cc1ccc(-n2c3ccccc3c3ccc(C(c4ccccc4)(c4ccccc4)c4ccc(-c5nc(-c6ccccc6)nc(-c6ccccc6)n5)cc4)cc32)cc1]

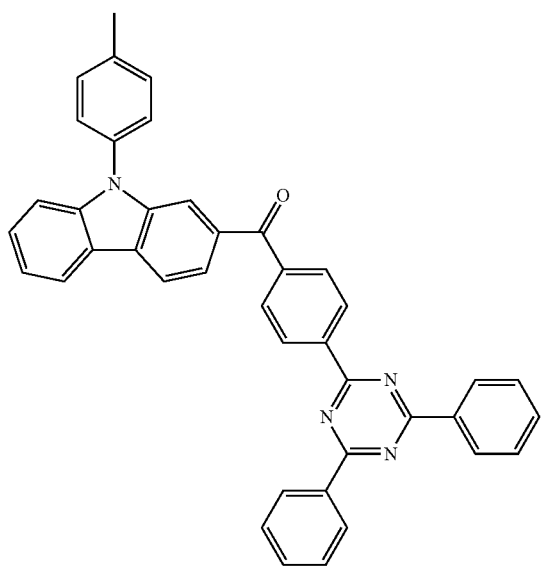 [SMILES: Cc1ccc(-n2c3ccccc3c3ccc(C(=O)c4ccc(-c5nc(-c6ccccc6)nc(-c6ccccc6)n5)cc4)cc32)cc1]
102
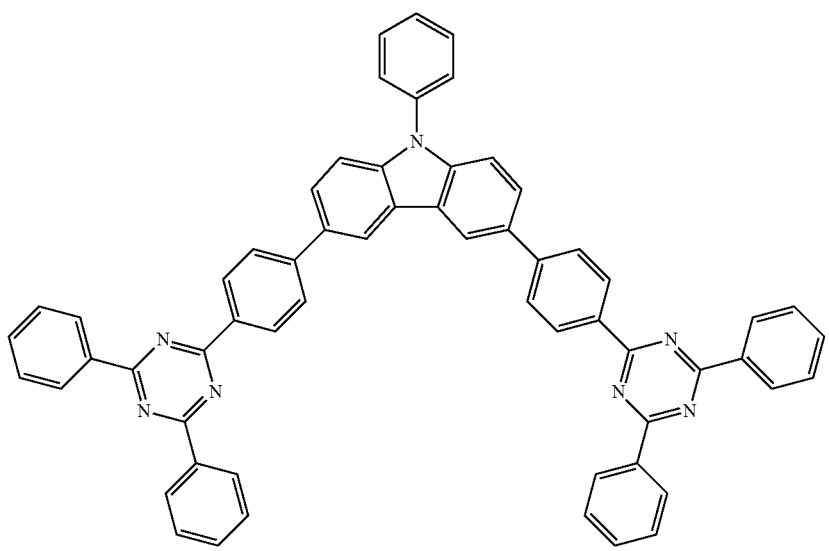 [SMILES: c1ccc(-c2nc(-c3ccccc3)nc(-c3ccc(-c4ccc5c(c4)c4cc(-c6ccc(-c7nc(-c8ccccc8)nc(-c8ccccc8)n7)cc6)ccc4n5-c4ccccc4)cc3)n2)cc1]
103
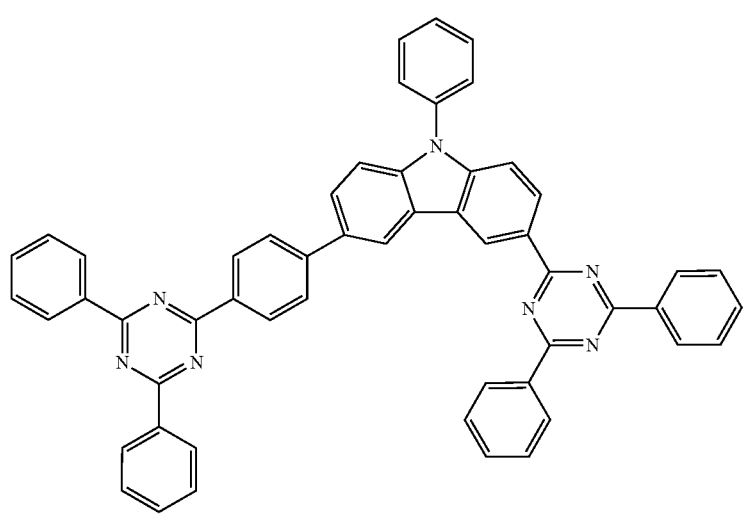 [SMILES: c1ccc(-c2nc(-c3ccccc3)nc(-c3ccc(-c4ccc5c(c4)c4cc(-c6nc(-c7ccccc7)nc(-c7ccccc7)n6)ccc4n5-c4ccccc4)cc3)n2)cc1]
104

105
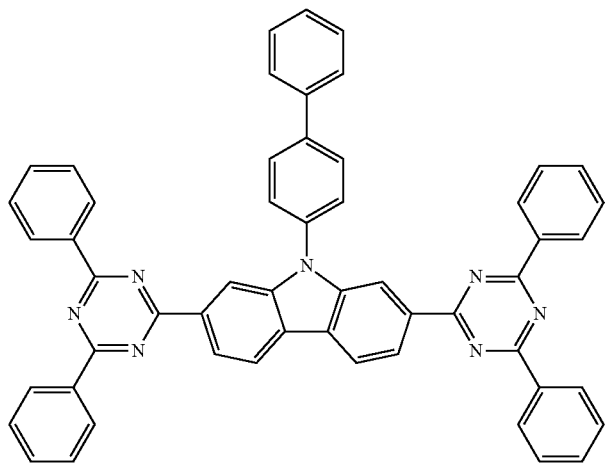 [SMILES: c1ccc(-c2ccc(-n3c4cc(-c5nc(-c6ccccc6)nc(-c6ccccc6)n5)ccc4c4ccc(-c5nc(-c6ccccc6)nc(-c6ccccc6)n5)cc43)cc2)cc1]
106
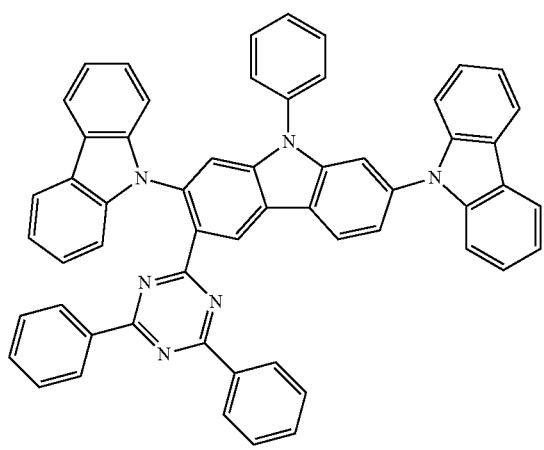 [SMILES: c1ccc(-c2nc(-c3ccccc3)nc(-c3cc4c5ccc(-n6c7ccccc7c7ccccc76)cc5n(-c5ccccc5)c4cc3-n3c4ccccc4c4ccccc43)n2)cc1]
107
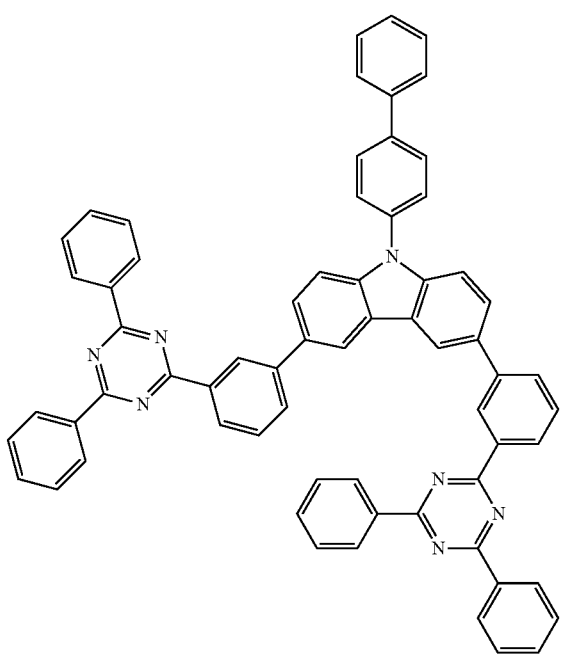 [SMILES: c1ccc(-c2ccc(-n3c4ccc(-c5cccc(-c6nc(-c7ccccc7)nc(-c7ccccc7)n6)c5)cc4c4cc(-c5cccc(-c6nc(-c7ccccc7)nc(-c7ccccc7)n6)c5)ccc43)cc2)cc1]

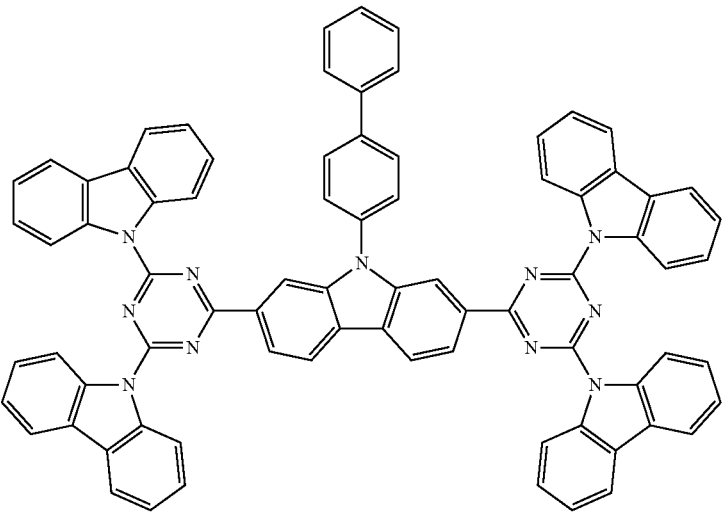 [SMILES: c1ccc(-c2ccc(-n3c4cc(-c5nc(-n6c7ccccc7c7ccccc76)nc(-n6c7ccccc7c7ccccc76)n5)ccc4c4ccc(-c5nc(-n6c7ccccc7c7ccccc76)nc(-n6c7ccccc7c7ccccc76)n5)cc43)cc2)cc1]
108
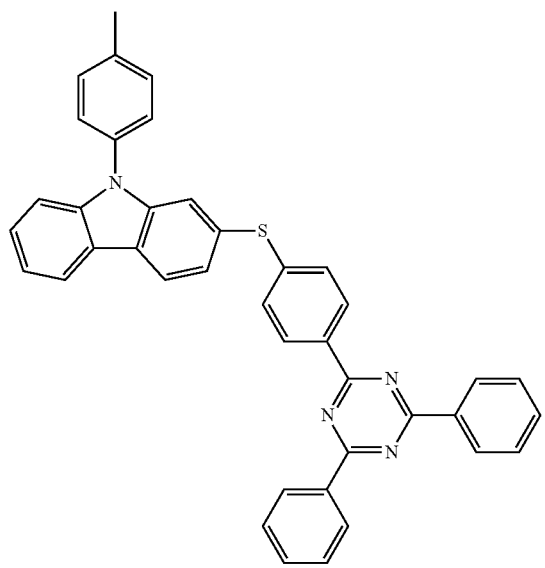 [SMILES: Cc1ccc(-n2c3ccccc3c3ccc(Sc4ccc(-c5nc(-c6ccccc6)nc(-c6ccccc6)n5)cc4)cc32)cc1]
109
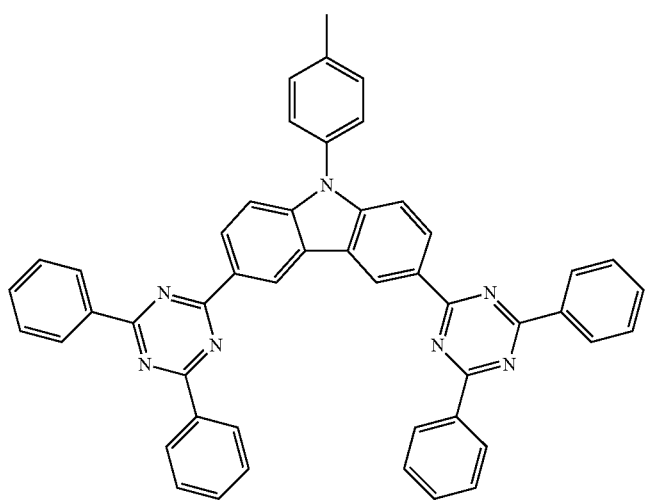 [SMILES: Cc1ccc(-n2c3ccc(-c4nc(-c5ccccc5)nc(-c5ccccc5)n4)cc3c3cc(-c4nc(-c5ccccc5)nc(-c5ccccc5)n4)ccc32)cc1]
110

111
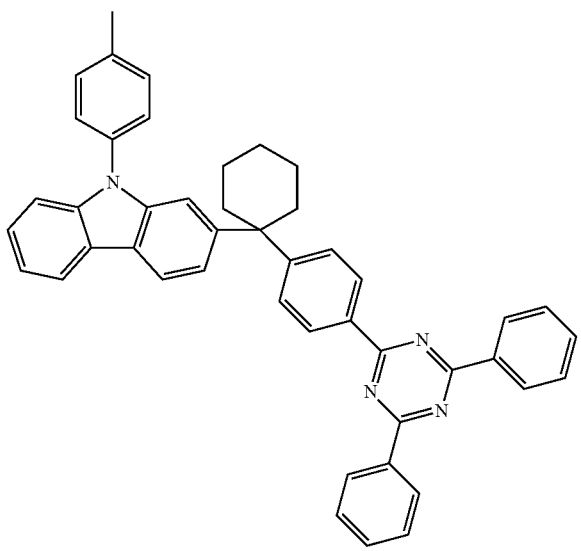 [SMILES: Cc1ccc(-n2c3ccccc3c3ccc(C4(c5ccc(-c6nc(-c7ccccc7)nc(-c7ccccc7)n6)cc5)CCCCC4)cc32)cc1]
112
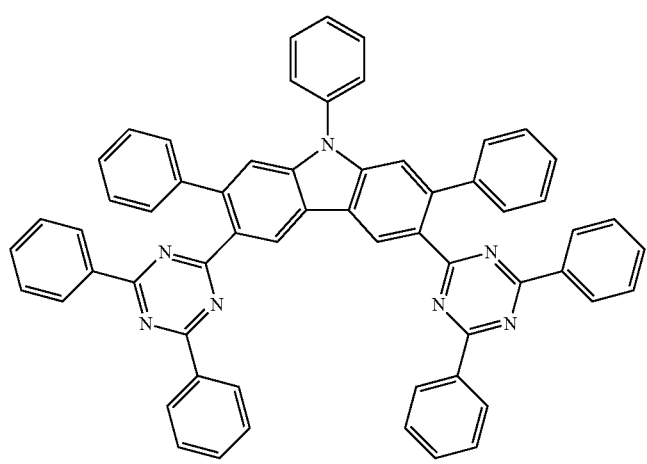 [SMILES: c1ccc(-c2nc(-c3ccccc3)nc(-c3cc4c5cc(-c6nc(-c7ccccc7)nc(-c7ccccc7)n6)c(-c6ccccc6)cc5n(-c5ccccc5)c4cc3-c3ccccc3)n2)cc1]
113
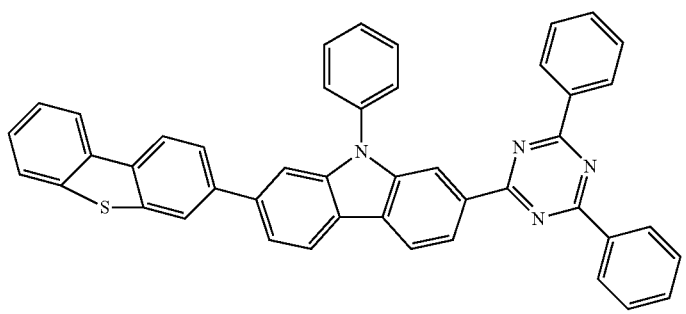 [SMILES: c1ccc(-c2nc(-c3ccccc3)nc(-c3ccc4c5ccc(-c6ccc7c(c6)sc6ccccc67)cc5n(-c5ccccc5)c4c3)n2)cc1]

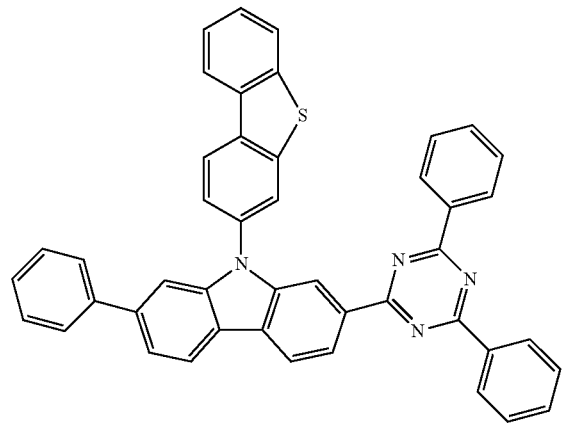 [SMILES: c1ccc(-c2ccc3c4ccc(-c5nc(-c6ccccc6)nc(-c6ccccc6)n5)cc4n(-c4ccc5c(c4)sc4ccccc45)c3c2)cc1]
114
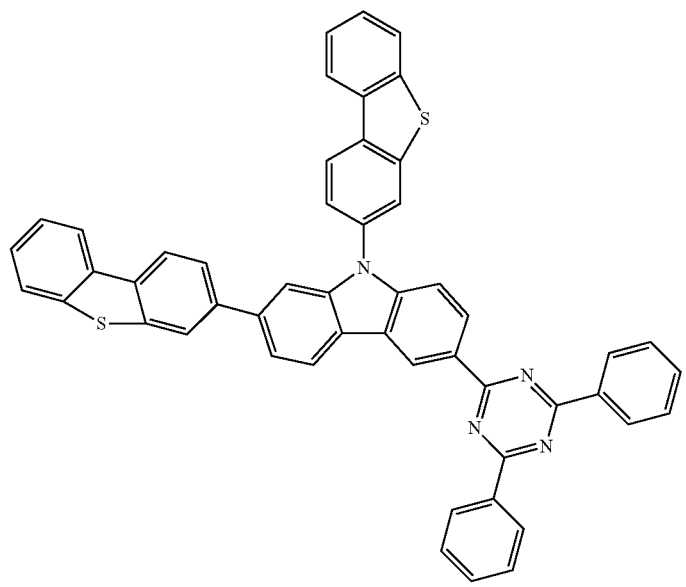 [SMILES: c1ccc(-c2nc(-c3ccccc3)nc(-c3ccc4c(c3)c3ccc(-c5ccc6c(c5)sc5ccccc56)cc3n4-c3ccc4c(c3)sc3ccccc34)n2)cc1]
115
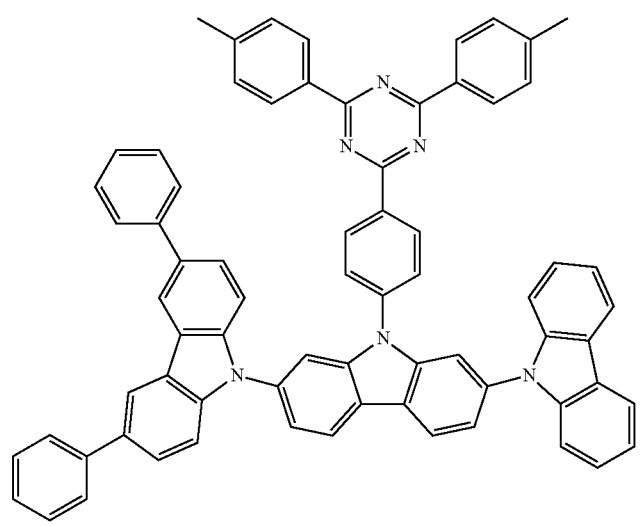 [SMILES: Cc1ccc(-c2nc(-c3ccc(C)cc3)nc(-c3ccc(-n4c5cc(-n6c7ccccc7c7ccccc76)ccc5c5ccc(-n6c7ccc(-c8ccccc8)cc7c7cc(-c8ccccc8)ccc76)cc54)cc3)n2)cc1]
116

-continued
117
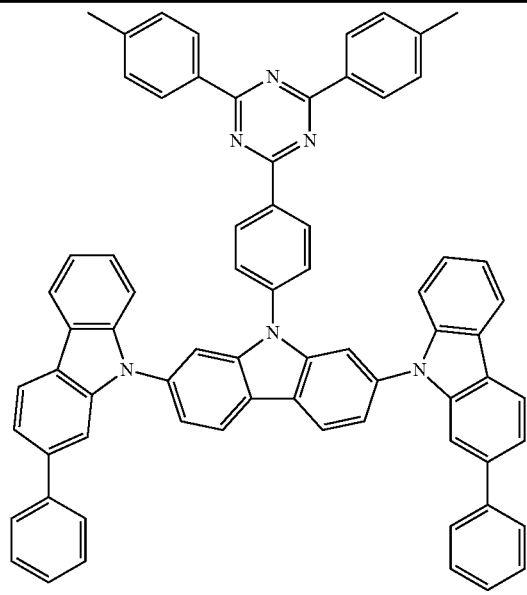
118
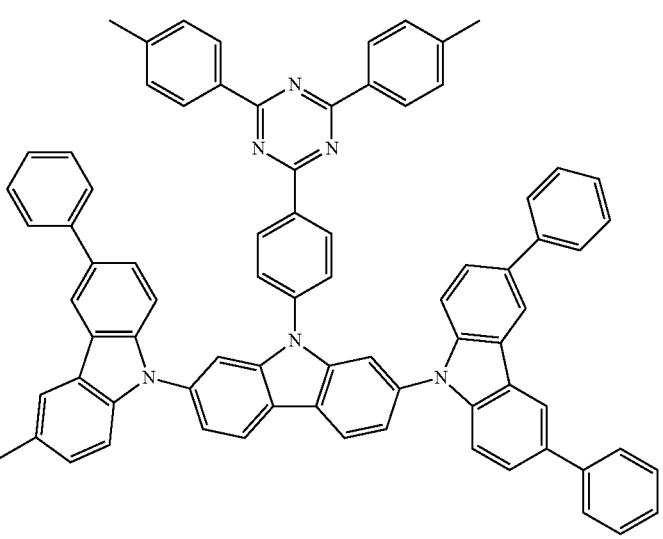
119
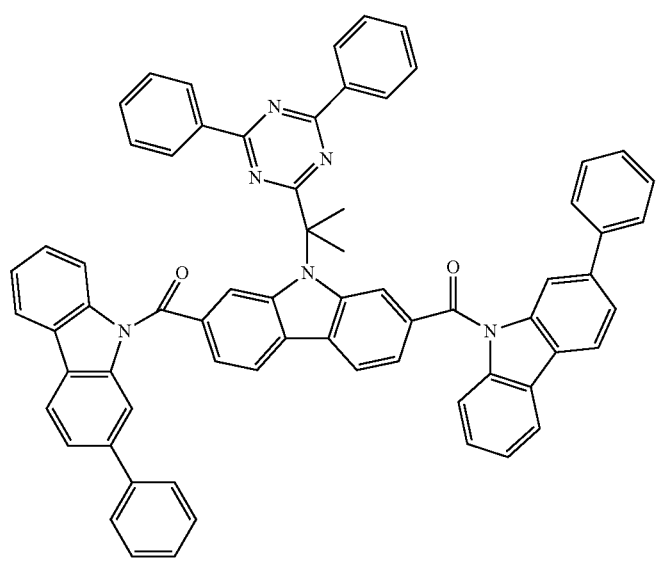 [SMILES: CC(C)(c1nc(-c2ccccc2)nc(-c2ccccc2)n1)n1c2cc(C(=O)n3c4ccccc4c4ccc(-c5ccccc5)cc43)ccc2c2ccc(C(=O)n3c4ccccc4c4ccc(-c5ccccc5)cc43)cc21]

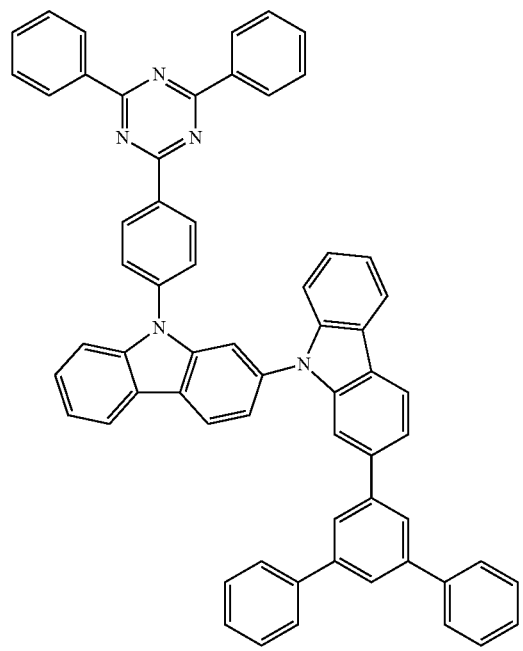 [SMILES: c1ccc(-c2cc(-c3ccccc3)cc(-c3ccc4c5ccccc5n(-c5ccc6c7ccccc7n(-c7ccc(-c8nc(-c9ccccc9)nc(-c9ccccc9)n8)cc7)c6c5)c4c3)c2)cc1]
120
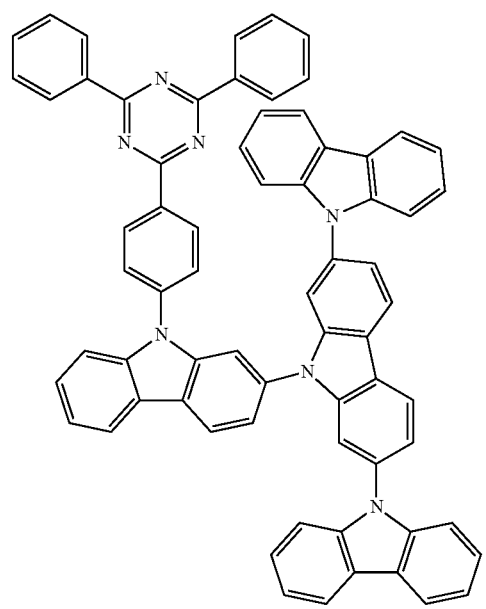 [SMILES: c1ccc(-c2nc(-c3ccccc3)nc(-c3ccc(-n4c5ccccc5c5ccc(-n6c7cc(-n8c9ccccc9c9ccccc98)ccc7c7ccc(-n8c9ccccc9c9ccccc98)cc76)cc54)cc3)n2)cc1]
121

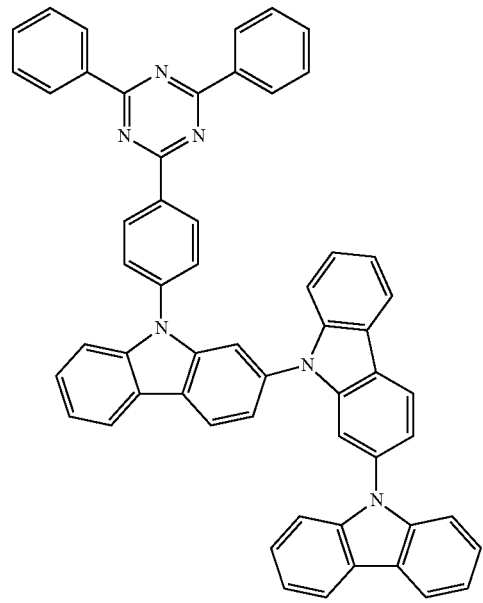 [SMILES: c1ccc(-c2nc(-c3ccccc3)nc(-c3ccc(-n4c5ccccc5c5ccc(-n6c7ccccc7c7ccc(-n8c9ccccc9c9ccccc98)cc76)cc54)cc3)n2)cc1]
122
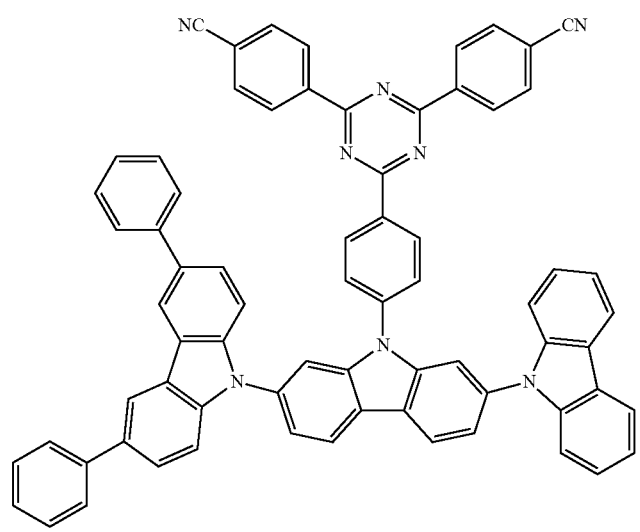 [SMILES: N#Cc1ccc(-c2nc(-c3ccc(C#N)cc3)nc(-c3ccc(-n4c5cc(-n6c7ccccc7c7ccccc76)ccc5c5ccc(-n6c7ccc(-c8ccccc8)cc7c7cc(-c8ccccc8)ccc76)cc54)cc3)n2)cc1]
123

124
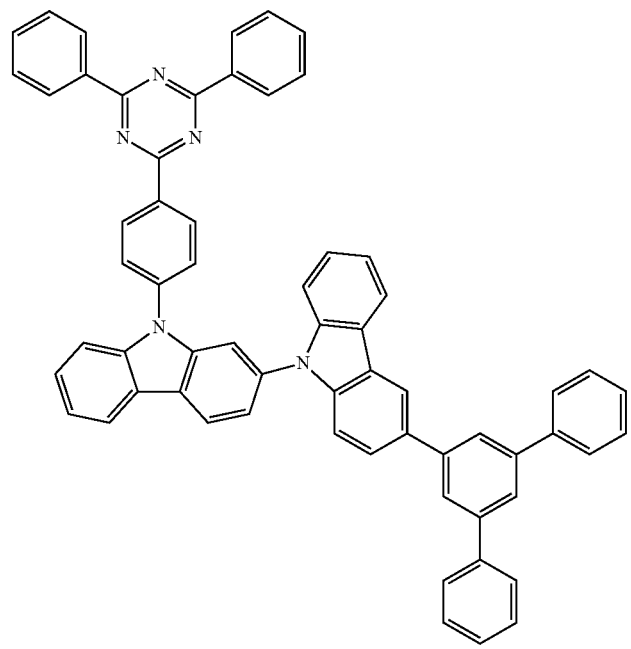 [SMILES: c1ccc(-c2cc(-c3ccccc3)cc(-c3ccc4c(c3)c3ccccc3n4-c3ccc4c5ccccc5n(-c5ccc(-c6nc(-c7ccccc7)nc(-c7ccccc7)n6)cc5)c4c3)c2)cc1]
125
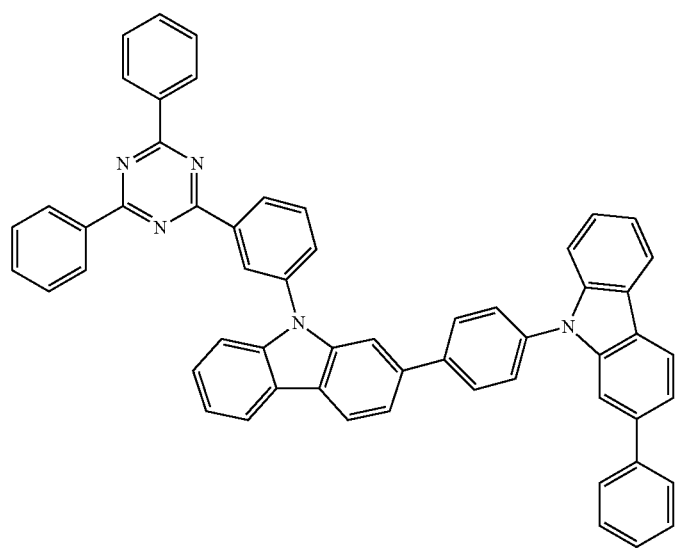 [SMILES: c1ccc(-c2ccc3c4ccccc4n(-c4ccc(-c5ccc6c7ccccc7n(-c7cccc(-c8nc(-c9ccccc9)nc(-c9ccccc9)n8)c7)c6c5)cc4)c3c2)cc1]

-continued
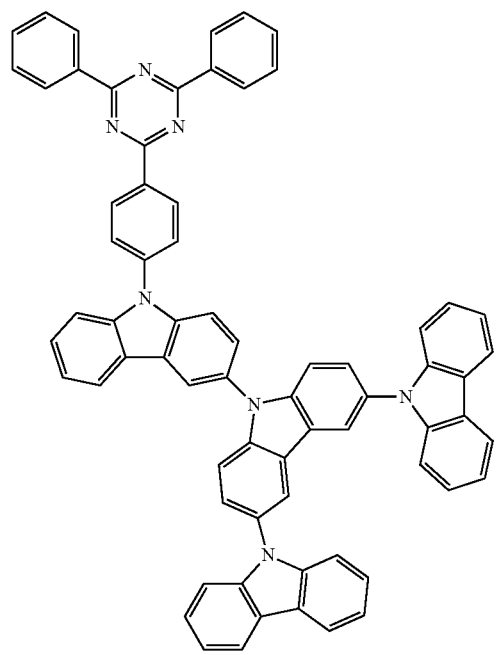 [SMILES: c1ccc(-c2nc(-c3ccccc3)nc(-c3ccc(-n4c5ccccc5c5cc(-n6c7ccc(-n8c9ccccc9c9ccccc98)cc7c7cc(-n8c9ccccc9c9ccccc98)ccc76)ccc54)cc3)n2)cc1]
126
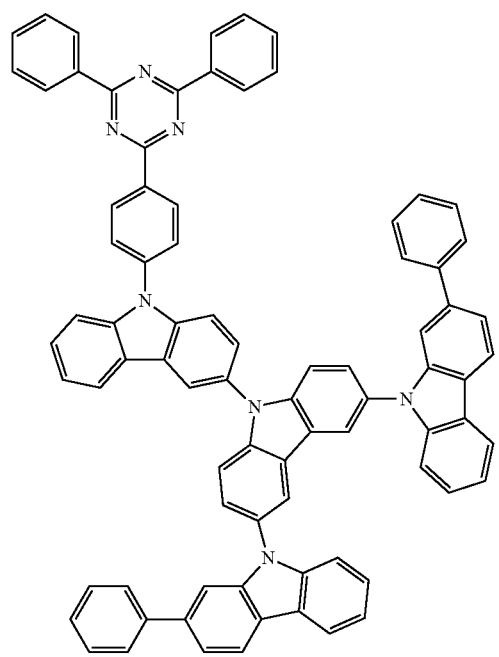 [SMILES: c1ccc(-c2ccc3c4ccccc4n(-c4ccc5c(c4)c4cc(-n6c7ccccc7c7ccc(-c8ccccc8)cc76)ccc4n5-c4ccc5c(c4)c4ccccc4n5-c4ccc(-c5nc(-c6ccccc6)nc(-c6ccccc6)n5)cc4)c3c2)cc1]
127

-continued
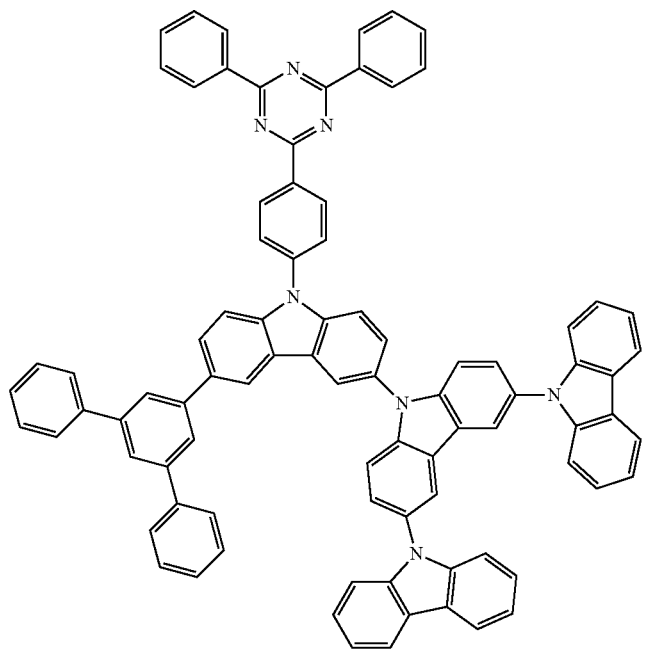 [SMILES: c1ccc(-c2cc(-c3ccccc3)cc(-c3ccc4c(c3)c3cc(-n5c6ccc(-n7c8ccccc8c8ccccc87)cc6c6cc(-n7c8ccccc8c8ccccc87)ccc65)ccc3n4-c3ccc(-c4nc(-c5ccccc5)nc(-c5ccccc5)n4)cc3)c2)cc1]
128
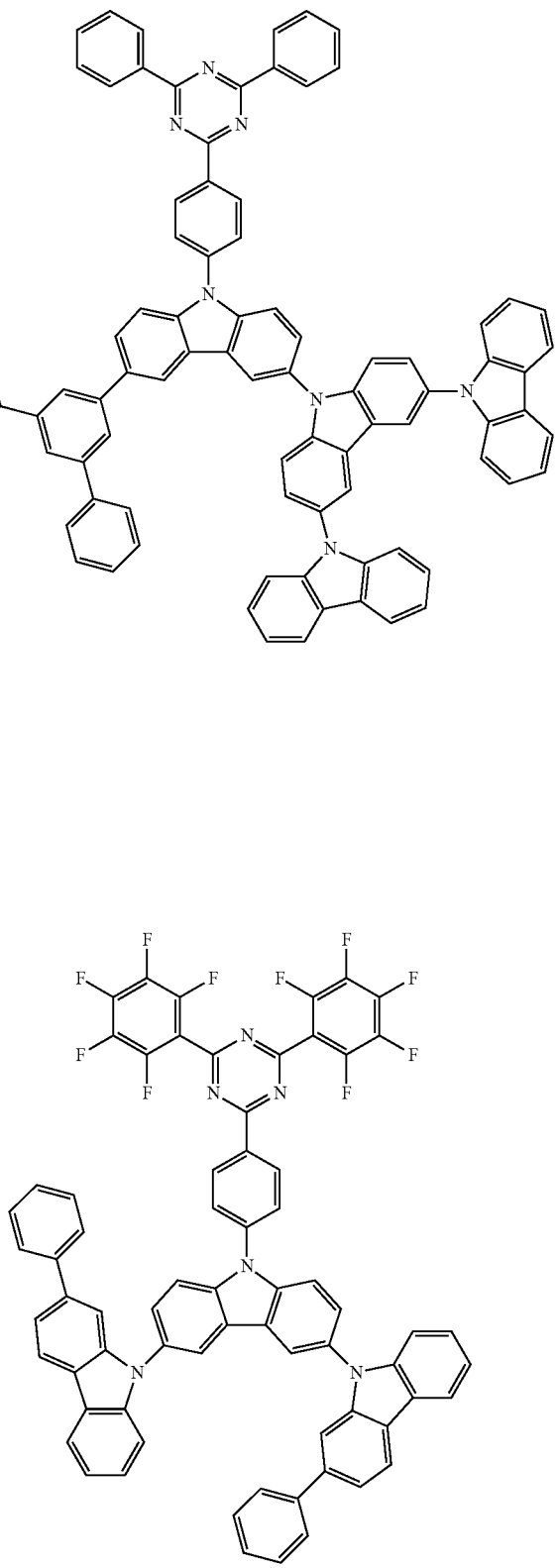
129

-continued
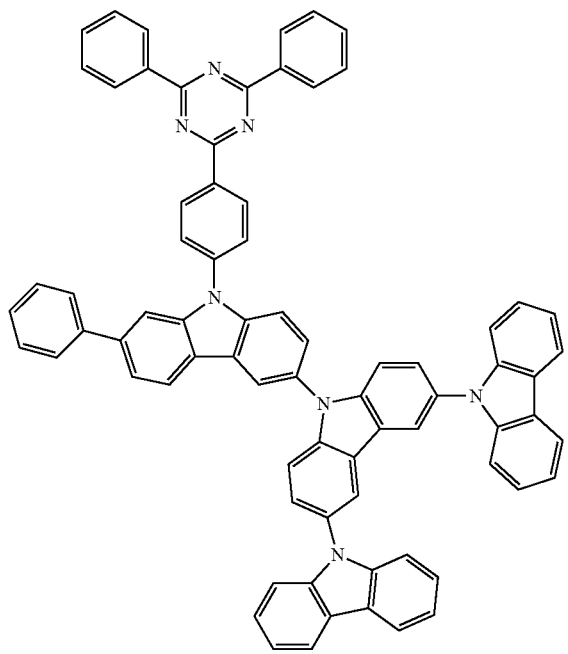 [SMILES: c1ccc(-c2ccc3c4cc(-n5c6ccc(-n7c8ccccc8c8ccccc87)cc6c6cc(-n7c8ccccc8c8ccccc87)ccc65)ccc4n(-c4ccc(-c5nc(-c6ccccc6)nc(-c6ccccc6)n5)cc4)c3c2)cc1]
130
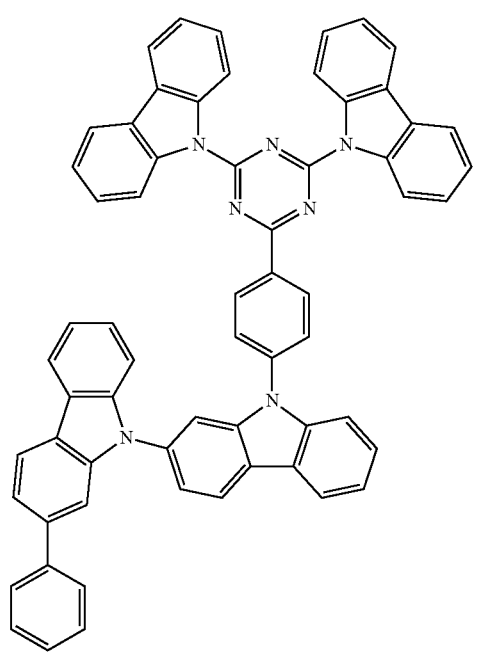 [SMILES: c1ccc(-c2ccc3c4ccccc4n(-c4ccc5c6ccccc6n(-c6ccc(-c7nc(-n8c9ccccc9c9ccccc98)nc(-n8c9ccccc9c9ccccc98)n7)cc6)c5c4)c3c2)cc1]
131

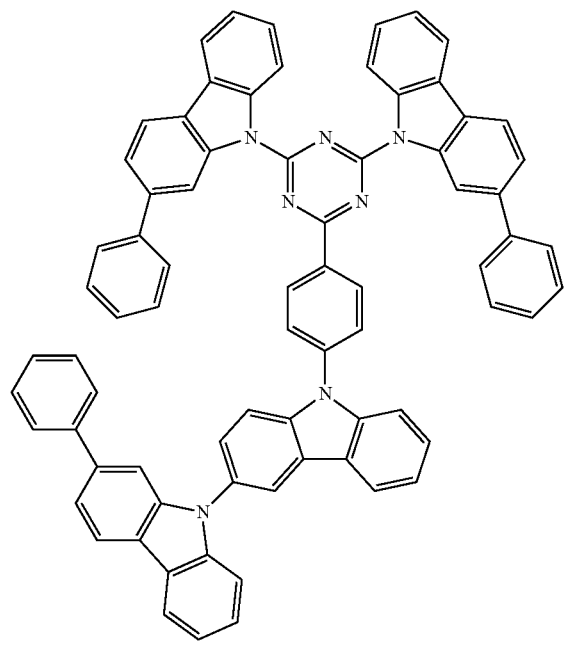 [SMILES: c1ccc(-c2ccc3c4ccccc4n(-c4ccc5c(c4)c4ccccc4n5-c4ccc(-c5nc(-n6c7ccccc7c7ccc(-c8ccccc8)cc76)nc(-n6c7ccccc7c7ccc(-c8ccccc8)cc76)n5)cc4)c3c2)cc1]
132
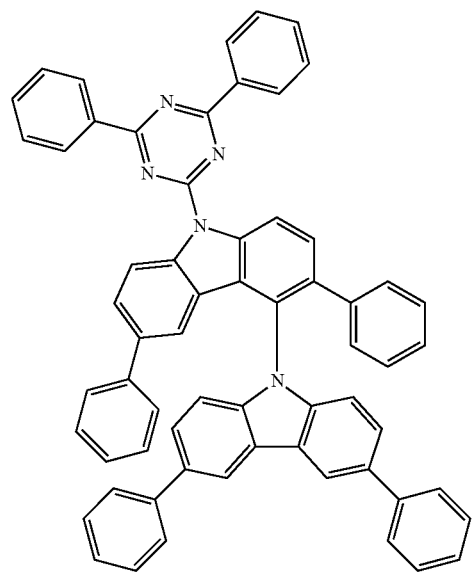 [SMILES: c1ccc(-c2ccc3c(c2)c2cc(-c4ccccc4)ccc2n3-c2c(-c3ccccc3)ccc3c2c2cc(-c4ccccc4)ccc2n3-c2nc(-c3ccccc3)nc(-c3ccccc3)n2)cc1]
133

-continued
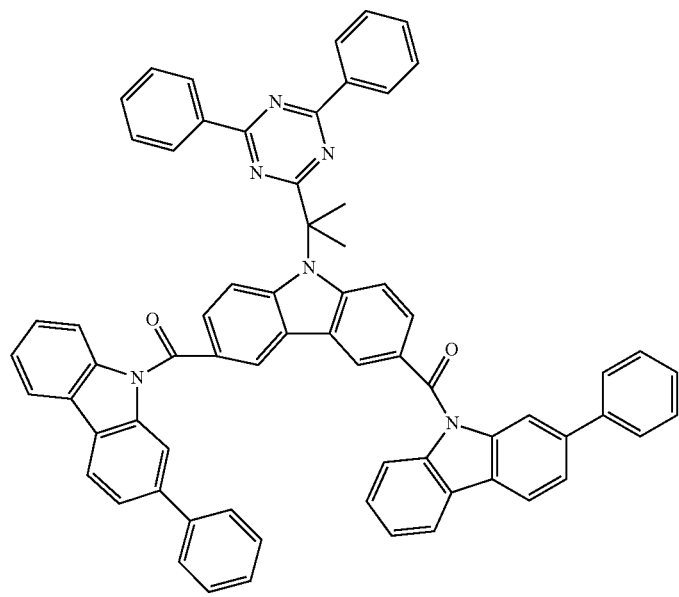 [SMILES: CC(C)(c1nc(-c2ccccc2)nc(-c2ccccc2)n1)n1c2ccc(C(=O)n3c4ccccc4c4ccc(-c5ccccc5)cc43)cc2c2cc(C(=O)n3c4ccccc4c4ccc(-c5ccccc5)cc43)ccc21]
134
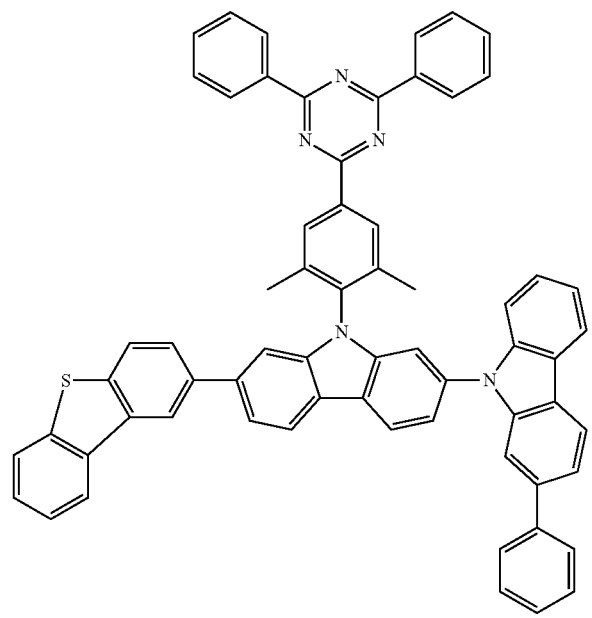 [SMILES: Cc1cc(-c2nc(-c3ccccc3)nc(-c3ccccc3)n2)cc(C)c1-n1c2cc(-c3ccc4sc5ccccc5c4c3)ccc2c2ccc(-n3c4ccccc4c4ccc(-c5ccccc5)cc43)cc21]
135

-continued
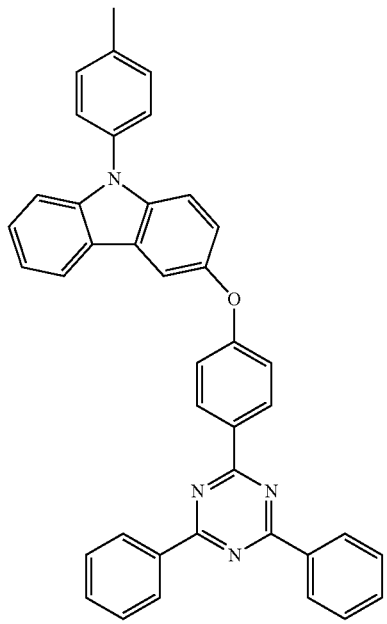 [SMILES: Cc1ccc(-n2c3ccccc3c3cc(Oc4ccc(-c5nc(-c6ccccc6)nc(-c6ccccc6)n5)cc4)ccc32)cc1]
136
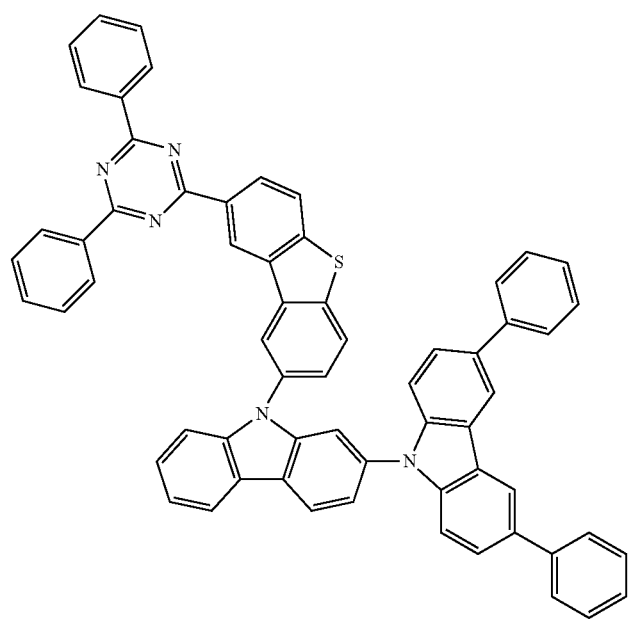 [SMILES: c1ccc(-c2ccc3c(c2)c2cc(-c4ccccc4)ccc2n3-c2ccc3c4ccccc4n(-c4ccc5sc6ccc(-c7nc(-c8ccccc8)nc(-c8ccccc8)n7)cc6c5c4)c3c2)cc1]
137
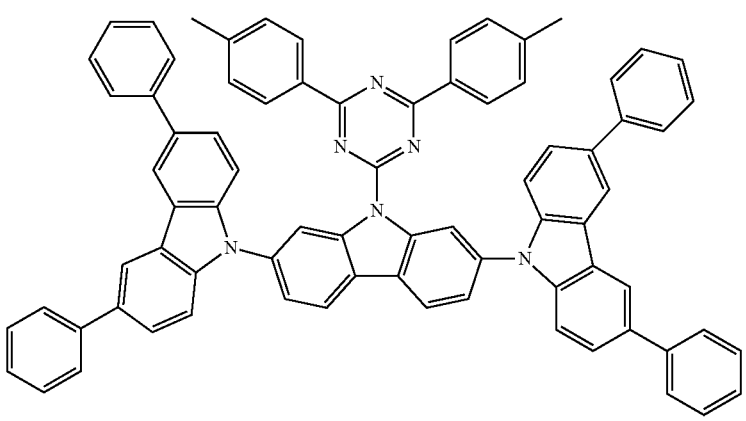 [SMILES: Cc1ccc(-c2nc(-c3ccc(C)cc3)nc(-n3c4cc(-n5c6ccc(-c7ccccc7)cc6c6cc(-c7ccccc7)ccc65)ccc4c4ccc(-n5c6ccc(-c7ccccc7)cc6c6cc(-c7ccccc7)ccc65)cc43)n2)cc1]
138

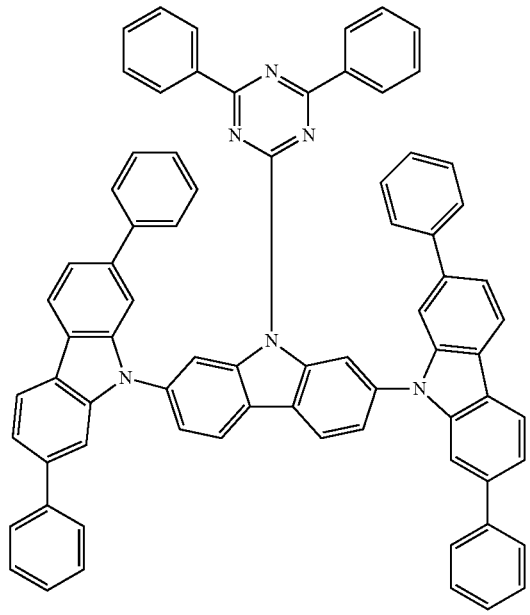 [SMILES: c1ccc(-c2ccc3c4ccc(-c5ccccc5)cc4n(-c4ccc5c6ccc(-n7c8cc(-c9ccccc9)ccc8c8ccc(-c9ccccc9)cc87)cc6n(-c6nc(-c7ccccc7)nc(-c7ccccc7)n6)c5c4)c3c2)cc1]
139
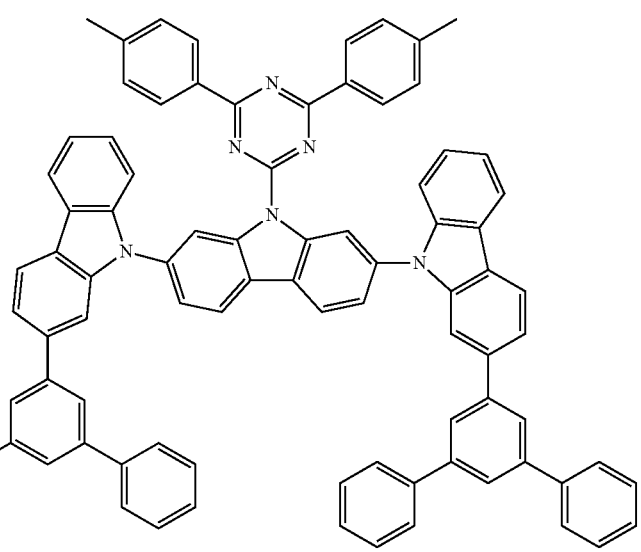
140
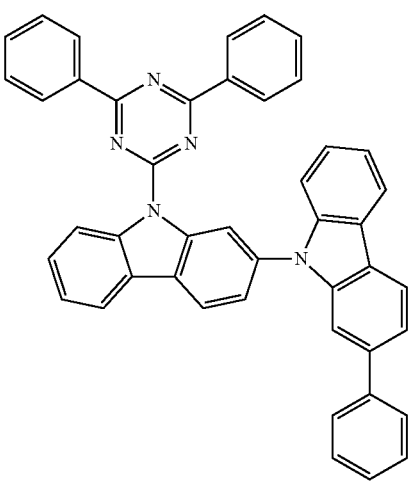 [SMILES: c1ccc(-c2ccc3c4ccccc4n(-c4ccc5c6ccccc6n(-c6nc(-c7ccccc7)nc(-c7ccccc7)n6)c5c4)c3c2)cc1]
141

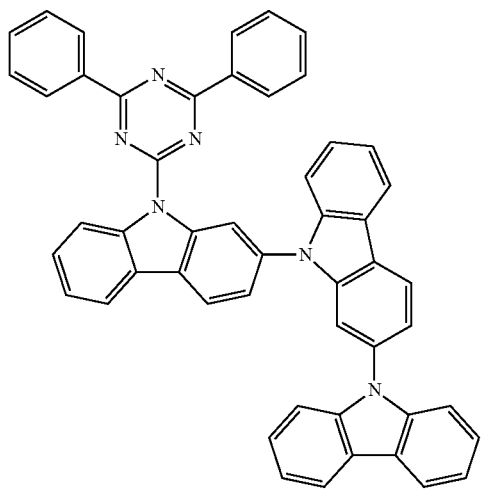 [SMILES: c1ccc(-c2nc(-c3ccccc3)nc(-n3c4ccccc4c4ccc(-n5c6ccccc6c6ccc(-n7c8ccccc8c8ccccc87)cc65)cc43)n2)cc1]
142
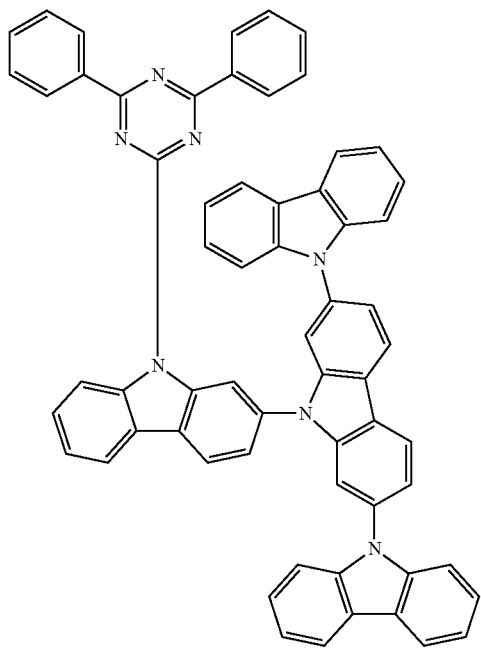 [SMILES: c1ccc(-c2nc(-c3ccccc3)nc(-n3c4ccccc4c4ccc(-n5c6cc(-n7c8ccccc8c8ccccc87)ccc6c6ccc(-n7c8ccccc8c8ccccc87)cc65)cc43)n2)cc1]
143
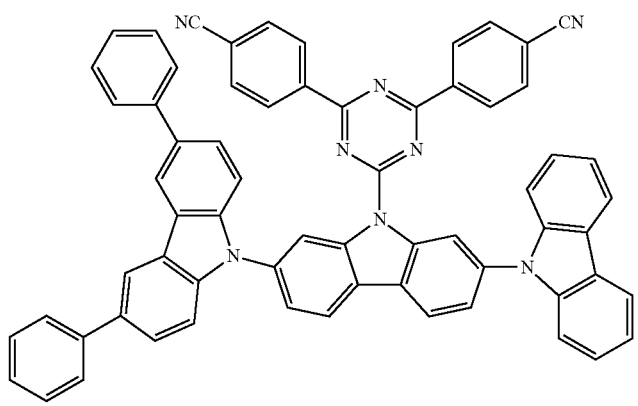 [SMILES: N#Cc1ccc(-c2nc(-c3ccc(C#N)cc3)nc(-n3c4cc(-n5c6ccccc6c6ccccc65)ccc4c4ccc(-n5c6ccc(-c7ccccc7)cc6c6cc(-c7ccccc7)ccc65)cc43)n2)cc1]
144

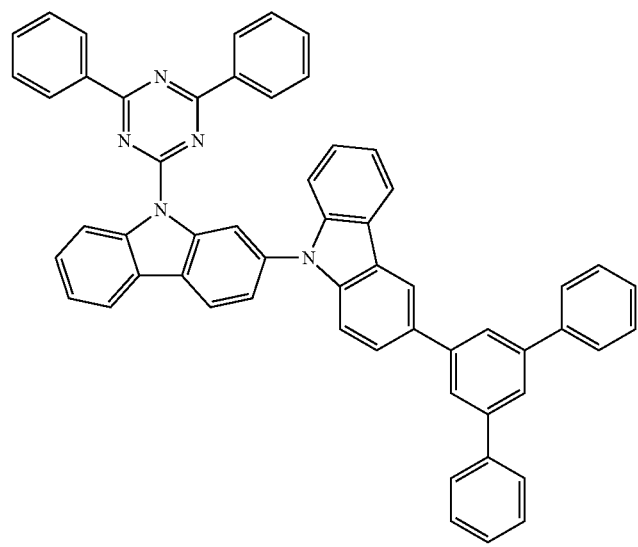 [SMILES: c1ccc(-c2cc(-c3ccccc3)cc(-c3ccc4c(c3)c3ccccc3n4-c3ccc4c5ccccc5n(-c5nc(-c6ccccc6)nc(-c6ccccc6)n5)c4c3)c2)cc1]
145
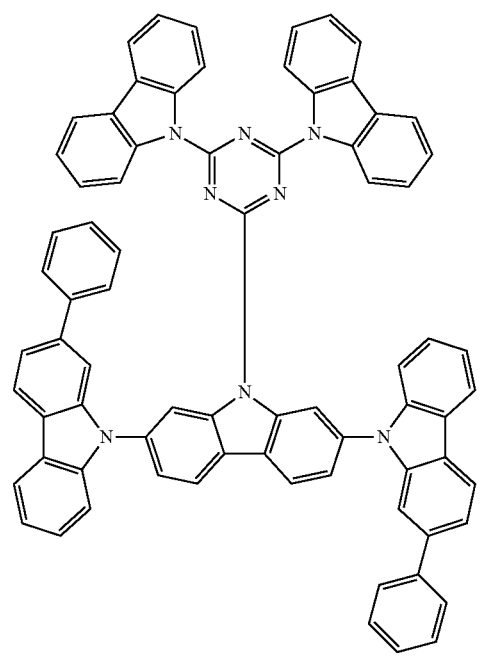 [SMILES: c1ccc(-c2ccc3c4ccccc4n(-c4ccc5c6ccc(-n7c8ccccc8c8ccc(-c9ccccc9)cc87)cc6n(-c6nc(-n7c8ccccc8c8ccccc87)nc(-n7c8ccccc8c8ccccc87)n6)c5c4)c3c2)cc1]
146

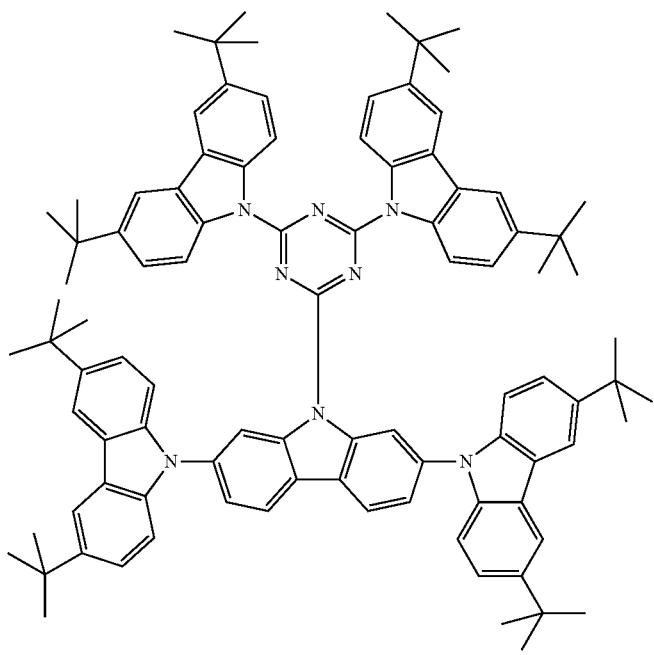 [SMILES: CC(C)(C)c1ccc2c(c1)c1cc(C(C)(C)C)ccc1n2-c1ccc2c3ccc(-n4c5ccc(C(C)(C)C)cc5c5cc(C(C)(C)C)ccc54)cc3n(-c3nc(-n4c5ccc(C(C)(C)C)cc5c5cc(C(C)(C)C)ccc54)nc(-n4c5ccc(C(C)(C)C)cc5c5cc(C(C)(C)C)ccc54)n3)c2c1]
147
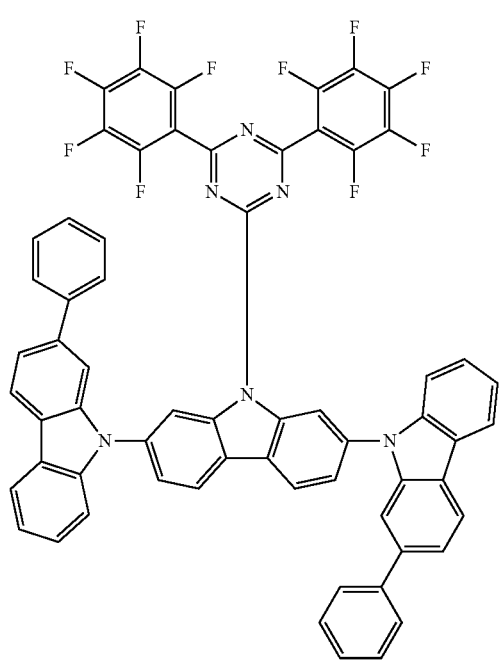 [SMILES: Fc1c(F)c(F)c(-c2nc(-c3c(F)c(F)c(F)c(F)c3F)nc(-n3c4cc(-n5c6ccccc6c6ccc(-c7ccccc7)cc65)ccc4c4ccc(-n5c6ccccc6c6ccc(-c7ccccc7)cc65)cc43)n2)c(F)c1F]
148

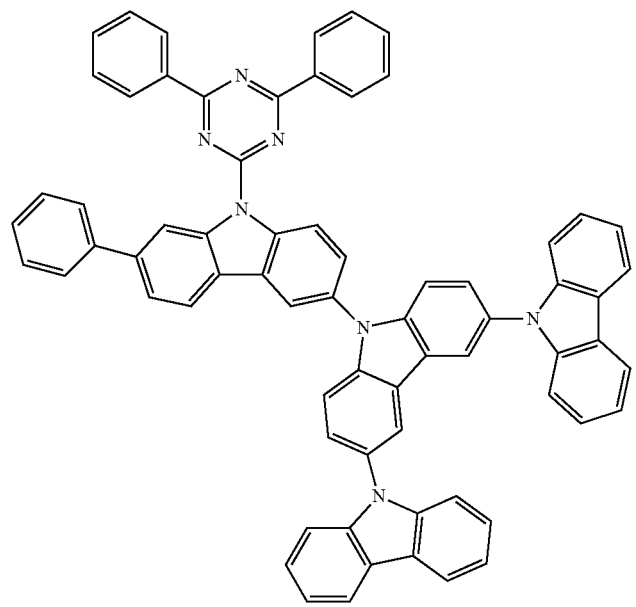 [SMILES: c1ccc(-c2ccc3c4cc(-n5c6ccc(-n7c8ccccc8c8ccccc87)cc6c6cc(-n7c8ccccc8c8ccccc87)ccc65)ccc4n(-c4nc(-c5ccccc5)nc(-c5ccccc5)n4)c3c2)cc1]
149
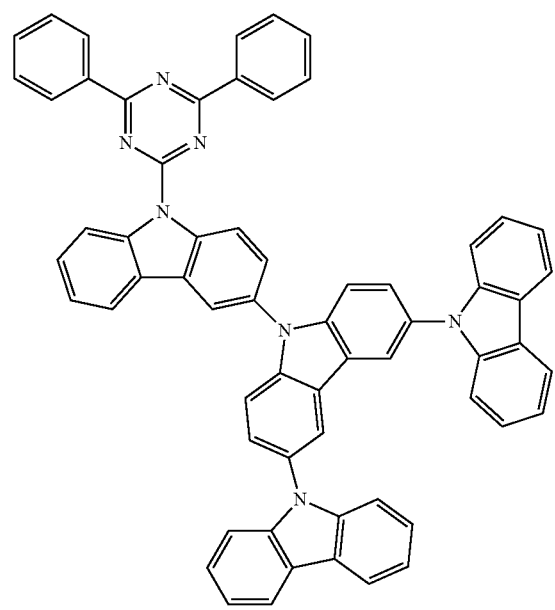 [SMILES: c1ccc(-c2nc(-c3ccccc3)nc(-n3c4ccccc4c4cc(-n5c6ccc(-n7c8ccccc8c8ccccc87)cc6c6cc(-n7c8ccccc8c8ccccc87)ccc65)ccc43)n2)cc1]
150

-continued
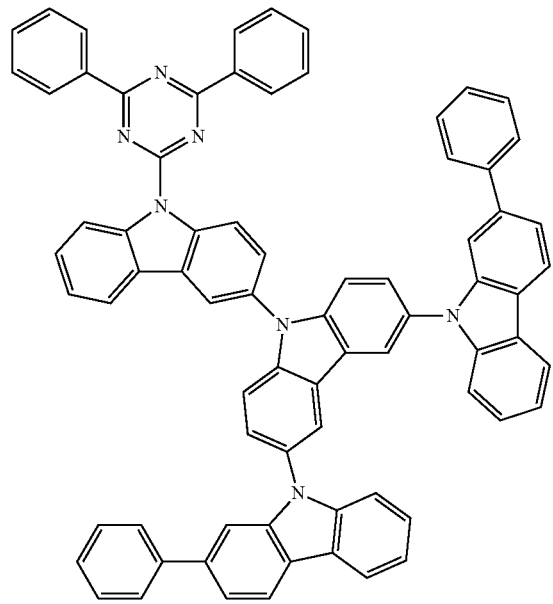 [SMILES: c1ccc(-c2ccc3c4ccccc4n(-c4ccc5c(c4)c4cc(-n6c7ccccc7c7ccc(-c8ccccc8)cc76)ccc4n5-c4ccc5c(c4)c4ccccc4n5-c4nc(-c5ccccc5)nc(-c5ccccc5)n4)c3c2)cc1]
151
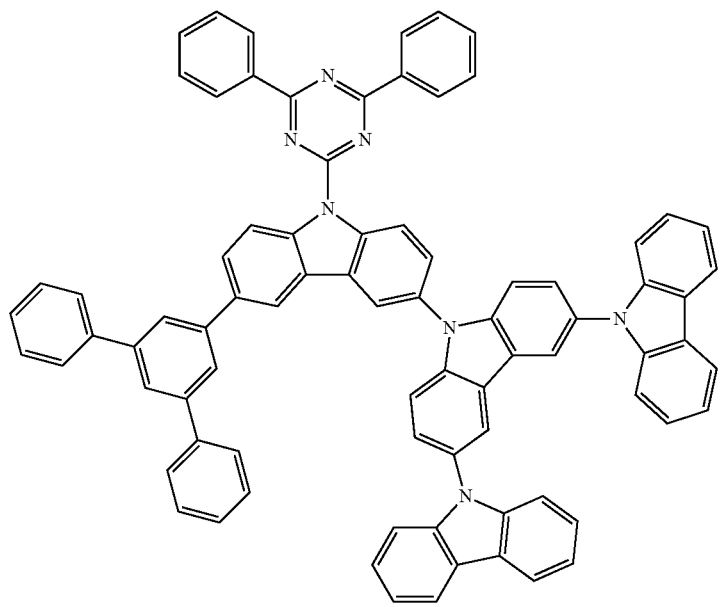 [SMILES: c1ccc(-c2cc(-c3ccccc3)cc(-c3ccc4c(c3)c3cc(-n5c6ccc(-n7c8ccccc8c8ccccc87)cc6c6cc(-n7c8ccccc8c8ccccc87)ccc65)ccc3n4-c3nc(-c4ccccc4)nc(-c4ccccc4)n3)c2)cc1]
152

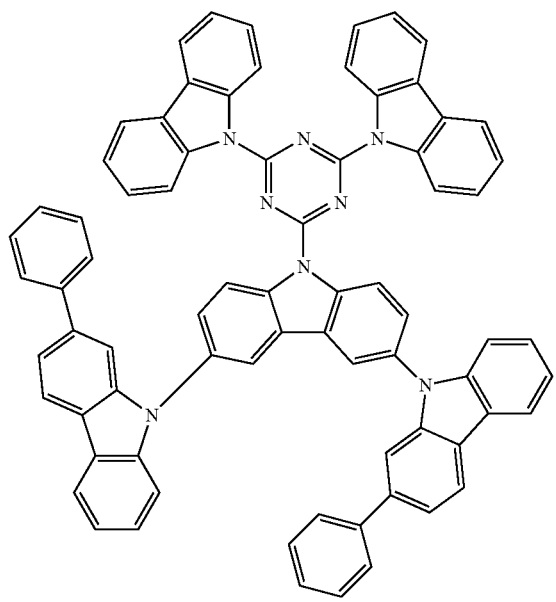 [SMILES: c1ccc(-c2ccc3c4ccccc4n(-c4ccc5c(c4)c4cc(-n6c7ccccc7c7ccc(-c8ccccc8)cc76)ccc4n5-c4nc(-n5c6ccccc6c6ccccc65)nc(-n5c6ccccc6c6ccccc65)n4)c3c2)cc1]
153
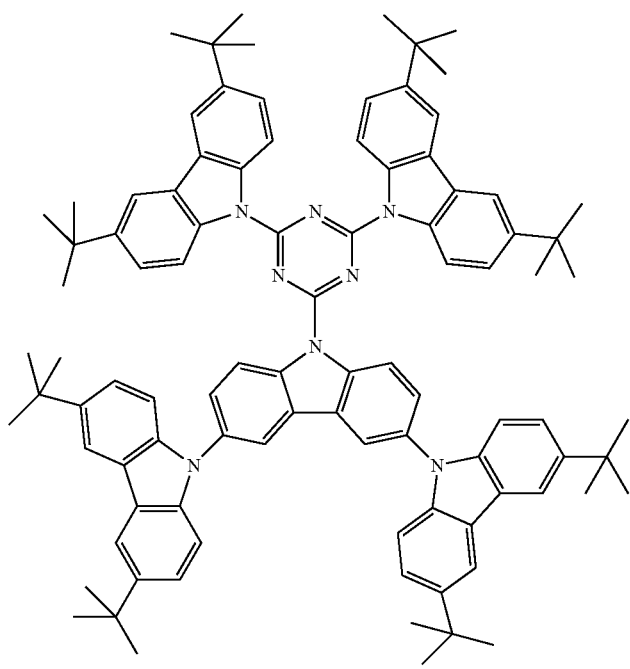 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1nc(-n2c3ccc(C(C)(C)C)cc3c3cc(C(C)(C)C)ccc32)nc(-n2c3ccc(C(C)(C)C)cc3c3cc(C(C)(C)C)ccc32)n1]
154

155
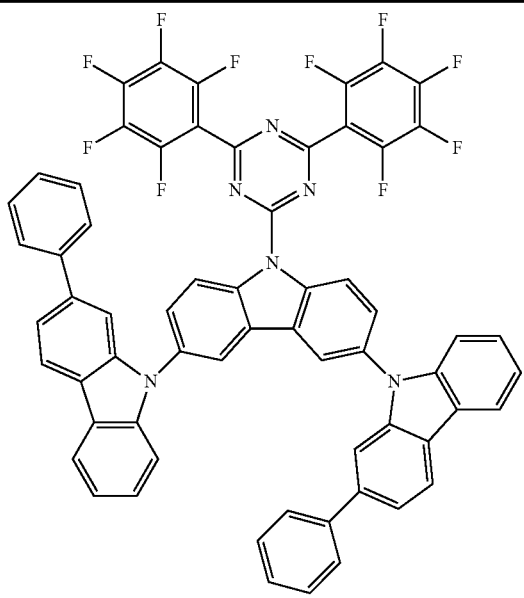
156
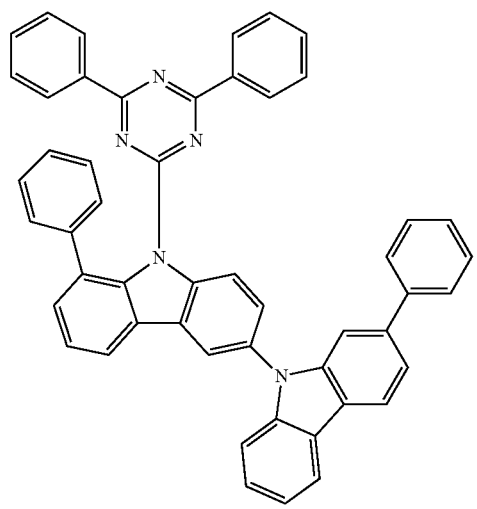 [SMILES: c1ccc(-c2ccc3c4ccccc4n(-c4ccc5c(c4)c4cccc(-c6ccccc6)c4n5-c4nc(-c5ccccc5)nc(-c5ccccc5)n4)c3c2)cc1]
157
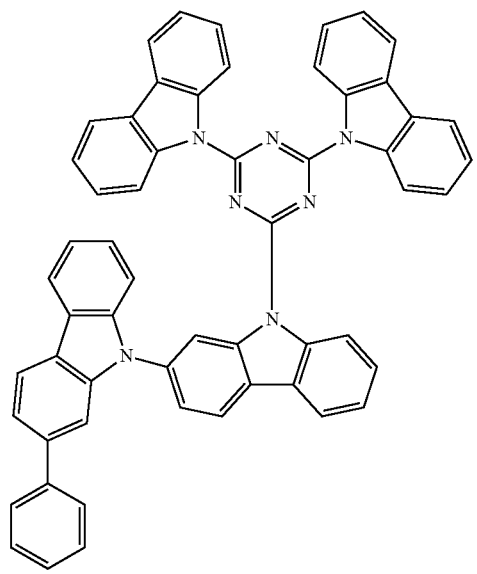 [SMILES: c1ccc(-c2ccc3c4ccccc4n(-c4ccc5c6ccccc6n(-c6nc(-n7c8ccccc8c8ccccc87)nc(-n7c8ccccc8c8ccccc87)n6)c5c4)c3c2)cc1]

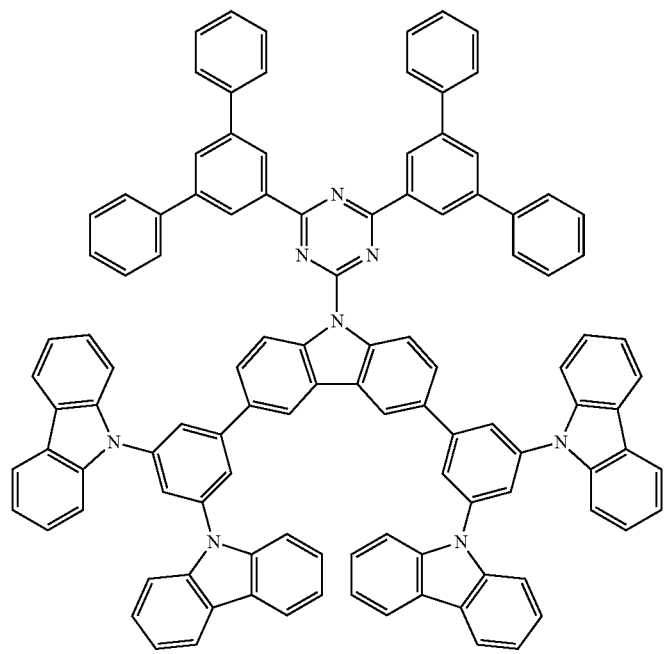 [SMILES: c1ccc(-c2cc(-c3ccccc3)cc(-c3nc(-c4cc(-c5ccccc5)cc(-c5ccccc5)c4)nc(-n4c5ccc(-c6cc(-n7c8ccccc8c8ccccc87)cc(-n7c8ccccc8c8ccccc87)c6)cc5c5cc(-c6cc(-n7c8ccccc8c8ccccc87)cc(-n7c8ccccc8c8ccccc87)c6)ccc54)n3)c2)cc1]
158
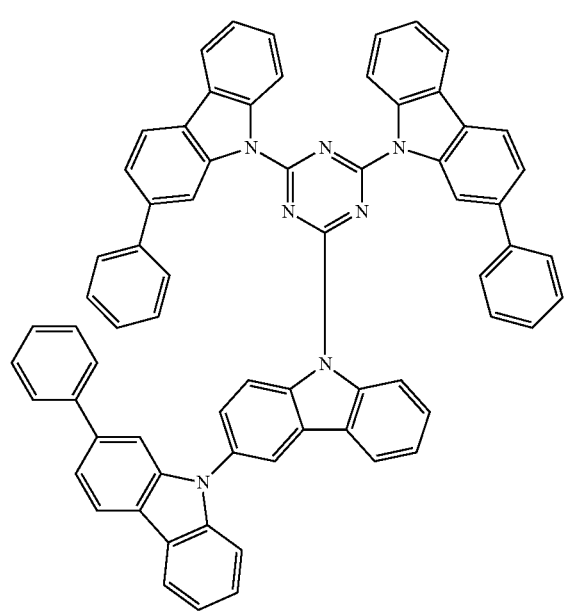 [SMILES: c1ccc(-c2ccc3c4ccccc4n(-c4ccc5c(c4)c4ccccc4n5-c4nc(-n5c6ccccc6c6ccc(-c7ccccc7)cc65)nc(-n5c6ccccc6c6ccc(-c7ccccc7)cc65)n4)c3c2)cc1]
159

-continued
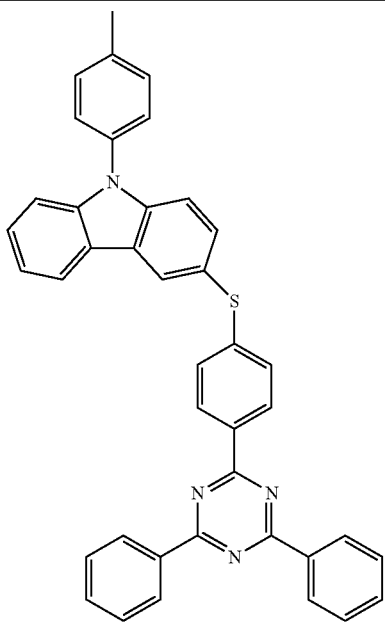
160
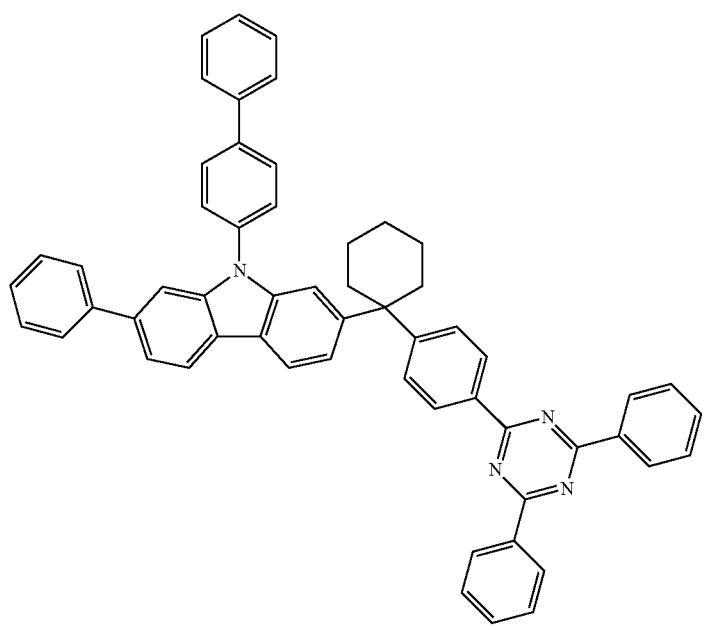 [SMILES: c1ccc(-c2ccc(-n3c4cc(-c5ccccc5)ccc4c4ccc(C5(c6ccc(-c7nc(-c8ccccc8)nc(-c8ccccc8)n7)cc6)CCCCC5)cc43)cc2)cc1]
161
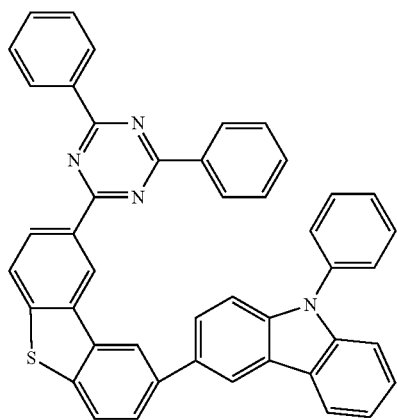 [SMILES: c1ccc(-c2nc(-c3ccccc3)nc(-c3ccc4sc5ccc(-c6ccc7c(c6)c6ccccc6n7-c6ccccc6)cc5c4c3)n2)cc1]
162

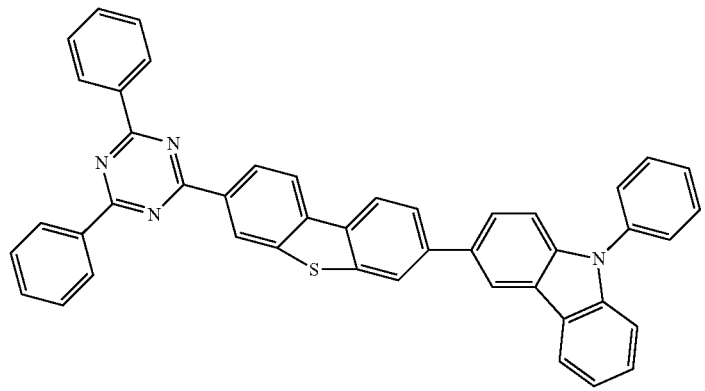 [SMILES: c1ccc(-c2nc(-c3ccccc3)nc(-c3ccc4c(c3)sc3cc(-c5ccc6c(c5)c5ccccc5n6-c5ccccc5)ccc34)n2)cc1]
163
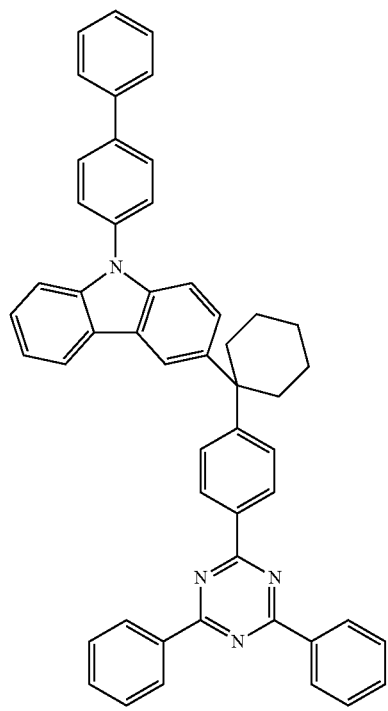 [SMILES: c1ccc(-c2ccc(-n3c4ccccc4c4cc(C5(c6ccc(-c7nc(-c8ccccc8)nc(-c8ccccc8)n7)cc6)CCCCC5)ccc43)cc2)cc1]
164
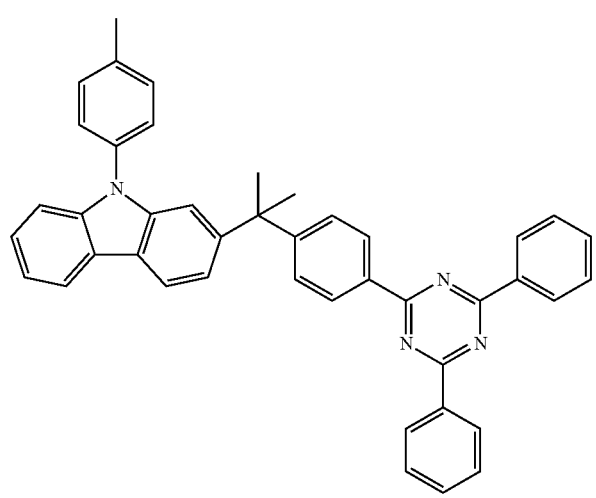 [SMILES: Cc1ccc(-n2c3ccccc3c3ccc(C(C)(C)c4ccc(-c5nc(-c6ccccc6)nc(-c6ccccc6)n5)cc4)cc32)cc1]
165

-continued
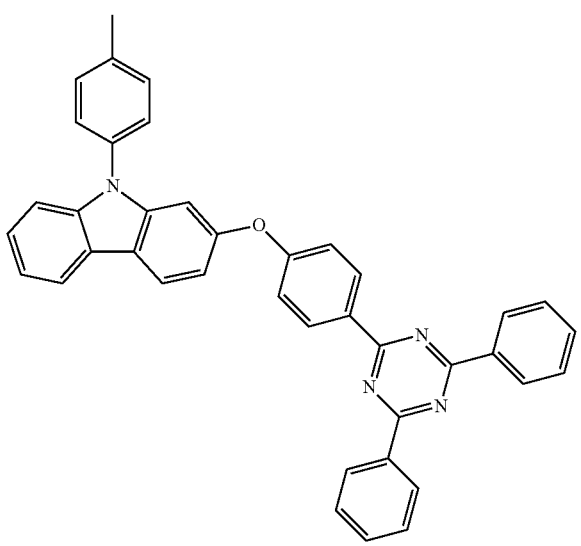 [SMILES: Cc1ccc(-n2c3ccccc3c3ccc(Oc4ccc(-c5nc(-c6ccccc6)nc(-c6ccccc6)n5)cc4)cc32)cc1]
166
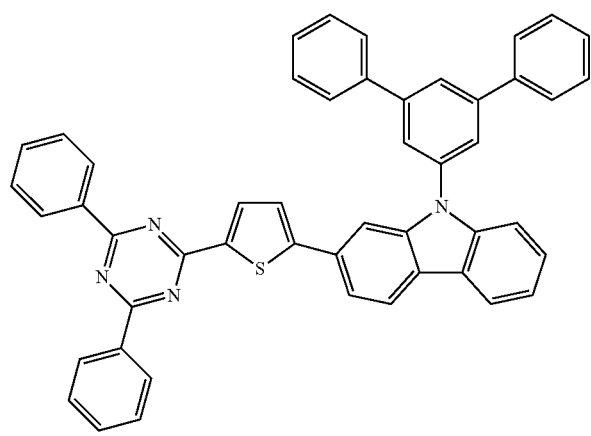 [SMILES: c1ccc(-c2cc(-c3ccccc3)cc(-n3c4ccccc4c4ccc(-c5ccc(-c6nc(-c7ccccc7)nc(-c7ccccc7)n6)s5)cc43)c2)cc1]
167
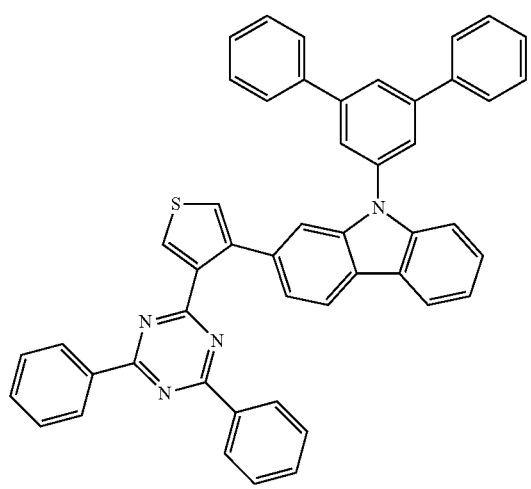 [SMILES: c1ccc(-c2cc(-c3ccccc3)cc(-n3c4ccccc4c4ccc(-c5cscc5-c5nc(-c6ccccc6)nc(-c6ccccc6)n5)cc43)c2)cc1]
168

169
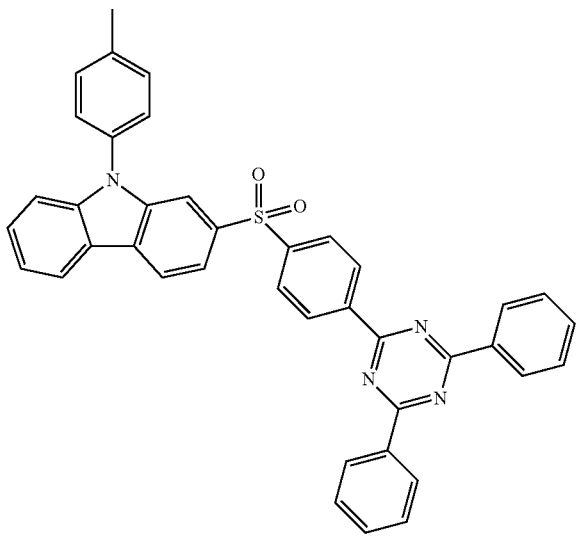 [SMILES: Cc1ccc(-n2c3ccccc3c3ccc(S(=O)(=O)c4ccc(-c5nc(-c6ccccc6)nc(-c6ccccc6)n5)cc4)cc32)cc1]
170
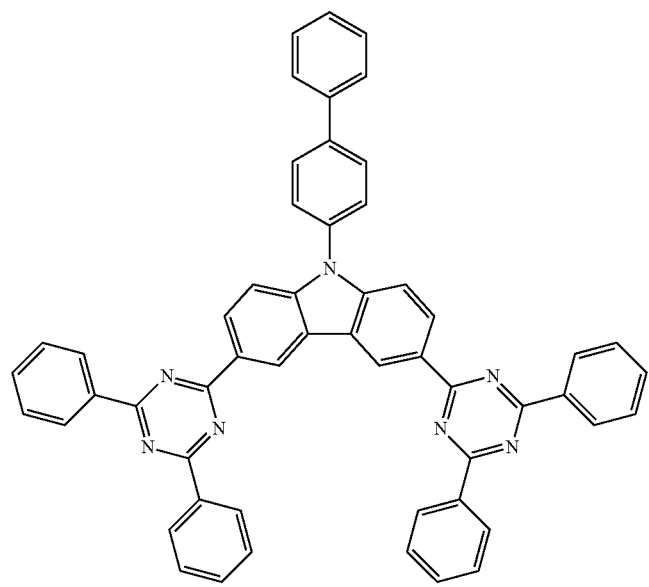 [SMILES: c1ccc(-c2ccc(-n3c4ccc(-c5nc(-c6ccccc6)nc(-c6ccccc6)n5)cc4c4cc(-c5nc(-c6ccccc6)nc(-c6ccccc6)n5)ccc43)cc2)cc1]
171
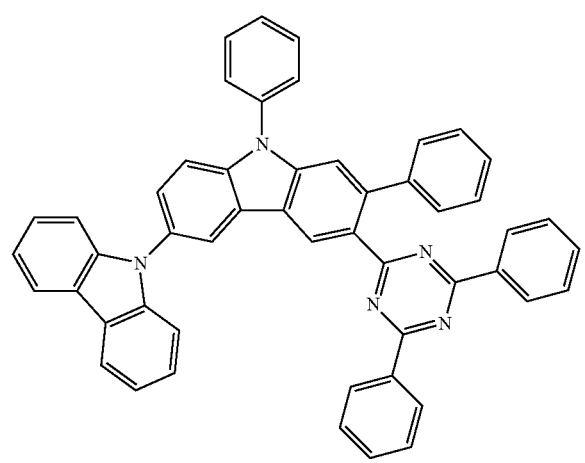 [SMILES: c1ccc(-c2nc(-c3ccccc3)nc(-c3cc4c5cc(-n6c7ccccc7c7ccccc76)ccc5n(-c5ccccc5)c4cc3-c3ccccc3)n2)cc1]

172
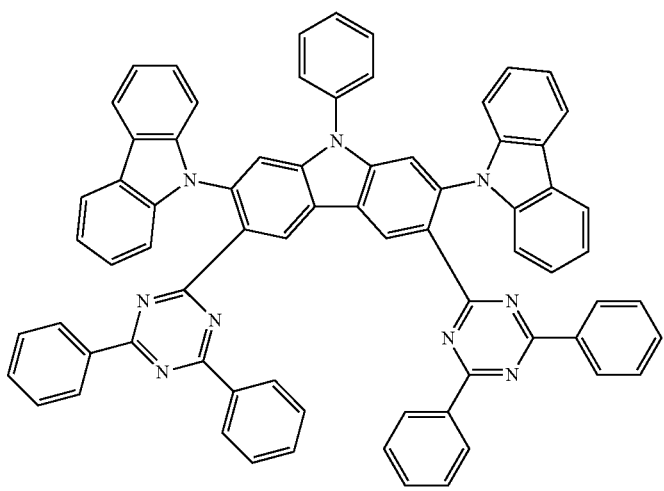 [SMILES: c1ccc(-c2nc(-c3ccccc3)nc(-c3cc4c5cc(-c6nc(-c7ccccc7)nc(-c7ccccc7)n6)c(-n6c7ccccc7c7ccccc76)cc5n(-c5ccccc5)c4cc3-n3c4ccccc4c4ccccc43)n2)cc1]
173
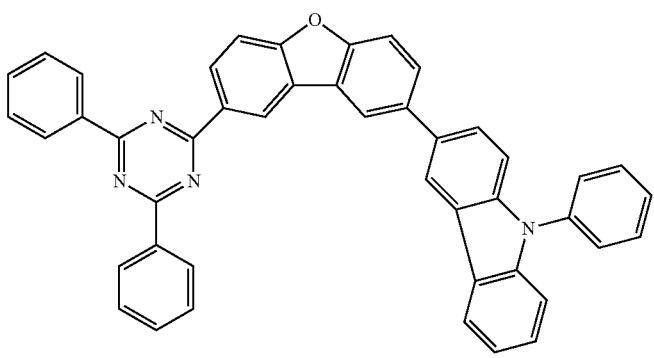
174
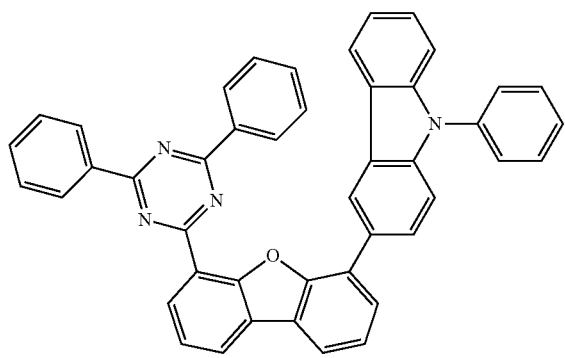 [SMILES: c1ccc(-c2nc(-c3ccccc3)nc(-c3cccc4c3oc3c(-c5ccc6c(c5)c5ccccc5n6-c5ccccc5)cccc34)n2)cc1]
175
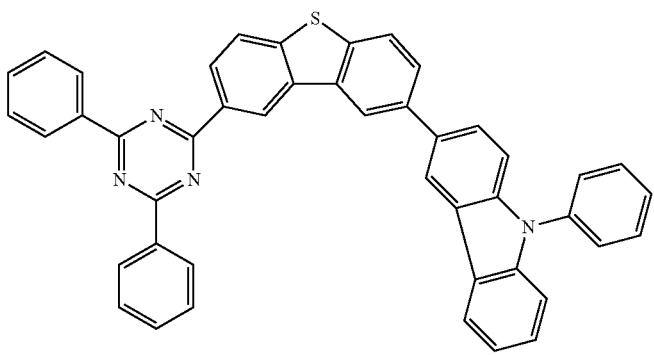 [SMILES: c1ccc(-c2nc(-c3ccccc3)nc(-c3ccc4sc5ccc(-c6ccc7c(c6)c6ccccc6n7-c6ccccc6)cc5c4c3)n2)cc1]

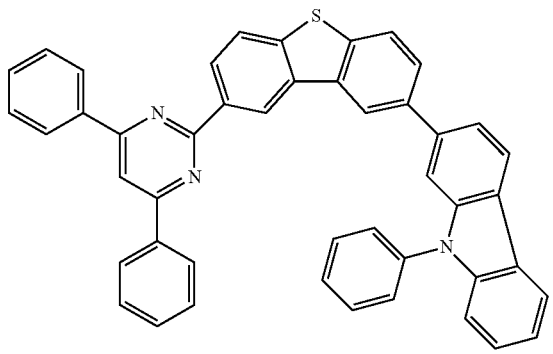 [SMILES: c1ccc(-c2cc(-c3ccccc3)nc(-c3ccc4sc5ccc(-c6ccc7c8ccccc8n(-c8ccccc8)c7c6)cc5c4c3)n2)cc1]
176
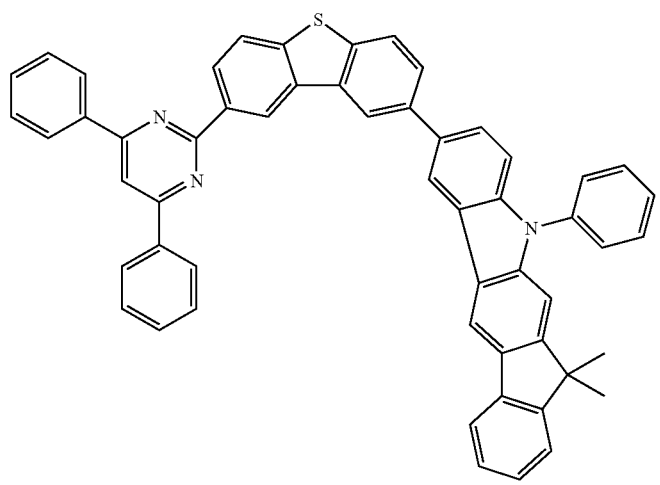 [SMILES: CC1(C)c2ccccc2-c2cc3c4cc(-c5ccc6sc7ccc(-c8nc(-c9ccccc9)nc(-c9ccccc9)n8)cc7c6c5)ccc4n(-c4ccccc4)c3cc21]
177
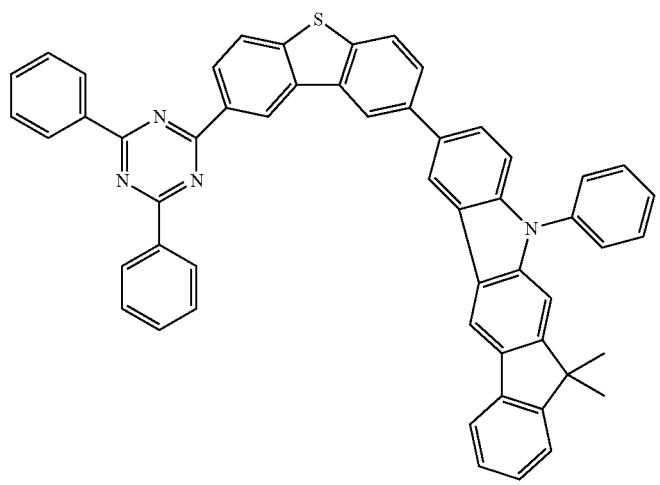
178
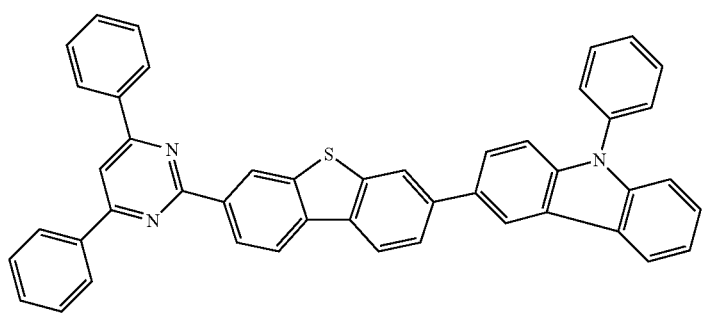 [SMILES: c1ccc(-c2cc(-c3ccccc3)nc(-c3ccc4c(c3)sc3cc(-c5ccc6c(c5)c5ccccc5n6-c5ccccc5)ccc34)n2)cc1]
179

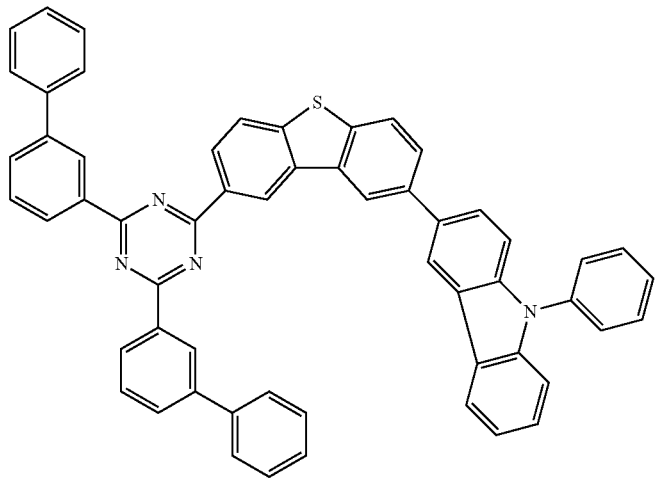 [SMILES: c1ccc(-c2cccc(-c3nc(-c4cccc(-c5ccccc5)c4)nc(-c4ccc5sc6ccc(-c7ccc8c(c7)c7ccccc7n8-c7ccccc7)cc6c5c4)n3)c2)cc1]
180
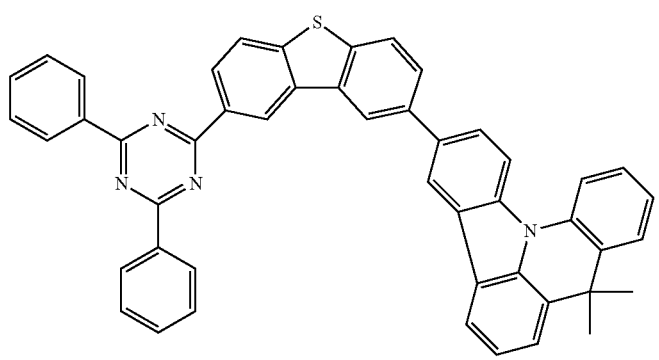 [SMILES: CC1(C)c2ccccc2-n2c3ccc(-c4ccc5sc6ccc(-c7nc(-c8ccccc8)nc(-c8ccccc8)n7)cc6c5c4)cc3c3cccc1c32]
181
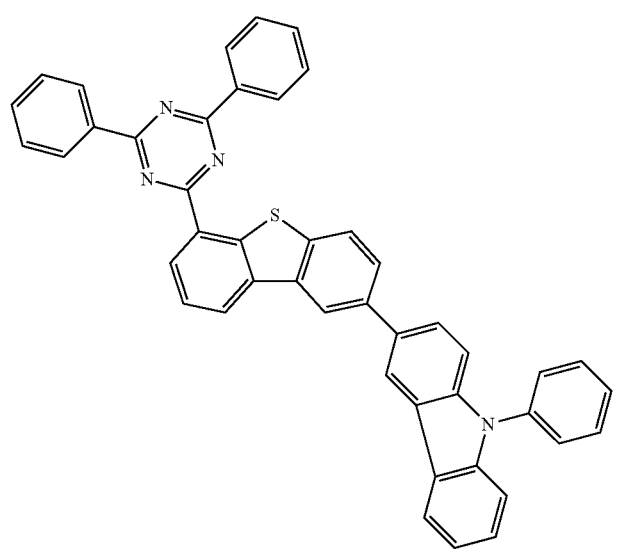 [SMILES: c1ccc(-c2nc(-c3ccccc3)nc(-c3cccc4c3sc3ccc(-c5ccc6c(c5)c5ccccc5n6-c5ccccc5)cc34)n2)cc1]
182

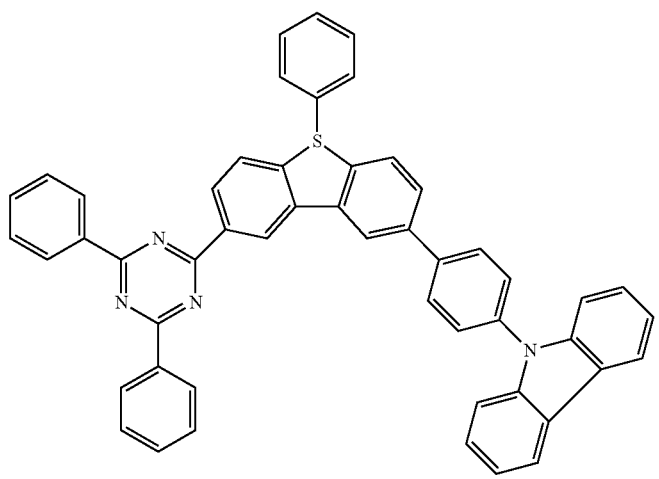
183
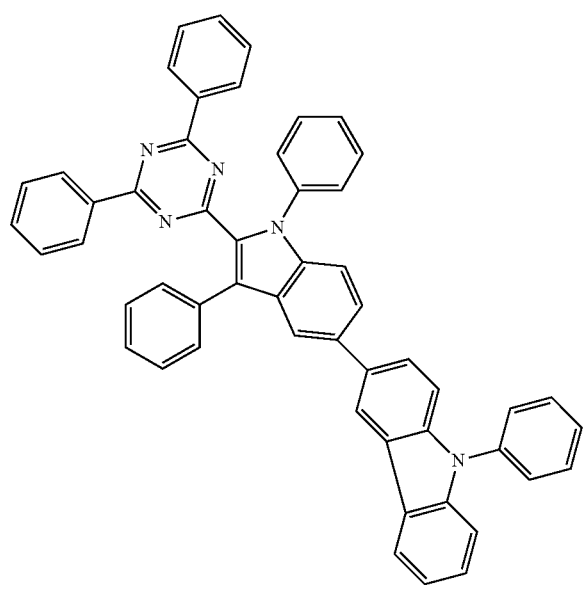 [SMILES: c1ccc(-c2nc(-c3ccccc3)nc(-c3c(-c4ccccc4)c4cc(-c5ccc6c(c5)c5ccccc5n6-c5ccccc5)ccc4n3-c3ccccc3)n2)cc1]
184
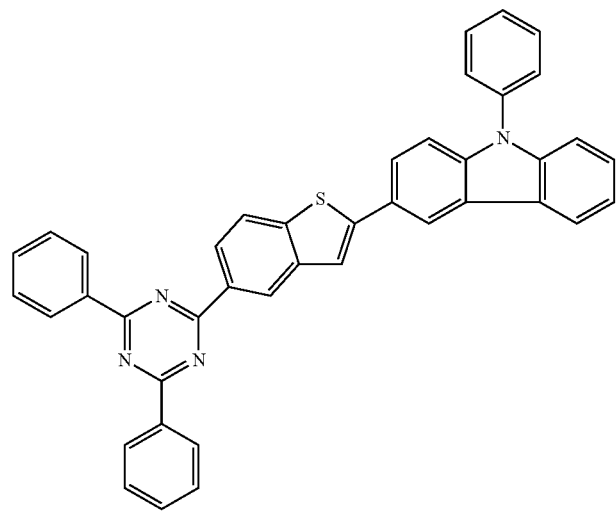 [SMILES: c1ccc(-c2nc(-c3ccccc3)nc(-c3ccc4sc(-c5ccc6c(c5)c5ccccc5n6-c5ccccc5)cc4c3)n2)cc1]
185

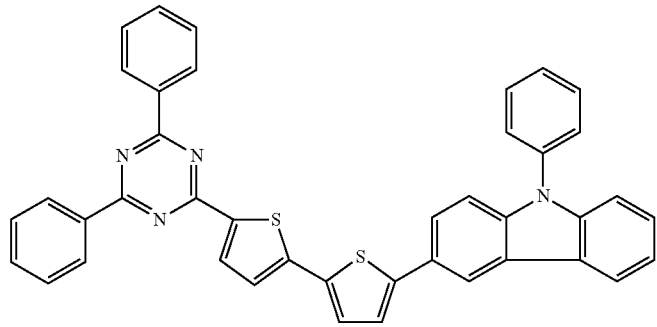 [SMILES: c1ccc(-c2nc(-c3ccccc3)nc(-c3ccc(-c4ccc(-c5ccc6c(c5)c5ccccc5n6-c5ccccc5)s4)s3)n2)cc1]
186
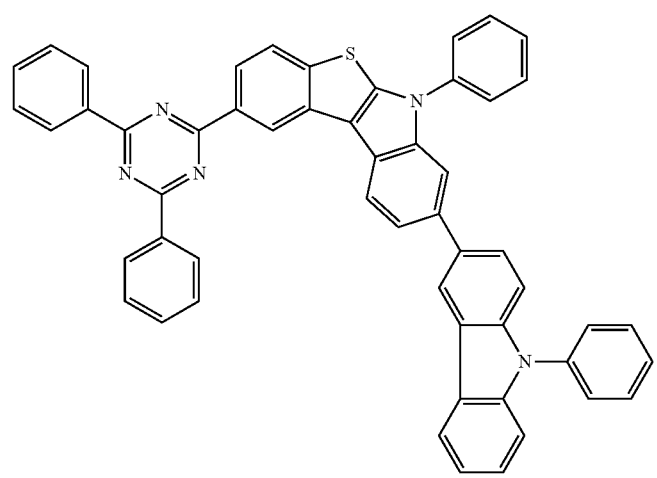 [SMILES: c1ccc(-c2nc(-c3ccccc3)nc(-c3ccc4sc5c(c4c3)c3ccc(-c4ccc6c(c4)c4ccccc4n6-c4ccccc4)cc3n5-c3ccccc3)n2)cc1]
187
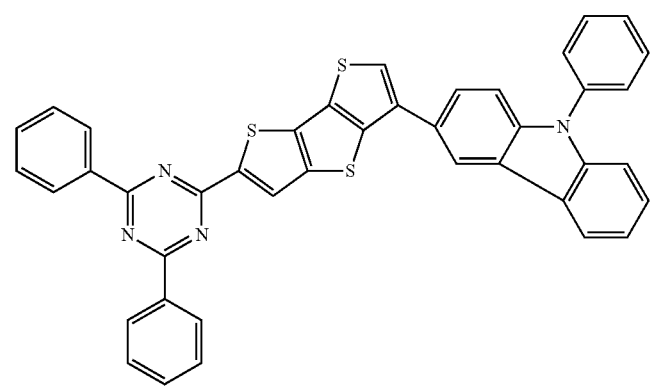 [SMILES: c1ccc(-c2nc(-c3ccccc3)nc(-c3cc4sc5c(-c6ccc7c(c6)c6ccccc6n7-c6ccccc6)csc5c4s3)n2)cc1]
188

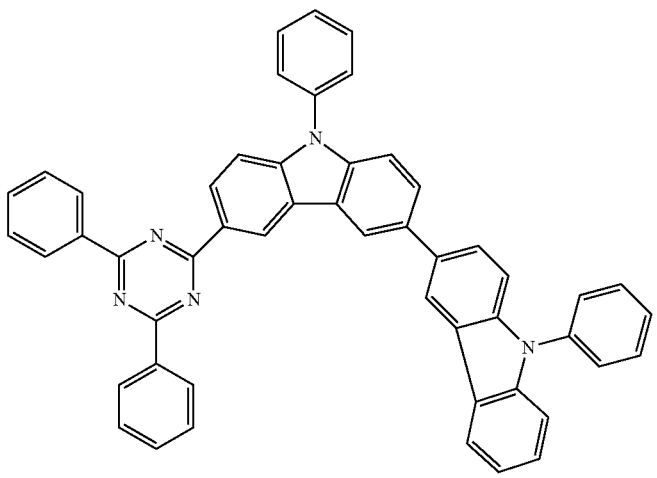 [SMILES: c1ccc(-c2nc(-c3ccccc3)nc(-c3ccc4c(c3)c3cc(-c5ccc6c(c5)c5ccccc5n6-c5ccccc5)ccc3n4-c3ccccc3)n2)cc1]
189
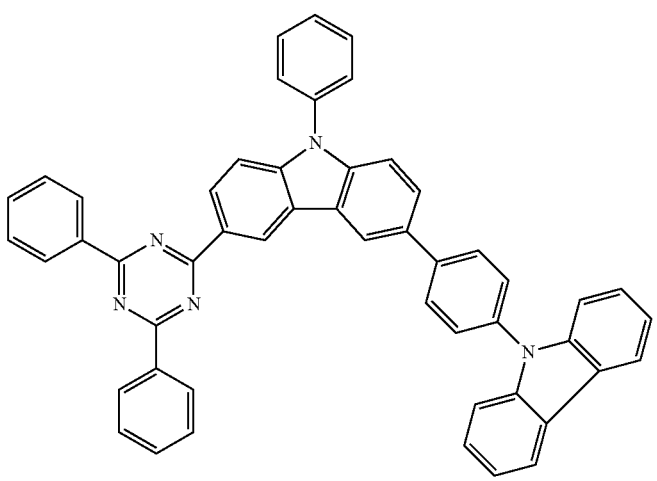
190
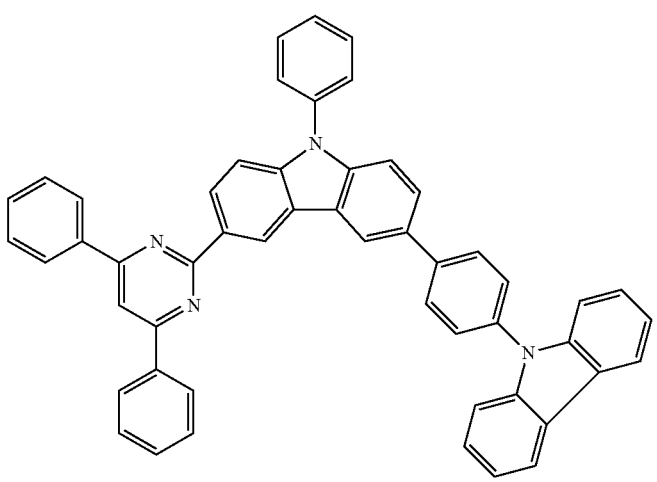
191

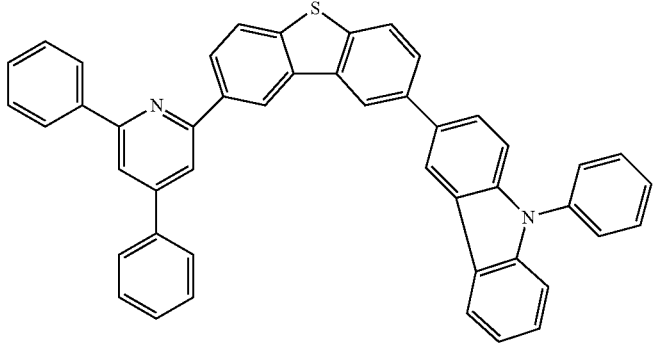
192
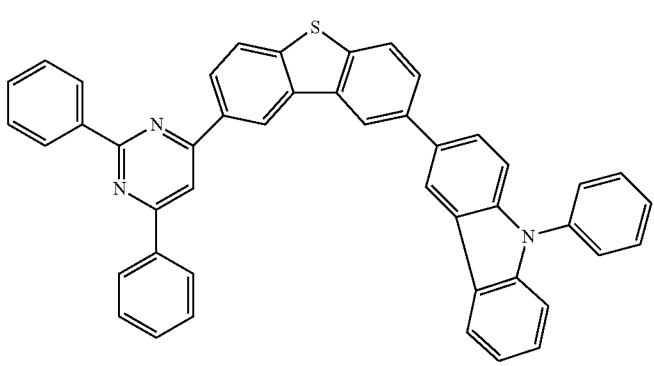 [SMILES: c1ccc(-c2cc(-c3ccc4sc5ccc(-c6ccc7c(c6)c6ccccc6n7-c6ccccc6)cc5c4c3)nc(-c3ccccc3)n2)cc1]
193
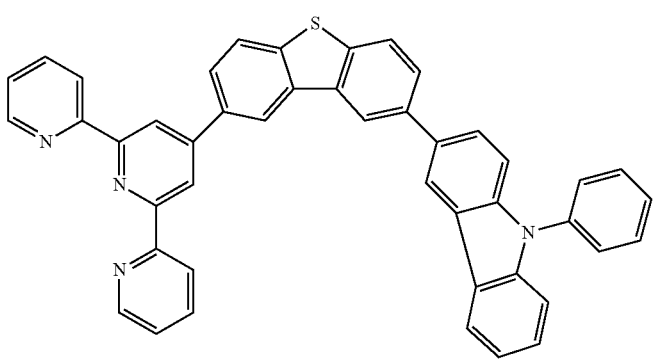 [SMILES: c1ccc(-n2c3ccccc3c3cc(-c4ccc5sc6ccc(-c7cc(-c8ccccn8)nc(-c8ccccn8)c7)cc6c5c4)ccc32)cc1]
194
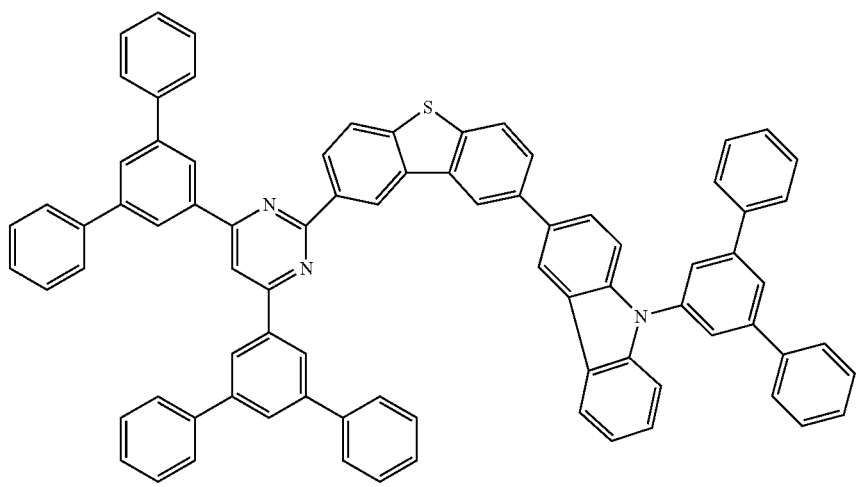 [SMILES: c1ccc(-c2cc(-c3ccccc3)cc(-c3cc(-c4cc(-c5ccccc5)cc(-c5ccccc5)c4)nc(-c4ccc5sc6ccc(-c7ccc8c(c7)c7ccccc7n8-c7cc(-c8ccccc8)cc(-c8ccccc8)c7)cc6c5c4)n3)c2)cc1]
195

196
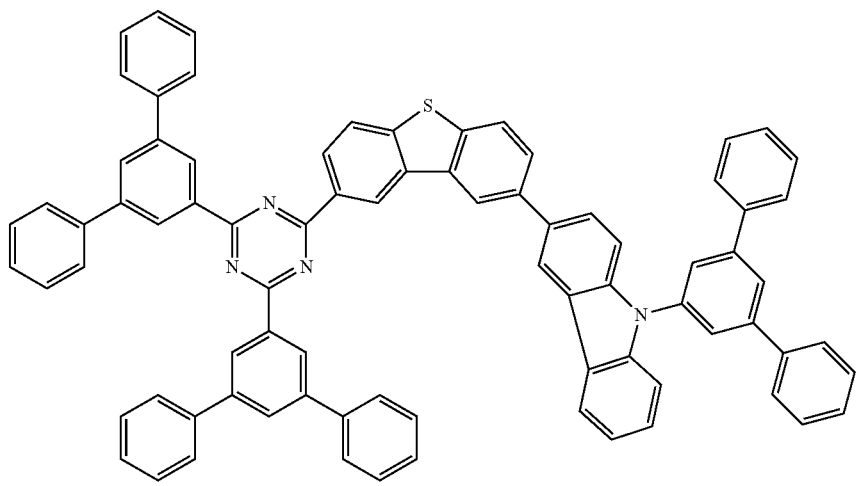 [SMILES: c1ccc(-c2cc(-c3ccccc3)cc(-c3nc(-c4cc(-c5ccccc5)cc(-c5ccccc5)c4)nc(-c4ccc5sc6ccc(-c7ccc8c(c7)c7ccccc7n8-c7cc(-c8ccccc8)cc(-c8ccccc8)c7)cc6c5c4)n3)c2)cc1]
197
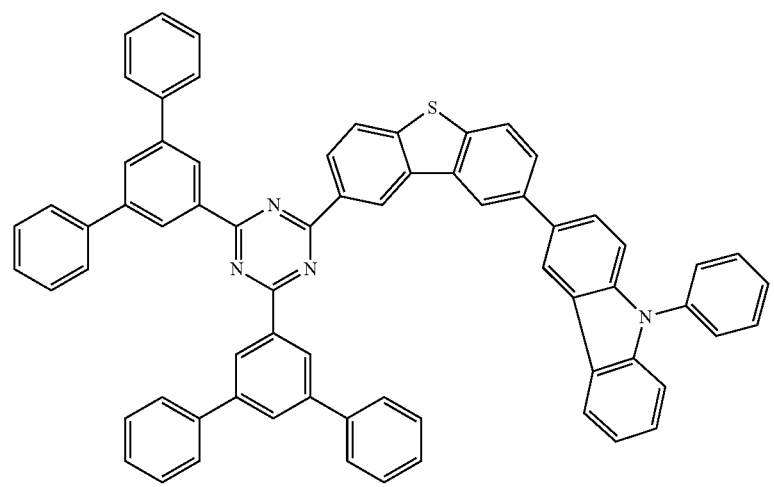 [SMILES: c1ccc(-c2cc(-c3ccccc3)cc(-c3nc(-c4cc(-c5ccccc5)cc(-c5ccccc5)c4)nc(-c4ccc5sc6ccc(-c7ccc8c(c7)c7ccccc7n8-c7ccccc7)cc6c5c4)n3)c2)cc1]
198
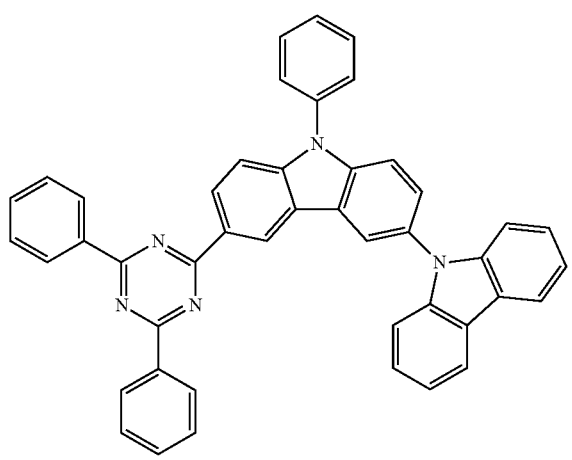 [SMILES: c1ccc(-c2nc(-c3ccccc3)nc(-c3ccc4c(c3)c3cc(-n5c6ccccc6c6ccccc65)ccc3n4-c3ccccc3)n2)cc1]

-continued
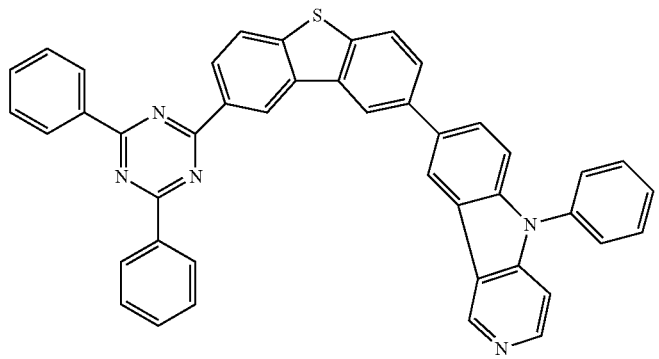 [SMILES: c1ccc(-c2nc(-c3ccccc3)nc(-c3ccc4sc5ccc(-c6ccc7c(c6)c6cnccc6n7-c6ccccc6)cc5c4c3)n2)cc1]
199
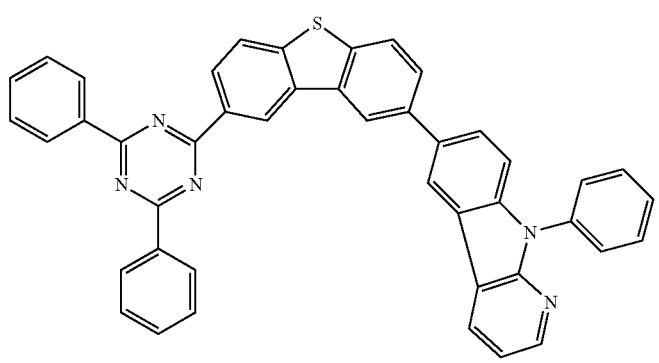 [SMILES: c1ccc(-c2nc(-c3ccccc3)nc(-c3ccc4sc5ccc(-c6ccc7c(c6)c6cccnc6n7-c6ccccc6)cc5c4c3)n2)cc1]
200
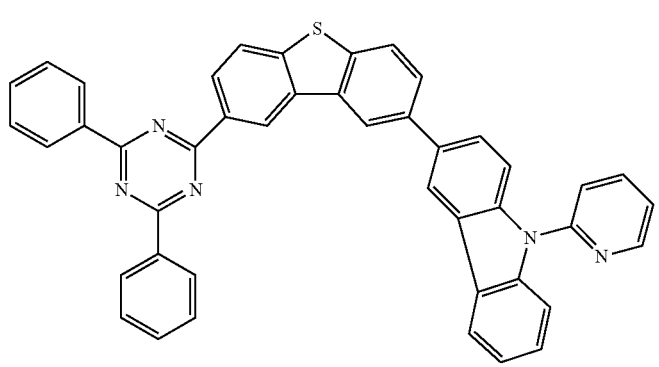 [SMILES: c1ccc(-c2nc(-c3ccccc3)nc(-c3ccc4sc5ccc(-c6ccc7c(c6)c6ccccc6n7-c6ccccn6)cc5c4c3)n2)cc1]
201
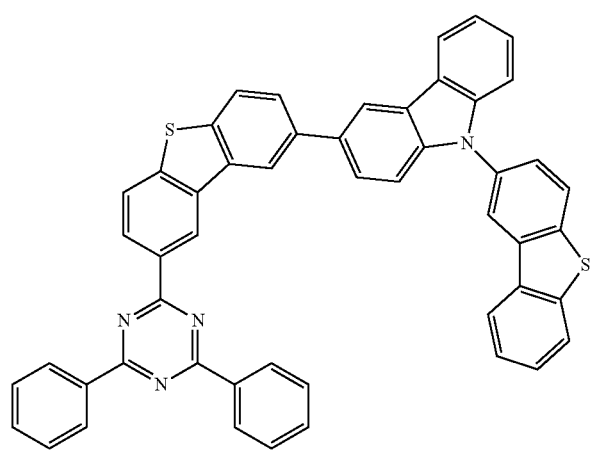 [SMILES: c1ccc(-c2nc(-c3ccccc3)nc(-c3ccc4sc5ccc(-c6ccc7c(c6)c6ccccc6n7-c6ccc7sc8ccccc8c7c6)cc5c4c3)n2)cc1]
202

203
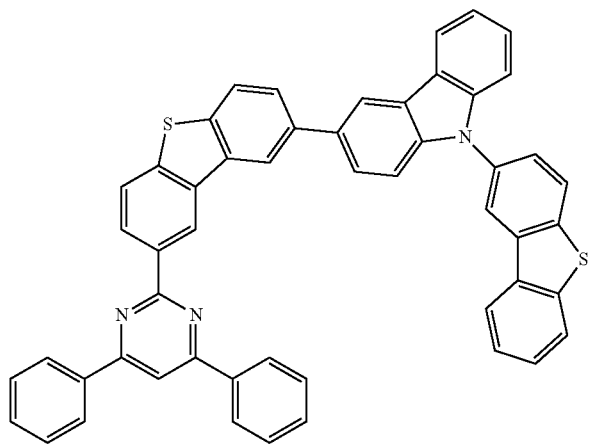 [SMILES: c1ccc(-c2cc(-c3ccccc3)nc(-c3ccc4sc5ccc(-c6ccc7c(c6)c6ccccc6n7-c6ccc7sc8ccccc8c7c6)cc5c4c3)n2)cc1]
204
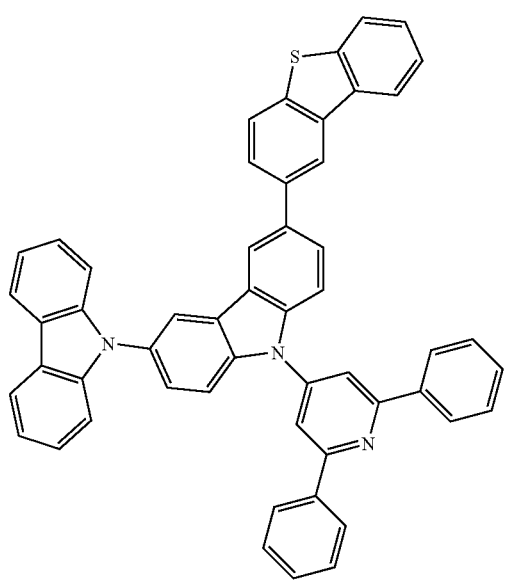 [SMILES: c1ccc(-c2cc(-n3c4ccc(-c5ccc6sc7ccccc7c6c5)cc4c4cc(-n5c6ccccc6c6ccccc65)ccc43)cc(-c3ccccc3)n2)cc1]
205
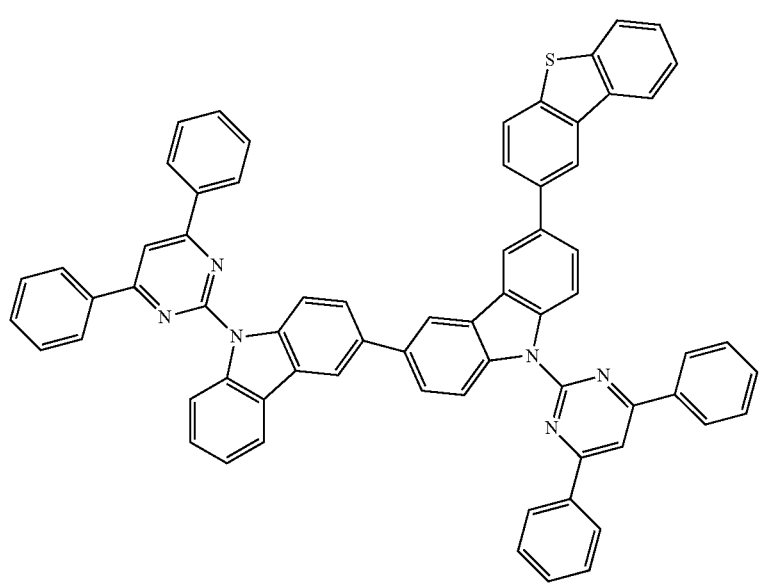 [SMILES: c1ccc(-c2cc(-c3ccccc3)nc(-n3c4ccccc4c4cc(-c5ccc6c(c5)c5cc(-c7ccc8sc9ccccc9c8c7)ccc5n6-c5nc(-c6ccccc6)cc(-c6ccccc6)n5)ccc43)n2)cc1]

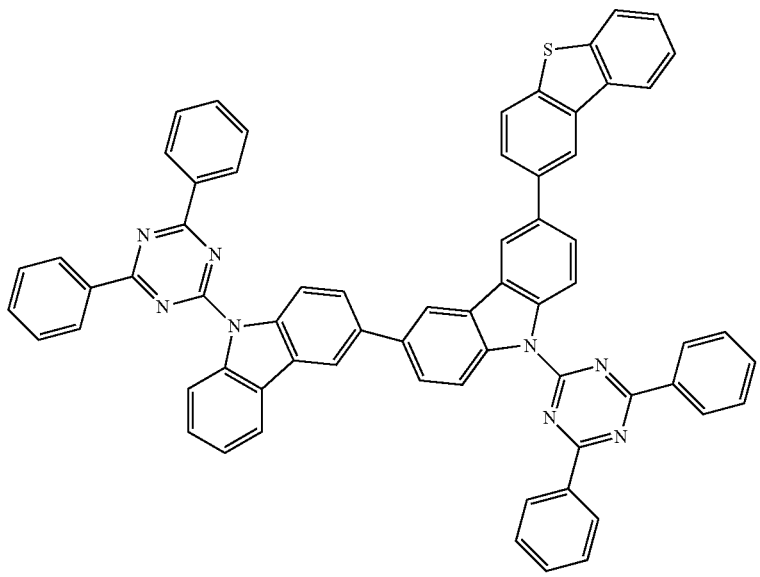 [SMILES: c1ccc(-c2nc(-c3ccccc3)nc(-n3c4ccccc4c4cc(-c5ccc6c(c5)c5cc(-c7ccc8sc9ccccc9c8c7)ccc5n6-c5nc(-c6ccccc6)nc(-c6ccccc6)n5)ccc43)n2)cc1]

206

The compounds according to the invention can be prepared by synthesis steps known to the person skilled in the art, such as, for example, halogenation, preferably bromination, and a subsequent organometallic coupling reaction, for example Suzuki coupling, Heck coupling or Hartwig-Buchwald coupling.

Examples of syntheses of compounds according to the invention are shown in the following two schemes:

Scheme 1

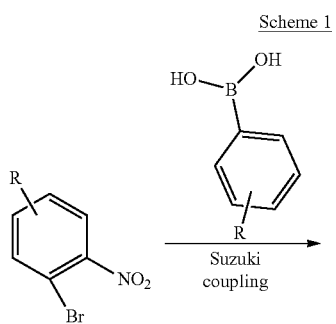

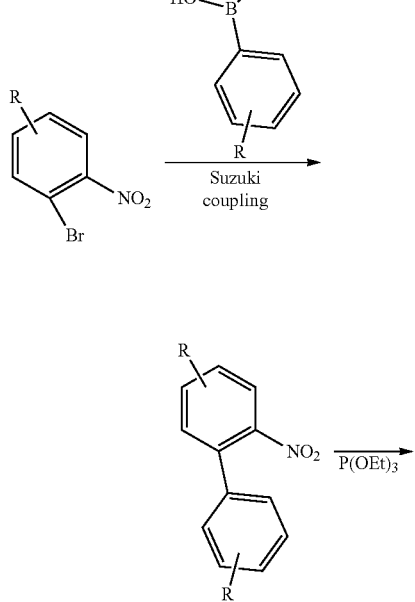

-continued

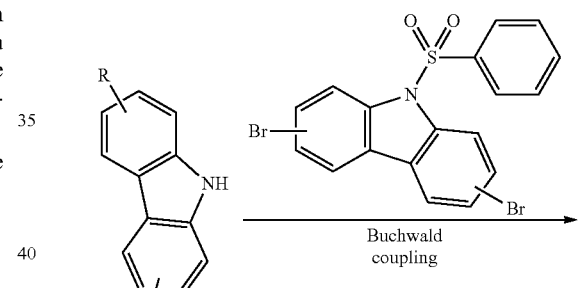

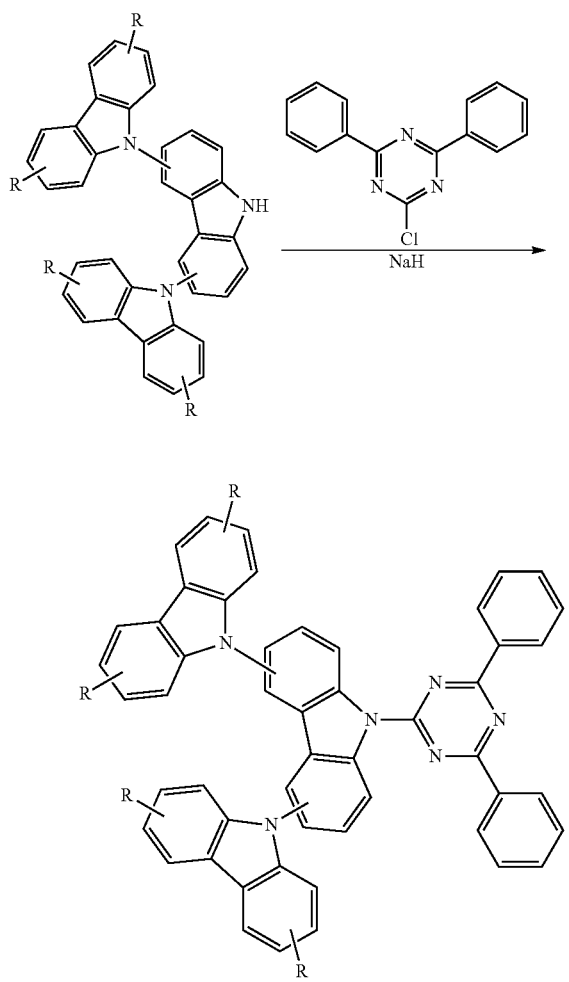

R = organic radical

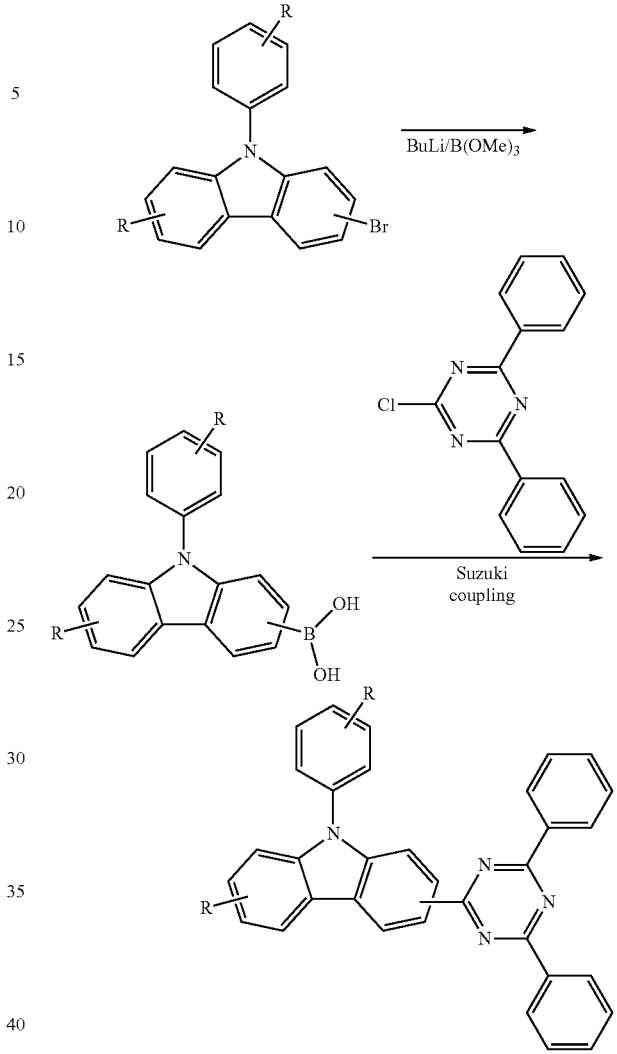

R = organic radical

The illustrative synthesis shown starts from substituted or unsubstituted carbazole derivatives (preparation, for example, in accordance with *Synthesis* 2005, 10, 1619-1624), which are reacted with an N-phenylsulfonyl-protected carbazole derivative which carries one or more halogen substituents in a Buchwald coupling (*Org. Biomol. Chem.* 2004, 2, 1476-1483). The phenylsulfonyl group is cleaved off under the action of KOH, and the free aromatic amino function of the carbazole can be reacted with a tri-derivative in a nucleophilic aromatic substitution reaction. In this way, other carbazole derivatives having substitution patterns not shown here can also be synthesised.

Scheme 2

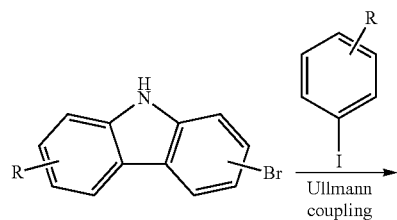

The synthesis shown starts from a bromocarbazole derivative, which is reacted with an iodoaryl compound (here by way of example a phenyl iodide derivative) in an Ullmann coupling. The bromine functionality is subsequently converted into a boronic acid functionality, enabling a Suzuki coupling to a chlorodiphenyltriazine to take place. In this way, carbazole derivatives which are substituted by aryl or heteroaryl groups on one or both aromatic rings of the carbazole group can be prepared. Carbazole derivatives having different substitution patterns not shown here can also be prepared in accordance with the scheme shown.

The person skilled in the art will be able, without being inventive, to modify the synthesis schemes shown above and use the processes shown for the synthesis of related structural classes according to the invention.

The invention thus furthermore relates to a process for the preparation of the compounds of the formula (I) or (II), comprising the following steps:
a) synthesis of a substituted carbazole derivative, optionally with introduction of halogen substituents,
b) coupling of the nitrogen atom of the carbazole derivative to an aryl or heteroaryl group in an organometallic coupling reaction or a nucleophilic aromatic substitution reaction, c) organometallic coupling reaction for the introduction of aryl or heteroaryl groups on one or both aromatic six-membered rings of the carbazole group, where steps b) and c) can also take place in the opposite sequence, and where, in addition, the introduction or removal of protecting groups may also be necessary.

The compounds according to the invention can furthermore be used for the preparation of polymers, oligomers or dendrimers. This is usually carried out via polymerisable functional groups. In particular, compounds which are substituted by reactive leaving groups, such as bromine, iodine, boronic acid, boronic acid ester, tosylate or triflate, are suitable for this purpose. These can also be used as comonomers for the generation of corresponding conjugated, partially conjugated or non-conjugated polymers, oligomers or also as the core of dendrimers. The polymerisation here is preferably carried out via the halogen functionality or the boronic acid functionality. The polymers may also have crosslinkable groups or be crosslinked via crosslinkable groups. Particularly suitable crosslinkable groups are those which are then crosslinked in the layer of the electronic device.

The invention thus furthermore relates to polymers, oligomers or dendrimers comprising one or more compounds of one of the formulae (I) and (II), where a bond to the polymer, oligomer or dendrimer occurs instead of one or more radicals or H atoms of the compounds defined above. The polymers, oligomers or dendrimers here may be conjugated, partially conjugated or non-conjugated. Likewise encompassed are mixtures (blends) of the polymers, oligomers or dendrimers according to the invention with further polymers, oligomers or dendrimers.

An oligomer in the sense of this invention is taken to mean a compound which has about three to nine recurring units. A polymer in the sense of this invention is taken to mean a compound which has ten or more recurring units.

These oligomers or polymers may comprise further recurring units. These further recurring units are preferably selected from the group consisting of fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or DE 102005037734) and/or metal complexes, in particular ortho-metallated iridium and platinum complexes. It should expressly be pointed out here that the polymers may also have a plurality of different recurring units selected from one or more of the groups mentioned above.

For application from solution, solutions or formulations of the compounds according to the invention are necessary.

The invention therefore furthermore relates to formulations comprising at least one compound of the formula (I) or (II) or at least one polymer, oligomer or dendrimer containing at least one unit of the formula (I) or (II) and at least one solvent, preferably an organic solvent.

The compounds of the formula (I) or (II) according to the invention are suitable for use in electronic devices, in particular in organic electroluminescent devices (OLEDs). Depending on the substitution, the compounds are employed in different functions and in different layers of the organic electroluminescent device.

The invention therefore furthermore relates to the use of the compounds according to the invention and the polymers, oligomers or dendrimers according to the invention in electronic devices, preferably organic electroluminescent devices.

In a preferred embodiment of the invention, the compounds of the formula (I) or (II) are employed as matrix material for phosphorescent dopants and/or as electron-transport material.

Compounds of one of the formulae (I) and (II) can also be employed in polymers, oligomers or dendrimers as electron-transporting unit and/or as matrix for phosphorescent emitters.

In a preferred embodiment of the invention, the compounds of the formula (I) or (II) are employed as matrix materials in an emitting layer. They are preferably employed here as matrix materials for one or more phosphorescent emitters.

The present invention therefore furthermore relates to mixtures comprising at least one phosphorescent emitter and at least one compound of one of the formulae (I) and (II).

The mixture of the compound according to the invention and the emitter which is employed in the emitting layer preferably comprises between 99 and 50% by vol., preferably between 98 and 50% by vol., particularly preferably between 97 and 60% by vol., in particular between 95 and 85% by vol., of the compound according to the invention, based on the mixture as a whole comprising emitter and matrix material. Correspondingly, the mixture comprises between 1 and 50% by vol., preferably between 2 and 50% by vol., particularly preferably between 3 and 40% by vol., in particular between 5 and 15% by vol., of the emitter, based on the mixture as a whole comprising emitter and matrix material.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as are used in accordance with the prior art for phosphorescent OLEDs and as are known to the person skilled in the art in the area of organic electroluminescence are suitable. The person skilled in the art will also be able to use further phosphorescent complexes without an inventive step.

Particularly suitable phosphorescent dopants are furthermore the compounds shown in the following table.

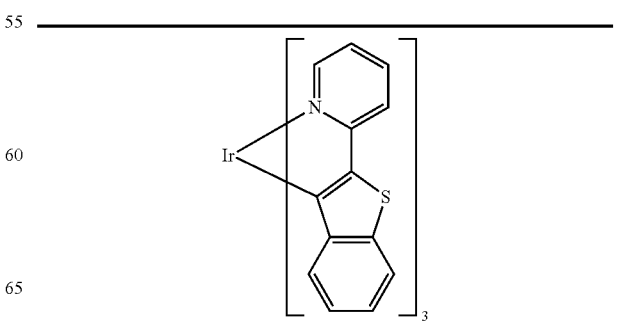

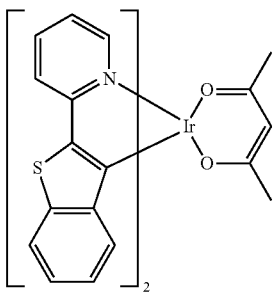
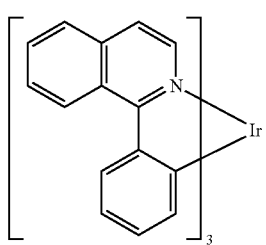
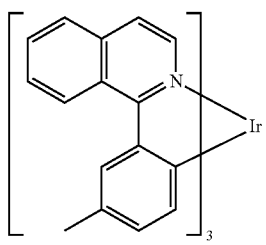
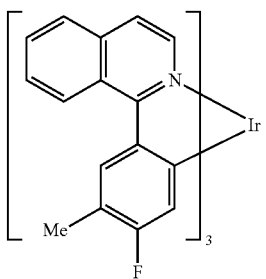
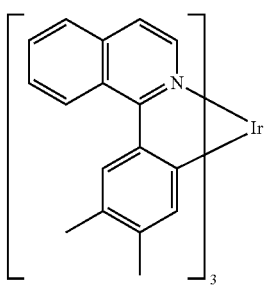
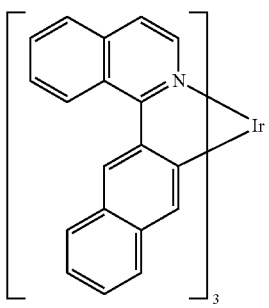
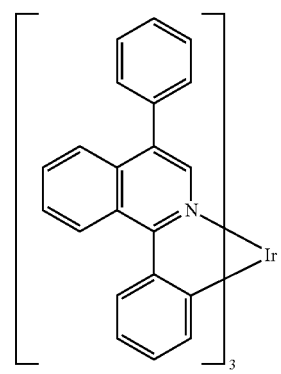
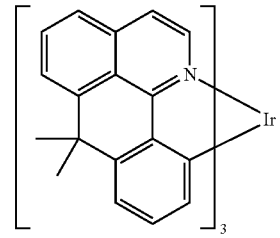
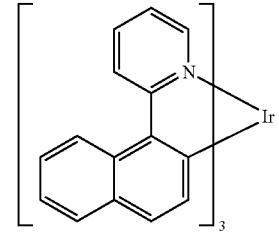
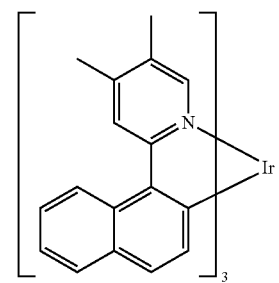

177
-continued
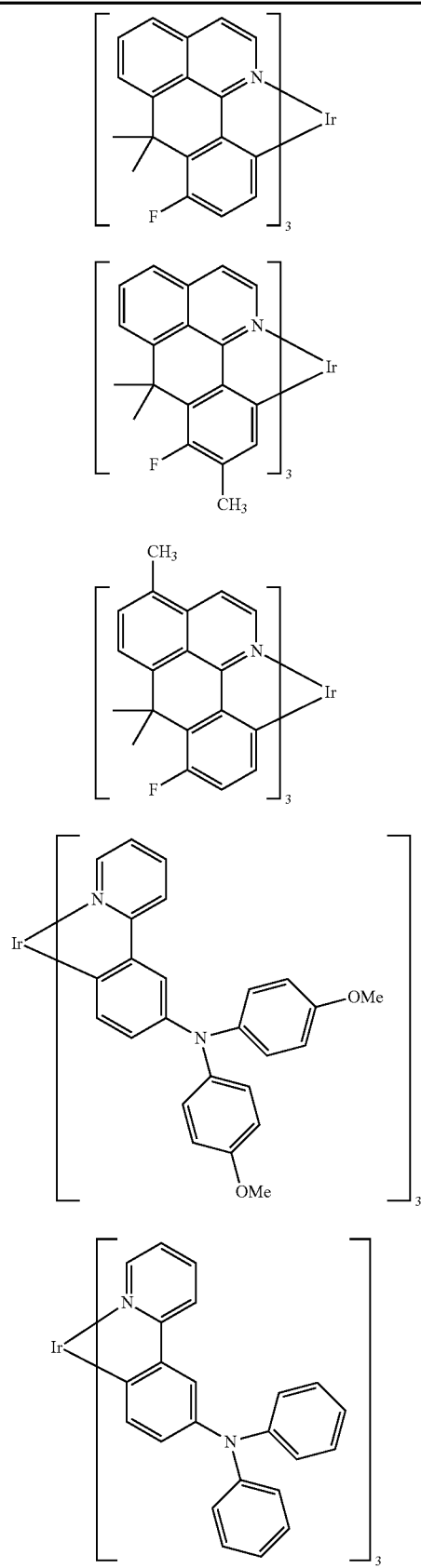
178
-continued
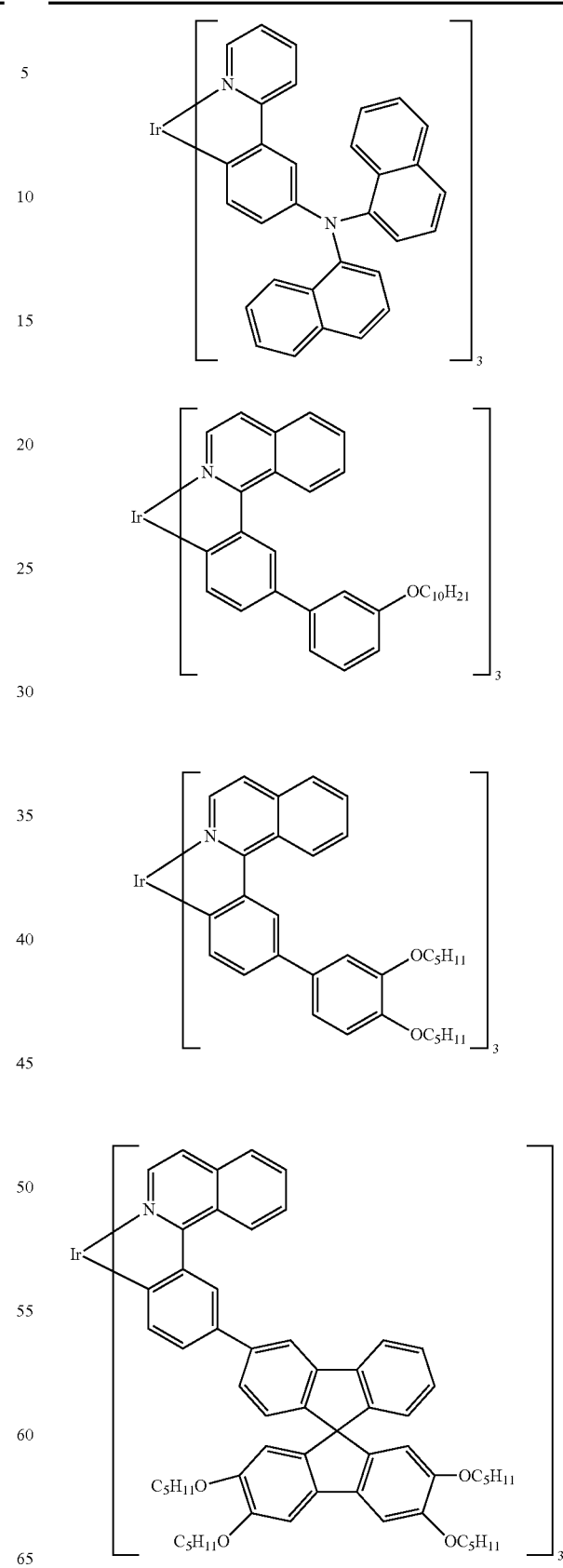

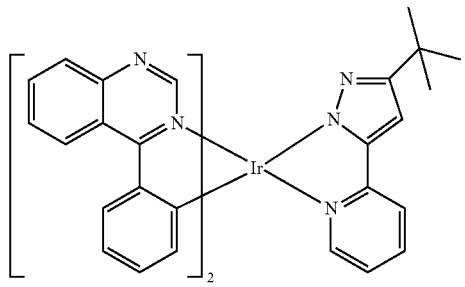
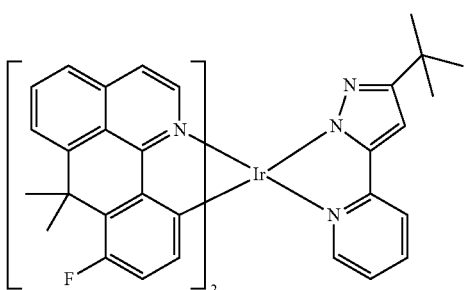
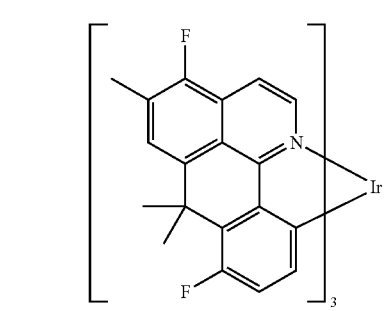
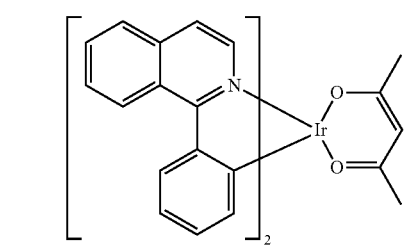
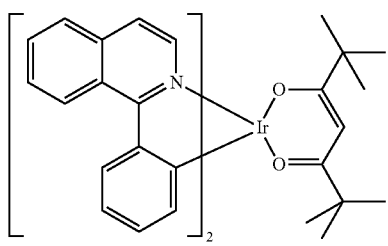
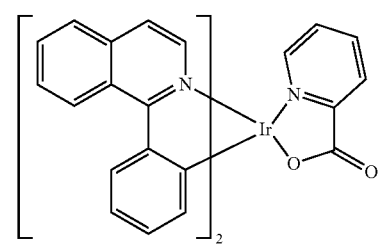
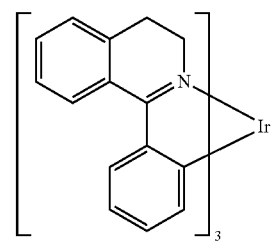
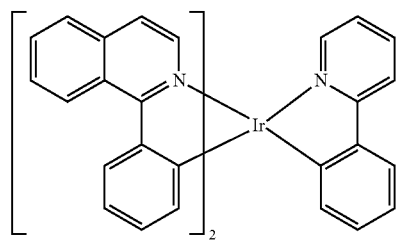
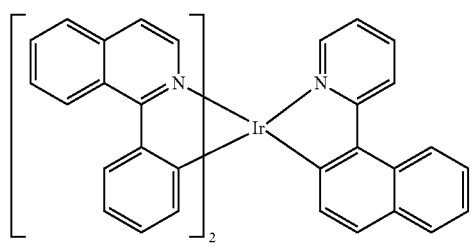
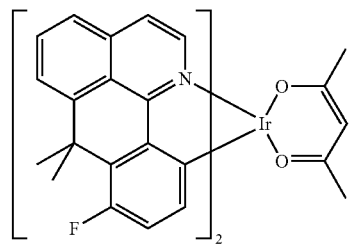
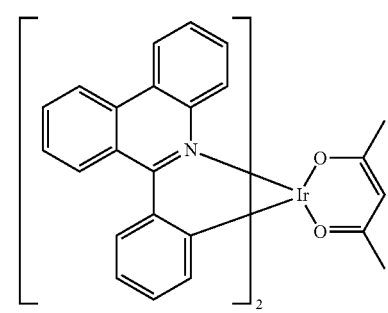
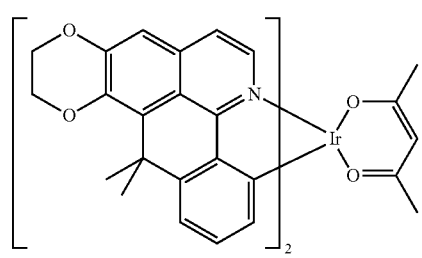

-continued
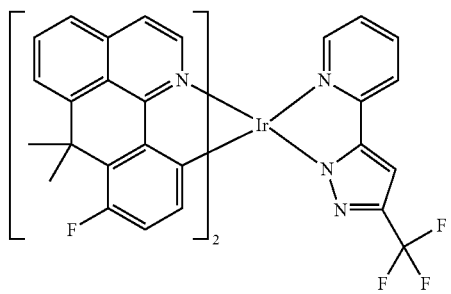
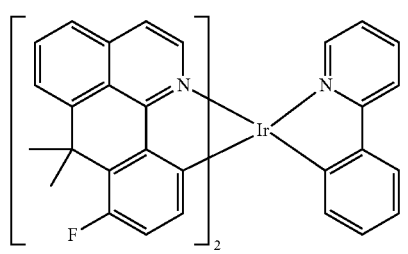
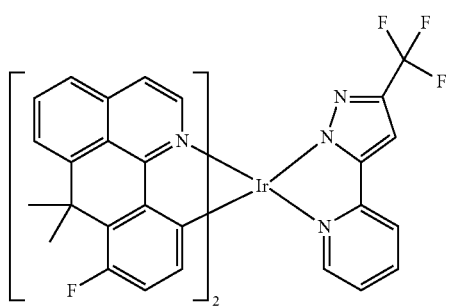
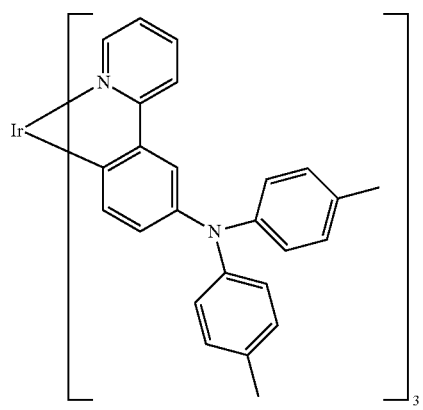
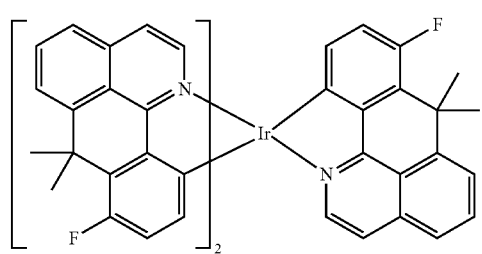
-continued
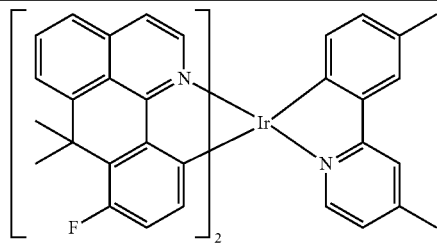
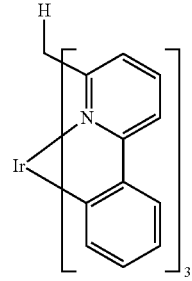
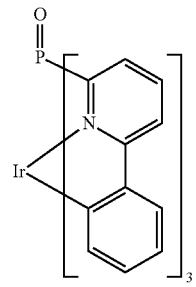
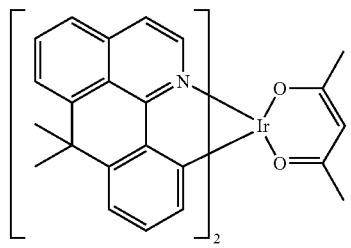
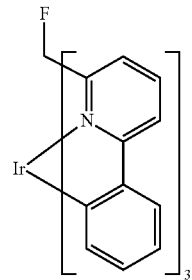
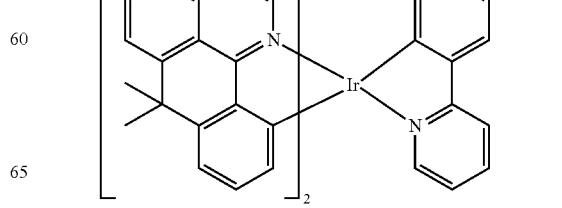

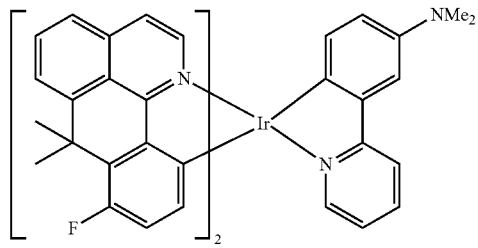
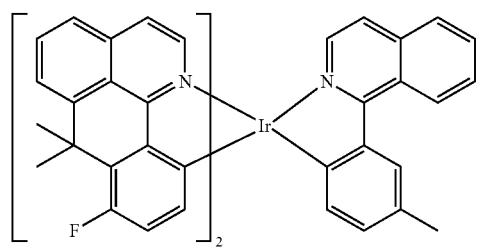
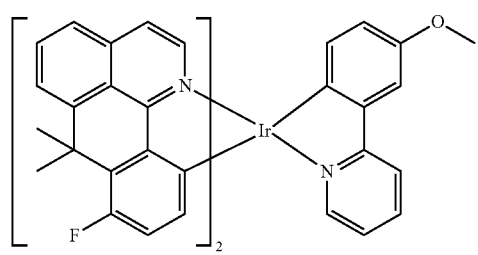
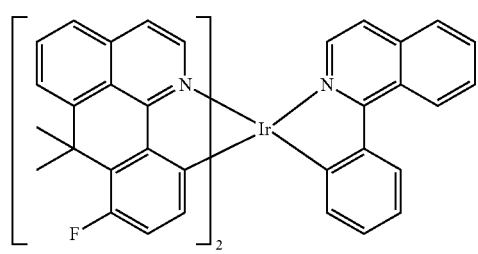
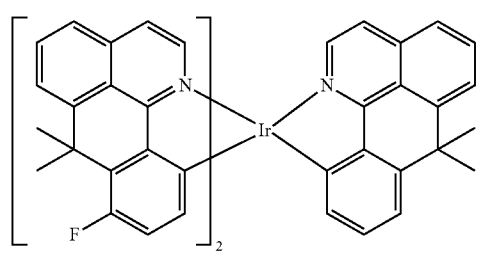
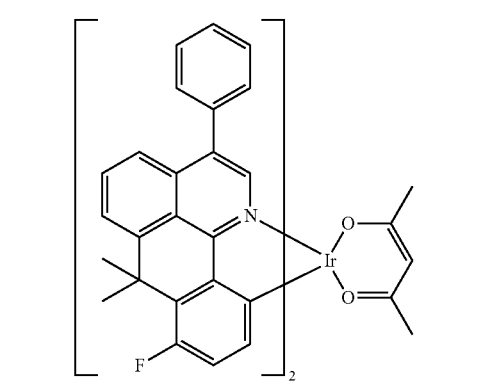
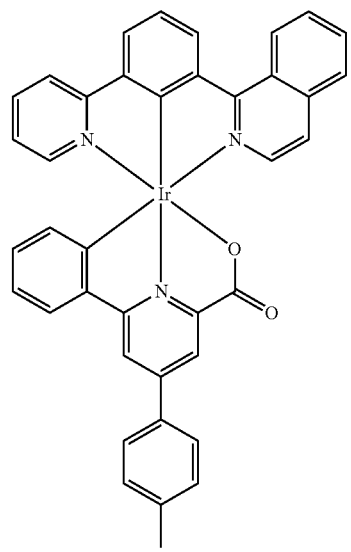
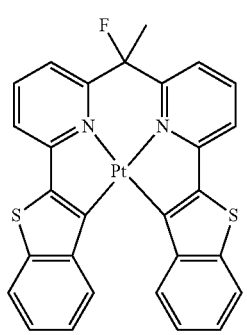
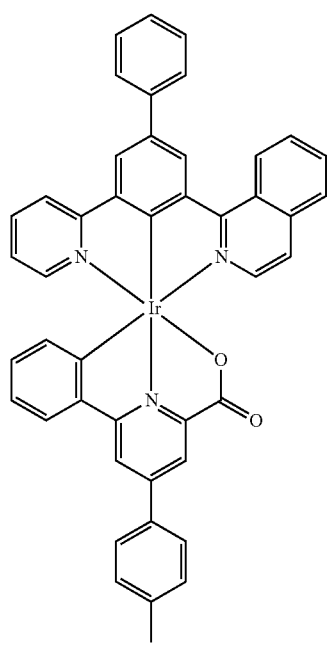

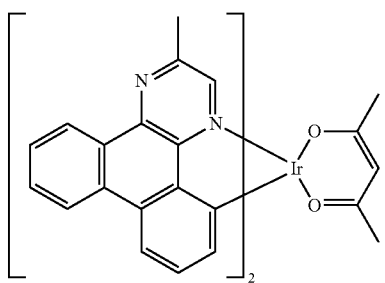
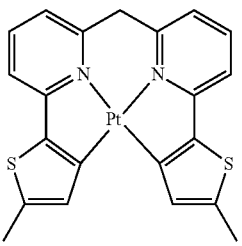
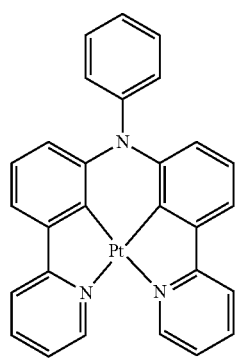
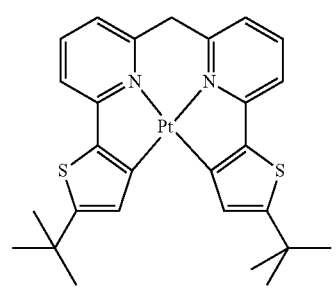
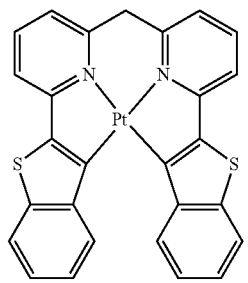
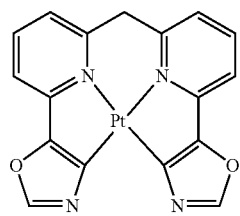
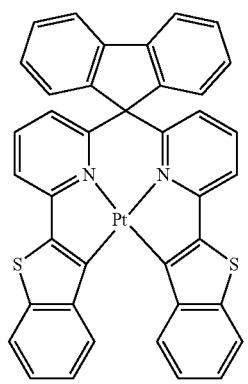
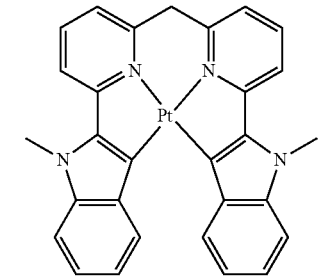
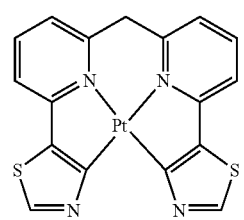
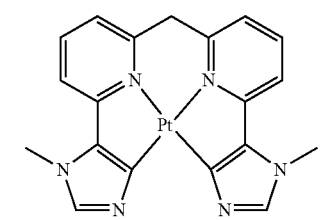

187
-continued
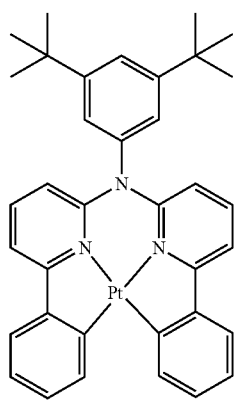
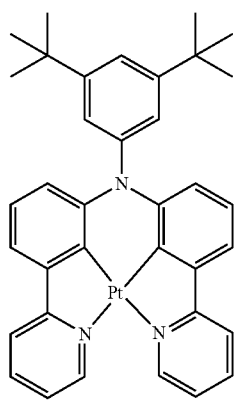
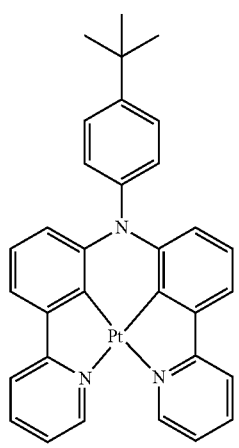
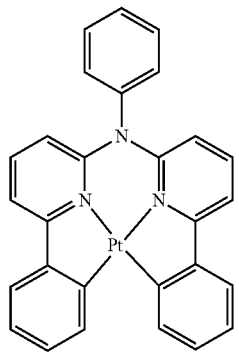
188
-continued
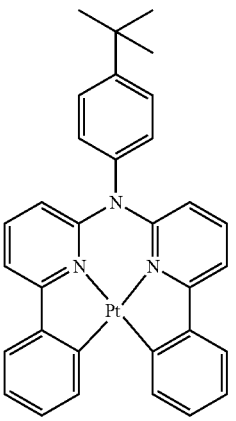
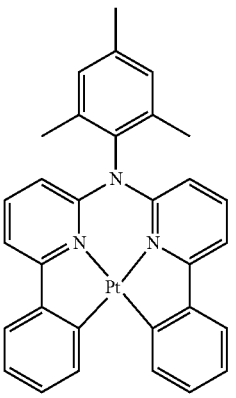
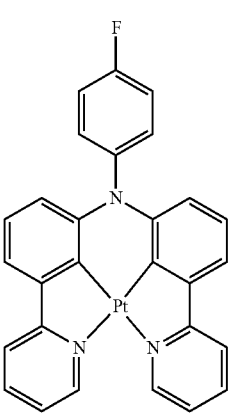
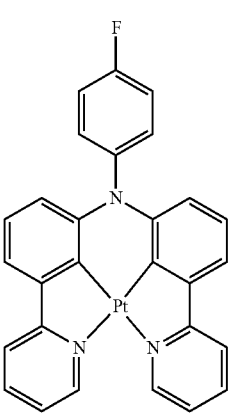

189
-continued
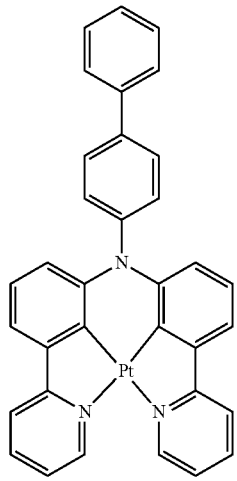
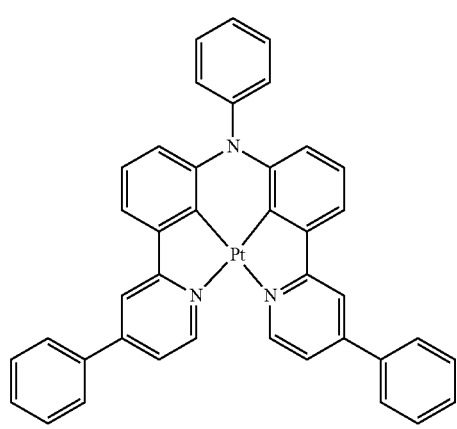
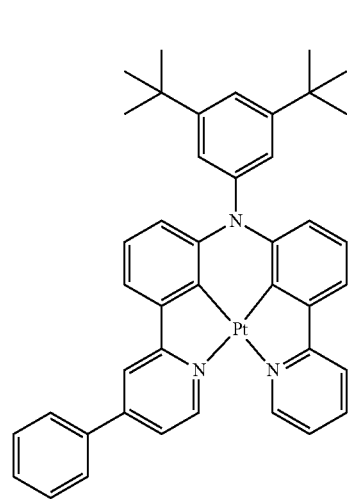
190
-continued
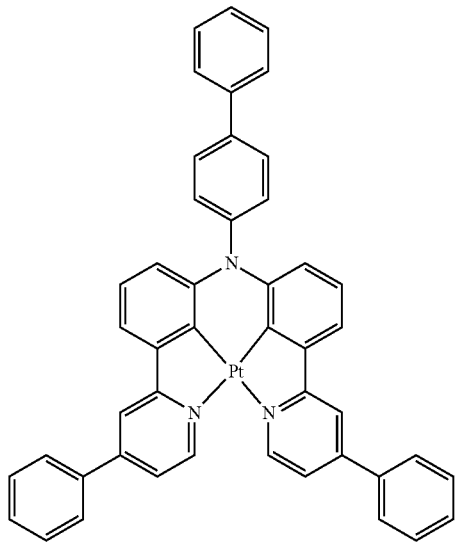
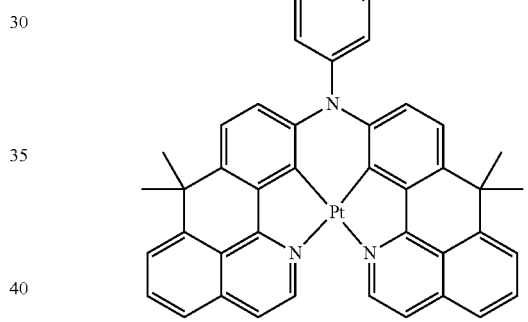
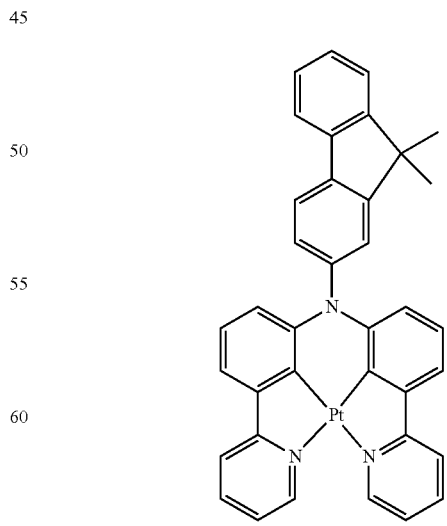

191
-continued
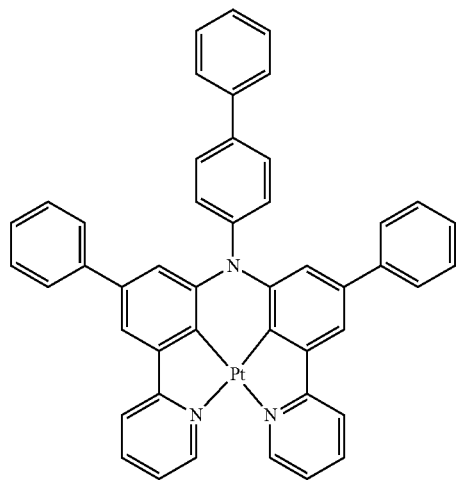
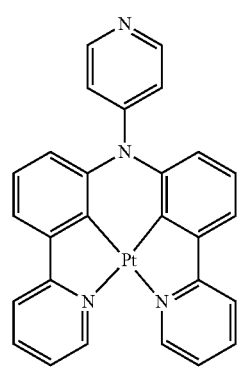
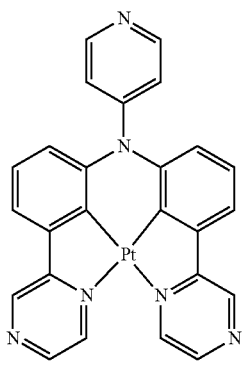
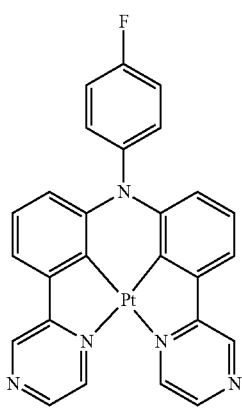
192
-continued
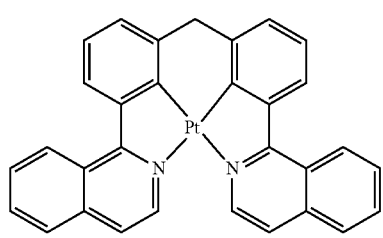
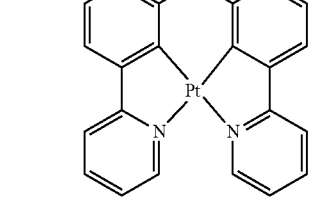
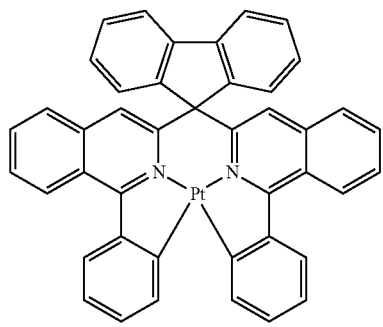
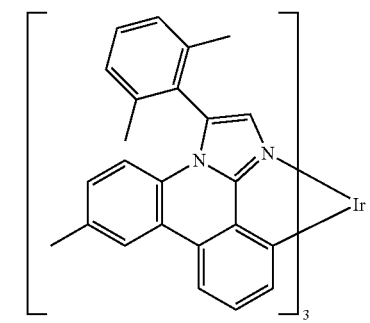
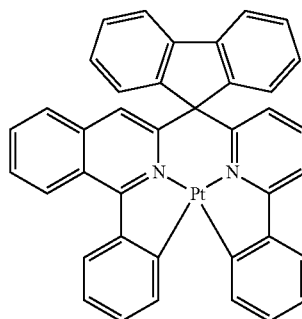

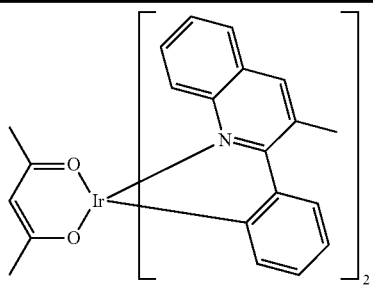
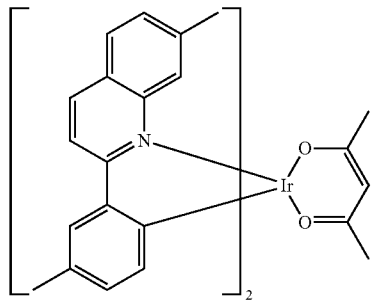
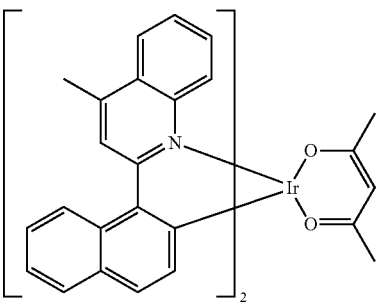
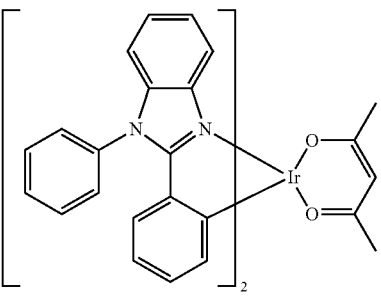
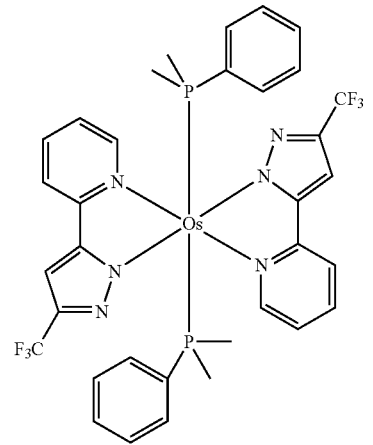
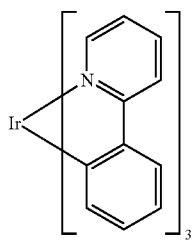
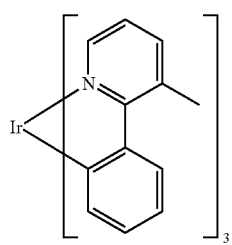
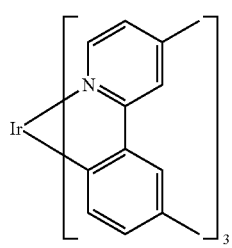
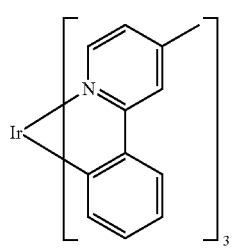
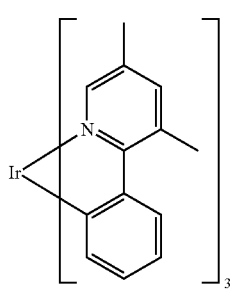
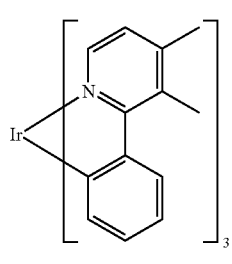

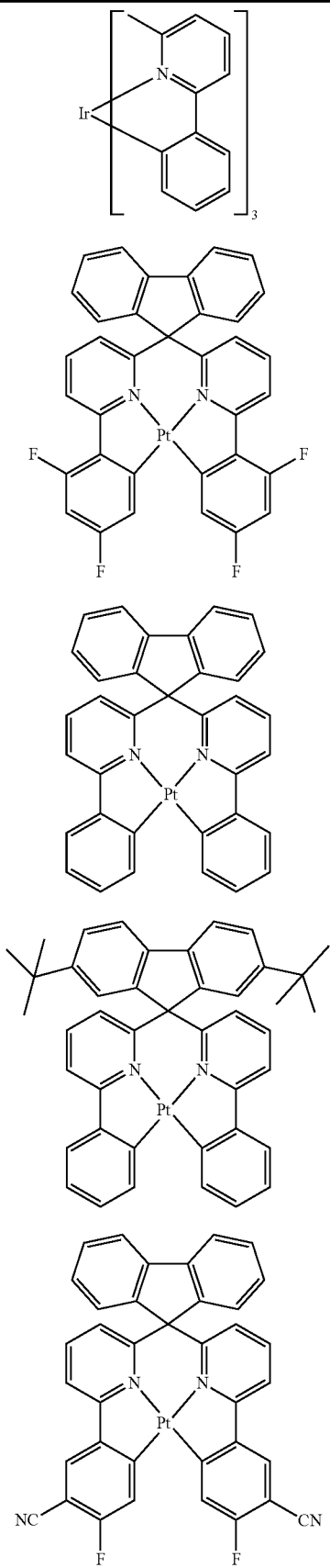
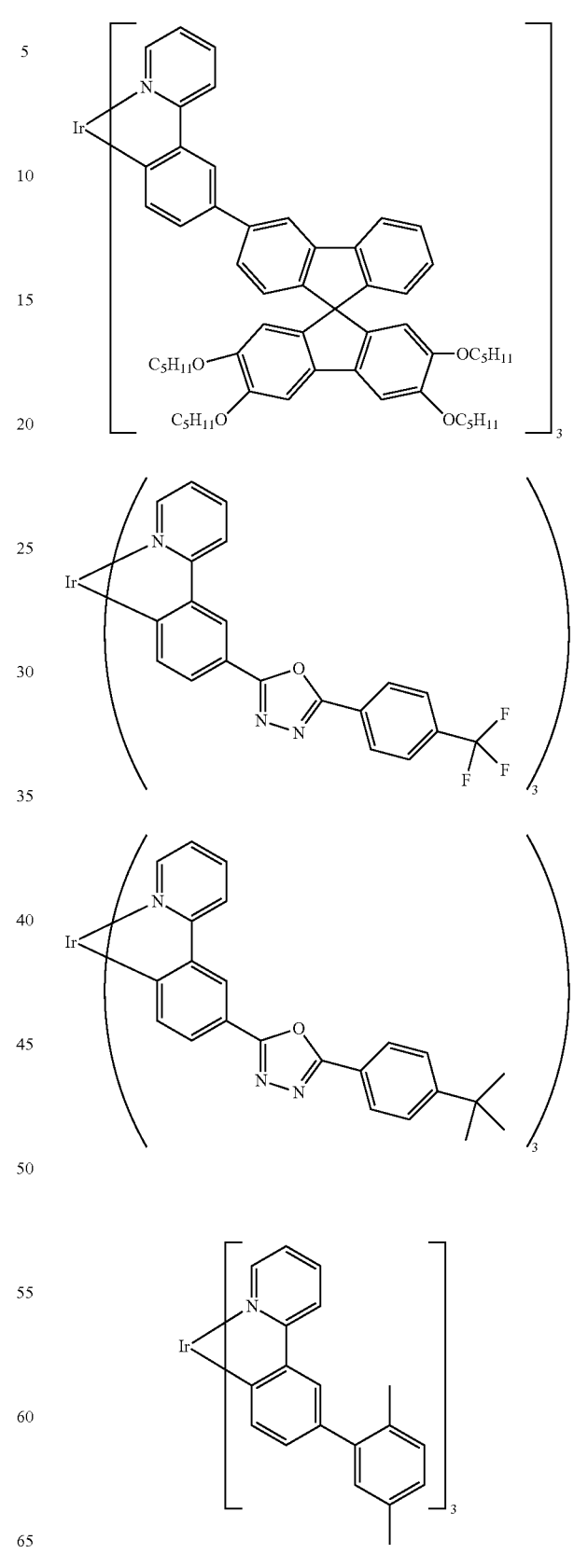

| 197 -continued | 198 -continued |
|---|---|
| 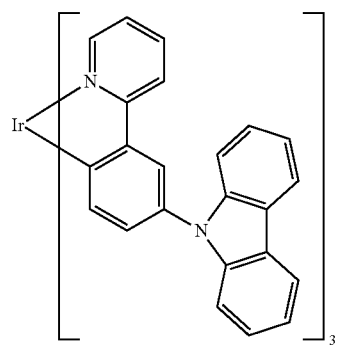 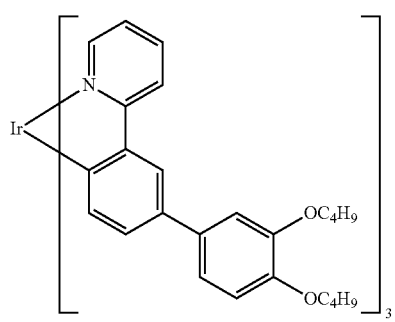 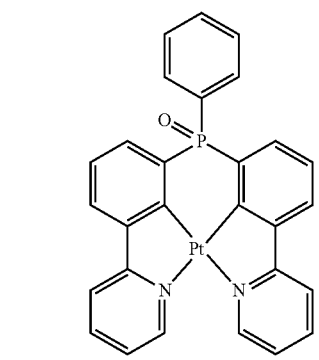 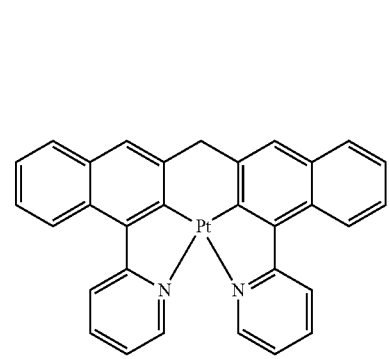 | 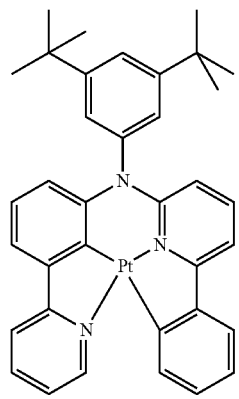 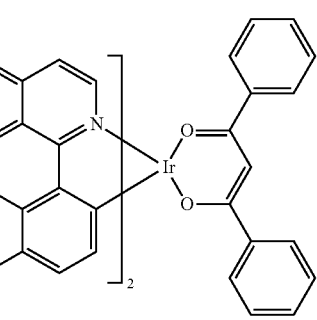 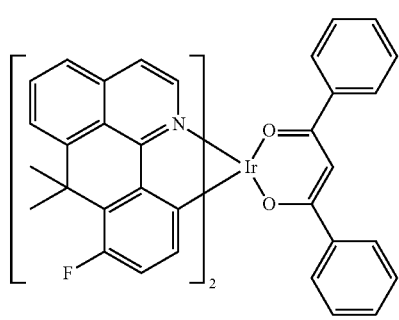 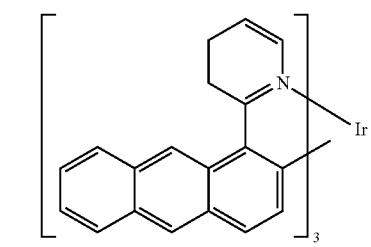 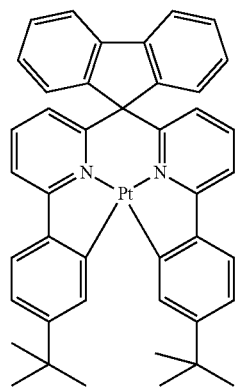 |

199
-continued
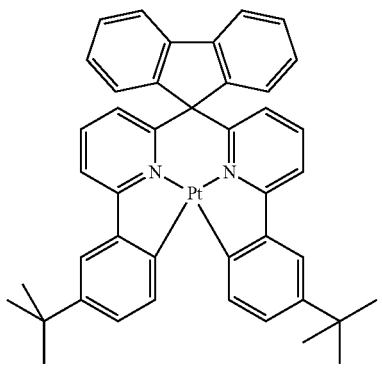
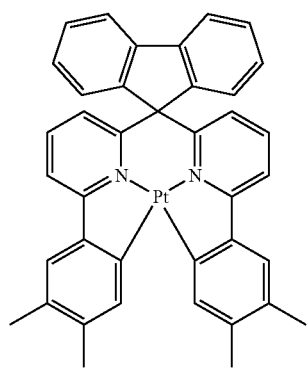
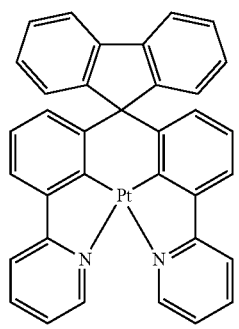
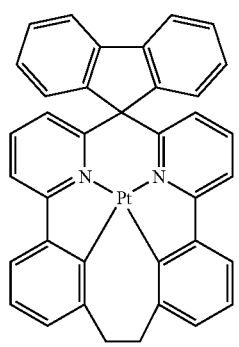
200
-continued
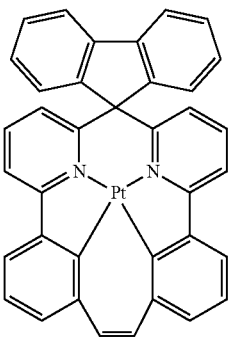
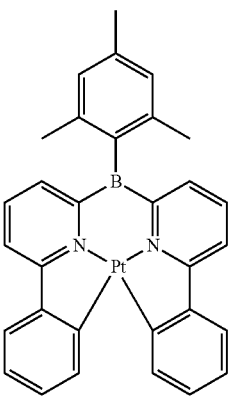
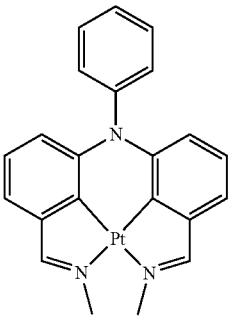
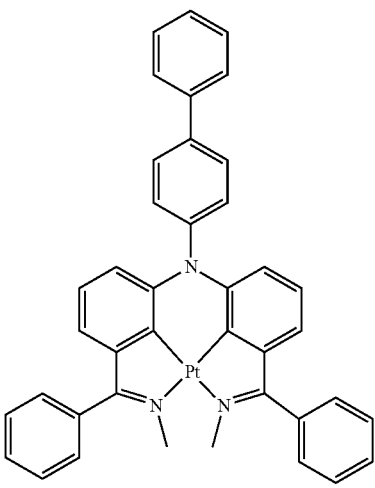

| 201 -continued | 202 -continued |
|---|---|
| 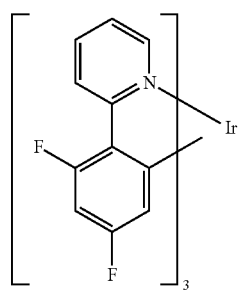 | 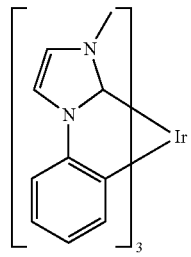 |
| 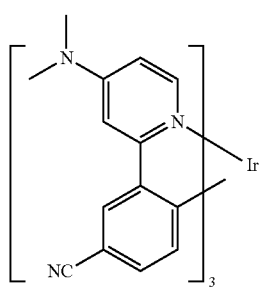 | 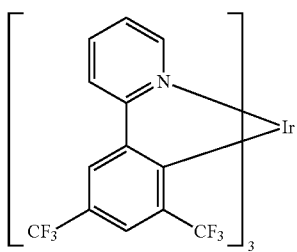 |
| 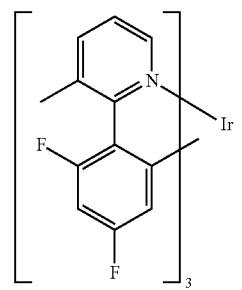 | 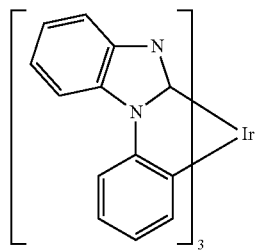 |
| 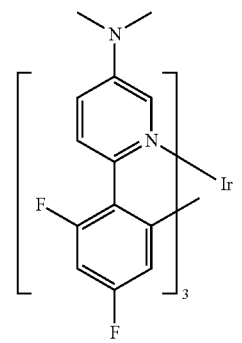 | 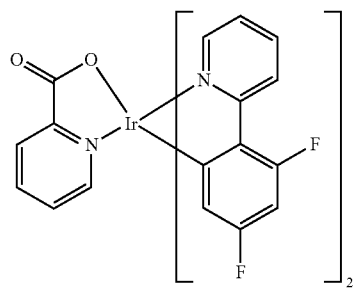 |
| 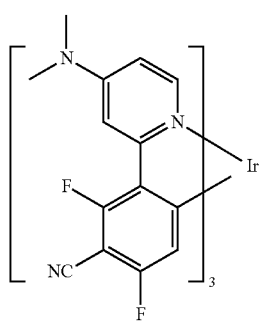 | 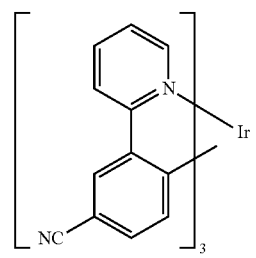 |
| | 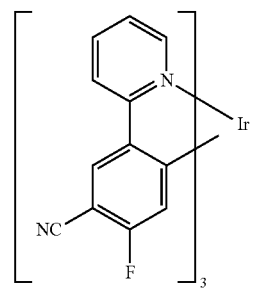 |

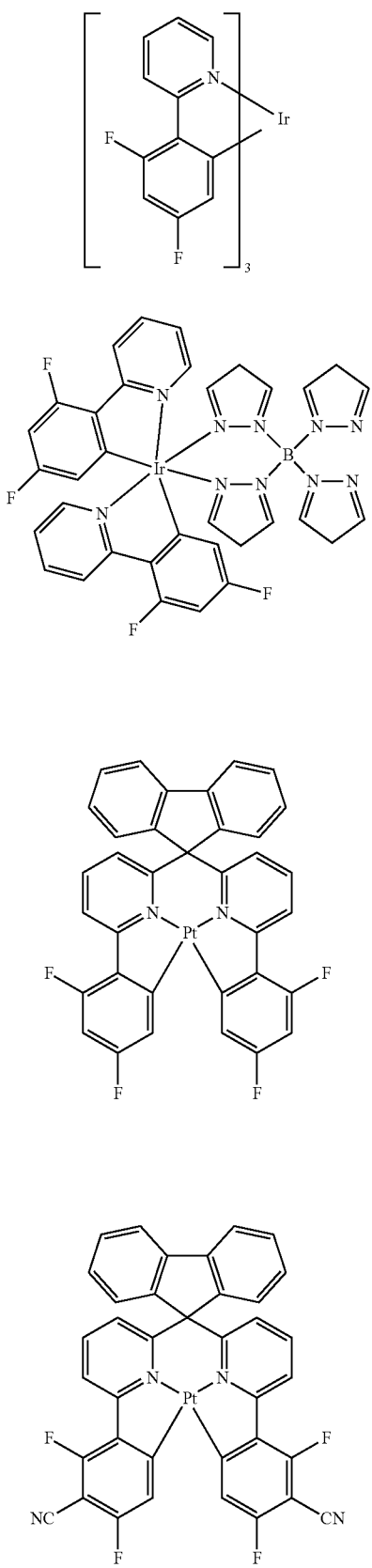
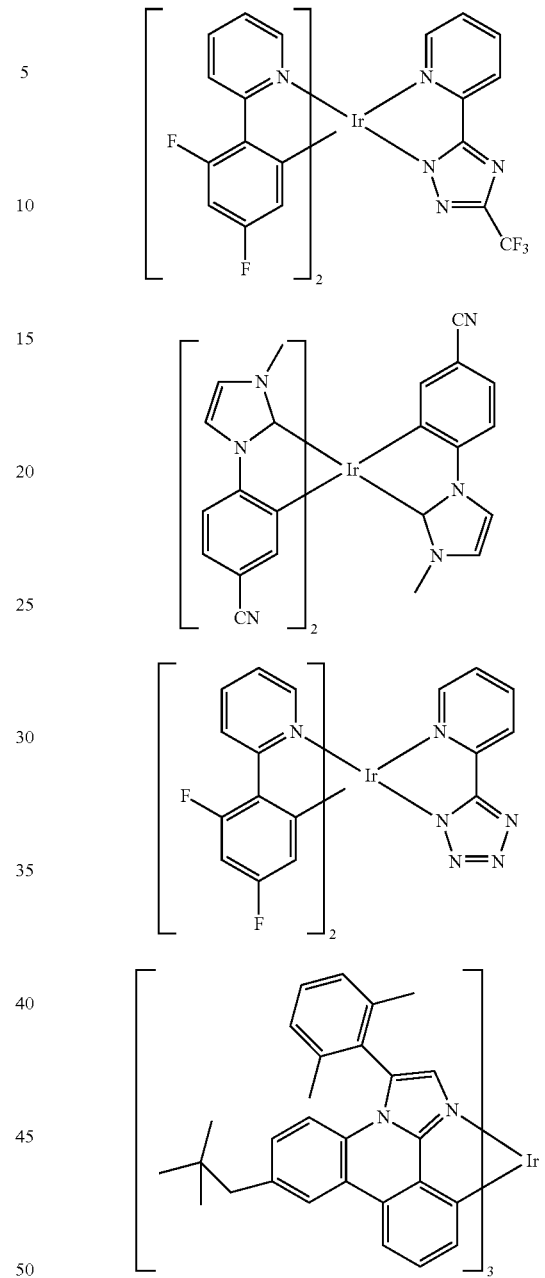

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 04/013080, WO 04/093207, WO 06/005627 or WO 10/006,680, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with WO 10/015,306, WO 07/063,754 or WO 08/056, 746, zinc complexes, for example in accordance with EP 652273 or WO 09/062,578, diazasilole or tetraazasilole derivatives, for example in accordance with WO 10/054,729, diazaphosphole derivatives, for example in accordance with WO 10/003,475, indenocarbazole derivatives, for example in accordance with the unpublished application DE 102009023155.2, or bridged carbazole derivatives, for example in accordance with the unpublished application DE 102009048791.3.

It may also be preferred to use two or more different phosphorescent emitters in an emitting layer, in particular emitters which have different emission maxima. Thus, the use of, for example, a green-phosphorescent emitter and a red-phosphorescent emitter enables red luminescence to be achieved with improved efficiency.

In a further preferred embodiment of the invention, the compounds of the formula (I) or (II) are employed as electron-transport material in an electron-transport layer. It is particularly preferred in this case for the compounds of the formula (I) or (II) to contain one or more electron-deficient heteroaromatic groups, example triazine or pyrimidine.

If the compounds according to the invention are employed as electron-transport material in an organic electroluminescent device, they can also be employed in accordance of the invention in combination with an organic or inorganic alkali-metal compound. "In combination with an organic alkali-metal compound" here means that the compounds according to the invention and the alkali-metal compound are either in the form of a mixture in one layer or are present separately in two successive layers. In a preferred embodiment of the invention, the compounds according to the invention and the organic alkali-metal compound are in the form of a mixture in one layer.

An organic alkali-metal compound in the sense of this invention is intended to be taken to mean a compound which contains a least one alkali metal, i.e. lithium, sodium, potassium, rubidium or caesium, and which furthermore contains at least one organic ligand. Suitable organic alkali-metal compounds are, for example, the compounds disclosed in WO 07/050,301, WO 07/050,334 and EP 1144543. These are incorporated into the present application by way of reference.

Preferred organic alkali-metal compounds are the compounds of the following formula (B):

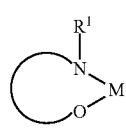

formula (B)

where $R^1$ has the same meaning as described above, the curved line represents two or three atoms and bonds which are necessary to make up a 5- or 6-membered ring with M, where these atoms may also be substituted by one or more radicals $R^1$, and M represents an alkali metal selected from the group consisting of lithium, sodium, potassium, rubidium and caesium.

It is possible here for the complex of the formula (B) to be in monomeric form, as depicted above, or for it to be in the form of aggregates, for example comprising two alkali-metal ions and two ligands, four alkali-metal ions and four ligands, six alkali-metal ions and six ligands, or other aggregates.

Preferred compounds of the formula (B) are the compounds of the following formulae (B') and (B"):

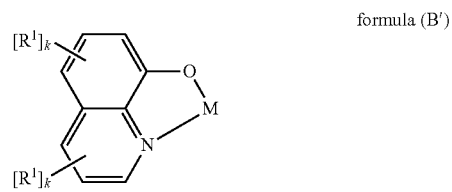

formula (B')

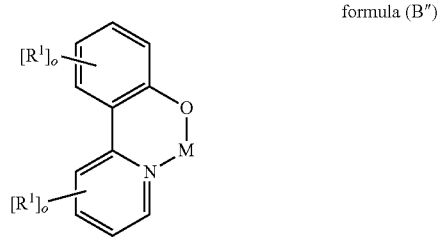

formula (B")

where k is equal to 0, 1, 2 or 3 and o is equal to 0, 1, 2, 3 or 4 and the other symbols used have the meanings given above.

Further preferred organic alkali-metal compounds are the compounds of the following formula (C):

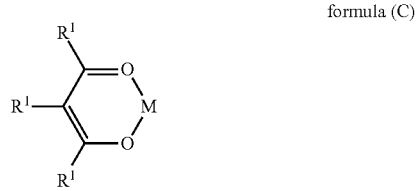

formula (C)

where the symbols used have the same meanings as described above.

The alkali metal M is preferably selected from lithium, sodium and potassium, particularly preferably lithium and sodium, very particularly preferably lithium.

Particular preference is given to a compound of the formula (B'), in particular where M=lithium. The index k is furthermore very particularly preferably =0. The compound is thus very particularly preferably unsubstituted lithium quinolinate.

The organic electroluminescent device very particularly preferably comprises a mixture of a compound according to the invention which contains an electron-deficient heteroaromatic group and an organic alkali-metal compound of the formula (B'), preferably where M=lithium, in particular unsubstituted lithium quinolinate.

Examples of suitable organic alkali-metal compounds are the structures shown in the following table.

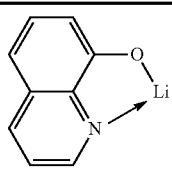

(1)

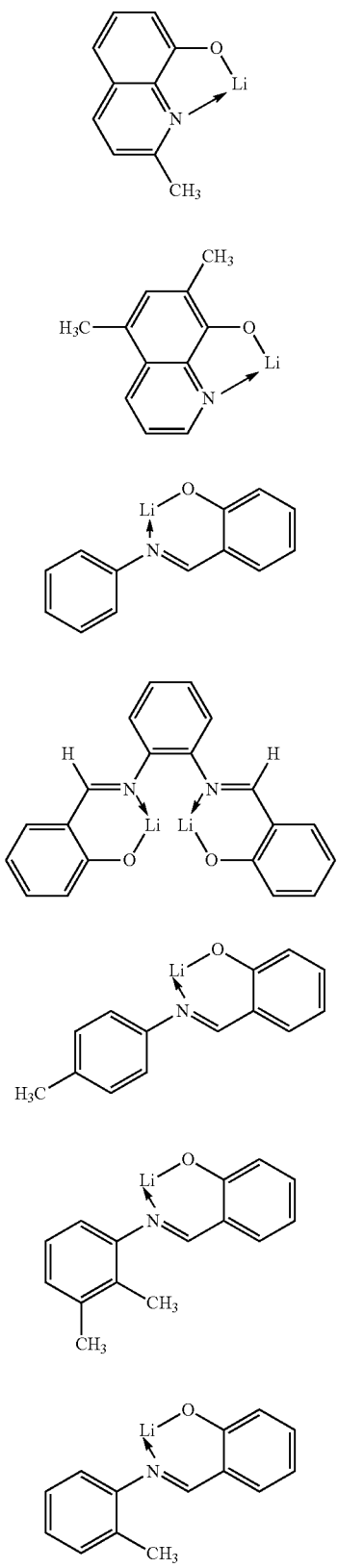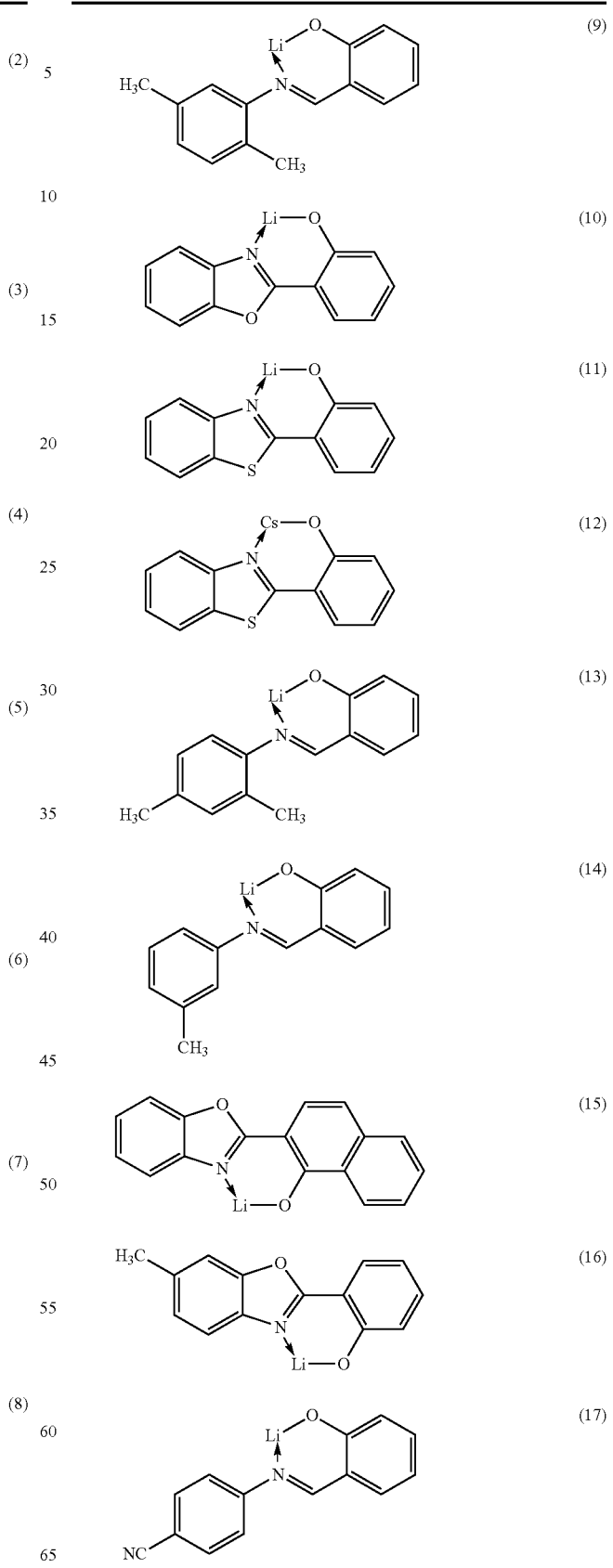

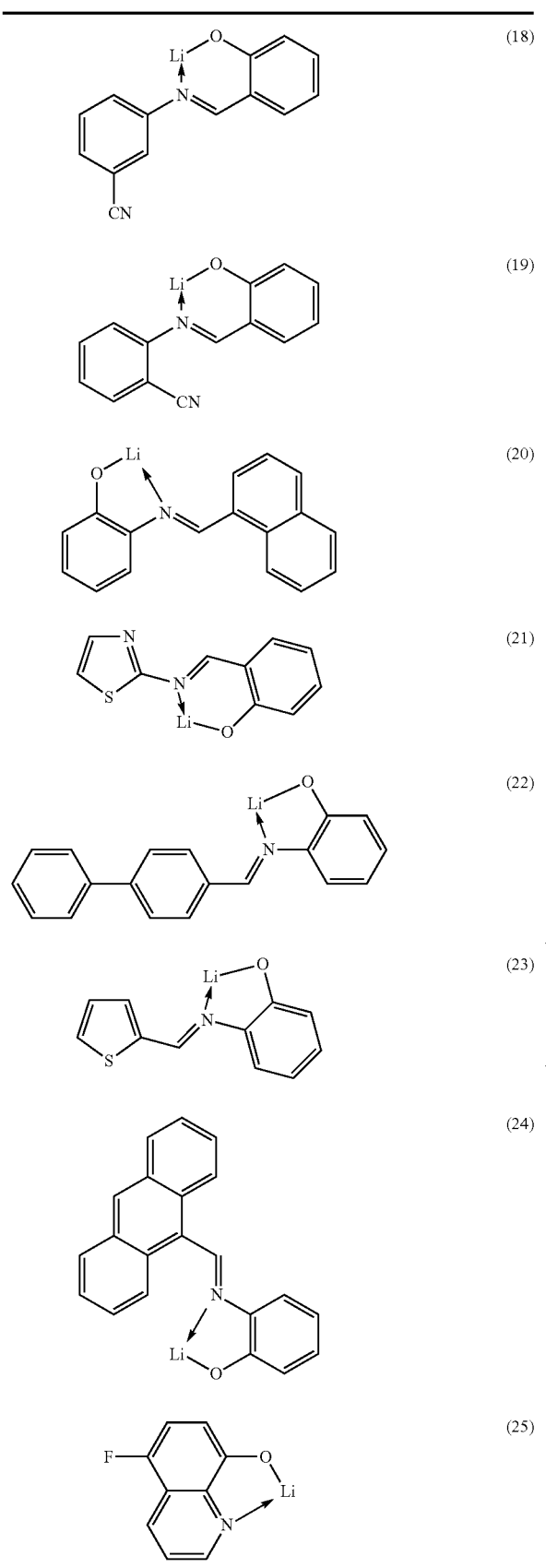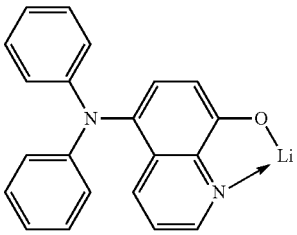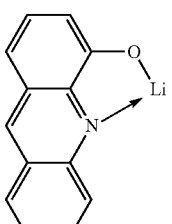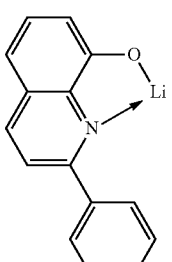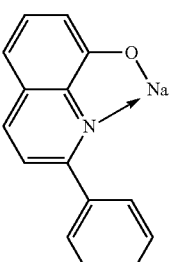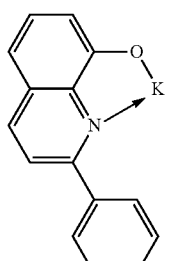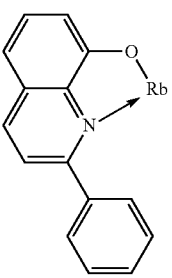

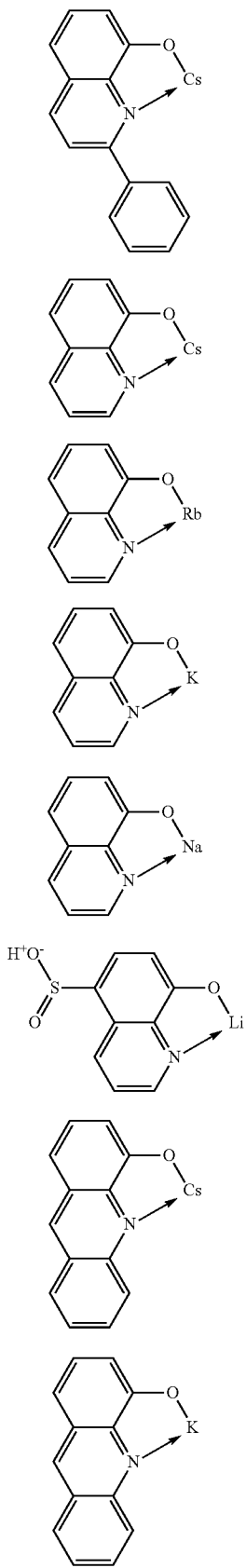

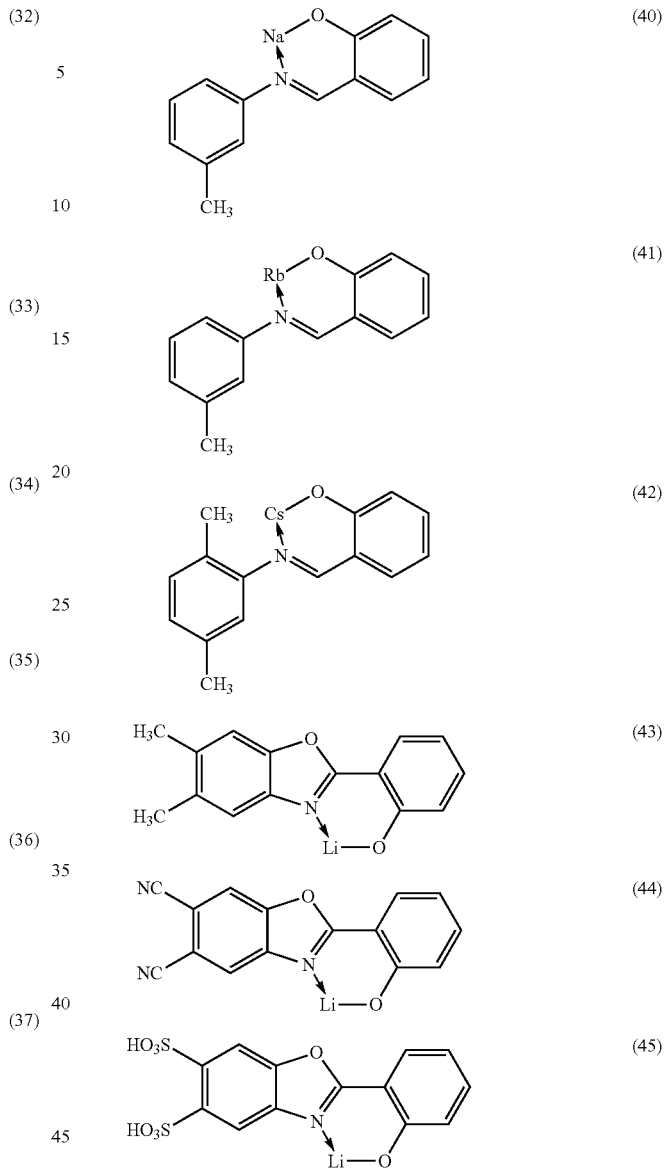

If the compound according to the invention and the organic or inorganic alkali-metal compound are in the form of a mixture, the ratio of the compound according to the invention to the organic alkali-metal compound is preferably 20:80 to 80:20, particularly preferably 30:70 to 70:30, very particularly preferably 30:70 to 50:50, in particular 30:70 to 45:55, in each case based on the volume. The organic alkali-metal compound is thus particularly preferably present in a higher proportion than the compound according to the invention.

If the compound according to the invention and the organic or inorganic alkali-metal compound are in the form of a mixture, the layer thickness of this electron-transport layer is preferably between 3 and 150 nm, particularly preferably between 5 and 100 nm, very particularly preferably between 10 and 60 nm, in particular between 15 and 40 nm.

If the compound according to the invention and the organic or inorganic alkali-metal compound are present in two successive layers, the layer thickness of the layer which comprises the compound according to the invention is preferably between 3 and 150 nm, particularly preferably between 5 and 100 nm, very particularly preferably between 10 and 60 nm, in particular between 15 and 40 nm. The layer thickness of the layer which comprises the organic or inorganic alkali-metal compound and which is arranged between the layer comprising the compound according to the invention and the cathode is preferably between 0.5 and 20 nm, particularly preferably between 1 and 10 nm, very particularly preferably between 1 and 5 nm, in particular between 1.5 and 3 nm.

It is furthermore a subject-matter of the present invention that the compounds according to the invention are employed as hole-blocking material. The compounds are then preferably employed in a hole-blocking layer, in particular in a phosphorescent OLED. A hole-blocking layer in the sense of this invention is a layer which is arranged between an emitting layer and an electron-transport layer.

It is furthermore a subject-matter of the present invention that the compounds according to the invention are employed as hole-transport material and/or as hole-injection material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer.

The invention furthermore relates to an electronic device comprising at least one compound of one of the formulae (I) and (II), or a polymer, oligomer or dendrimer as defined above.

The electronic device is preferably selected from the group consisting of organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or organic laser diodes (O-lasers), particularly preferably organic electroluminescent devices (OLEDs).

An organic electroluminescent device in the sense of the present invention is a device which comprises an anode, a cathode and at least one emitting layer, which is arranged between the anode and the cathode. In addition, in each case one or more electron-transport layers and/or hole-transport layers and/or further layers may also be present. An organic electroluminescent device according to the invention comprises at least one layer between the anode and the cathode which comprises one or more of the compounds or polymers, oligomers or dendrimers according to the invention.

Apart from the cathode, anode and at least one of the layers already mentioned above, the organic electroluminescent device may also comprise further layers. These can be, for example: a hole-injection layer, electron-blocking layer, exciton-blocking layer, hole-blocking layer, electron-injec-layer and/or charge-generation layer (T. Matsumoto et al., *Multiphoton Organic EL Device Having Charge Generation Layer*, IDMC 2003, Taiwan; Session 21 OLED (5)). However, it should be pointed out that each of these layers does not necessarily have to be present. Thus, in particular use of the compounds according to the invention with electron-conducting matrix materials, very good results are furthermore obtained if the organic electroluminescent device does not comprise a separate electron-transport layer and the emitting layer is directly adjacent to the electron-injection layer or to the cathode. Alternatively, the matrix material may also simultaneously serve as electron-transport material in an electron-transport layer. It may likewise be preferred for the organic electroluminescent device not to comprise a separate hole-transport layer and for the emitting layer to be directly adjacent to the hole-injection layer or to the anode.

The present invention also relates to organic electroluminescent devices which are characterised in that a plurality of emitting compounds are used in the same layer or in different layers. The compound according to the invention can be employed here, for example, as matrix material in an emitting layer or as electron-transport material in an electron-transport layer or as hole-transport material in a hole-transport layer. Compounds according to the invention can also be employed in a plurality of the said layers.

The organic electroluminescent device may also comprise a plurality of emitting layers. These emission layers particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where one or more of these layers may comprise a compound of the formula (I) or (II) as matrix material and where the three layers exhibit blue, green and orange or red emission (for the basic structure see, for example, WO 05/011013). The use of more than three emitting layers may also be preferred. Emitters which have broadband emission bands and thus exhibit white emission are likewise suitable for white emission. Alternatively and/or additionally, the compounds according to the invention may also be present in a hole-transport layer or electron-transport layer or in another layer in such systems.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, example, in WO 05/053051. It is furthermore possible to use a metal complex which is identical or similar to the metal complex in the emitting layer, as hole-transport or hole-injection material directly adjacent to the emitting layer, as described, for example, in WO 09/030,981.

The cathode preferably comprises metals having a low work function, metal alloys or multilayered structures comprising different metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, may also be used in addition to the said metals, in which case combinations of the metals, such as, for example, Ca/Ag or Ba/Ag, are then generally used. Preference is likewise given to metal alloys, in particular alloys comprising an alkali metal or alkaline-earth metal and silver, particularly preferably an alloy comprising Mg and Ag. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, CsF, $Cs_2CO_3$, $BaF_2$, MgO, NaF, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$, WoO$_3$) may also be preferred. For some applications, at least one of the electrodes must be transparent in order to enable either the irradiation of the organic material (O-SCs) or the coupling-out of light (OLEDs, PLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is correspondingly (depending on the application) structured, provided with contacts and finally hermetically sealed, since the lifetime of the devices according to the invention is shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it should be noted that the initial pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of one of the formula (I) and (II) are necessary for this purpose. High solubility can be achieved through suitable substitution of the compounds. These processes for the production of layers are also particularly suitable for polymers, oligomers or dendrimers The organic electroluminescent device can also be produced as a hybrid system by applying one or more layers from solution and applying one or more other layers by vapour deposition. Thus, for example, it is possible to apply an emitting layer comprising a compound of one of the formula (I) and (II) and a phosphorescent dopant from solution and to apply a hole-blocking layer and/or an electron-transport layer on top by vacuum vapour deposition. The emitting layer comprising one of the compounds according to the invention and a phosphorescent dopant can likewise be applied by vacuum vapour deposition, and one or more other layers can be applied from solution. Alternatively or additionally, it is, for example, also possible to apply an emitting layer from solution and to apply an electron-transport layer comprising a compound according to the invention, optionally in combination with an organic alkali-metal compound, on top by vacuum vapour deposition.

These processes are generally known to the person skilled in the art and can be applied by him without problems to organic electroluminescent devices comprising compounds of one of the formula (I) and (II) or the preferred embodiments mentioned above.

The compounds according to the invention have the following surprising advantages over the prior art on use in organic electroluminescent devices:

1. The compounds according to the invention are very highly suitable for use as matrix material for phosphorescent emitters and result in good efficiencies, long lifetimes and low operating voltages in this use.
2. The power efficiency of corresponding devices becomes higher compared with systems in accordance with the prior art, in particular on use of thick layers. This applies, in particular, on use of the compound according to the invention in an electron-transport layer.
3. The stability of corresponding devices becomes higher compared systems in accordance with the prior art, which is evident, in particular, from a significantly longer lifetime, in particular on use of thick layers.
4. The organic electroluminescent devices according to the invention simultaneously have a reduced operating voltage.
5. The organic electroluminescent devices according to the invention have very high efficiency. The improved efficiency is possibly attributable to improved electron injection from the electron-transport layer into the emitting layer.

Finally, it should be noted that all the preferred features of the compounds according to the invention mentioned above and the features that are not explicitly mentioned as preferred, the use thereof in electronic devices, and the electronic devices themselves can be combined with one another as desired. All resultant combinations are likewise part of this invention.

The invention is now explained in greater detail by the following examples, without wishing it to be restricted thereby.

WORKING EXAMPLES

The following syntheses are carried out, unless indicated otherwise, under a protective-gas atmosphere in dried solvents.

The starting point for the syntheses can be, for example, 2-phenylcarbazole (Synthesis 2005, 10, 1619-1624), 3,6-dibromo-9-(phenylsulfonyl)-9H-carbazole (Organic & Biomolecular Chemistry 2004, 2, 1476-1483), 9-phenyl-9H-carbazole-3-boronic acid (Synlett 2006, 17, 2841-2845), 2,8-dibromodibenzothiophene (Journal of Organic Chemistry 2004, 69, 8177-8182) or 7-bromo-12,12-dimethyl-10-phenyl-10,12-dihydro-10-azaindeno-[2,1-b]fluorene (not yet published application DE 102009023155.2).

Synthesis Examples Step A 3,3'''-Bis(phenyl)-9'-[(phenyl)sulfonyl]-9,3':6',9''-ter-9H-carbazole (A1)

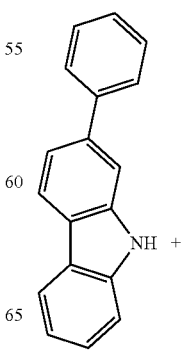

217
-continued

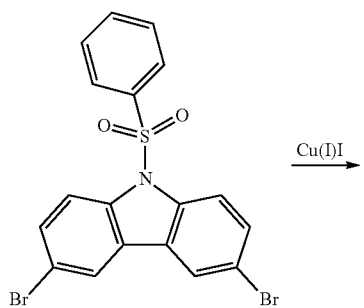

218
-continued

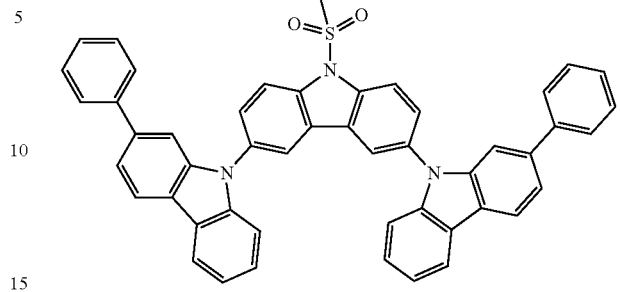

8.0 g (42.2 mmol) of copper(I) iodide and 11.7 ml (97.5 mmol) of trans-cyclohexanediamine are added to a vigorously stirred suspension of 56.9 g (234 mmol) of 2-phenylcarbazole, 54.4 g (117 mmol) of 3,6-dibromo-9-(phenylsulfonyl)-9H-carbazole and 416.4 g (1961 mmol) of potassium phosphate in 1170 ml of dioxane, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol. Yield: 80 g (101 mmol), 86%.

The following compounds are prepared analogously (if present, the CAS number is indicated for starting materials):

| Ex. | Starting material 1 | Starting material 2 | Product | Yield |
|---|---|---|---|---|
| A2 | 56525-79-2 | | | 74% |
| A3 | 78750-83-1 | | | 63% |

| Ex. | Starting material 1 | Starting material 2 | Product | Yield |
|---|---|---|---|---|
| A4 | 223713-94-8 | | A4 | 55% |

Synthesis Examples Step B 3,3"-Bis(phenyl)-9,3':6',9"-ter-9H-carbazole (B1)

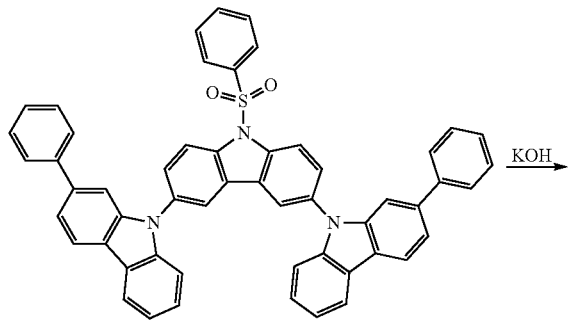

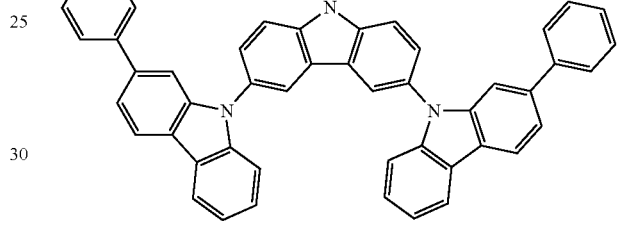

97 g (123 mmol) of 3,3"-bis(phenyl)-9'-[(phenyl)sulfonyl]-9,3':6',9"-ter-9H-carbazole and 48 g (856 mmol) of potassium hydroxide in 65 ml of dimethyl sulfoxide and 21 ml of water are heated under reflux for 1 h. The mixture is subsequently cooled to room temperature and neutralised using 1 M HCl solution. The mixture is then extracted with dichloromethane. The solvent is evaporated in vacuo, and the residue is purified by chromatography (heptane/ethyl acetate 10:1). Yield: 64.8 g (100 mmol), 80%.

The following compounds are prepared analogously:

| Ex. | Starting material | Product | Yield |
|---|---|---|---|
| B2 | A2 | B2 | 81% |

-continued
| Ex. | Starting material | Product | Yield |
|---|---|---|---|
| B3 | 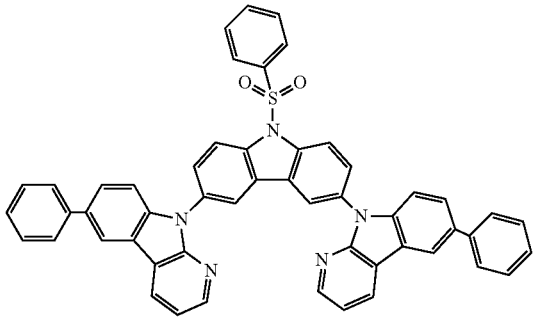<br>A3 | 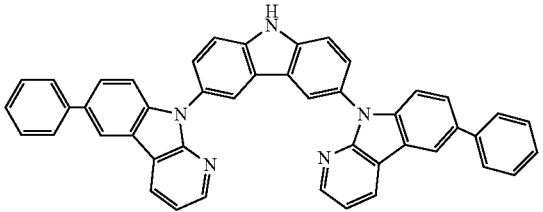<br>B3 | 79% |
| B4 | 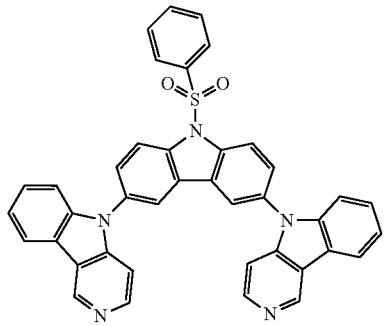<br>A4 | 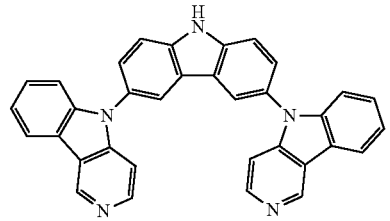<br>B4 | 80% |
Synthesis Examples Step C
Compounds According to the Invention
3,3''-Bis(4,6-diphenyl-1,3,5-triazin-2-yl)-9,3':6',9''-ter-9H-carbazole (C1)
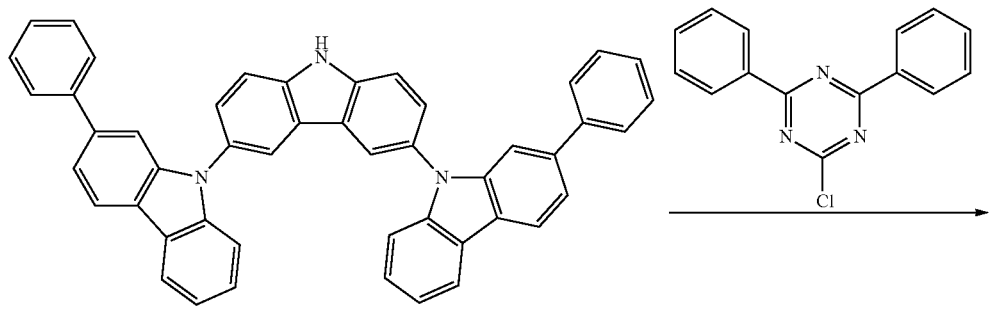

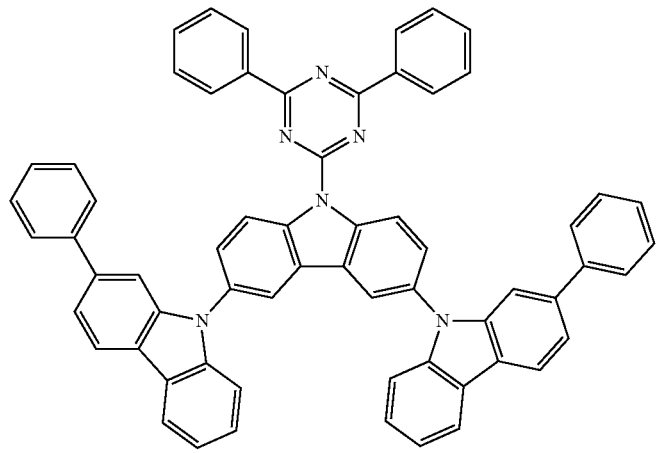

1.6 g (40 mmol) of NaH (60% in oil) are initially introduced in 150 ml of DMF. A solution of 19.9 g (30 mmol) of 3,3''-bis(phenyl)-9,3':6',9''-ter-9H-carbazole in 50 ml of DMF is added dropwise thereto at RT. After 1 h, 9 g (33 mmol) of 2-chloro-4,6-diphenyl-1,3,5-triazine are added, and the mixture is stirred at RT for 8 h. The precipitated solid is recrystallised from toluene. The deposited crystals are filtered off with suction, washed with a little MeOH and dried in vacuo; yield: 17.8 g (20 mmol), 66%; purity: 99.9% according to HPLC.

The following compounds are prepared analogously:

| Ex. | Starting material 1 | Starting material 2 | Product | Yield |
|---|---|---|---|---|
| C2 | | | | 81% |

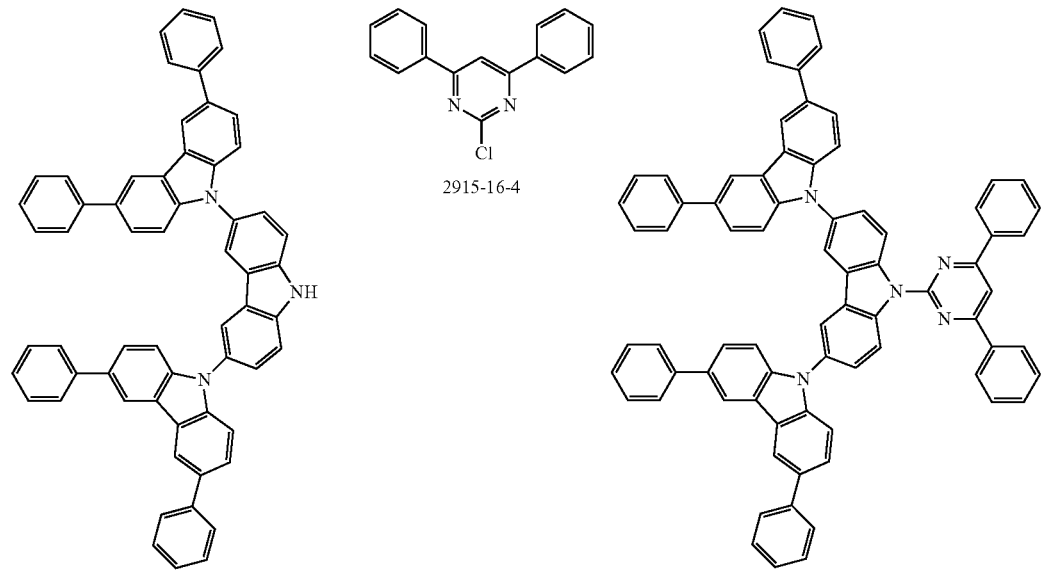

-continued

| Ex. | Starting material 1 | Starting material 2 | Product | Yield |
|---|---|---|---|---|
| C3 | B3 | 2915-16-4 | C3 | 79% |
| C4 | B4 | | C4 | 80% |

Synthesis Examples Step D

Starting Material for Step E7

8,8-Dimethyl-8H-indolo[3,2,1-de]acridine-3-boronic acid (D1)

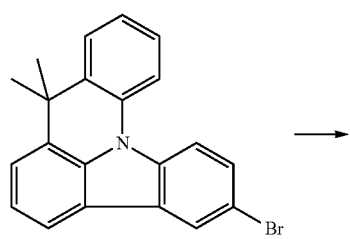

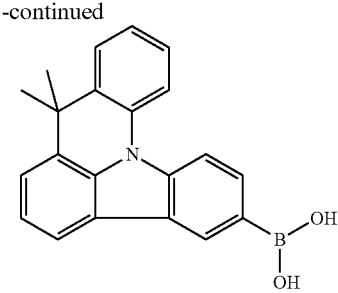

-continued 93.9 g (259 mmol) of 3-bromo-8,8-dimethyl-8H-indolo[3,2,1-de]acridine are dissolved in 1500 ml of dry THF. 135 ml (337 mmol) of a 2.5 M solution of n-butyllithium in cyclohexane are added dropwise at −70° C., and, after 1 h, 37 ml of trimethyl borate (336 mmol) are added dropwise. The mixture is allowed to come to room temperature over the course of 1 h, and the solvent is removed. The residue, which is uniform according to ¹H-NMR, is employed in the subsequent reaction without further purification. The yield is 77 g (235 mmol), corresponding to 91% of theory.

Synthesis Examples Step E 3-(6-Bromodibenzothiophen-3-yl)-9-phenyl-9H-carbazole (E1)

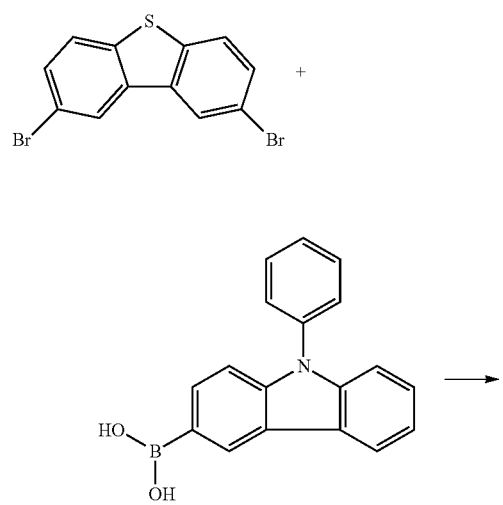

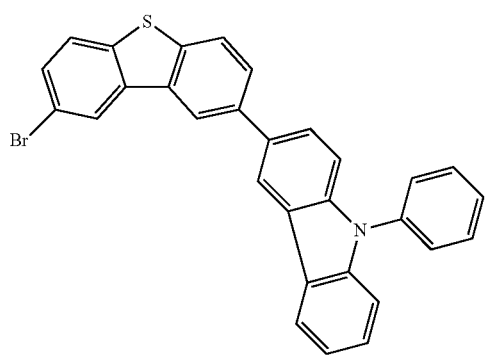

2.47 g (8.1 mmol) of tetrakistriphenylphosphinopalladium (0) are added to a vigorously stirred suspension of 6.8 g (20 mmol) of 3,6-dibromodibenzothiophene, 15 g (40 mmol) of 9-phenyl-9H-carbazole-3-boronic acid and 63.9 g (127 mmol) of $Na_2CO_3$ in 500 ml of DMF, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol and recrystallised three times from DMF (about 15 ml/g). Yield 17.4 g (33 mmol), 86.0%, purity 99.9% (HPLC).

The following compounds are prepared analogously:

| Ex. | Starting material 1 | Starting material 2 | Product | Yield |
|---|---|---|---|---|
| E2 | 10016-52-1 | | | 67% |
| E3 | 201138-91-2 | | | 61% |

-continued
| Ex. | Starting material 1 | Starting material 2 | Product | Yield |
|---|---|---|---|---|
| E4 | 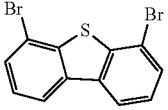<br>669773-34-6 | 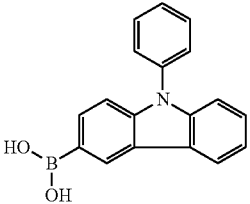 [SMILES: OB(O)c1ccc2c(c1)c1ccccc1n2-c1ccccc1] | 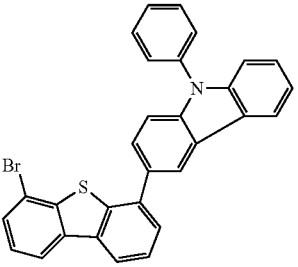<br>E4 | 65% |
| E5 | 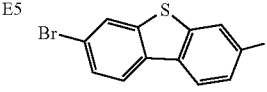<br>83834-10-0 | 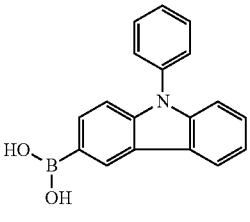 [SMILES: OB(O)c1ccc2c(c1)c1ccccc1n2-c1ccccc1] | 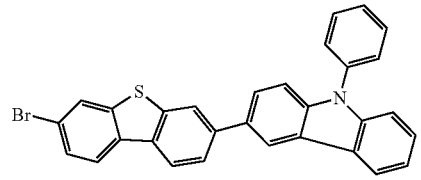<br>E5 | 63% |
| E6 | 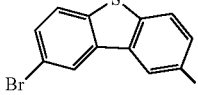 | 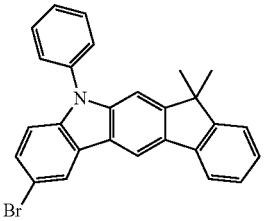 [SMILES: CC1(C)c2ccccc2-c2cc3c4cc(Br)ccc4n(-c4ccccc4)c3cc21] | 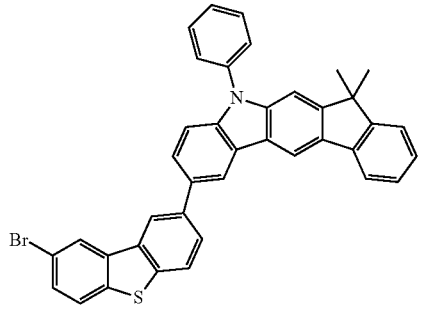<br>E6 | 62% |
| E7 | 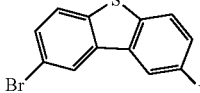 | 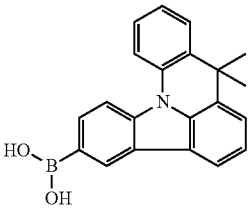<br>D1 | 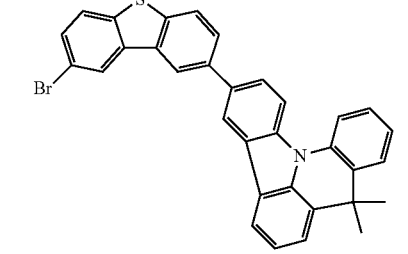<br>E7 | 69% |

-continued

| Ex. | Starting material 1 | Starting material 2 | Product | Yield |
|---|---|---|---|---|
| E8 | 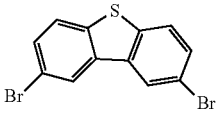 [SMILES: Brc1ccc2sc3ccc(Br)cc3c2c1] | 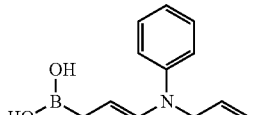  1001911-63-2 | 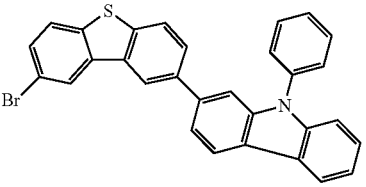 E8 | 62% |
| E9 | 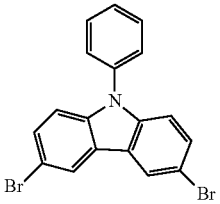 57103-20-5 | 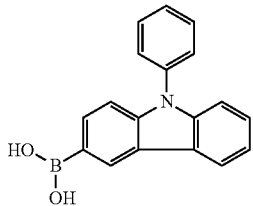 [SMILES: OB(O)c1ccc2c(c1)c1ccccc1n2-c1ccccc1] | 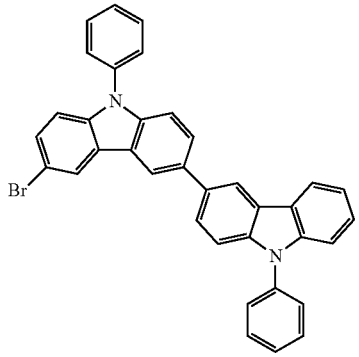 E9 | 66% |

Synthesis Examples Step F 6-(9-Phenyl-9H-carbazol-3-yl)dibenzothiophene-3-boronic acid (F1)

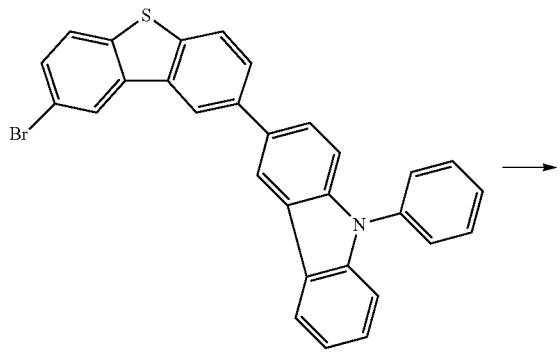

→

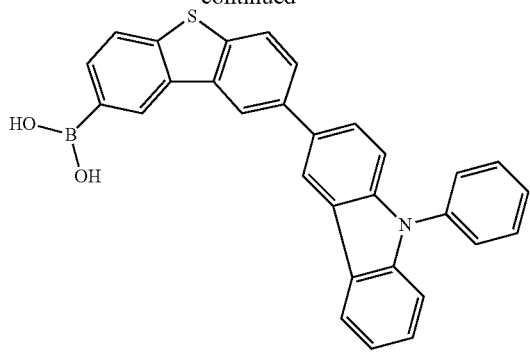

52 ml (130 mmol) of n-butyllithium (2.5 M in n-hexane) are added dropwise with vigorous stirring at −78° C. to a suspension of 50.4 g (100 mmol) of 3-(6-bromodibenzothiophen-3-yl)-9-phenyl-9H-carbazole in 1000 ml of THF, and the mixture is stirred for a further 2 h. 16.7 ml (150 mmol) of trimethyl borate are added (in one portion) to the red solution with vigorous stirring, the mixture is stirred at −78° C. for a further 30 min, then warmed to room temperature over the course of 3 h, 300 ml of water are added, and the mixture is stirred for 30 min. The organic phase is separated off and evaporated to dryness in vacuo. The solid is taken up in 100 ml of n-hexane, filtered off with suction, washed once with 100 ml of hexane and dried in vacuo. Yield: 39 g (38 mmol), 84%, purity about 90% (NMR) of boronic acid, with varying amounts of boronic anhydride and boronic acid. The boronic acid can be used in this form without further purification.

The following compounds are prepared analogously:

| Ex. | Starting material | Product | Yield |
|---|---|---|---|
| F2 | E2 | F2 | 59% |
| F3 | E3 | F3 | 58% |
| F4 | E4 | F4 | 55% |
| F5 | E5 | F5 | 53% |

-continued

| Ex. | Starting material | Product | Yield |
|---|---|---|---|
| F6 | E6 | F6 | 62% |
| F7 | E7 | F7 | 61% |
| F8 | E8 | F8 | 63% |
| F9 | E9 | F9 | 66% |

Synthesis Examples Step G

Compounds According to the Invention

3-[6-(4,6-Diphenyl-1,3,5-triazin-2-yl)dibenzothiophen-3-yl]-9-phenyl-9H-carbazole (G1)

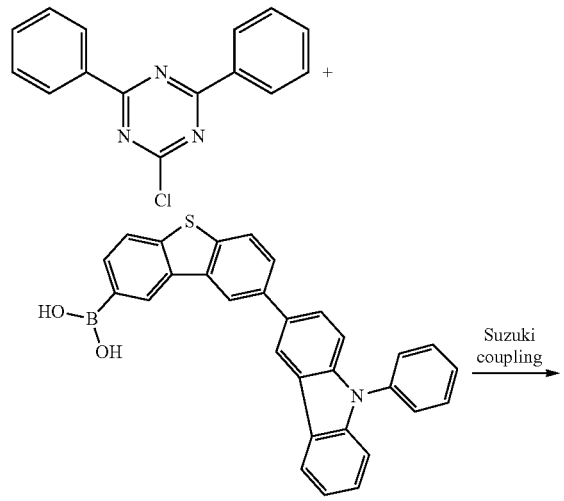

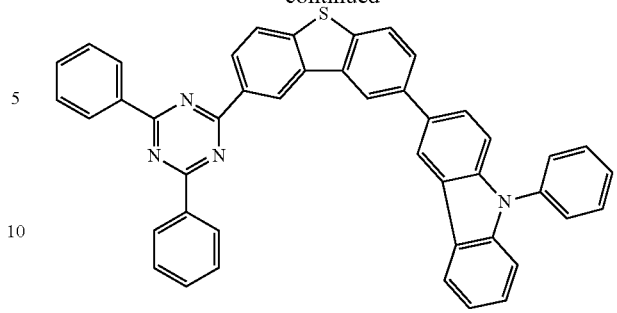

51.5 g (110.0 mmol) of 6-(9-phenyl-9H-carbazol-3-yl)dibenzothiophene-3-boronic acid, 29.5 g (110.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum ($p=5\times10^{-5}$ mbar). The purity is 99.9%. The yield is 58 g (88.9 mmol), corresponding to 81% of theory.

The following compounds are prepared analogously:

| Ex. | Starting material 1 | Starting material 2 | Product | Yield |
|---|---|---|---|---|
| G2 | F2 | | G2 | 59% |
| G3 | F3 | 915-16-4 | G3 | 58% |

-continued

| Ex. | Starting material 1 | Starting material 2 | Product | Yield |
|---|---|---|---|---|
| G4 | F4 | | G4 | 55% |
| G5 | F5 | | G5 | 53% |
| G6 | F6 | | G6 | 50% |
| G7 | F7 | | G7 | 61% |
| G8 | F8 | | G8 | 63% |

-continued

| Ex. | Starting material 1 | Starting material 2 | Product | Yield |
|---|---|---|---|---|
| G9 | F9 | | G9 | 66% |
| G10 | F1 | | G10 | 68% |
| G11 | F7 | | G11 | 61% |
| G12 | F6 | | G12 | 57% |

| Ex. | Starting material 1 | Starting material 2 | Product | Yield |
|---|---|---|---|---|
| G13 | F6 | 9509-91-9 | G13 | 57% |

Device Examples

Production of OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in Examples C1 to I27 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin-coating from water; purchased from H. C. Starck, Goslar, Germany) for improved processing. These coated glass plates form the substrates to which the OLEDs are applied. The OLEDs have basically the following layer structure: substrate/hole-injection layer (HIL)/electron-blocking layer (EBL)/emission layer (EML)/optional hole-blocking layer (HBL)/electron-transport layer (ETL)/option al electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by coevaporation. A specification such as ST1:CBP:TER1 (55%:35%:10%) here means that material ST1 is present in the layer in a proportion by volume of 55%, CBP is present in the layer in a proportion of 35% and TER1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminance characteristic lines (IUL characteris-lines), and the lifetime are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m$^2$. CE1000 and PE1000 denote the current and power efficiencies achieved at 1000 cd/m$^2$. Finally, EQE1000 is the external quantum efficiency at an operating luminous density of 1000 cd/m$^2$. The lifetime LT is defined as the time after which the luminous density has dropped from the initial luminous density L0 to a certain proportion L1 on operation at constant current. A specification of L0=4000 cd/m$^2$ and L1=80% in Table 2 means that the lifetime indicated in column LT corresponds to the time after which the initial luminous density of the corresponding OLEDs has dropped from 4000 cd/m$^2$ to 3200 cd/m$^2$. The values for the lifetime can be converted a specification for other initial luminous densities with the aid of conversion formulae known to the person skilled in the art. The lifetime for an initial luminous density of 1000 cd/m$^2$ is a usual specification here.

The data for the various OLEDs are summarised in Table 2. Examples C1-C5 are comparative examples in accordance with the prior art, Examples I1-I27 show data of OLEDs comprising materials according to the invention.

Some of the examples are explained in greater detail below in order to illustrate the advantages of the compounds according to the invention. However, it should be pointed out that this only represents a selection of the data shown in Table 2. As revealed by the table, significant improvements over the prior art are also achieved on use of the compounds according to the invention which are not described in greater detail, in some cases in all parameters, but in some cases only an improvement in the efficiency or voltage or lifetime is observed. However, even the improvement of one of the said parameters represents a significant advance, since different applications require optimisation with respect to different parameters.

Use of Compounds According to the Invention as Matrix Materials in Phosphorescent OLEDs The compounds according to the invention can be employed, in particular, as matrix materials (host materials) for phosphorescent dopants. Compounds C1-C4 and G1-G13 according to the invention are used in the present examples. Compound ST1, which is known from the prior art, is used as comparison. Data of OLEDs comprising the green-emitting dopant TEG1 and the red-emitting dopants TER1 and TER2 are shown. The data of the OLEDs are summarised in Table 2.

It can be seen that the advantages of the novel materials lie, in particular, in a reduction in the operating voltage and an improvement in the lifetime. This applies, for example, to compound G1, for which an advantage of somewhat greater than 10% with respect to the power efficiency in the case of green emission can be seen compared with the prior art. The lifetime is improved by about 35% (see Examples C4 and 13).

Even greater improvements in green-emitting OLEDs are obtained on use of compounds G6 and G12 according to the invention. The improvement in the lifetime here is up to about 40% compared with ST1, and the power efficiency can be increased by somewhat more than 25% (Ex. I12, I21 and C4).

In the case of red emission, an even clearer improvement in the lifetime (compared with the case of green emission) by about 50% is observed on use of compound G1 according to the invention (see Examples 11 and 12 and compared with C1 and C3). A significant increase in the power efficiency by about 10% is also evident here. Compound G12 allows similarly good lifetimes and power efficiencies in the case of red emission (Ex. 118-120).

The examples show that significant advantages arise on use of compounds according to the invention, especially in relation to the operating voltage and the lifetime.

Use of Compounds According to the Invention as Electron-Transport Material

Use of G1 as electron-transport material in combination with LiQ as electron-injection material gives a power efficiency and lifetime which are improved by about 10% compared with ETM1:LiQ (50%:50%) (Ex. I27, C5).

TABLE 1

Structure of the OLEDs

| Ex. | HTL thickness | EBL thickness | EML thickness | HBL thickness | ETL thickness | EIL thickness |
|---|---|---|---|---|---|---|
| C1 | SPA1 20 nm | NPB 20 nm | ST1:TER1 (85%:15%) 30 nm | — | Alq3 20 nm | LiF 1 nm |
| C2 | SPA1 20 nm | NPB 20 nm | ST1:TER2 (85%:15%) 30 nm | — | Alq3 20 nm | LiF 1 nm |
| C3 | SPA1 20 nm | NPB 20 nm | ST1:CBP:TER1 (45%:45%:10%) 30 nm | ST1 10 nm | Alq3 20 nm | LiF 1 nm |
| C4 | SPA1 160 nm | BPA1 20 nm | ST1:TEG1 (90%:10%) 30 nm | ST1 10 nm | ETM1:LiQ (50%:50%) 40 nm | — |
| C5 | SPA1 160 nm | BPA1 20 nm | ST1:TEG1 (90%:10%) 30 nm | — | ETM1:LiQ (50%:50%) 40 nm | — |
| I1 | SPA1 20 nm | NPB 20 nm | G1:TER1 (85%:15%) 30 nm | — | Alq3 20 nm | LiF 1 nm |
| I2 | SPA1 20 nm | NPB 20 nm | G1:CBP:TER1 (45%:45%:10%) 30 nm | ST1 10 nm | Alq3 20 nm | LiF 1 nm |
| I3 | SPA1 160 nm | BPA1 20 nm | G1:TEG1 (90%:10%) 30 nm | ST1 10 nm | ETM1:LiQ (50%:50%) 40 nm | — |
| I4 | SPA1 160 nm | BPA1 20 nm | G1:TEG1 (90%:10%) 30 nm | — | ETM1:LiQ (50%:50%) 40 nm | — |
| I5 | SPA1 160 nm | BPA1 20 nm | C1:TEG1 (90%:10%) 30 nm | ST1 10 nm | ETM1:LiQ (50%:50%) 40 nm | — |
| I6 | SPA1 160 nm | BPA1 20 nm | C1:TEG1 (90%:10%) 30 nm | — | ETM1:LiQ (50%:50%) 40 nm | — |
| I7 | SPA1 160 nm | BPA1 20 nm | G2:TEG1 (90%:10%) 30 nm | ST1 10 nm | ETM1:LiQ (50%:50%) 40 nm | — |
| I8 | SPA1 160 nm | BPA1 20 nm | G3:TEG1 (90%:10%) 30 nm | ST1 10 nm | ETM1:LiQ (50%:50%) 40 nm | — |
| I9 | SPA1 20 nm | NPB 20 nm | G4:TER1 (85%:15%) 30 nm | — | Alq3 20 nm | LiF 1 nm |
| I10 | SPA1 20 nm | NPB 20 nm | G5:TER1 (85%:15%) 30 nm | — | Alq3 20 nm | LiF 1 nm |
| I11 | SPA1 20 nm | NPB 20 nm | G5:TER2 (85%:15%) 30 nm | — | Alq3 20 nm | LiF 1 nm |
| I12 | SPA1 160 nm | BPA1 20 nm | G6:TEG1 (90%:10%) 30 nm | ST1 10 nm | ETM1:LiQ (50%:50%) 40 nm | — |
| I13 | SPA1 160 nm | BPA1 20 nm | G7:TEG1 (90%:10%) 30 nm | ST1 10 nm | ETM1:LiQ (50%:50%) 40 nm | — |
| I14 | SPA1 160 nm | BPA1 20 nm | G8:TEG1 (90%:10%) 30 nm | ST1 10 nm | ETM1:LiQ (50%:50%) 40 nm | — |
| I15 | SPA1 160 nm | BPA1 20 nm | G9:TEG1 (90%:10%) 30 nm | ST1 10 nm | ETM1:LiQ (50%:50%) 40 nm | — |
| I16 | SPA1 160 nm | BPA1 20 nm | G10:TEG1 (90%:10%) 30 nm | ST1 10 nm | ETM1:LiQ (50%:50%) 40 nm | — |
| I17 | SPA1 160 nm | BPA1 20 nm | G11:TEG1 (90%:10%) 30 nm | ST1 10 nm | ETM1:LiQ (50%:50%) 40 nm | — |
| I18 | SPA1 20 nm | NPB 20 nm | G12:TER1 (85%:15%) 30 nm | — | Alq3 20 nm | LiF 1 nm |
| I19 | SPA1 20 nm | NPB 20 nm | G12:TER2 (85%:15%) 30 nm | — | Alq3 20 nm | LiF 1 nm |
| I20 | SPA1 20 nm | NPB 20 nm | G12:CBP:TER1 (45%:45%:10%) 30 nm | ST1 10 nm | Alq3 20 nm | LiF 1 nm |
| I21 | SPA1 160 nm | BPA1 20 nm | G12:TEG1 (90%:10%) 30 nm | ST1 10 nm | ETM1:LiQ (50%:50%) 40 nm | — |
| I22 | SPA1 160 nm | BPA1 20 nm | G12:TEG1 (90%:10%) 30 nm | — | ETM1:LiQ (50%:50%) 40 nm | — |
| I23 | SPA1 160 nm | BPA1 20 nm | G13:TEG1 (90%:10%) 30 nm | ST1 10 nm | ETM1:LiQ (50%:50%) 40 nm | — |

TABLE 1-continued

Structure of the OLEDs

| Ex. | HTL thickness | EBL thickness | EML thickness | HBL thickness | ETL thickness | EIL thickness |
|---|---|---|---|---|---|---|
| I24 | SPA1 20 nm | NPB 20 nm | C2:TER1 (85%:15%) 30 nm | — | Alq3 20 nm | LiF 1 nm |
| I25 | SPA1 160 nm | BPA1 20 nm | C3:TEG1 (90%:10%) 30 nm | ST1 10 nm | ETM1:LiQ (50%:50%) 40 nm | — |
| I26 | SPA1 160 nm | BPA1 20 nm | C4:TEG1 (90%:10%) 30 nm | ST1 10 nm | ETM1:LiQ (50%:50%) 40 nm | — |
| I27 | SPA1 160 nm | BPA1 20 nm | ST1:TEG1 (90%:10%) 30 nm | — | G1 40 nm | LiQ 3 nm |

TABLE 2

Data of the OLEDs

| Ex. | U1000 (V) | CE1000 (cd/A) | PE1000 (lm/W) | CIE x/y bei 1000 cd/m$^2$ | L0 (cd/m$^2$) | L1 % | LT (h) |
|---|---|---|---|---|---|---|---|
| C1 | 5.0 | 7.2 | 4.5 | 0.69/0.31 | 4000 | 80 | 230 |
| C2 | 6.5 | 9.0 | 4.3 | 0.66/0.33 | 4000 | 80 | 280 |
| C3 | 5.2 | 8.1 | 4.9 | 0.68/0.32 | 4000 | 80 | 250 |
| C4 | 4.7 | 55 | 37 | 0.36/0.61 | 4000 | 80 | 440 |
| C5 | 4.6 | 54 | 37 | 0.37/0.60 | 4000 | 80 | 400 |
| I1 | 4.8 | 7.8 | 5.1 | 0.69/0.31 | 4000 | 80 | 350 |
| I2 | 4.9 | 8.5 | 5.4 | 0.69/0.31 | 4000 | 80 | 380 |
| I3 | 4.3 | 57 | 42 | 0.36/0.61 | 4000 | 80 | 590 |
| I4 | 4.3 | 52 | 38 | 0.36/0.61 | 4000 | 80 | 510 |
| I5 | 4.5 | 51 | 36 | 0.37/0.60 | 4000 | 80 | 530 |
| I6 | 4.4 | 53 | 38 | 0.38/0.59 | 4000 | 80 | 520 |
| I7 | 4.1 | 50 | 38 | 0.36/0.60 | 4000 | 80 | 460 |
| I8 | 4.4 | 58 | 42 | 0.37/0.61 | 4000 | 80 | 490 |
| I9 | 4.7 | 7.3 | 4.8 | 0.69/0.31 | 4000 | 80 | 330 |
| I10 | 4.7 | 7.9 | 5.2 | 0.69/0.31 | 4000 | 80 | 360 |
| I11 | 5.2 | 10.2 | 6.4 | 0.66/0.33 | 4000 | 80 | 340 |
| I12 | 4.0 | 61 | 47 | 0.36/0.61 | 4000 | 80 | 620 |
| I13 | 4.1 | 60 | 47 | 0.36/0.61 | 4000 | 80 | 610 |
| I14 | 4.7 | 48 | 32 | 0.36/0.60 | 4000 | 80 | 490 |
| I15 | 4.1 | 50 | 38 | 0.36/0.61 | 4000 | 80 | 450 |
| I16 | 4.4 | 55 | 40 | 0.36/0.61 | 4000 | 80 | 560 |
| I17 | 4.2 | 57 | 43 | 0.37/0.61 | 4000 | 80 | 530 |
| I18 | 4.7 | 7.8 | 5.2 | 0.69/0.31 | 4000 | 80 | 340 |
| I19 | 5.8 | 9.2 | 5.0 | 0.66/0.33 | 4000 | 80 | 380 |
| I20 | 5.0 | 8.3 | 5.3 | 0.68/0.32 | 4000 | 80 | 360 |
| I21 | 4.2 | 59 | 45 | 0.36/0.61 | 4000 | 80 | 610 |
| I22 | 4.2 | 57 | 43 | 0.36/0.61 | 4000 | 80 | 580 |
| I24 | 5.2 | 6.6 | 2.5 | 0.69/0.31 | 4000 | 80 | 260 |
| I25 | 4.4 | 48 | 35 | 0.36/0.61 | 4000 | 80 | 390 |
| I26 | 4.9 | 46 | 30 | 0.36/0.61 | 4000 | 80 | 470 |
| I27 | 4.1 | 54 | 42 | 0.36/0.60 | 4000 | 80 | 430 |

TABLE 3

Structural formulae of the materials for the OLEDs

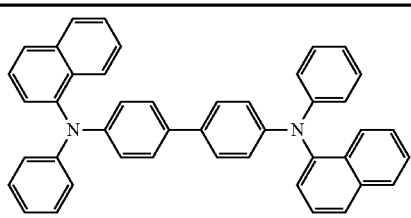

NPB

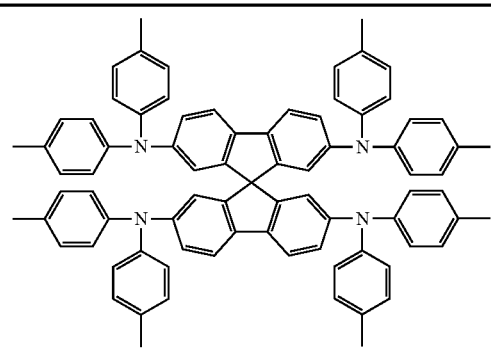

SpA1

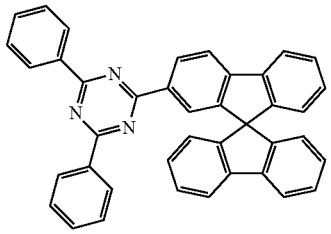

ST1 (prior art)

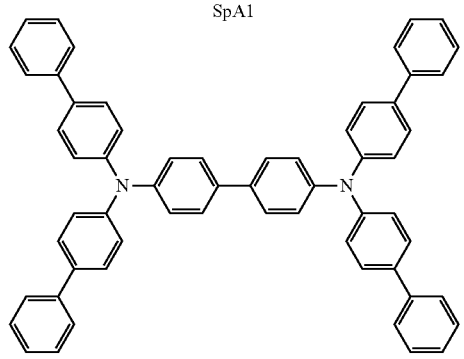

BPA1

TABLE 3-continued
Structural formulae of the materials for the OLEDs
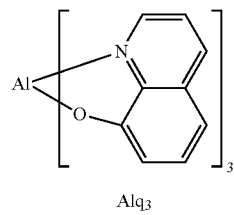
Alq3
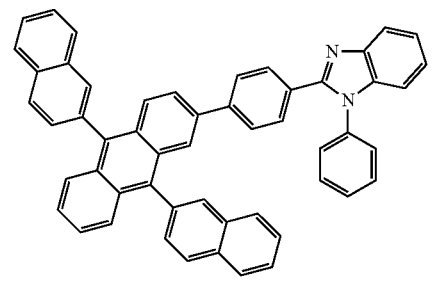
ETM1 (prior art)
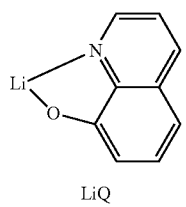
LiQ
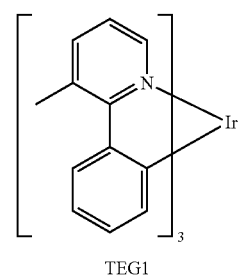
TEG1
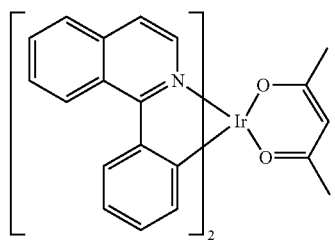
TER1
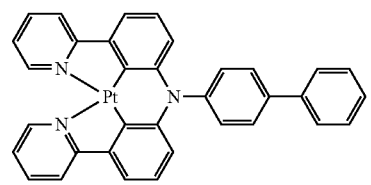
TER2
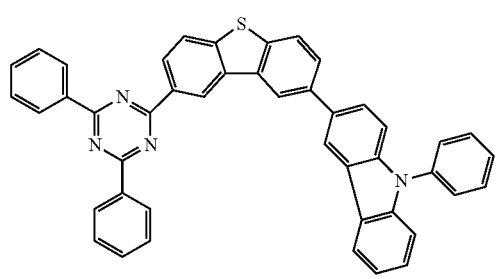
G1
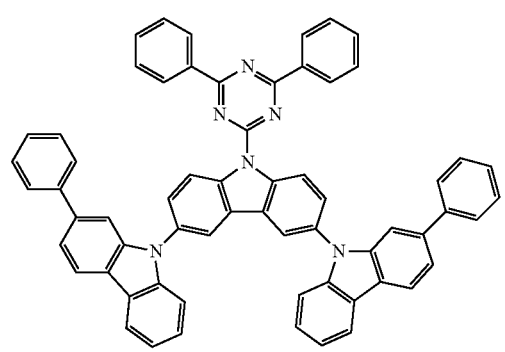
C1

TABLE 3-continued
Structural formulae of the materials for the OLEDs
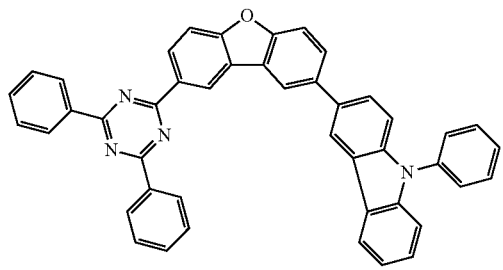
G2
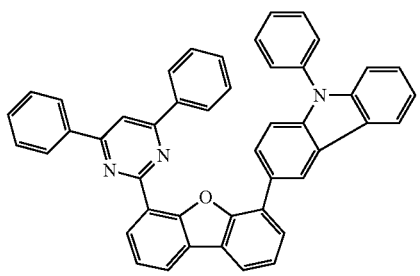
G3
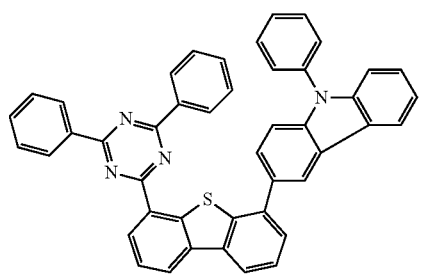
G4
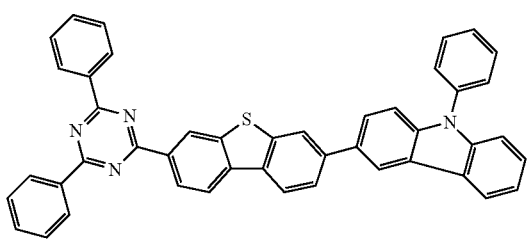
G5
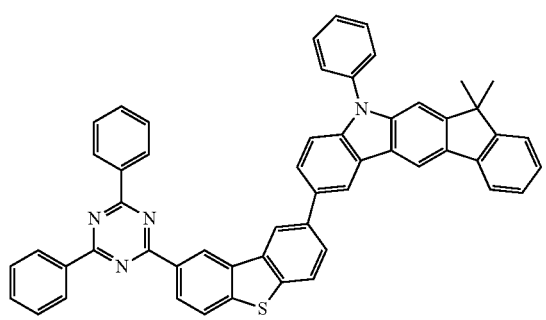
G6
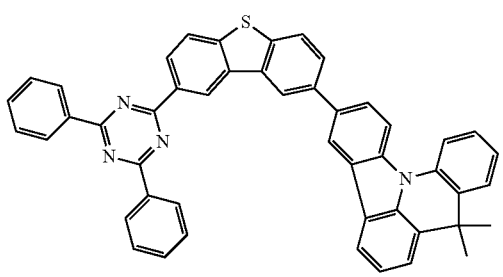
G7
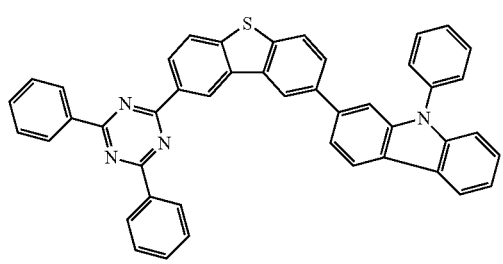
G8
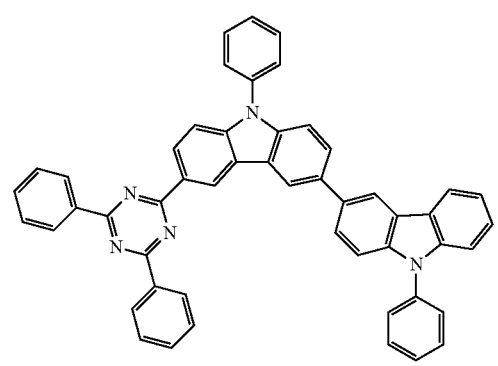
G9

TABLE 3-continued
Structural formulae of the materials for the OLEDs
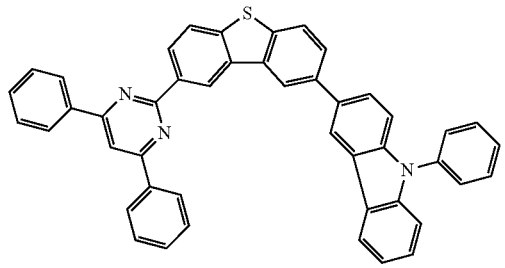
G10
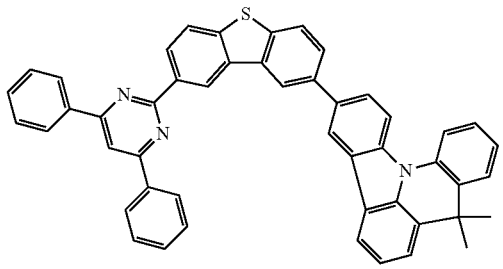
G11
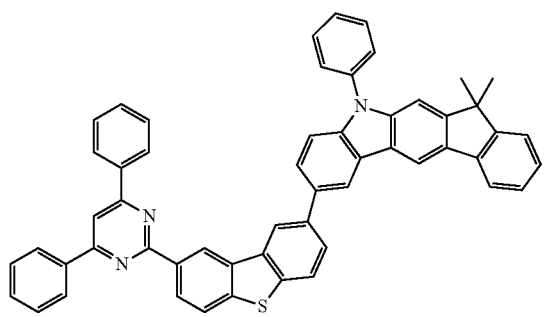
G12
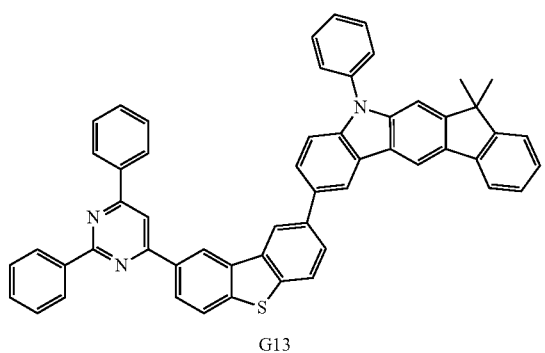 [SMILES: CC1(C)c2ccccc2-c2cc3c4cc(-c5ccc6sc7ccc(-c8cc(-c9ccccc9)nc(-c9ccccc9)n8)cc7c6c5)ccc4n(-c4ccccc4)c3cc21]
G13
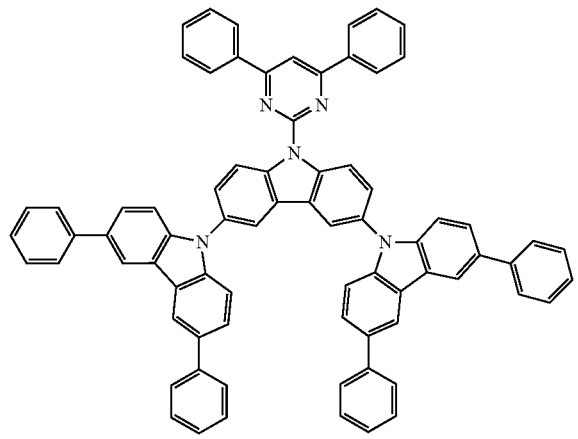
C2
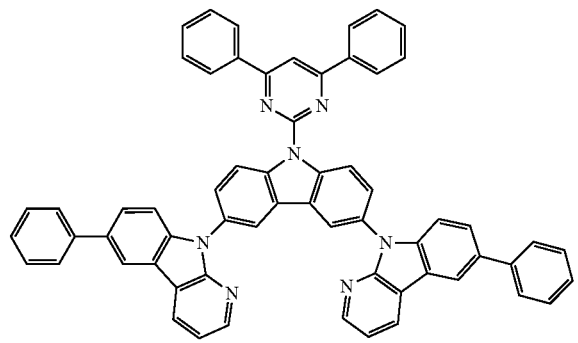
C3
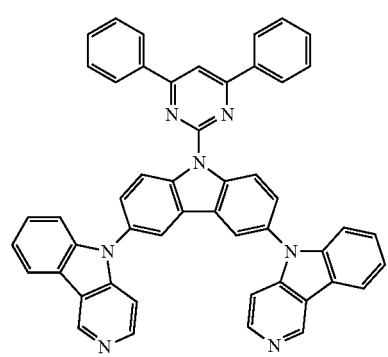
C4

The invention claimed is:
1. A compound of formula (II-1a)

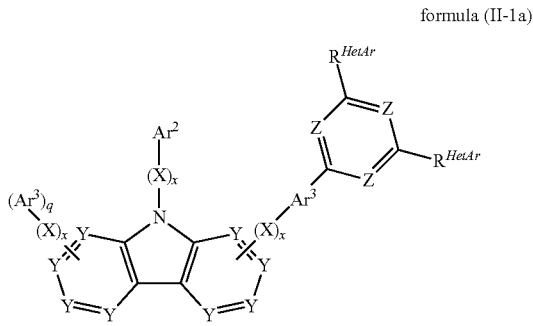

formula (II-1a)

where the symbols and indices occurring are defined as follows:
$Ar^2$ is on each occurrence, identically or differently, an aromatic ring system having 6 to 30 aromatic ring atoms, which is optionally substituted by one or more radicals $R^1$;
$Ar^3$ is on each occurrence, identically or differently, a heteroaromatic ring system having 5 to 30 aromatic ring atoms, which is optionally substituted by one or more radicals $R^1$;
X is selected on each occurrence, identically or differently, and is —B($R^1$)—, —N($R^1$)—, —P($R^1$)—, —P($R^1$)$_3$—, —P(=O)($R^1$)—, —C($R^1$)$_2$—, —Si($R^1$)$_2$—, C=O, C=N$R^1$, C=C($R^1$)$_2$, —O—, —S—, —Se—, —S(=O)— or —S(=O)$_2$—;
Y is on each occurrence, identically or differently, $CR^{Cz}$ or N, or is C if a group X or $Ar^1$ or $Ar^3$ or Cz is bonded to this group;
Z is on each occurrence N;
x is on each occurrence, identically or differently, 0 or 1, where, in the case where x=0, the two groups bonded to the group X in question are bonded directly to one another;
$R^1$, $R^{HetAr}$ and $R^{Cz}$ are on each occurrence, identically or differently, H, D, F, Cl, Br, I, N($R^2$)$_2$, CN, NO$_2$, Si($R^2$)$_3$, B(O$R^2$)$_2$, C(=O)$R^2$, P(=O)($R^2$)$_2$, S(=O)$_2R^2$, OSO$_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkoxy or thioalkoxy group having 3 to 40 C atoms, each of which is optionally substituted by one or more radicals $R^2$, where one or more CH$_2$ groups is optionally replaced by —$R^2$C=C$R^2$—, —Si($R^2$)$_2$—, —Ge($R^2$)$_2$—, —Sn($R^2$)$_2$—, C=O, C=S, C=Se, C=N$R^2$, —P(=O)($R^2$)—, —S(=O)—, —S(=O)$_2$—, —N($R^2$)—, —O—, —S—, —C(=O)O— or —C(=O)N$R^2$—, or an aromatic or heteroaromatic ring system having 5 to 60 aromatic ring atoms, which is optionally in each case be substituted by one or more radicals $R^2$, or an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which may in each case be substituted by one or more radicals $R^2$; two or more substituents $R^1$, $R^{HetAr}$ or $R^{Cz}$ here is optionally linked to one another and may optionally form a mono- or polycyclic aliphatic, aromatic or heteroaromatic ring system;
$R^2$ is on each occurrence, identically or differently, H, D or an aliphatic, aromatic or heteroaromatic organic radical having 1 to 20 C atoms, in which, in addition, one or more H atoms is optionally replaced by D or F; two or more radicals $R^2$ here is optionally linked to one another and may optionally form a mono- or polycyclic aliphatic, aromatic or heteroaromatic ring system.

2. The compound according to claim 1, wherein no groups Y, or one or two groups Y, per six-membered ring of the carbazole derivative stand for N, and all other groups Y stand for $CR^{Cz}$ or C.

3. The compound according to claim 1, wherein for the formula (II-1a) one or more groups Y stand for N.

4. The compound according to claim 1, wherein X is selected on each occurrence, identically or differently, from N($R^1$), C($R^1$)$_2$, C=O, C=N$R^1$, O, S, S(=O) and S(=O)$_2$.

5. A process for the preparation of the compound according to claim 1, which comprises the following steps:
a) synthesis of a substituted carbazole derivative, optionally with introduction of halogen substituents,
b) coupling of the nitrogen atom of the carbazole derivative to an aryl or heteroaryl group in an organometallic coupling reaction or a nucleophilic aromatic substitution reaction,
c) organometallic coupling reaction for the introduction of aryl or heteroaryl groups on one or both aromatic six-membered rings of the carbazole group.

6. An oligomer, polymer or dendrimer comprising one or more compounds according to claim 1, where a bond to the polymer, oligomer or dendrimer occurs instead of one or more radicals or H atoms of the compounds.

7. A formulation comprising at least one compound according to claim 1 and at least one solvent.

8. A formulation comprising the oligomer, polymer or dendrimer according to claim 6 and at least one solvent.

9. An electronic device which comprises the compounds according to claim 1.

10. An electronic device which comprises the oligomer, dendrimer or polymer according to claim 6.

11. The electronic device as claimed in claim 9, wherein the device is an organic electroluminescent device (OLED), organic field-effect transistor (O-FET), organic thin-film transistor (O-TFT), organic light-emitting transistor (O-LET), organic integrated circuit (O-IC), organic solar cell (O-SC), organic field-quench device (O-FQD), light-emitting electrochemical cell (LEC), organic laser diode (O-laser) or organic photoreceptor.

12. An organic electroluminescent device which comprises the compound according to claim 1 is employed as a matrix material.

13. An organic electroluminescent device which comprises the compound according to claim 1 is employed as a matrix material for phosphorescent dopants, or as electron-transport material.

14. An organic electroluminescent device comprising a compound of Formula II as a matrix material formula (II)

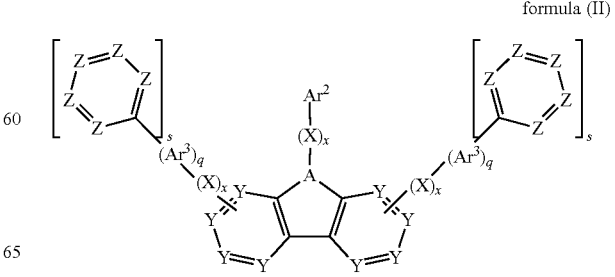

where the symbols and indices occurring are defined as follows:

Ar$^2$ is on each occurrence, identically or differently, an aromatic or heteroaromatic ring system having 6 to 60 aromatic ring atoms, which is optionally substituted by one or more radicals R$^1$;

Ar$^3$ is on each occurrence, identically or differently, an aromatic or heteroaromatic ring system having 5 to 60 aromatic ring atoms, which is optionally substituted by one or more radicals R$^1$;

A is N or P;

X is selected on each occurrence, identically or differently, and is —B(R$^1$)—, —N(R$^1$)—, —P(R$^1$)—, —P(R$^1$)$_3$—, —C(R$^1$)$_2$—, —Si(R$^1$)$_2$—, C=O, C=NR$^1$, C=C(R$^1$)$_2$, —O—, —S—, —Se—, —S(=O)— or —S(=O)$_2$—;

Y is on each occurrence, identically or differently, CR$^{Cz}$ or N, or is C if a group X or Ar$^1$ or Ar$^3$ or Cz is bonded to this group;

Z is on each occurrence, identically or differently, CR$^{HetAr}$ or N, where at least one Z per six-membered ring is equal to N;

q is on each occurrence, identically or differently, 0 or 1, where, in the case where q=0, the two groups bonded to the group Ar$^1$ or Ar$^3$ in question are bonded directly to one another;

s is on each occurrence, identically or differently, 0 or 1, with the proviso that at least one index s is equal to 1;

x is on each occurrence, identically or differently, 0 or 1, where, in the case where x=0, the two groups bonded to the group X in question are bonded directly to one another;

R$^1$, R$^{HetAr}$ and R$^{Cz}$ are on each occurrence, identically or differently, H, D, F, Cl, Br, I, N(R$^2$)$_2$, CN, NO$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkoxy or thioalkoxy group having 3 to 40 C atoms, each of which is optionally substituted by one or more radicals R$^2$, where one or more CH$_2$ groups is optionally replaced by —R$^2$C=CR$^2$—, —Si(R$^2$)$_2$—, —Ge(R$^2$)$_2$—, —Sn(R$^2$)$_2$—, C=O, C=S, C=Se, C=NR$^2$, —P(=O)(R$^2$)—, —S(=O)—, —S(=O)$_2$—, —N(R$^2$)—, —O—, —S—, —C(=O)O— or —C(=O)NR$^2$—, or an aromatic or heteroaromatic ring system having 5 to 60 aromatic ring atoms, which is optionally in each case be substituted by one or more radicals R$^2$, or an aryloxy or heteroaryloxy group having 5 to 60 aromatic ring atoms, which is optionally substituted by one or more radicals R$^2$, or an aralkyl or heteroaralkyl group having 5 to 60 aromatic ring atoms, which may in each case be substituted by one or more radicals R$^2$; two or more substituents R$^1$, R$^{HetAr}$ or R$^{Cz}$ here is optionally linked to one another and may optionally form a mono- or polycyclic aliphatic, aromatic or heteroaromatic ring system;

R$^2$ is on each occurrence, identically or differently, H, D or an aliphatic, aromatic or heteroaromatic organic radical having 1 to 20 C atoms, in which, in addition, one or more H atoms is optionally replaced by D or F; two or more radicals R$^2$ here is optionally linked to one another and may optionally form a mono- or polycyclic aliphatic, aromatic or heteroaromatic ring system.

15. The electroluminescent device according to claim 14, wherein no groups Y, or one or two groups Y, per six-membered ring of the carbazole derivative stand for N, and all other groups Y stand for CR$^{Cz}$ or C.

16. The electroluminescent device according to claim 14, wherein A is N.

17. The electroluminescent device according to claim 14, wherein one or more groups Y is N.

18. The electroluminescent device according to claim 14, wherein all indices s adopt the value 1.

19. The electroluminescent device according to claim 14, wherein the group

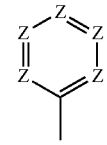

of the formula (II) represents triazine, pyrazine, pyridazine, pyrimidine or pyridine, which is optionally substituted by one or more radicals R$^{HetAr}$.

20. The electroluminescent device according to claim 14, wherein X is on each occurrence, identically or differently, selected from N(R$^1$), C(R$^1$)$_2$, C=O, C=NR$^1$, O, S, S(=O) or S(=O)$_2$.

21. The electroluminescent device according to claim 14, wherein the compound conforms to one of the following formulae:

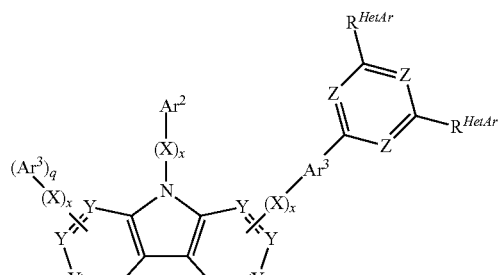

formula (II-1a)

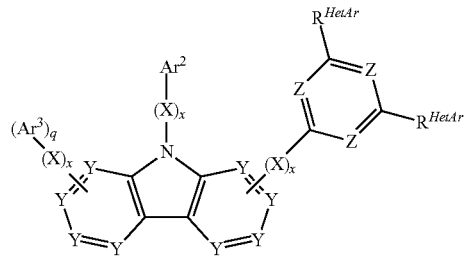

formula (II-1b)

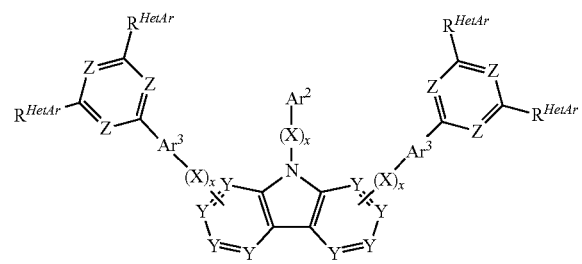

formula (II-2a)

-continued
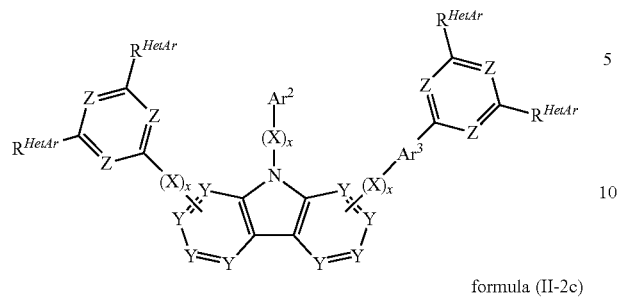
formula (II-2b)
formula (II-2c)
where the symbols and indices occurring are as defined in claim 14.
* * * * *